(12) United States Patent
Sigurdsson

(10) Patent No.: US 10,988,528 B2
(45) Date of Patent: Apr. 27, 2021

(54) ANTIBODY-BASED MOLECULES SPECIFIC FOR THE TRUNCATED ASP421 EPITOPE OF TAU AND THEIR USES IN THE DIAGNOSIS AND TREATMENT OF TAUOPATHY

(71) Applicant: New York University, New York, NY (US)

(72) Inventor: Einar Sigurdsson, Scarsdale, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/750,975

(22) PCT Filed: Aug. 11, 2016

(86) PCT No.: PCT/US2016/046513
§ 371 (c)(1),
(2) Date: Feb. 7, 2018

(87) PCT Pub. No.: WO2017/027685
PCT Pub. Date: Feb. 16, 2017

(65) Prior Publication Data
US 2019/0315841 A1   Oct. 17, 2019

Related U.S. Application Data

(60) Provisional application No. 62/211,123, filed on Aug. 28, 2015, provisional application No. 62/204,699, filed on Aug. 13, 2015.

(51) Int. Cl.
| | | |
|---|---|---|
| C07K 16/18 | (2006.01) | |
| A61P 25/28 | (2006.01) | |
| G01N 33/532 | (2006.01) | |
| A61K 38/00 | (2006.01) | |

(52) U.S. Cl.
CPC .............. *C07K 16/18* (2013.01); *A61P 25/28* (2018.01); *G01N 33/532* (2013.01); *A61K 38/00* (2013.01); *C07K 2317/622* (2013.01); *C07K 2317/92* (2013.01); *G01N 2800/2821* (2013.01)

(58) Field of Classification Search
CPC .............. C07K 16/18; C07K 2317/622; C07K 2317/92; A61P 25/28; A61P 9/00; A61P 29/00; A61P 25/16; A61P 25/02; A61P 25/00; A61P 21/04; A61P 17/02; G01N 33/532; G01N 2800/2821; A61K 38/00
See application file for complete search history.

(56) References Cited

U.S. PATENT DOCUMENTS

| | | |
|---|---|---|
| 4,179,337 A | 12/1979 | Davis et al. |
| 4,495,285 A | 1/1985 | Shimizu et al. |
| 4,609,546 A | 9/1986 | Hiratani |
| 4,681,581 A | 7/1987 | Coates |
| 4,735,210 A | 4/1988 | Goldenberg |
| 4,766,106 A | 8/1988 | Katre et al. |
| 5,101,827 A | 4/1992 | Goldenberg |
| 5,102,990 A | 4/1992 | Rhodes |
| 5,225,539 A | 7/1993 | Winter |
| 5,434,050 A | 7/1995 | Maggio |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,585,089 A | 12/1996 | Queen et al. |
| 5,589,466 A | 12/1996 | Feigner et al. |
| 5,625,126 A | 4/1997 | Lonberg et al. |
| RE35,500 E | 5/1997 | Rhodes |
| 5,633,425 A | 5/1997 | Lonberg et al. |
| 5,648,471 A | 7/1997 | Buttmm et al. |
| 5,661,016 A | 8/1997 | Lonberg et al. |
| 5,670,477 A | 9/1997 | Poduslo et al. |

(Continued)

FOREIGN PATENT DOCUMENTS

| | | |
|---|---|---|
| WO | 92/03918 | 3/1992 |
| WO | 92/22645 | 12/1992 |
| WO | 93/11231 | 6/1993 |
| WO | 94/25585 | 11/1994 |
| WO | 98/22120 | 5/1998 |

(Continued)

OTHER PUBLICATIONS

International Search Report PCT/US2016/046513 (WO 2017/027685) (2017) (5 pages).

(Continued)

*Primary Examiner* — Gregory S Emch

(74) *Attorney, Agent, or Firm* — Jeffrey I. Auerbach; AuerbachSchrot LLC

(57) ABSTRACT

The present invention relates to antibody-based molecules (including single domain antibody fragment, scFv molecules, antibodies, antibody fragments, diabodies, and the epitope-binding domains thereof) that are capable of immunospecifically and selectively binding to the truncated Asp421 epitope of Tau. Such antibody-based molecules are useful to detect pathological Tau protein conformer if present in a biological sample, especially in conjunction with the diagnosis and/or treatment of Alzheimer's disease or other tauopathy, and thus provide a diagnostic for Alzheimer's disease and other Tau pathologies. The antibody-based molecules of the present invention have particular utility as diagnostic markers for, Alzheimer's disease and related tauopathies and as pharmaceutical compositions for the treatment of such conditions.

17 Claims, 13 Drawing Sheets

Specification includes a Sequence Listing.

(56) References Cited

U.S. PATENT DOCUMENTS

| | | | |
|---|---|---|---|
| 5,697,902 | A | 12/1997 | Goldenberg |
| 5,721,106 | A | 2/1998 | Maggio |
| 5,733,743 | A | 3/1998 | Johnson et al. |
| 5,741,957 | A | 4/1998 | Deboer et al. |
| 5,750,172 | A | 5/1998 | Meade et al. |
| 5,756,687 | A | 5/1998 | Denman et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,827,690 | A | 10/1998 | Meade et al. |
| 5,837,473 | A | 11/1998 | Maggio et al. |
| 5,859,205 | A | 1/1999 | Adair et al. |
| 5,874,299 | A | 2/1999 | Lonberg et al. |
| 5,877,397 | A | 3/1999 | Lonberg et al. |
| 5,973,972 | A | 10/1999 | Kwon et al. |
| 6,077,835 | A | 6/2000 | Hanson et al. |
| 6,207,153 | B1 | 3/2001 | Dan et al. |
| 6,265,150 | B1 | 7/2001 | Terstappen et al. |
| 6,407,213 | B1 | 6/2002 | Carter et al. |
| 6,471,960 | B1 | 10/2002 | Anderson |
| 6,821,504 | B2 | 11/2004 | Wisniewski et al. |
| 6,881,557 | B2 | 4/2005 | Foote |
| 7,446,180 | B2 | 11/2008 | Novak |
| 8,012,936 | B2 | 9/2011 | Sigurdsson et al. |
| 8,748,386 | B2 | 6/2014 | Sigurdsson |
| 9,139,643 | B2 | 9/2015 | Sigurdsson |
| 10,132,818 | B2 | 11/2018 | Sigurdsson |
| 2003/0147811 | A1 | 8/2003 | Wisniewskki et al. |
| 2008/0050383 | A1 | 2/2008 | Sigurdsson et al. |
| 2008/0220449 | A1 | 9/2008 | Vasan et al. |
| 2009/0098155 | A1 | 4/2009 | Garsky et al. |
| 2009/0317805 | A1 | 12/2009 | Wang et al. |
| 2010/0316564 | A1 | 12/2010 | Sigurdsson et al. |
| 2011/0318358 | A1 | 12/2011 | Sigurdsson et al. |

FOREIGN PATENT DOCUMENTS

| | | | |
|---|---|---|---|
| WO | 98/24884 | 6/1998 | |
| WO | 02/064084 | 8/2002 | |
| WO | 2007/059782 | 5/2007 | |
| WO | 2009/033743 | 3/2009 | |
| WO | WO-2009033743 A1 * | 3/2009 | ............ C07K 16/18 |
| WO | 2010/106127 | 9/2010 | |
| WO | 2010/115843 | 10/2010 | |
| WO | 2011/013034 | 2/2011 | |
| WO | 2015/067432 | 5/2015 | |
| WO | 2017/189963 | 11/2017 | |

OTHER PUBLICATIONS

Written Opinion of the International Searching Authority PCT/US2016/046513 (WO 2017/027685) (2017) (6 pages).

Adams, G.P. et al. (1998) "*Prolonged in vivo Tumour Retention of a Human Diabody Targeting the Extracellular Domain of Human HER2/neu*," Brit. J. Cancer 77(9):1405-1412.

Ahmad, Z.A. et al. (2012) "*scFv Antibody: Principles and Clinical Application*," Clin. Dev. Immunol. 2012:980250.

Alt, M. et al. (1999) "*Novel Tetravalent and Bispecific IgG-like Antibody Molecules Combining Single-Chain Diabodies with the Immunoglobulin γl Fc or CH3 Region*," Febs Lett. 454:90-94.

Altschul, S.F. (1991) "*Amino Acid Substitution Matrices from an Information Theoretic Perspective*," J. Mol. Biol. 219: 555-565.

Andorfer, C. et al. (2003) "*Hyperphosphorylation and Aggregation of Tau in Mice Expressing Normal Human Tau Isoforms*," J. Neurochem. 86:582-590.

Asuni, A.A. et al. (2006) "*Tau-Based Immunotherapy for Dementia*," Alzheimer's & Dementia 2(3):S40-S41 02-05-04.

Asuni, A.A. et al. (2007) "*Immunotherapy Targeting Pathological Tau Conformers in A Tangle Mouse Model Reduces Brain Pathology with Associated Functional Improvements*," J. Neurosci. 27:9115-9129.

Barderas, R. et al. (2008) "*Affinity Maturation Of Antibodies Assisted by in Silico Modeling*," Proc. Natl. Acad. Sci. (USA) 105(26):9029-9034.

Basurto-Islas, G. et al. (2008) "Accumulation of Aspartic Acid(421)- and Glutamic Acid(391-Cleaved Tau in Neurofibrillary Tangles Correlates with Progression in Alzheimer's Disease," J Neuropathol Exp Neuro! 67(5):169-179.

Bekris, L.M. et al. (2010) "*Genetics of Alzheimer Disease*," J. Geriatr. Psychiatry Neurol. 23(4):213-227.

Benvenisty N. et al., "*Direct Introduction of Genes into Rates and Expression of the Genes*," Proc. Natl. Acad. Sci. (USA) 83: 9551-9555.

Beny, R.W. et al. (2003) "*Inhibition of Tau Polymerization by Its Carboxy-Terminal Caspase Cleavage Fragment*," Biochemistry 42(27):8325-8331.

Bhaskar, S. et al. (2010) "*Multifunctional Nanocarriers for Diagnostics, Drug Delivery and Targeted Treatment Across Blood-Brain Barrier: Perspectives on Tracking and Neuroimaging*," Part. Fibre. Toxicol. 7:3 pp. 1-25.

Bi, M. et al. (2011) "*Tau-Targeted Immunization Impedes Progression of Neurofibrillary Histopathology in Aged P301L Tau Transgenic Mice*," PLoS One. 6:e26860.

Bibl, M. et al. (2012) "*Neurochemical Biomarkers in Alzheimer's Disease and Related Disorders*," Ther Adv Neurolog Disorders 5(6):455-476.

Bickel, U. et al. (2001) "*Delivery of Peptides and Proteins Through the Blood-Brain Barrier*," Adv. Drug Deliv. Rev. 46:247-279.

Bird, R.E. et al. (1988) "*Single-Chain Antigen-Binding Proteins*," Science 242:423-426.

Bitter, G.A. et al. (1987) "*Expression and Secretion Vectors for Yeast*," Methods Enzymol. 153, 516544 (1987).

Biundo, F. et al. (2017) "*Abolishing Tau Cleavage by Caspases At Aspartate421 Causes Memory/Synaptic Plasticity Deficits and Pre-Pathological Tau Alterations*," Transl. Psychiatry 7:e1198 (pp. 1-11).

Blennow, K. et al. (2010)"*Cerebrospinal Fluid and Plasma Biomarkers in Alzheimer Disease*," Nat. Rev. Neurol. 6: 131-144.

Boado, R.J. et al. (2010) "*IgG-Single Chain Fv Fusion Protein Therapeutic for Alzheimer's Disease: Expression in CHO cells and Pharmacokinetics and Brain Delivery in the Rhesus Monkey*," Biotechnol. Bioeng. 105:627-635.

Boimel, M. et al. (2010) "*Efficacy and Safety of Immunization with Phosphorylated Tau Against Neurofibrillary Tangles in Mice*," Exp. Neurol. 224, 472-485.

Bostrom, J. et al. (2009) "*Improving Antibody Binding Affinity and Specificity for Therapeutic Development*," Methods Mol. Biol. 525:353-376.

Boutajangout, A. et al. (2010) "*Immunotherapy Targeting Pathological Tau Prevents Cognitive Decline in a New Tangle Mouse Model*," J. Neurosci. 30:16559-16566.

Boutajangout, a. et al. (2011) "*Passive Immunization Targeting Pathological Phospho-Tau Protein in a Mouse Model Reduces Functional Decline and Clears Tau Aggregates From the Brain*," J. Neurochem. 118:658-667.

Boutajangout, A. et al. (2011) "*Passive Tau Immunotherapy Diminishes Functional Decline and Clears Tau Aggregates in Mouse Model of Tauopahty*," Alzheimer's & Dementia 6(4):S578:P3-427 (1 page).

Budson, A.E. et al. (2012) "*New Criteria for Alzheimer Disease and Mild Cognitive Impairment: Implications for the Practicing Clinician*," Neurologist 18(6):356-363.

Calignon A et al. (2010) "*Caspase Activation Precedes and Leads to Tangles*," Nature 464:1201-1205.

Carrillo, M.C. et al. (2013) "*Revisiting the Framework of the National Institute on Aging-Alzheimer 's Association Diagnostic Criteria*," Alzheimers Dement. 9(5):594-601.

Carter, P. et al. (1992) "*Humanization Of An Anti-p185her2 Antibody for Human Cancer Therapy*," Proc. Natl. Acad. Sci. (U.S.A.) 89:4285-4289.

Castillo-Carranza, D.L. et al. (2014) "*Passive Immunization with Tau Oligomer Monoclonal Antibody Reverses Tauopathy Phenotypes without Affecting Hyperphosphorylated Neurofibrillary Tangles*," J. Neurosci. 34:4260-4272.

(56) References Cited

OTHER PUBLICATIONS

Castillo-Carranza, D.L. et al. (2014) "*Specific Targeting of Tau Oligomers in Htau Mice Prevents Cognitive Impairment and Tau Toxicity Following Injection With Brain-Derived Tau Oligomeric Seeds,*" J. Alzheimers. Dis. 40:S97-S111.
Chai, X. et al. (2011) "*Passive Immunization With Anti-Tau Antibodies in Two Transgenic Models: Reduction of Tau Pathology and Delay of Disease Progression,*" J. Biol Chem. 286:34457-34467.
Chen et al. (1993) "*B Cell Development in Mice That Lack One or Both Immunoglobulin Kappa Light Chain Genes,*" Embo J. 12:821-830.
Chen, J. et al. (1993) "*Immunoglobulin gene rearrangement in B cell deficient mice generated by targeted deletion of the JH locus,*" International Immunology 5:647-656.
Chien, D.T. (2013) "*Early Clinical PET Imaging Results With the Novel PHF-Tau Radioligand [F18]-T807,*" J. Alzheimers. Dis. 34(2):457-468.
Chien, D.T. (2014) "*Early Clinical Pet Imaging Results With the Novel PHF-Tau Radioligand [F18]-T808,*" J. Alzheimers. Dis. 38:171-184.
Cho, J.H. et al. (2004) "*Glycogen Synthase Kinase 3 Beta Induces Caspase-Cleaved Tau Aggregation In Situ,*" J. Biol. Chem. 279(52):54716-54723.
Chothia, C. et al. (1987) "*Canonical Structures for the Hypervariable Regions of Immunoglobulins,*" J. Mol. Biol. 196:901-917.
Co, M. S. et al. (1991) "*Humanized Antibodies for Antiviral Therapy,*" Proc. Natl. Acad. Sci. (U.S.A.) 88:2869-2873.
Congdon, E. E. et al. (2013) "*Antibody Uptake into Neurons Occurs Primarily via Clathrin-dependent Fcgamma Receptor Endocytosis and Is a Prerequisite for Acute Tau Protein Clearance,*" J. Biol Chem. 288:35452-35465.
Congdon, E.E. (2014) "*Harnessing the Immune System for Treatment and Detection of Tau Pathology,*" J. Alzheimers Dis. 40:S113-S121.
Corsaro, C.M. et al. (1981) "*Enhancing the efficiency of DNA-mediated gene transfer in mammalian cells,*" Somatic Cell Genetics 7(5):603-616.
Cribbs, D.H. et al. (2004) "*Caspase-Mediated Degeneration in Alzheimer's Disease,*" Amer. J. Pathol. 165(2):353-355.
d'Abramo, C. et al. (2013) "*Tau Passive Immunotherapy in Mutant P301L Mice: Antibody Affinity versus Specificity,*" PLoS One 8:e62402.
Davis, J. et al. (2004) "*Early-Onset and Robust Cerebral Microvascular Accumulation of Amyloid Beta-Protein in Transgenic Mice Expressing Low Levels Of A Vasculotropic Dutch/Iowa Mutant Form Of Amyloid Beta-Protein Precursor,*" J Biol Chem 279:20296-20306.
Dincq, S. et al. (2001) "*Expression and Purification Of Monospecific and Bispecific Recombinant Antibody Fragments Derived From Antibodies That Block the CD80/CD86-CD28 Costimulatory Pathway,*" Protein Express. Purificat. 22(1):11-24.
Eddy, S.R. (2004) "*Where Did the BLOSUM62 Alignment Score Matrix Come From?,*" Nature Biotechnol. 22(8):1035-1036.
Eurasian Patent Search Report Appln No. 201171397 (2012) (4 pages).
Evans et al. (1995) "*Rapid expression of an anti-human C5 chimeric Fab utilizing a vector that replicates in COS and 293 cells,*" J. Immunol. Meth. 184, 123-138.
Extended European Search Report EP 16835896.8 (2019) pp. 1-11.
Fagan, a.M. et al. (2010) "*Upcoming Candidate Cerebrospinal Fluid Biomarkers of Alzheimer's Disease,*" Biomarkers Med 6(4):455-476.
Fasulo, L. et al. (2005) "*Apoptotic Effect of Caspase-3 Cleaved Tau in Hippocampal Neurons and Its Potentiation by Tau FTDP-Mutation N279K,*" J. Alzheimers. Dis. 7(1):3-13.
Finlay, W.J. et al. (2009) "*Affinity Maturation Of A Humanized Rat Antibody for Anti-Rage Therapy: Comprehensive Mutagenesis Reveals a High Level Of Mutational Plasticity Both Inside and Outside the Complementarity-Determining Regions,*" J. Mol. Biol. 388(3):541-558.

Fisher, a. et al. (2009) "*Efficient Isolation of Soluble Intracellular Single-Chain Antibodies Using the Twin Arginine Translocation Machinery,*" J. Mol. Biol. 385(1):299-311.
Fishwild, D. et al. (1996) "*High Avidity Human IgG Kappa Monoclonal Antibodies From a Novel Strain of Minilocus Transgenic Mice,*" Nature Biotechnol. 14:845-851.
Fodero-Tavoletti, M. T. et al. (2011) "*18F-THK523: A Novel in Vivo Tau Imaging Ligand for Alzheimer's Disease,*" Brain 134:1089-1100.
Fodero-Tavoletti, M. T. et al. (2014) "*Assessing THK523 Selectivity for Tau Deposits in Alzheimer's Disease and Non-Alzheimer's Disease Tauopathies,*" Alzheimer's Res. Ther. 6:11.
Fraser, K.J. et al. (1972) "*Specific Cleavage Between Variable and Constant Domains of Rabbit Antibody Light Chains by Dilute Acid Hydrolysis,*" Biochemistry 11(26):4974-4977.
Gamblin, T.C. et al. (2003) "*Caspase Cleavage of Tau: Linking Amyloid and Neurofibrillary Tangles in Alzheimer's Disease,*" Proc. Natl. Acad. Sci. (U.S.A.) 100(17):10032-10037.
GenBank Accession No. EAW93567 (Dec. 18, 2006).
Glaser, S.M. et al. (1992) "*Antibody Engineering by Codon-Based Mutagenesis in a Filamentous Phage Vector System,*" J. Immunology 149:3903-3913.
Gonzales, N. R. et al. (2004) "*SDR Grafting of a Murine Antibody Using Multiple Human Germline Templates to Minimize Its Immunogenicity,*" Mol. Immunol. 41:863-872.
Gorman, S. D. et al. (1991) "*Reshaping a Therapeutic CD4 Antibody,*" Proc. Natl. Acad. Sci. (U.S.A.) 88:4181-4185.
Gu, J. et al. (2013) "*Two Novel Tau Antibodies Targeting the 396/404 Region are Primarily Taken Up by Neurons and Reduce Tau Protein Pathology,*" J. Biol. Chem. 288(46):33081-33095.
Guillozet-Bongaarts, A.L. et al. (2005) "*Tau Truncation During Neurofibrillary Tangle Evolution in Alzheimer's Disease,*" Neurobiol. Aging ;26(7):1015-1022.
Guillozet-Bongaarts, A.L. et al. (2006) "*Pseudophosphorylation of Tau At Serine 422 Inhibits Caspase Cleavage: in Vitro Evidence and Implications for Tangle Formation in vivo,*" J. Neurochem. 97(4):1005-1014.
Gustchina, E. et al. (2009) "*Affinity Maturation by Targeted Diversification of the CDR-H2 Loop of a Monoclonal Fab Derived From a Synthetic Naïve Human Antibody Library and Directed Against the Internal Trimeric Coiled-Coil of Gp41 Yields a Set of Fabs With Improved HIV-1 Neutralization Potency and Breadth,*" Virology 393(1):112-119.
Hackel, B.J. et al. (2010) "*Stability and CDR Composition Biases Enrich Binder Functionality Landscapes,*" J. Mol. Biol. 401(1):84-96.
Hales, C.M. et al. (2013) "*From Frontotemporal Lobar Degeneration Pathology to Frontotemporal Lobar Degeneration Biomarkers,*" Int. Rev. Psychiatry 25:210-220.
Hanes, et al. (1997) "*New advances in microsphere-based single-dose vaccines,*" Advanced Drug Delivery Reviews 28:97-119.
Harada, R., et al. (2013) "*Comparison of the Binding Characteristics of [18E]THK-523 and Other Amyloid Imaging Tracers to Alzheimer's Disease Pathology,*" Eur. J. Nucl. Med. Mol. Imaging 40:125-132.
Harding, F., et al. (1995) "*Class Switching in Human Immunoglobulin Transgenic Mice,*" Ann. N. Y. Acad. Sci. 764 536-546.
Henikoff, J.G. et al. (1992) "Amino acid substitution matrices from protein blocks," Proc. Natl. Acad. Sci. (USA) 89:10915-10919.
Herve, F. et al. (2008) "*CNS Delivery Via Adsorptive Transcytosis,*" AAPS J. 10(3):455-472.
Hoffmann R et al. (1997) "*Unique Alzheimer's Disease Paired Helical Filaments Specific Epitopes. Involve Double Phosphorylation at Specific Sites,*" Biochemistry 36(26):8114-8124.
Holliger, P. et al. (1993) "'*Diabodies': Small Bivalent and Bispecific Antibody Fragments,*" Proc. Natl. Acad. Sci. (U.S.A.) 90(14), 6444-6448.
Holt, L.J. et al. (2003) "*Domain Antibodies: Proteins for Therapy,*" Trends Biotechnol. 21(11):484490.
Huang, L. et al. (2013) "*Single-Chain Fragment Variable Passive Immunotherapies for Neurodegenerative Diseases,*" Int. J. Mol. Sci. 14(9):19109-19127.

(56) References Cited

OTHER PUBLICATIONS

Huhalov, A. et al. (2004) "*Engineered Single-Chain Antibody Fragments for Radioimmunotherapy*," Q. J. Nucl. Med. Mol. Imaging 48(4):279-288.

Husain, M.M. (2005) "*Clinical Diagnosis and Management of Alzheimer's Disease*," Neuroimag. Clin. N. Am. 15(4):767-777.

Hussein, A.H. et al. (2007) "*Construction and Characterization of Single-Chain Variable Fragment Antibodies Directed against the Bordetella pertussis Surface Adhesins Filamentous Hemagglutinin and Pertactin*," Infect. Immun. 75(11):5476-5482.

Huston, J.S. et al. (1988) "*Protein Engineering ofAntibody Binding Sites: Recovery of Specific Activity in an Anti-Digoxin Single-Chain Fv Analogue Produced in Escherichia coli*," Proc. Natl. Acad. Sci. (U.S.A.) 85:5879-5883.

International Search Report for PCT/US2010/038184 (Mar. 29, 2011); 7 pages.

International Search Report for PCT/US2016/046513 (2017); 5 pages.

Jarero-Basulto, J.J. et al. (2013) "*Proteolytic Cleavage of Polymeric Tau Protein by Caspase-3: Implications for Alzheimer Disease*," J. Neuropathol. Exp. Neurol. 72(12):1145-1161.

Jevsevar, S. et al. (2010) "*PEGylation of Therapeutic Proteins*," Biotechnol. J. 5(1):113-228.

Johnson, G.V.W. et al. (2004) "*Tau Phosphorylation in Neuronal Cell Fraction and Dysfunction*," J Cell Sci 117(24):5721-5729.

Jones, A.R. et al. (2007) "*Blood-Brain Barrier Transport of Therapeutics Via Receptor-Mediation*," Pharm. Res. 24(9):1759-1771.

Kandimalla, K. K. et al. (2006) "*Physiological and Biophysical Factors That Influence Alzheimer's Disease Amyloid Plaque Targeting of Native and Putrescine Modified Human Amyloid Beta40*," J. Pharmacol. Exp. Ther. 318:17-25.

Karlin, S. et al. (1990) "*Methods for Assessing the Statistical Significance of Molecular Sequence Features by Using General Scoring Schemes*," Proc. Natl. Acad. Sci. (USA) 87:2264-2268.

Kaur, S. et al. (2012) "*Recent Trends in Antibody-Based Oncologic Imaging*," Cancer Lett. 315, 97-111.

Kettleborough, C. A. et al. (1991) "*Humanization Of A Mouse Monoclonal Antibody by CDR-Grafting: The Importance of Framework Residues on Loop Conformation*," Protein Engineering 4:773-3783.

Kfoury, N. et al. (2012) "*Trans-cellular Propagation of Tau Aggregation by Fibrillar Species*," J. Biol. Chem. 287:19440-19451.

Knopman, D.S. et al. (2001) "*Practice Parameter: Diagnosis of Dementia (An Evidence-Based Review) Report of the Quality Standards Subcommittee of the American Academy of Neurology*," Neurology 56:1143-1153.

Krause, J.C. et al. (2011) "*An Insertion Mutation That Distorts Antibody Binding Site Architecture Enhances Function of a Human Antibody*," MBio. 2(1) pii: e00345-10. doi: 10.1128/mBio.00345-10.

Krishnamurthy, P.K. et al. (2009) "*Immunotherapy Targeting Alzheimer's Phospho-Tau Epitope Within the Microtubule Binding Region of Tau Clears Pathological Tau and Prevents Functional Decline in a Mouse Model of Tauopathy*," Alzheimer's & Dementia: The Journal of the Alzheimer's Association 5(4):P112 Feb. 5, 2001 (1 page).

Krishnamurthy, P.K. et al. (2011) "*Mechanistic Studies of Antibody-Mediated Clearance of Tau Aggregates Using an Ex Vivo Brain Slice Model*," Front. Psychiatry 2:59.

Krishnaswamy S. et al. (2014) "*Antibody-Derived in vivo Imaging of Tau Pathology*," J. Neurosci. 34:16835-16850.

Krishnaswamy, S. et al. (2009) "*Cloning Antifungal Single Chain Fragment Variable Antibodies by Phage Display and Competitive Panning Elution*," Anal. Biochem. 395:16-24.

Krishnaswamy, S. et al. (2011) "*Isolation and Characterization of Recombinant Single Chain Fragment Variable Anti-Idiotypic Antibody Specific to Aspergillus fumigatus Membrane Protein*," J. Immunol. Methods 366:60-68.

Kuan, C.T. et al. (2010) "*Affinity-Matured Anti-Glycoprotein Nmb Recombinant Immunotoxins Targeting Malignant Gliomas and Melanomas*," Int. J. Cancer 10.1002/ijc.25645.

Kufer, P. et al. (2004) "*A Revival of Bispecific Antibodies*," Trends Biotechnol. 22(5):238-244.

Kurth, M. et al. (1993) "*Site-Specific Conjugation of a Radioiodinated Phenethylamine Derivative to a Monoclonal Antibody Results in Increased Radioactivity Localization in Tumor*," J. Med. Chem. 36(9):1255-1261.

Lajoie, J.M. et al. (2015) "*Targeting Receptor-Mediated Transport for Delivery of Biologics Across the Blood-Brain Barrier*," Annu Rev. Pharmacol. Toxicol. 55:613-631.

Langer, R. et al. (1990) "*New Methods of Drug Delivery*," Science 249:1527-1533.

Le Gall, F. et al. (1999) "*Di-, Tri-And Tetrameric Single-Chain Fv Antibody Fragments Against Human CD19: Effect of Valency on Cell Binding*," FEBS Letters 453(1):164-168.

Lemere, C.A. et al. (2010) "*Can Alzheimer Disease Be Prevented by Amyloid-Beta Immunotherapy?*," Nat. Rev. Neurol. 6:108-119.

Lerchundi, R. et al. (2011) "*Tau Cleavage At D421 by Caspase-3 Is Induced in Neurons and Astrocytes Infected With Herpes Simplex Virus Type 1*," J. Alzheimers Dis. 23(3):513-520.

Lewis, J. et al. (2000) "*Neurofibrillary Tangles, Amyotrophy and Progressive Motor Disturbance in Mice Expressing Mutant (P301L) Tau Protein*," Nat. Genet. 25:402-405.

Lindegren, S. et al. (1998) "*Chloramine-T in High-Specific-Activity Radioiodination Of Antibodies Using N-Succinimidyl-3-(Trimethylstannyl)Benzoate As an Intermediate*," Nucl. Med. Biol. 25(7):659-665.

LoBuglio, A.F. et al. (1989) "*Mouse/Human Chimeric Monoclonal Antibody in Man: Kinetics and Immune Response*," Proc. Natl. Acad. Sci. (U.S.A.) 86:4220-4224.

Lonberg, N. et al. (1994) "*Antigen-specific human antibodies from mice comprising four distinct genetic modifications*," Nature 368:856-859.

Lonberg, N. et al. (1995) "*Human Antibodies From Transgenic Mice*," Intern. Rev. Immunol. 13(1):65-93.

Maeda, H. et al. (1991) "*Construction of Reshaped Human Antibodies with HIV-Neutralizing Activity*," Hum. Antibod. Hybridomas 2:124-134.

Maggio, J.E. et al. (1992) "*Reversible in Vivo Growth of Alzheimer Disease b-Amyloid Plaques by Deposition of Labeled Amyloid Peptide*," Proc Natl Acad Sci U.S.A. 89:5462-5466.

Maruyama, M.H. et al. (2013) "*Imaging of Tau Pathology in a Tauopathy Mouse Model and in Alzheimer Patients Compared to Normal Controls*," Neuron 79:1094-1108.

Mason, N. S. et al. (2013) "*Positron Emission Tomography Radioligands for in Vivo Imaging of ABeta Plaques*," J. Labelled Comp. Radiopharm. 56:89-95.

Mathupala, S.P. et al. (2009) "*Delivery of Small-Interfering RNA (siRNA) To The Brain*," Expert Opin. Ther. Pat. 19(2):137-140.

Mondragón-Rodríguez, S. et al. (2008) "*Cleavage and Conformational Changes of Tau Protein Follow Phosphorylation During Alzheimer's Disease*," Int. J. Exp. Pathol. 89(2):81-90.

Mondragón-Rodríguez, S. et al. (2008) "*Conformational Changes and Cleavage of Tau in Pick Bodies Parallel the Early Processing of Tau Found in Alzheimer Pathology*," Neuropathol. Appl. Neurobiol. 34(1):62-75.

Mondragón-Rodríguez, S. et al. (2014) "*Phosphorylation of Tau Protein At Sites Ser(396-404) Is One of the Earliest Events in Alzheimer's Disease and Down Syndrome*," Neuropathol. Appl. Neurobiol. 40(2):121-135.

Montgomery, D.L. et al. (2009) "*Affinity Maturation and Characterization of A Human Monoclonal Antibody Against HIV-1 gp41*," mAbs 1(5):462-474.

Moosmann, A. et al. (2014) "*Purification of PEGylated Proteins, with the Example of PEGylated Lysozyme and PEGylated scFv*," Methods Mol. Biol. 1129:527-538.

Müller, M.R. et al. (2012) "*Improving the Pharmacokinetic Properties of Biologics by Fusion to an Anti-HSA Shark VNAR Domain*," mAbs. 4(6):673-685.

Novak, M. (1994) "*Truncated Tau Protein as a New Marker for Alzheimer's Disease*," Acta Virologica 38:173-189.

(56) References Cited

OTHER PUBLICATIONS

Novak, M. (2009) "Tau Vaccine Active Immunization with Misfolded Tau Protein Attenuates Tau Pathology in the Transgenic Rat Model of Tauopathy," Alzheimers & Dementia 5(4)Supp:1-2.
Novak, M. et al. (1993) "*Molecular Characterization of the Minimal Protease Resistant Tau Unit of the Alzheimer's Disease Paired Helical Filament,*" EMBO J 12(1):365-370.
Okamura, N. et al. (2005) "*Quinoline and Benzimidazole Derivatives: Candidate Probes for in Vivo Imaging of Tau Pathology in Alzheimer's Disease,*" J. Neurosci. 25:10857-10862.
Okamura, N. et al. (2014) "*Non Invasive Assessment Of Alzheimer's Disease Neurofibrillary Pathology Using 18F-THK5105 PET,*" Brain 137:1762-1771.
Olafsen, T. et al. (2010) "*Antibody Vectors for Imaging,*" Semin. Nucl. Med. 40:167-181.
Ono, M. et al. (2011) "*Rhodanine and Thiohydantoin Derivatives for Detecting Tau Pathology in Alzheimer's Brains,*" ACS Chem. Neurosci. 2:269-275.
Pardridge, W. M. (2102) "*Drug Transport Across the Blood-Brain Barrier,*" J. Cereb. Blood Flow Metab. 32(11):1959-1972.
Park, S.-Y. et al. (2005) "*The Generation of 17 kDa Neurotoxic Fragment: an Alternative Mechanism by Which Tau Mediates Beta-Amyloid-Induced Neurodegeneration,*" J Neucosci 25(22):5365-5375.
Pedersen, J.T. et al. (2015) "*Tau Immunotherapy for Alzheimer's Disease,*" Trends Mol. Med. 21(6):394-402.
Perez, M. et al. (2001) "*In Vitro Assembly of Tau Protein: Mapping the Regions Involved in Filament Formation,*" Biochemistry 40:5983-5991.
Piszkiewicz, D. et al. (1970) "*Anomalous Cleavage Of Aspartyl-Proline Peptide Bonds During Amino Acid Sequence Determinations,*" Biochem. Biophys. Res. Commun. 40(5):1173-1178.
Poulson, K. et al. (1972) "*An Active Derivative of Rabbit Antibody Light Chain Composed of the Constant and the Variable Domains Held Together Only by a Native Disulfide Bond,*" Proc. Natl. Acad. Sci. (U.S.A.) 69(9):2495-2499.
Quintanilla, R.A. et al. (2009) "*Caspase-Cleaved Tau Expression Induces Mitochondrial Dysfunction In Immortalized Cortical Neurons: Implications for the Pathogenesis Of Alzheimer Disease,*" J. Biol. Chem. 284(28):18754-18766.
Rao, K.S. et al. (2009) "*Targeting- Anti-HIV Drugs to the CNS,*" Expert Opin. Drug Deliv. 6(8):771784.
Rea, D.W. et al. (1990) "*Site-specifically radioiodinated antibody for targeting tumors,*" Cancer Res. 50(3 Suppl):857s-861s.
Revets, H. et al. (2005) "*Nanobodies as Novel Agents for Cancer Terapy,*" Expert Opin Biol Ther. 5(1):111-124.
Richard, J.P. et al. (2003) "*Cell-Penetrating Peptides. A Reevaluation of the Mechanism of Cellular Uptake,*" J. Biol. Chem. 278:585-590.
Riechmann, L et al. (1988) "*Reshaping Human Antibodies for Therapy,*" Nature 332:323-327.
Rissman, R.A. et al. (2004) "*Caspase-Cleavage of Tau Is an Early Event in Alzheimer Disease Tangle Pathology,*" J. Clin. Invest. 114(1):121-130.
Rosenmann, H. et al. (2006) "*Tauopahy-Like Abnormalities and Neurologic Deficits in Mice Immunized with Neuronal Tau Protein,*" Arch Neurol 63:1459-1467.
Rudikoff, S. et al. (1982) "*Single Amino Acid Substitution Altering Antigen-Binding Specificity,*" Proc. Natl. Acad. Sci. (USA) 79(6):1979-1983.
Sarazin, M. et al. (2012) "*Clinical and Research Diagnostic Criteria for Alzheimer's Disease,*" Neuroimaging Clin. N. Amer. 22(1):23-32.
Sato, K. et al. (1993) "*Reshaping a human antibody to inhibit the interleukin 6-dependent tumor cell growth,*" Cancer Res. 53:851-856.
Schakowski, F. et al. (2001) "*A novel minimal-size vector (MIDGE) improves transgene expression in colon carcinoma cells and avoids transfection of undesired DNA,*" Mol Ther 3, 793-800.
Schenk, D. et al. (1999) "*Immunization With Amyloid-β Attenuates Alzheimer-Disease-Like Pathology in the PDAPP Mouse,*" Nature 400:173-177.
Schier et al. (1996) "*Isolation of Picomolar Affinity Anti-c-erbB-2 Single-chain Fv by Molecular Evolution of the Complementarity Determining Regions in the Center of the Antibody Binding Site,*" J. Mol. Bio. 263:551-567.
Sigurdsson, E.M. et al. (2000) "*In Vivo Reversal of Amyloid-β Lesions in Rat Brain,*" J Neuropathology and Neurology 59(1): 11-17.
Sigurdsson, E.M. (2008) "*Immunotherapy Targeting Pathological Tau Protein in Alzheimer's Disease and Related Tauopathies,*" J Alzheimers Dis 15(2):157-168.
Sigurdsson, E.M. (2008) "*Tau Immunotherapy Prevents Cognitive Decline and Clears Pathological Tau in a Tangle Mouse Model,*" Alzheimer's & Dementia: The Journal of the Alzheimer's Association 4(4):T191-T192 (2 pages).
Sigurdsson, E.M. (2009) "*Tau-Focused Immunotherapy for Alzheimer's Disease and Related Tauopathies,*" Curr Alzheimer Res 6:446-450.
Small, G.W. et al. (1997) "*Diagnosis and Treatment Of Alzheimer Disease and Related Disorders. Consensus Statement of the American Association for Geriatric Psychiatry, The Alzheimer's Association, and The American Geriatrics Society,*" JAMA 278(16):1363-1371.
Soto, C et al. (1996) "*Inhibition of Alzheimer's Amyloidosis by Peptides that Prevent β-Sheet Conformation,*" Biochem Biophys Res Com 226(3):672-680.
Steidl, S. et al. (2008) "*In Vitro Affinity Maturation of Human GM-CSF Antibodies by Targeted CDR-Diversification,*" Mol. Immunol. 46(1):135-144.
Stork, R. et al. (2008) "*N-Glycosylation as Novel Strategy to Improve Pharmacokinetic Properties of Bispecific Single-Chain Diabodies,*" J. Biol. Chem. 283:7804-7812.
Supplemental Search Report EP 10786852.3 PCT/US2010/038184 (Oct. 9, 2013) pp. 1-16.
Sykes, K.F. et al. (1999) "*Linear expression elements: a rapid, in vivo, method to screen for gene functions,*" Nat. Biotechnol. 12, 355-359.
Taniguchi, T. et al. (2005) "*Effects of Different Anti-Tau Antibodies on Tau Fibrogenesis: RTA-1 and RTA-2 Counteract Tau Aggregation,*" FEBS Lett 579(6):1399-1404.
Taylor, L.D. et al. (1992) *A transgenic mouse that expresses a diversity of human sequence heavy and light chain immunoglobulins*, Nucleic Acids Res. 20 (23), 6287-6295.
Taylor, L.D. et al. (1994) "*Human immunoglobulin transgenes undergo rearrangement, somatic mutation and class switching in mice that lack endogenous IgM,*" Int. Immunol. 6(4): 579-591.
Tempest, P.R. et al. (1991) "*Reshaping A Human Monoclonal Antibody to Inhibit Human Respiratory Syncytial Virus Infection in vivo,*" Nature BioTechnol 9:266-271.
Temsamani, J. et al. (2004) "*The Use of Cell-Penetrating Peptides for Drug Delivery,*" Drug Discov. Today 9:1012-1019.
Theunis, C. et al. (2013) "*Efficacy and Safety of a Liposome-Based Vaccine Against Protein Tau, Assessed in Tau.P301L Mice That Model Tauopathy,*" PLoS One. 8:e72301.
Troquier et al. (2010) "*Immunotherapy Targeting Tau,*" The Biology and Pathology of Tau and its Role in Toauopahies, Biochemical Society, Cambridge, UK, Jan. 7-8, 2010 P016 (Abstract ePub Dec. 2009).
Troquier, L. et al. (2012) "*Targeting Phospho-Ser422 by Active Tau Immunotherapy in the THY-Tau22 Mouse Model: A Suitable Therapeutic Approach,*" Curr. Alzheimer Res. 9: 397-405.
Tuaillon et al. (1994), "*Biased utilization of DHQ52 and JH4 gene segments in a human Ig transgenic minilocus is independent of antigenic selection,*" J. Immunol. 152: 2912-2920.
Tuma, P.L. et al. (2003) "*Transcytosis: Crossing Cellular Barriers,*" Physiol. Rev. 83:871-932.
Van Heeke, G. et al. (1989), "*Expression of Human Asparagine Synthetase in Escherichia coli,*" J Biol Chem 264(10):5503-5509.
Verghese, P.B. et al. (2011) "*Apolipoprotein E in Alzheimer's Disease and Other Neurological Disorders,*" Lancet Neurol. 10(3):241-252.

(56) References Cited

OTHER PUBLICATIONS

Verhoeyen, M. et al. (1988) "*Reshaping Human Antibodies: Grafting an Antilysozyme Activity,*" Science 239:1534-1536.

Villemagne, V.L. et al. (2014) "*In Vivo Evaluation of A Novel Tau Imaging Tracer for Alzheimer's Disease,*" Eur. J. Nucl. Med. Mol. Imaging 41:816-826.

Wadia, J.S. et al. (2004) "*Transducible TAT-HA Fusogenic Peptide Enhances Escape of TAT-Fusion Proteins After Lipid Raft Macropinocytosis,*" Nat. Med. 10:310-315.

Wang, Y.Y. et al. (2009) "*Receptor-Mediated Therapeutic Transport Across the Blood-Brain Barrier,*" Immunotherapy 1(6):983-993.

Ward, E.S. et al. (1989) "*Binding Activities Of A Repertoire of Single Immunoglobulin Variable Domains Secreted From Escherichia coli,*" Nature 341:544-546.

Weiner et al. (2013) "*The Alzheimer's Disease Neuroimaging Initiative: a Review of Papers Published Since Its Inception,*" Alzheimers Dement. 9(5): ell 1-e194.

Wengenack, T.M. et al. (2000) "*Targeting Alzheimer Amyloid Plaques in Vivo,*" Nature Biotechnol 18:868-872.

Wesseling, H. et al. (2020) "*Tau PTM Profiles Identify Patient Heterogeneity and Stages of Alzheimer's Disease,*" Cell 183:1699-1713.

Whitlow, M. et al. (1993) "*An Improved Linker for Single-Chain Fv With Reduced Aggregation and Enhanced Proteolytic Stability,*" Protein Eng. 6:989-995.

Wigler, M. et al (1978) "*Biochemical transfer of single-copy eucaryotic genes using total cellular DNA as donor,*" Cell 14:725-731.

Winter, G. et al. (1994) "*Making Antibodies by Phage Display Technology,*" Annu. Rev. Immunol. 12.433-455.

Written Opinion of the International Searching Authority for PCT/US2010/038184, (Mar. 29, 2011) 5 pages.

Written Opinion of the International Searching Authority for PCT/US2016/046513 (2017); 6 pages.

Wu, H. et al. (1998) "*Stepwise in vitro affinity maturation of Vitaxin, an alphav beta3-specific humanized mAb,*" Proc. Natl. Acad. Sci. (U.S.A.) 95:6037-6042.

Xia, C.F. et al. (2013) "*[(18)F]T807, A Novel Tau Positron Emission Tomography Imaging Agent for Alzheimer's Disease,*" Alzheimers Dement. 9:666-676.

Xiong, C.-Y. et al. (2006) "*Development of Tumor Targeting Anti-MUC-1 Multimer: Effects of di-scFv Unpaired Cysteine Location on PEGylation and Tumor Binding,*" Protein Engineering Design and Selection 19(8):359-367.

Yanamandra, K. et al. (2013) "*Anti-Tau Antibodies That Block Tau Aggregate Seeding in vitro Markedly Decrease Pathology and Improve Cognition in vivo,*" Neuron 80:402-414.

Yelton et al. (1995) "*Affinity maturation of the BR96 anti-carcinoma antibody by codon-based mutagenesis,*" J. Immunology 155:1994-2004.

Zhang, W. et al. (2012) "*A Highly Selective and Specific Pet Tracer for Imaging of Tau Pathologies,*" J. Alzheimers. Dis. 31:601-612 (1 page Abstract Only).

Zilka et al. (2008) "*Chaperone-Like Antibodies Targeting Misfolded Tau Protein: New Vistas in the Immunotherapy of Neurodegenerative Foldopathies,*" J Alzheimers Disease 15:169-179.

Zou, Y.-R. et al. (1993) "*Gene targeting in the Ig kappa locus: efficient generation of lambda chain-expressing B cells, independent of gene rearrangements in Ig kappa,*" Embo J. 12(3):811-820.

\* cited by examiner

SEQUENCE LISTING

<160> NUMBER OF SEQ ID NOS: 105

<210> SEQ ID NO 1
<211> LENGTH: 441
<212> TYPE: PRT
<213> ORGANISM: Homo sapiens -continued

```
<220> FEATURE:
<221> NAME/KEY: MISC_FEATURE
<222> LOCATION: (1)..(441)
<223> OTHER INFORMATION: Tau Protein

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380
```

```
Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440

<210> SEQ ID NO 2
<211> LENGTH: 15
<212> TYPE: PRT
<213> ORGANISM: Artificial Sequence
<220> FEATURE:
<223> OTHER INFORMATION: Linker Peptide

<400> SEQUENCE: 2

Gly Gly Gly Gly Ser Gly Gly Gly Ser Gly Gly Gly Gly Ser
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Linker Peptide

<400> SEQUENCE: 3

Gly Ser Thr Ser Gly Ser Gly Lys Pro Gly Ser Gly Glu Gly Ser Thr
1               5                   10                  15

Lys Gly

<210> SEQ ID NO 4
<211> LENGTH: 18
<212> TYPE: PRT
<213> ORGANISM: Artificial Sequence
<220> FEATURE:
<223> OTHER INFORMATION: Linker Peptide

<400> SEQUENCE: 4

Ser Ser Gly Gly Gly Gly Ser Gly Gly Gly Gly Gly Gly Ser Ser Arg
1               5                   10                  15

Ser Ser

<210> SEQ ID NO 5
<211> LENGTH: 6
<212> TYPE: PRT
<213> ORGANISM: Artificial Sequence
<220> FEATURE:
<223> OTHER INFORMATION: His Tag Peptide

<400> SEQUENCE: 5

His His His His His His
1               5

<210> SEQ ID NO 6
<211> LENGTH: 12
<212> TYPE: PRT
<213> ORGANISM: Artificial Sequence
<220> FEATURE:
<223> OTHER INFORMATION: HA Tag Peptide
```

<400> SEQUENCE: 6

Gly Ala Tyr Pro Tyr Asp Val Pro Asp Tyr Ala Ser
1               5                   10

<210> SEQ ID NO 7
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: Amino Acid Residues 407-421 of Tau Protein (SEQ
      ID NO:1)

<400> SEQUENCE: 7

His Leu Ser Asn Val Ser Ser Thr Gly Ser Ile Asp Met Val Asp
1               5                   10                  15

<210> SEQ ID NO 8
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Light Chain Variable Domain of Antibody 1G10D2

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu Asn Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 9
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: Light Chain CDR1 of Antibody 1G10D2

<400> SEQUENCE: 9

Arg Ser Ser Gln Ser Ile Leu Asn Ser Asn Gly Asn Thr Tyr Leu Glu
1               5                   10                  15

<210> SEQ ID NO 10
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Light Chain CDR2 of Antibody 1G10D2

```
<400> SEQUENCE: 10

Lys Val Ser Asn Arg Phe Ser
1               5

<210> SEQ ID NO 11
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Light Chain CDR3 of Antibody 1G10D2

<400> SEQUENCE: 11

Phe Gln Gly Ser His Val Pro Trp Thr
1               5

<210> SEQ ID NO 12
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: Heavy Chain Variable Domain of Antibody 1G10D2

<400> SEQUENCE: 12

Glu Val Lys Leu Val Glu Ser Gly Gly Asp Leu Val Thr Pro Gly Gly
1               5                   10                  15

Ser Leu Lys Val Ser Cys Ala Ala Ser Gly Leu Thr Phe Ser Asp Ser
            20                  25                  30

Ala Met Ser Trp Val Arg Leu Thr Pro Glu Lys Arg Leu Glu Trp Val
        35                  40                  45

Ala Ser Ile Ser Thr Gly Gly Ala Thr Tyr Tyr Pro Asp Gly Leu Lys
    50                  55                  60

Gly Arg Phe Thr Ile Ser Arg Asp Asp Ala Arg Asn Ile Leu Phe Leu
65                  70                  75                  80

Gln Met Asn Ser Leu Arg Ser Glu Asp Thr Ala Met Tyr Tyr Cys Thr
                85                  90                  95

Arg Arg Gly Val Ser Ser Gly Asn Leu Phe Thr Tyr Trp Gly Gln Gly
            100                 105                 110

Thr Leu Val Thr Val Ser Ala
        115

<210> SEQ ID NO 13
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: Heavy Chain CDR1 of Antibody 1G10D2

<400> SEQUENCE: 13

Asp Ser Ala Met Ser
1               5

<210> SEQ ID NO 14
<211> LENGTH: 16
<212> TYPE: PRT
<213> ORGANISM: Mus musculus
```

```
<220> FEATURE:
<221> NAME/KEY: MISC_FEATURE
<222> LOCATION: (1)..(16)
<223> OTHER INFORMATION: Heavy Chain CDR2 of Antibody 1G10D2

<400> SEQUENCE: 14

Ser Ile Ser Thr Gly Gly Ala Thr Tyr Tyr Pro Asp Gly Leu Lys Gly
1               5                   10                  15

<210> SEQ ID NO 15
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Heavy Chain CDR3 of Antibody 1G10D2

<400> SEQUENCE: 15

Arg Gly Val Ser Ser Gly Asn Leu Phe Thr Tyr
1               5                   10

<210> SEQ ID NO 16
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Light Chain Variable Domain of Antibody 1G11A10

<400> SEQUENCE: 16

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Ile Asn Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 17
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: Light Chain CDR1 of Antibody 1G11A10

<400> SEQUENCE: 17

Arg Ser Ser Gln Ser Ile Ile Asn Ser Asn Gly Asn Thr Tyr Leu Glu
1               5                   10                  15

<210> SEQ ID NO 18
<211> LENGTH: 7
<212> TYPE: PRT
<213> ORGANISM: Mus musculus
```

-continued

```
<220> FEATURE:
<221> NAME/KEY: MISC_FEATURE
<222> LOCATION: (1)..(7)
<223> OTHER INFORMATION: Light Chain CDR2 of Antibody 1G11A10

<400> SEQUENCE: 18

Lys Val Ser Asn Arg Phe Ser
1               5

<210> SEQ ID NO 19
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Light Chain CDR3 of Antibody 1G11A10

<400> SEQUENCE: 19

Phe Gln Gly Ser His Val Pro Trp Thr
1               5

<210> SEQ ID NO 20
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: Heavy Chain Variable Domain of Antibody 1G11A10

<400> SEQUENCE: 20

Glu Val Lys Leu Val Glu Ser Gly Gly Gly Leu Met Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Ser Ile Ser Ser Gly Gly Gln Thr Tyr Ser Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Arg Asn Leu Arg Ser Glu Asp Thr Ala Met Tyr Tyr Cys Ala
                85                  90                  95

Ser Arg Gly Asp Pro Thr Met Thr Ala Thr Leu Phe Val Tyr Trp Gly
            100                 105                 110

Gln Gly Thr Leu Val Thr Val Ser
        115                 120

<210> SEQ ID NO 21
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: Heavy Chain CDR1 of Antibody 1G11A10

<400> SEQUENCE: 21

Ser Tyr Ala Met Ser
1               5
```

```
<210> SEQ ID NO 22
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: Heavy Chain CDR2 of Antibody 1G11A10

<400> SEQUENCE: 22

Ser Ile Ser Ser Gly Gly Gln Thr Tyr Ser Pro Asp Ser Val Lys Gly
1               5                   10                  15

<210> SEQ ID NO 23
<211> LENGTH: 13
<212> TYPE: PRT
<213> ORGANISM: Mus musculus
<220> FEATURE:
<221> NAME/KEY: MISC_FEATURE
<222> LOCATION: (1)..(13)
<223> OTHER INFORMATION: Heavy Chain CDR3 of Antibody 1G11A10

<400> SEQUENCE: 23

Arg Gly Asp Pro Thr Met Thr Ala Thr Leu Phe Val Tyr
1               5                   10

<210> SEQ ID NO 24
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Light Chain VL1 Variable Domain of Antibody
      5B3C11

<400> SEQUENCE: 24

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Ser Ile Leu His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Ile Pro Trp Thr Phe Gly Gly Gly Thr Lys Leu Glu Ile Lys
            100                 105                 110

<210> SEQ ID NO 25
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: Light Chain VL1 CDR1 of Antibody 5B3C11

<400> SEQUENCE: 25

Arg Ser Asn Gln Ser Ile Leu His Ser Asn Gly Asn Thr Tyr Leu Asp
1               5                   10                  15
```

```
<210> SEQ ID NO 26
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Light Chain VL1 CDR2 of Antibody 5B3C11

<400> SEQUENCE: 26

Lys Val Ser Asn Arg Phe Ser
1               5

<210> SEQ ID NO 27
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Light Chain VL1 CDR3 of Antibody 5B3C11

<400> SEQUENCE: 27

Phe Gln Gly Ser His Ile Pro Trp Thr
1               5

<210> SEQ ID NO 28
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: Light Chain VL2 Variable Domain of Antibody
      5B3C11

<400> SEQUENCE: 28

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Arg Thr Phe Gly Gly Gly Thr Lys Leu Glu Ile Lys
            100                 105

<210> SEQ ID NO 29
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: Light Chain VL2 CDR1 of Antibody 5B3C11

<400> SEQUENCE: 29

Arg Ala Ser Ser Ser Val Ser Ser Ser Tyr Leu His
1               5                   10
```

```
<210> SEQ ID NO 30
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Light Chain VL2 CDR2 of Antibody 5B3C11

<400> SEQUENCE: 30

Ser Thr Ser Asn Leu Ala Ser
1               5

<210> SEQ ID NO 31
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Light Chain VL2 CDR3 of Antibody 5B3C11

<400> SEQUENCE: 31

Gln Gln Tyr Ser Gly Tyr Pro Arg Thr
1               5

<210> SEQ ID NO 32
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: Heavy Chain VL2 Variable Domain of Antibody
      5B3C11

<400> SEQUENCE: 32

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Leu Ser Trp Val Arg Gln Thr Pro Glu Lys Arg Leu Glu Trp Val
        35                  40                  45

Ala Ser Ile Ser Ser Gly Gly Asn Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Phe Tyr Cys Thr
                85                  90                  95

Ser Arg Gly Asp Thr Thr Leu Ile Thr Thr Leu Phe Thr Tyr Trp Gly
            100                 105                 110

Gln Gly Thr Leu Val Thr Val Ser Ala
        115                 120

<210> SEQ ID NO 33
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: Heavy Chain CDR1 of Antibody 5B3C11
```

```
<400> SEQUENCE: 33

Asn Tyr Ala Leu Ser
1               5

<210> SEQ ID NO 34
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: Heavy Chain CDR2 of Antibody 5B3C11

<400> SEQUENCE: 34

Ser Ile Ser Ser Gly Gly Asn Thr Tyr Tyr Pro Asp Ser Val Lys Gly
1               5                   10                  15

<210> SEQ ID NO 35
<211> LENGTH: 13
<212> TYPE: PRT
<213> ORGANISM: Mus musculus
<220> FEATURE:
<221> NAME/KEY: MISC_FEATURE
<222> LOCATION: (1)..(13)
<223> OTHER INFORMATION: Heavy Chain CDR3 of Antibody 5B3C11

<400> SEQUENCE: 35

Arg Gly Asp Thr Thr Leu Ile Thr Thr Leu Phe Thr Tyr
1               5                   10

<210> SEQ ID NO 36
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: Light Chain Variable Domain of Antibody 5G2A3

<400> SEQUENCE: 36

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Arg
            20                  25                  30

Asn Gly Asn Thr Tyr Leu Asp Trp Phe Leu Leu Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 37
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: Light Chain CDR1 of Antibody 5G2A3
```

-continued

<400> SEQUENCE: 37

Arg Ser Ser Gln Ser Ile Leu His Arg Asn Gly Asn Thr Tyr Leu Asp
1               5                   10                  15

<210> SEQ ID NO 38
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Light Chain CDR2 of Antibody 5G2A3

<400> SEQUENCE: 38

Lys Val Ser Asn Arg Phe Ser
1               5

<210> SEQ ID NO 39
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Light Chain CDR3 of Antibody 5G2A3

<400> SEQUENCE: 39

Phe Gln Gly Ser His Val Pro Trp Thr
1               5

<210> SEQ ID NO 40
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: Heavy Chain Variable Domain of Antibody 5G2A3

<400> SEQUENCE: 40

Glu Val Lys Leu Val Glu Ser Gly Gly Gly Leu Val Lys Pro Gly Gly
1               5                   10                  15

Ser Leu Thr Leu Ser Cys Ala Ala Ser Gly Phe Thr Phe Ser Ser Tyr
                20                  25                  30

Ala Met Ser Trp Val Arg Gln Thr Pro Glu Lys Ser Leu Glu Trp Val
            35                  40                  45

Ala Ser Ile Ser Ser Gly Gly Asn Thr Phe Tyr Pro Asp Thr Val Lys
        50                  55                  60

Gly Arg Phe Thr Ile Ser Arg Asp Asn Ala Arg Asn Ile Leu Tyr Leu
65                  70                  75                  80

Gln Met Ser Gly Leu Arg Ser Glu Asp Thr Ala Ile Tyr Tyr Cys Ala
                85                  90                  95

Arg Arg Gly Asp Pro Asn Met Ile Thr Thr Leu Phe Gly Tyr Trp Gly
            100                 105                 110

Gln Gly Thr Leu Val Thr Ile Ser Ala
        115                 120

<210> SEQ ID NO 41
<211> LENGTH: 5
<212> TYPE: PRT
<213> ORGANISM: Mus musculus

```
<220> FEATURE:
<221> NAME/KEY: MISC_FEATURE
<222> LOCATION: (1)..(5)
<223> OTHER INFORMATION: Heavy Chain CDR1 of Antibody 5G2A3

<400> SEQUENCE: 41

Ser Tyr Ala Met Ser
1               5

<210> SEQ ID NO 42
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: Heavy Chain CDR2 of Antibody 5G2A3

<400> SEQUENCE: 42

Ser Ile Ser Ser Gly Gly Asn Thr Phe Tyr Pro Asp Thr Val Lys Gly
1               5                   10                  15

<210> SEQ ID NO 43
<211> LENGTH: 13
<212> TYPE: PRT
<213> ORGANISM: Mus musculus
<220> FEATURE:
<221> NAME/KEY: MISC_FEATURE
<222> LOCATION: (1)..(13)
<223> OTHER INFORMATION: Heavy Chain CDR3 of Antibody 5G2A3

<400> SEQUENCE: 43

Arg Gly Asp Pro Asn Met Ile Thr Thr Leu Phe Gly Tyr
1               5                   10

<210> SEQ ID NO 44
<211> LENGTH: 28
<212> TYPE: PRT
<213> ORGANISM: Artificial Sequence
<220> FEATURE:
<223> OTHER INFORMATION: N-terminal Leader Peptide

<400> SEQUENCE: 44

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala
            20                  25

<210> SEQ ID NO 45
<211> LENGTH: 15
<212> TYPE: PRT
<213> ORGANISM: Artificial Sequence
<220> FEATURE:
<223> OTHER INFORMATION: C-terminal peptide portion

<400> SEQUENCE: 45

Ala Lys Thr Thr Pro Pro Ser Val Thr Ser Gly Gln Ala Gly Gln
1               5                   10                  15

<210> SEQ ID NO 46
<211> LENGTH: 33
<212> TYPE: PRT
<213> ORGANISM: Artificial Sequence
<220> FEATURE:
<223> OTHER INFORMATION: Preferred C-terminal Peptide
```

<400> SEQUENCE: 46

Ala Lys Thr Thr Pro Pro Ser Val Thr Ser Gly Gln Ala Gly Gln His
1               5                   10                  15

His His His His His Gly Ala Tyr Pro Tyr Asp Val Pro Asp Tyr Ala
                20                  25                  30

Ser

<210> SEQ ID NO 47
<211> LENGTH: 249
<212> TYPE: PRT
<213> ORGANISM: Artificial Sequence
<220> FEATURE:
<223> OTHER INFORMATION: scFv Molecule Generated from Antibody 1G10D2

<400> SEQUENCE: 47

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu Asn Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110

Ser Ser Gly Gly Gly Gly Ser Gly Gly Gly Gly Ser Gly Ser Ser Arg
            115                 120                 125

Ser Ser Glu Val Lys Leu Val Glu Ser Gly Gly Asp Leu Val Thr Pro
    130                 135                 140

Gly Gly Ser Leu Lys Val Ser Cys Ala Ala Ser Gly Leu Thr Phe Ser
145                 150                 155                 160

Asp Ser Ala Met Ser Trp Val Arg Leu Thr Pro Glu Lys Arg Leu Glu
                165                 170                 175

Trp Val Ala Ser Ile Ser Thr Gly Gly Ala Thr Tyr Tyr Pro Asp Gly
                180                 185                 190

Leu Lys Gly Arg Phe Thr Ile Ser Arg Asp Asp Ala Arg Asn Ile Leu
            195                 200                 205

Phe Leu Gln Met Asn Ser Leu Arg Ser Glu Asp Thr Ala Met Tyr Tyr
    210                 215                 220

Cys Thr Arg Arg Gly Val Ser Ser Gly Asn Leu Phe Thr Tyr Trp Gly
225                 230                 235                 240

Gln Gly Thr Leu Val Thr Val Ser Ala
                245

<210> SEQ ID NO 48
<211> LENGTH: 277
<212> TYPE: PRT
<213> ORGANISM: Artificial Sequence
<220> FEATURE:
<223> OTHER INFORMATION: scFv Molecule Generated from Antibody 1G10D2
<220> FEATURE:
<221> NAME/KEY: MISC_FEATURE
<222> LOCATION: (1)..(28)
<223> OTHER INFORMATION: N-terminal Leader Peptide

```
<220> FEATURE:
<221> NAME/KEY: MISC_FEATURE
<222> LOCATION: (29)..(277)
<223> OTHER INFORMATION: scFv Molecule Generated from Antibody 1G10D2

<400> SEQUENCE: 48

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Leu Asn Ser Asn Gly Asn Thr
50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
            100                 105                 110

Ala Glu Asp Leu Gly Val Tyr Tyr Cys Phe Gln Gly Ser His Val Pro
        115                 120                 125

Trp Thr Phe Gly Gly Gly Thr Lys Leu Glu Ile Lys Ser Ser Gly Gly
130                 135                 140

Gly Gly Ser Gly Gly Gly Gly Gly Ser Ser Arg Ser Ser Glu Val
145                 150                 155                 160

Lys Leu Val Glu Ser Gly Gly Asp Leu Val Thr Pro Gly Gly Ser Leu
                165                 170                 175

Lys Val Ser Cys Ala Ala Ser Gly Leu Thr Phe Ser Asp Ser Ala Met
            180                 185                 190

Ser Trp Val Arg Leu Thr Pro Glu Lys Arg Leu Glu Trp Val Ala Ser
        195                 200                 205

Ile Ser Thr Gly Gly Ala Thr Tyr Tyr Pro Asp Gly Leu Lys Gly Arg
210                 215                 220

Phe Thr Ile Ser Arg Asp Asp Ala Arg Asn Ile Leu Phe Leu Gln Met
225                 230                 235                 240

Asn Ser Leu Arg Ser Glu Asp Thr Ala Met Tyr Tyr Cys Thr Arg Arg
                245                 250                 255

Gly Val Ser Ser Gly Asn Leu Phe Thr Tyr Trp Gly Gln Gly Thr Leu
            260                 265                 270

Val Thr Val Ser Ala
        275

<210> SEQ ID NO 49
<211> LENGTH: 264
<212> TYPE: PRT
<213> ORGANISM: Artificial Sequence
<220> FEATURE:
<223> OTHER INFORMATION: scFv Molecule Generated from Antibody 1G10D2
<220> FEATURE:
<221> NAME/KEY: MISC_FEATURE
<222> LOCATION: (1)..(249)
<223> OTHER INFORMATION: scFv Molecule Generated from Antibody 1G10D2
<220> FEATURE:
<221> NAME/KEY: MISC_FEATURE
<222> LOCATION: (250)..(264)
<223> OTHER INFORMATION: C-terminal Peptide
```

<400> SEQUENCE: 49

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu Asn Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Gly Ser Ser Arg
            115                 120                 125

Ser Ser Glu Val Lys Leu Val Glu Ser Gly Gly Asp Leu Val Thr Pro
130                 135                 140

Gly Gly Ser Leu Lys Val Ser Cys Ala Ala Ser Gly Leu Thr Phe Ser
145                 150                 155                 160

Asp Ser Ala Met Ser Trp Val Arg Leu Thr Pro Glu Lys Arg Leu Glu
                165                 170                 175

Trp Val Ala Ser Ile Ser Thr Gly Gly Ala Thr Tyr Tyr Pro Asp Gly
            180                 185                 190

Leu Lys Gly Arg Phe Thr Ile Ser Arg Asp Asp Ala Arg Asn Ile Leu
        195                 200                 205

Phe Leu Gln Met Asn Ser Leu Arg Ser Glu Asp Thr Ala Met Tyr Tyr
    210                 215                 220

Cys Thr Arg Arg Gly Val Ser Ser Gly Asn Leu Phe Thr Tyr Trp Gly
225                 230                 235                 240

Gln Gly Thr Leu Val Thr Val Ser Ala Ala Lys Thr Thr Pro Pro Ser
                245                 250                 255

Val Thr Ser Gly Gln Ala Gly Gln
            260

<210> SEQ ID NO 50
<211> LENGTH: 255
<212> TYPE: PRT
<213> ORGANISM: Artificial Sequence
<220> FEATURE:
<223> OTHER INFORMATION: scFv Molecule Generated from Antibody 1G10D2
<220> FEATURE:
<221> NAME/KEY: MISC_FEATURE
<222> LOCATION: (1)..(249)
<223> OTHER INFORMATION: scFv Molecule Generated from Antibody 1G10D2
<220> FEATURE:
<221> NAME/KEY: MISC_FEATURE
<222> LOCATION: (250)..(255)
<223> OTHER INFORMATION: His Tag

<400> SEQUENCE: 50

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu Asn Ser
            20                  25                  30

Asn Gly Asn Thr Tyr Leu Glu Trp Tyr Leu Gln Lys Pro Gly Gln Ser
        35                  40                  45

```
Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
                100                 105                 110

Ser Ser Gly Gly Gly Gly Ser Gly Gly Gly Gly Ser Ser Arg
                115                 120                 125

Ser Ser Glu Val Lys Leu Val Glu Ser Gly Gly Asp Leu Val Thr Pro
130                 135                 140

Gly Gly Ser Leu Lys Val Ser Cys Ala Ala Ser Gly Leu Thr Phe Ser
145                 150                 155                 160

Asp Ser Ala Met Ser Trp Val Arg Leu Thr Pro Glu Lys Arg Leu Glu
                165                 170                 175

Trp Val Ala Ser Ile Ser Thr Gly Gly Ala Thr Tyr Tyr Pro Asp Gly
                180                 185                 190

Leu Lys Gly Arg Phe Thr Ile Ser Arg Asp Asp Ala Arg Asn Ile Leu
                195                 200                 205

Phe Leu Gln Met Asn Ser Leu Arg Ser Glu Asp Thr Ala Met Tyr Tyr
210                 215                 220

Cys Thr Arg Arg Gly Val Ser Gly Asn Leu Phe Thr Tyr Trp Gly
225                 230                 235                 240

Gln Gly Thr Leu Val Thr Val Ser Ala His His His His His
                245                 250                 255
```

<210> SEQ ID NO 51
<211> LENGTH: 261
<212> TYPE: PRT
<213> ORGANISM: Artificial Sequence
<220> FEATURE:
<223> OTHER INFORMATION: scFv molecule generated from Antibody 1G10D2
<220> FEATURE:
<221> NAME/KEY: MISC_FEATURE
<222> LOCATION: (1)..(249)
<223> OTHER INFORMATION: scFv molecule generated from Antibody 1G10D2
<220> FEATURE:
<221> NAME/KEY: MISC_FEATURE
<222> LOCATION: (250)..(261)
<223> OTHER INFORMATION: HA Tag Peptide

<400> SEQUENCE: 51

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Leu Asn Ser
                 20                  25                  30

Asn Gly Asn Thr Tyr Leu Glu Trp Tyr Leu Gln Lys Pro Gly Gln Ser
                 35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
                100                 105                 110
```

```
Ser Ser Gly Gly Gly Gly Ser Gly Gly Gly Gly Ser Ser Arg
        115                 120                 125

Ser Ser Glu Val Lys Leu Val Glu Ser Gly Gly Asp Leu Val Thr Pro
    130                 135                 140

Gly Gly Ser Leu Lys Val Ser Cys Ala Ala Ser Gly Leu Thr Phe Ser
145                 150                 155                 160

Asp Ser Ala Met Ser Trp Val Arg Leu Thr Pro Glu Lys Arg Leu Glu
                165                 170                 175

Trp Val Ala Ser Ile Ser Thr Gly Gly Ala Thr Tyr Tyr Pro Asp Gly
                180                 185                 190

Leu Lys Gly Arg Phe Thr Ile Ser Arg Asp Asp Ala Arg Asn Ile Leu
            195                 200                 205

Phe Leu Gln Met Asn Ser Leu Arg Ser Glu Asp Thr Ala Met Tyr Tyr
        210                 215                 220

Cys Thr Arg Arg Gly Val Ser Ser Gly Asn Leu Phe Thr Tyr Trp Gly
225                 230                 235                 240

Gln Gly Thr Leu Val Thr Val Ser Ala Gly Ala Tyr Pro Tyr Asp Val
                245                 250                 255

Pro Asp Tyr Ala Ser
            260

<210> SEQ ID NO 52
<211> LENGTH: 282
<212> TYPE: PRT
<213> ORGANISM: Artificial Sequence
<220> FEATURE:
<223> OTHER INFORMATION: scFv Molecule Generated from Antibody 1G10D2
<220> FEATURE:
<221> NAME/KEY: MISC_FEATURE
<222> LOCATION: (1)..(249)
<223> OTHER INFORMATION: scFv Molecule Generated from Antibody 1G10D2
<220> FEATURE:
<221> NAME/KEY: MISC_FEATURE
<222> LOCATION: (250)..(282)
<223> OTHER INFORMATION: Preferred C-terminal Peptide

<400> SEQUENCE: 52

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu Asn Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Ser Ser Arg
        115                 120                 125

Ser Ser Glu Val Lys Leu Val Glu Ser Gly Gly Asp Leu Val Thr Pro
    130                 135                 140

Gly Gly Ser Leu Lys Val Ser Cys Ala Ala Ser Gly Leu Thr Phe Ser
145                 150                 155                 160
```

-continued

Asp Ser Ala Met Ser Trp Val Arg Leu Thr Pro Glu Lys Arg Leu Glu
                165                 170                 175

Trp Val Ala Ser Ile Ser Thr Gly Gly Ala Thr Tyr Tyr Pro Asp Gly
        180                 185                 190

Leu Lys Gly Arg Phe Thr Ile Ser Arg Asp Asp Ala Arg Asn Ile Leu
    195                 200                 205

Phe Leu Gln Met Asn Ser Leu Arg Ser Glu Asp Thr Ala Met Tyr Tyr
210                 215                 220

Cys Thr Arg Arg Gly Val Ser Ser Gly Asn Leu Phe Thr Tyr Trp Gly
225                 230                 235                 240

Gln Gly Thr Leu Val Thr Val Ser Ala Ala Lys Thr Thr Pro Pro Ser
                245                 250                 255

Val Thr Ser Gly Gln Ala Gly Gln His His His His His His Gly Ala
            260                 265                 270

Tyr Pro Tyr Asp Val Pro Asp Tyr Ala Ser
            275                 280

<210> SEQ ID NO 53
<211> LENGTH: 292
<212> TYPE: PRT
<213> ORGANISM: Artificial Sequence
<220> FEATURE:
<223> OTHER INFORMATION: scFv Molecule Generated from Antibody 1G10D2
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(277)
<223> OTHER INFORMATION: scFv Molecule Generated from Antibody 1G10D2
<220> FEATURE:
<221> NAME/KEY: MISC_FEATURE
<222> LOCATION: (278)..(292)
<223> OTHER INFORMATION: C-terminal Leader Peptide

<400> SEQUENCE: 53

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Leu Asn Ser Asn Gly Asn Thr
    50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
            100                 105                 110

Ala Glu Asp Leu Gly Val Tyr Tyr Cys Phe Gln Gly Ser His Val Pro
        115                 120                 125

Trp Thr Phe Gly Gly Gly Thr Lys Leu Glu Ile Lys Ser Ser Gly Gly
    130                 135                 140

Gly Gly Ser Gly Gly Gly Gly Ser Ser Arg Ser Ser Glu Val
145                 150                 155                 160

Lys Leu Val Glu Ser Gly Gly Asp Leu Val Thr Pro Gly Gly Ser Leu
                165                 170                 175

```
Lys Val Ser Cys Ala Ala Ser Gly Leu Thr Phe Ser Asp Ser Ala Met
                180                 185                 190

Ser Trp Val Arg Leu Thr Pro Glu Lys Arg Leu Glu Trp Val Ala Ser
        195                 200                 205

Ile Ser Thr Gly Gly Ala Thr Tyr Tyr Pro Asp Gly Leu Lys Gly Arg
        210                 215                 220

Phe Thr Ile Ser Arg Asp Asp Ala Arg Asn Ile Leu Phe Leu Gln Met
225                 230                 235                 240

Asn Ser Leu Arg Ser Glu Asp Thr Ala Met Tyr Tyr Cys Thr Arg Arg
                245                 250                 255

Gly Val Ser Ser Gly Asn Leu Phe Thr Tyr Trp Gly Gln Gly Thr Leu
                260                 265                 270

Val Thr Val Ser Ala Ala Lys Thr Thr Pro Pro Ser Val Thr Ser Gly
        275                 280                 285

Gln Ala Gly Gln
        290

<210> SEQ ID NO 54
<211> LENGTH: 283
<212> TYPE: PRT
<213> ORGANISM: Artificial Sequence
<220> FEATURE:
<223> OTHER INFORMATION: scFv Molecule Generated from Antibody 1G10D2
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(277)
<223> OTHER INFORMATION: scFv Molecule Generated from Antibody 1G10D2
<220> FEATURE:
<221> NAME/KEY: MISC_FEATURE
<222> LOCATION: (278)..(283)
<223> OTHER INFORMATION: His Tag Peptide

<400> SEQUENCE: 54

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
                20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Leu Asn Ser Asn Gly Asn Thr
    50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
                100                 105                 110

Ala Glu Asp Leu Gly Val Tyr Tyr Cys Phe Gln Gly Ser His Val Pro
            115                 120                 125

Trp Thr Phe Gly Gly Gly Thr Lys Leu Glu Ile Lys Ser Ser Gly Gly
        130                 135                 140

Gly Gly Ser Gly Gly Gly Gly Gly Ser Ser Arg Ser Ser Glu Val
145                 150                 155                 160

Lys Leu Val Glu Ser Gly Gly Asp Leu Val Thr Pro Gly Gly Ser Leu
                165                 170                 175
```

```
Lys Val Ser Cys Ala Ala Ser Gly Leu Thr Phe Ser Asp Ser Ala Met
            180                 185                 190

Ser Trp Val Arg Leu Thr Pro Glu Lys Arg Leu Glu Trp Val Ala Ser
        195                 200                 205

Ile Ser Thr Gly Gly Ala Thr Tyr Tyr Pro Asp Gly Leu Lys Gly Arg
    210                 215                 220

Phe Thr Ile Ser Arg Asp Asp Ala Arg Asn Ile Leu Phe Leu Gln Met
225                 230                 235                 240

Asn Ser Leu Arg Ser Glu Asp Thr Ala Met Tyr Tyr Cys Thr Arg Arg
                245                 250                 255

Gly Val Ser Ser Gly Asn Leu Phe Thr Tyr Trp Gly Gln Gly Thr Leu
            260                 265                 270

Val Thr Val Ser Ala His His His His His His
            275                 280

<210> SEQ ID NO 55
<211> LENGTH: 289
<212> TYPE: PRT
<213> ORGANISM: Artificial Sequence
<220> FEATURE:
<223> OTHER INFORMATION: scFv Molecule Generated from Antibody 1G10D2
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(277)
<223> OTHER INFORMATION: scFv Molecule Gnerated from Antibody 1G10D2
<220> FEATURE:
<221> NAME/KEY: MISC_FEATURE
<222> LOCATION: (278)..(289)
<223> OTHER INFORMATION: HA Tag Peptide

<400> SEQUENCE: 55

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Leu Asn Ser Asn Gly Asn Thr
    50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
            100                 105                 110

Ala Glu Asp Leu Gly Val Tyr Tyr Cys Phe Gln Gly Ser His Val Pro
        115                 120                 125

Trp Thr Phe Gly Gly Gly Thr Lys Leu Glu Ile Lys Ser Ser Gly Gly
    130                 135                 140

Gly Gly Ser Gly Gly Gly Gly Gly Ser Ser Arg Ser Ser Glu Val
145                 150                 155                 160

Lys Leu Val Glu Ser Gly Gly Asp Leu Val Thr Pro Gly Gly Ser Leu
                165                 170                 175

Lys Val Ser Cys Ala Ala Ser Gly Leu Thr Phe Ser Asp Ser Ala Met
            180                 185                 190
```

```
Ser Trp Val Arg Leu Thr Pro Glu Lys Arg Leu Glu Trp Val Ala Ser
            195                 200                 205

Ile Ser Thr Gly Gly Ala Thr Tyr Tyr Pro Asp Gly Leu Lys Gly Arg
210                 215                 220

Phe Thr Ile Ser Arg Asp Asp Ala Arg Asn Ile Leu Phe Leu Gln Met
225                 230                 235                 240

Asn Ser Leu Arg Ser Glu Asp Thr Ala Met Tyr Tyr Cys Thr Arg Arg
            245                 250                 255

Gly Val Ser Ser Gly Asn Leu Phe Thr Tyr Trp Gly Gln Gly Thr Leu
                260                 265                 270

Val Thr Val Ser Ala Gly Ala Tyr Pro Tyr Asp Val Pro Asp Tyr Ala
            275                 280                 285

Ser

<210> SEQ ID NO 56
<211> LENGTH: 310
<212> TYPE: PRT
<213> ORGANISM: Artificial Sequence
<220> FEATURE:
<223> OTHER INFORMATION: scFv Molecule Generated from Antibody 1G10D2
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(277)
<223> OTHER INFORMATION: scFv Molecule Generated from Antibody 1G10D2
<220> FEATURE:
<221> NAME/KEY: MISC_FEATURE
<222> LOCATION: (278)..(310)
<223> OTHER INFORMATION: Preferred C-terminal Peptide

<400> SEQUENCE: 56

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Leu Asn Ser Asn Gly Asn Thr
50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
            100                 105                 110

Ala Glu Asp Leu Gly Val Tyr Tyr Cys Phe Gln Gly Ser His Val Pro
        115                 120                 125

Trp Thr Phe Gly Gly Gly Thr Lys Leu Glu Ile Lys Ser Ser Gly Gly
130                 135                 140

Gly Gly Ser Gly Gly Gly Gly Gly Ser Ser Arg Ser Ser Glu Val
145                 150                 155                 160

Lys Leu Val Glu Ser Gly Gly Asp Leu Val Thr Pro Gly Gly Ser Leu
                165                 170                 175

Lys Val Ser Cys Ala Ala Ser Gly Leu Thr Phe Ser Asp Ser Ala Met
            180                 185                 190
```

Ser Trp Val Arg Leu Thr Pro Glu Lys Arg Leu Glu Trp Val Ala Ser
        195                 200                 205

Ile Ser Thr Gly Gly Ala Thr Tyr Tyr Pro Asp Gly Leu Lys Gly Arg
        210                 215                 220

Phe Thr Ile Ser Arg Asp Asp Ala Arg Asn Ile Leu Phe Leu Gln Met
225                 230                 235                 240

Asn Ser Leu Arg Ser Glu Asp Thr Ala Met Tyr Tyr Cys Thr Arg Arg
                245                 250                 255

Gly Val Ser Ser Gly Asn Leu Phe Thr Tyr Trp Gly Gln Gly Thr Leu
                260                 265                 270

Val Thr Val Ser Ala Ala Lys Thr Thr Pro Pro Ser Val Thr Ser Gly
        275                 280                 285

Gln Ala Gly Gln His His His His His His Gly Ala Tyr Pro Tyr Asp
        290                 295                 300

Val Pro Asp Tyr Ala Ser
305                 310

<210> SEQ ID NO 57
<211> LENGTH: 250
<212> TYPE: PRT
<213> ORGANISM: Artificial Sequence
<220> FEATURE:
<223> OTHER INFORMATION: scFv Molecule Generated from Antibody 1G11A10

<400> SEQUENCE: 57

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Ile Asn Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Gly Ser Ser Arg
        115                 120                 125

Ser Ser Glu Val Lys Leu Val Glu Ser Gly Gly Gly Leu Met Lys Pro
        130                 135                 140

Gly Gly Ser Leu Lys Leu Ser Cys Ala Ala Ser Gly Phe Thr Phe Ser
145                 150                 155                 160

Ser Tyr Ala Met Ser Trp Val Arg Gln Ser Pro Glu Lys Arg Leu Glu
                165                 170                 175

Trp Val Ala Ser Ile Ser Ser Gly Gly Gln Thr Tyr Ser Pro Asp Ser
            180                 185                 190

Val Lys Gly Arg Phe Thr Ile Ser Arg Asp Asn Ala Arg Asn Ile Leu
        195                 200                 205

Tyr Leu Gln Met Arg Asn Leu Arg Ser Glu Asp Thr Ala Met Tyr Tyr
    210                 215                 220

Cys Ala Ser Arg Gly Asp Pro Thr Met Thr Ala Thr Leu Phe Val Tyr
225                 230                 235                 240

Trp Gly Gln Gly Thr Leu Val Thr Val Ser
            245                 250

<210> SEQ ID NO 58
<211> LENGTH: 278
<212> TYPE: PRT
<213> ORGANISM: Artificial Sequence
<220> FEATURE:
<223> OTHER INFORMATION: scFv Molecule Generated from Antibody 1G11A10
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(278)
<223> OTHER INFORMATION: scFv Molecule Generated from Antibody 1G11A10

<400> SEQUENCE: 58

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Ile Asn Ser Asn Gly Asn Thr
    50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
            100                 105                 110

Thr Glu Asp Leu Gly Ile Tyr Tyr Cys Phe Gln Gly Ser His Val Pro
        115                 120                 125

Trp Thr Phe Gly Gly Gly Thr Lys Leu Glu Ile Lys Ser Ser Gly Gly
    130                 135                 140

Gly Gly Ser Gly Gly Gly Gly Gly Ser Ser Arg Ser Ser Glu Val
145                 150                 155                 160

Lys Leu Val Glu Ser Gly Gly Gly Leu Met Lys Pro Gly Gly Ser Leu
                165                 170                 175

Lys Leu Ser Cys Ala Ala Ser Gly Phe Thr Phe Ser Ser Tyr Ala Met
            180                 185                 190

Ser Trp Val Arg Gln Ser Pro Glu Lys Arg Leu Glu Trp Val Ala Ser
        195                 200                 205

Ile Ser Ser Gly Gly Gln Thr Tyr Ser Pro Asp Ser Val Lys Gly Arg
    210                 215                 220

Phe Thr Ile Ser Arg Asp Asn Ala Arg Asn Ile Leu Tyr Leu Gln Met
225                 230                 235                 240

Arg Asn Leu Arg Ser Glu Asp Thr Ala Met Tyr Tyr Cys Ala Ser Arg
                245                 250                 255

Gly Asp Pro Thr Met Thr Ala Thr Leu Phe Val Tyr Trp Gly Gln Gly
            260                 265                 270

Thr Leu Val Thr Val Ser
        275

-continued

<210> SEQ ID NO 59
<211> LENGTH: 265
<212> TYPE: PRT
<213> ORGANISM: Artificial Sequence
<220> FEATURE:
<223> OTHER INFORMATION: scFv Molecule Generated from Antibody 1G11A10
<220> FEATURE:
<221> NAME/KEY: MISC_FEATURE
<222> LOCATION: (1)..(249)
<223> OTHER INFORMATION: scFv Molecule Generated from Antibody 1G11A10
<220> FEATURE:
<221> NAME/KEY: MISC_FEATURE
<222> LOCATION: (251)..(265)
<223> OTHER INFORMATION: C-terminal Peptide

<400> SEQUENCE: 59

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Ile Asn Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Ser Ser Arg
        115                 120                 125

Ser Ser Glu Val Lys Leu Val Glu Ser Gly Gly Gly Leu Met Lys Pro
    130                 135                 140

Gly Gly Ser Leu Lys Leu Ser Cys Ala Ala Ser Gly Phe Thr Phe Ser
145                 150                 155                 160

Ser Tyr Ala Met Ser Trp Val Arg Gln Ser Pro Glu Lys Arg Leu Glu
                165                 170                 175

Trp Val Ala Ser Ile Ser Ser Gly Gly Gln Thr Tyr Ser Pro Asp Ser
            180                 185                 190

Val Lys Gly Arg Phe Thr Ile Ser Arg Asp Asn Ala Arg Asn Ile Leu
        195                 200                 205

Tyr Leu Gln Met Arg Asn Leu Arg Ser Glu Asp Thr Ala Met Tyr Tyr
    210                 215                 220

Cys Ala Ser Arg Gly Asp Pro Thr Met Thr Ala Thr Leu Phe Val Tyr
225                 230                 235                 240

Trp Gly Gln Gly Thr Leu Val Thr Val Ser Ala Lys Thr Thr Pro Pro
                245                 250                 255

Ser Val Thr Ser Gly Gln Ala Gly Gln
            260                 265

<210> SEQ ID NO 60
<211> LENGTH: 256
<212> TYPE: PRT
<213> ORGANISM: Artificial Sequence
<220> FEATURE:
<223> OTHER INFORMATION: scFv molecule generated from Antibody 1G11A10
<220> FEATURE:
<221> NAME/KEY: MISC_FEATURE
<222> LOCATION: (1)..(250)
<223> OTHER INFORMATION: scFv Molecule Generated from Antibody 1G11A10

```
<220> FEATURE:
<221> NAME/KEY: MISC_FEATURE
<222> LOCATION: (251)..(256)
<223> OTHER INFORMATION: His Tag Peptide

<400> SEQUENCE: 60

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Ile Asn Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Ser Ser Arg
            115                 120                 125

Ser Ser Glu Val Lys Leu Val Glu Ser Gly Gly Gly Leu Met Lys Pro
130                 135                 140

Gly Gly Ser Leu Lys Leu Ser Cys Ala Ala Ser Gly Phe Thr Phe Ser
145                 150                 155                 160

Ser Tyr Ala Met Ser Trp Val Arg Gln Ser Pro Glu Lys Arg Leu Glu
                165                 170                 175

Trp Val Ala Ser Ile Ser Ser Gly Gly Gln Thr Tyr Ser Pro Asp Ser
            180                 185                 190

Val Lys Gly Arg Phe Thr Ile Ser Arg Asp Asn Ala Arg Asn Ile Leu
        195                 200                 205

Tyr Leu Gln Met Arg Asn Leu Arg Ser Glu Asp Thr Ala Met Tyr Tyr
    210                 215                 220

Cys Ala Ser Arg Gly Asp Pro Thr Met Thr Ala Thr Leu Phe Val Tyr
225                 230                 235                 240

Trp Gly Gln Gly Thr Leu Val Thr Val Ser His His His His His His
                245                 250                 255

<210> SEQ ID NO 61
<211> LENGTH: 262
<212> TYPE: PRT
<213> ORGANISM: Artificial Sequence
<220> FEATURE:
<223> OTHER INFORMATION: scFv Molecule Generated from Antibody 1G11A10
<220> FEATURE:
<221> NAME/KEY: MISC_FEATURE
<222> LOCATION: (1)..(250)
<223> OTHER INFORMATION: scFv Molecule Generated from Antibody 1G11A10
<220> FEATURE:
<221> NAME/KEY: MISC_FEATURE
<222> LOCATION: (251)..(262)
<223> OTHER INFORMATION: HA Tag Peptide

<400> SEQUENCE: 61

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Ile Asn Ser
            20                  25                  30
```

```
Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Thr Glu Asp Leu Gly Ile Tyr Tyr Cys Phe Gln Gly
                 85                  90                  95

Ser His Val Pro Trp Thr Phe Gly Gly Gly Thr Lys Leu Glu Ile Lys
             100                 105                 110

Ser Ser Gly Gly Gly Gly Ser Gly Gly Gly Gly Gly Ser Ser Arg
         115                 120                 125

Ser Ser Glu Val Lys Leu Val Glu Ser Gly Gly Gly Leu Met Lys Pro
     130                 135                 140

Gly Gly Ser Leu Lys Leu Ser Cys Ala Ala Ser Gly Phe Thr Phe Ser
145                 150                 155                 160

Ser Tyr Ala Met Ser Trp Val Arg Gln Ser Pro Glu Lys Arg Leu Glu
             165                 170                 175

Trp Val Ala Ser Ile Ser Ser Gly Gly Gln Thr Tyr Ser Pro Asp Ser
             180                 185                 190

Val Lys Gly Arg Phe Thr Ile Ser Arg Asp Asn Ala Arg Asn Ile Leu
         195                 200                 205

Tyr Leu Gln Met Arg Asn Leu Arg Ser Glu Asp Thr Ala Met Tyr Tyr
     210                 215                 220

Cys Ala Ser Arg Gly Asp Pro Thr Met Thr Thr Leu Phe Val Tyr
225                 230                 235                 240

Trp Gly Gln Gly Thr Leu Val Thr Val Ser Gly Ala Tyr Pro Tyr Asp
             245                 250                 255

Val Pro Asp Tyr Ala Ser
         260

<210> SEQ ID NO 62
<211> LENGTH: 283
<212> TYPE: PRT
<213> ORGANISM: Artificial Sequence
<220> FEATURE:
<223> OTHER INFORMATION: scFv Molecule Generated from Antibody 1G11A10
<220> FEATURE:
<221> NAME/KEY: MISC_FEATURE
<222> LOCATION: (1)..(250)
<223> OTHER INFORMATION: scFv Molecule Generated from Antibody 1G11A10
<220> FEATURE:
<221> NAME/KEY: MISC_FEATURE
<222> LOCATION: (251)..(283)
<223> OTHER INFORMATION: Preferred C-terminal Peptide

<400> SEQUENCE: 62

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Ile Asn Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80
```

-continued

Ser Arg Val Glu Thr Glu Asp Leu Gly Ile Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Ser Ser Arg
        115                 120                 125

Ser Ser Glu Val Lys Leu Val Glu Ser Gly Gly Gly Leu Met Lys Pro
        130                 135                 140

Gly Gly Ser Leu Lys Leu Ser Cys Ala Ala Ser Gly Phe Thr Phe Ser
145                 150                 155                 160

Ser Tyr Ala Met Ser Trp Val Arg Gln Ser Pro Glu Lys Arg Leu Glu
            165                 170                 175

Trp Val Ala Ser Ile Ser Ser Gly Gly Gln Thr Tyr Ser Pro Asp Ser
            180                 185                 190

Val Lys Gly Arg Phe Thr Ile Ser Arg Asp Asn Ala Arg Asn Ile Leu
        195                 200                 205

Tyr Leu Gln Met Arg Asn Leu Arg Ser Glu Asp Thr Ala Met Tyr Tyr
    210                 215                 220

Cys Ala Ser Arg Gly Asp Pro Thr Met Thr Ala Thr Leu Phe Val Tyr
225                 230                 235                 240

Trp Gly Gln Gly Thr Leu Val Thr Val Ser Ala Lys Thr Thr Pro Pro
                245                 250                 255

Ser Val Thr Ser Gly Gln Ala Gly Gln His His His His His His Gly
            260                 265                 270

Ala Tyr Pro Tyr Asp Val Pro Asp Tyr Ala Ser
            275                 280

<210> SEQ ID NO 63
<211> LENGTH: 293
<212> TYPE: PRT
<213> ORGANISM: Artificial Sequence
<220> FEATURE:
<223> OTHER INFORMATION: scFv Molecule Generated from Antibody 1G11A10
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(278)
<223> OTHER INFORMATION: scFv Molecule Generated From Antibody 1G11A10
<220> FEATURE:
<221> NAME/KEY: MISC_FEATURE
<222> LOCATION: (279)..(293)
<223> OTHER INFORMATION: C-terminal Peptide

<400> SEQUENCE: 63

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Ile Asn Ser Asn Gly Asn Thr
    50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

```
Gly Ser Gly Ser Gly Thr Asp Phe Thr Leu Lys Ile Ser Arg Val Glu
            100                 105                 110

Thr Glu Asp Leu Gly Ile Tyr Tyr Cys Phe Gln Gly Ser His Val Pro
        115                 120                 125

Trp Thr Phe Gly Gly Gly Thr Lys Leu Glu Ile Lys Ser Ser Gly Gly
    130                 135                 140

Gly Gly Ser Gly Gly Gly Gly Ser Ser Arg Ser Ser Glu Val
145                 150                 155                 160

Lys Leu Val Glu Ser Gly Gly Leu Met Lys Pro Gly Gly Ser Leu
                165                 170                 175

Lys Leu Ser Cys Ala Ala Ser Gly Phe Thr Phe Ser Ser Tyr Ala Met
            180                 185                 190

Ser Trp Val Arg Gln Ser Pro Glu Lys Arg Leu Glu Trp Val Ala Ser
        195                 200                 205

Ile Ser Ser Gly Gly Gln Thr Tyr Ser Pro Asp Ser Val Lys Gly Arg
    210                 215                 220

Phe Thr Ile Ser Arg Asp Asn Ala Arg Asn Ile Leu Tyr Leu Gln Met
225                 230                 235                 240

Arg Asn Leu Arg Ser Glu Asp Thr Ala Met Tyr Tyr Cys Ala Ser Arg
                245                 250                 255

Gly Asp Pro Thr Met Thr Ala Thr Leu Phe Val Tyr Trp Gly Gln Gly
            260                 265                 270

Thr Leu Val Thr Val Ser Ala Lys Thr Thr Pro Pro Ser Val Thr Ser
        275                 280                 285

Gly Gln Ala Gly Gln
        290

<210> SEQ ID NO 64
<211> LENGTH: 284
<212> TYPE: PRT
<213> ORGANISM: Artificial Sequence
<220> FEATURE:
<223> OTHER INFORMATION: scFv Molecule Generated from Antibody 1G11A10
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(278)
<223> OTHER INFORMATION: scFv Molecule Generated from Antibody 1G11A10
<220> FEATURE:
<221> NAME/KEY: MISC_FEATURE
<222> LOCATION: (279)..(284)
<223> OTHER INFORMATION: C-terminal Peptide

<400> SEQUENCE: 64

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Ile Asn Ser Asn Gly Asn Thr
    50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95
```

Gly Ser Gly Ser Gly Thr Asp Phe Thr Leu Lys Ile Ser Arg Val Glu
            100                 105                 110

Thr Glu Asp Leu Gly Ile Tyr Tyr Cys Phe Gln Gly Ser His Val Pro
        115                 120                 125

Trp Thr Phe Gly Gly Gly Thr Lys Leu Glu Ile Lys Ser Ser Gly Gly
130                 135                 140

Gly Gly Ser Gly Gly Gly Gly Gly Ser Ser Arg Ser Ser Glu Val
145                 150                 155                 160

Lys Leu Val Glu Ser Gly Gly Gly Leu Met Lys Pro Gly Gly Ser Leu
            165                 170                 175

Lys Leu Ser Cys Ala Ala Ser Gly Phe Thr Phe Ser Ser Tyr Ala Met
        180                 185                 190

Ser Trp Val Arg Gln Ser Pro Glu Lys Arg Leu Glu Trp Val Ala Ser
    195                 200                 205

Ile Ser Ser Gly Gly Gln Thr Tyr Ser Pro Asp Ser Val Lys Gly Arg
        210                 215                 220

Phe Thr Ile Ser Arg Asp Asn Ala Arg Asn Ile Leu Tyr Leu Gln Met
225                 230                 235                 240

Arg Asn Leu Arg Ser Glu Asp Thr Ala Met Tyr Tyr Cys Ala Ser Arg
            245                 250                 255

Gly Asp Pro Thr Met Thr Ala Thr Leu Phe Val Tyr Trp Gly Gln Gly
        260                 265                 270

Thr Leu Val Thr Val Ser His His His His His
            275                 280

<210> SEQ ID NO 65
<211> LENGTH: 290
<212> TYPE: PRT
<213> ORGANISM: Artificial Sequence
<220> FEATURE:
<223> OTHER INFORMATION: scFv Molecule Generated from Antibody 1G11A10
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(278)
<223> OTHER INFORMATION: scFv Molecule Generated from Antibody 1G11A10
<220> FEATURE:
<221> NAME/KEY: MISC_FEATURE
<222> LOCATION: (279)..(290)
<223> OTHER INFORMATION: HA Tag Peptide

<400> SEQUENCE: 65

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Ile Asn Ser Asn Gly Asn Thr
    50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
            85                  90                  95

Gly Ser Gly Ser Gly Thr Asp Phe Thr Leu Lys Ile Ser Arg Val Glu
            100                 105                 110

-continued

```
Thr Glu Asp Leu Gly Ile Tyr Tyr Cys Phe Gln Gly His Val Pro
            115                 120                 125

Trp Thr Phe Gly Gly Gly Thr Lys Leu Glu Ile Lys Ser Ser Gly Gly
130                 135                 140

Gly Gly Ser Gly Gly Gly Gly Ser Ser Arg Ser Ser Glu Val
145                 150                 155                 160

Lys Leu Val Glu Ser Gly Gly Gly Leu Met Lys Pro Gly Gly Ser Leu
                165                 170                 175

Lys Leu Ser Cys Ala Ala Ser Gly Phe Thr Phe Ser Ser Tyr Ala Met
                180                 185                 190

Ser Trp Val Arg Gln Ser Pro Glu Lys Arg Leu Glu Trp Val Ala Ser
                195                 200                 205

Ile Ser Ser Gly Gly Gln Thr Tyr Ser Pro Asp Ser Val Lys Gly Arg
210                 215                 220

Phe Thr Ile Ser Arg Asp Asn Ala Arg Asn Ile Leu Tyr Leu Gln Met
225                 230                 235                 240

Arg Asn Leu Arg Ser Glu Asp Thr Ala Met Tyr Tyr Cys Ala Ser Arg
                245                 250                 255

Gly Asp Pro Thr Met Thr Ala Thr Leu Phe Val Tyr Trp Gly Gln Gly
                260                 265                 270

Thr Leu Val Thr Val Ser Gly Ala Tyr Pro Tyr Asp Val Pro Asp Tyr
                275                 280                 285

Ala Ser
    290

<210> SEQ ID NO 66
<211> LENGTH: 311
<212> TYPE: PRT
<213> ORGANISM: Artificial Sequence
<220> FEATURE:
<223> OTHER INFORMATION: scFv Molecule Generated from Antibody 1G11A10
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(278)
<223> OTHER INFORMATION: scFv Molecule Generated from Antibody 1G10D2
<220> FEATURE:
<221> NAME/KEY: MISC_FEATURE
<222> LOCATION: (279)..(311)
<223> OTHER INFORMATION: Preferred C-terminal Peptide

<400> SEQUENCE: 66

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
                20                  25                  30

Thr Gln Thr Pro Leu Ser Leu Pro Val Ser Leu Gly Asp Gln Ala Ser
                35                  40                  45

Ile Ser Cys Arg Ser Ser Gln Ser Ile Ile Asn Ser Asn Gly Asn Thr
    50                  55                  60

Tyr Leu Glu Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
                100                 105                 110
```

```
Thr Glu Asp Leu Gly Ile Tyr Tyr Cys Phe Gln Ser His Val Pro
            115                 120                 125

Trp Thr Phe Gly Gly Gly Thr Lys Leu Glu Ile Lys Ser Ser Gly Gly
        130                 135                 140

Gly Gly Ser Gly Gly Gly Gly Ser Ser Arg Ser Ser Glu Val
145                 150                 155                 160

Lys Leu Val Glu Ser Gly Gly Leu Met Lys Pro Gly Gly Ser Leu
                165                 170                 175

Lys Leu Ser Cys Ala Ala Ser Gly Phe Thr Phe Ser Ser Tyr Ala Met
            180                 185                 190

Ser Trp Val Arg Gln Ser Pro Glu Lys Arg Leu Glu Trp Val Ala Ser
        195                 200                 205

Ile Ser Ser Gly Gly Gln Thr Tyr Ser Pro Asp Ser Val Lys Gly Arg
210                 215                 220

Phe Thr Ile Ser Arg Asp Asn Ala Arg Asn Ile Leu Tyr Leu Gln Met
225                 230                 235                 240

Arg Asn Leu Arg Ser Glu Asp Thr Ala Met Tyr Tyr Cys Ala Ser Arg
            245                 250                 255

Gly Asp Pro Thr Met Thr Ala Thr Leu Phe Val Tyr Trp Gly Gln Gly
        260                 265                 270

Thr Leu Val Thr Val Ser Ala Lys Thr Thr Pro Pro Ser Val Thr Ser
275                 280                 285

Gly Gln Ala Gly Gln His His His His His Gly Ala Tyr Pro Tyr
            290                 295                 300

Asp Val Pro Asp Tyr Ala Ser
305                 310

<210> SEQ ID NO 67
<211> LENGTH: 251
<212> TYPE: PRT
<213> ORGANISM: Artificial Sequence
<220> FEATURE:
<223> OTHER INFORMATION: scFv Molecule Generated Antibody 5B3C11 (VL1)

<400> SEQUENCE: 67

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Ser Ile Leu His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Ile Pro Trp Thr Phe Gly Gly Gly Thr Lys Leu Glu Ile Lys
            100                 105                 110

Ser Ser Gly Gly Gly Gly Ser Gly Gly Gly Gly Gly Ser Ser Arg
        115                 120                 125

Ser Ser Glu Val Gln Leu Val Glu Ser Gly Gly Gly Leu Val Lys Pro
    130                 135                 140

Gly Gly Ser Leu Lys Leu Ser Cys Ala Ala Ser Gly Phe Thr Phe Ser
145                 150                 155                 160
```

```
Asn Tyr Ala Leu Ser Trp Val Arg Gln Thr Pro Glu Lys Arg Leu Glu
            165                 170                 175

Trp Val Ala Ser Ile Ser Ser Gly Gly Asn Thr Tyr Tyr Pro Asp Ser
        180                 185                 190

Val Lys Gly Arg Phe Thr Ile Ser Arg Asp Asn Ala Arg Asn Ile Leu
        195                 200                 205

Tyr Leu Gln Met Ser Ser Leu Arg Ser Glu Asp Thr Ala Met Phe Tyr
        210                 215                 220

Cys Thr Ser Arg Gly Asp Thr Thr Leu Ile Thr Thr Leu Phe Thr Tyr
225                 230                 235                 240

Trp Gly Gln Gly Thr Leu Val Thr Val Ser Ala
                245                 250
```

<210> SEQ ID NO 68
<211> LENGTH: 279
<212> TYPE: PRT
<213> ORGANISM: Artificial Sequence
<220> FEATURE:
<223> OTHER INFORMATION: scFv Molecule Generated Antibody 5B3C11 (VL1)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated Antibody 5B3C11 (VL1)

<400> SEQUENCE: 68

```
Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Asn Gln Ser Ile Leu His Ser Asn Gly Asn Thr
    50                  55                  60

Tyr Leu Asp Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Arg Ile Ser Arg Val Glu
            100                 105                 110

Ala Glu Asp Leu Gly Val Tyr Tyr Cys Phe Gln Gly Ser His Ile Pro
        115                 120                 125

Trp Thr Phe Gly Gly Gly Thr Lys Leu Glu Ile Lys Ser Ser Gly Gly
    130                 135                 140

Gly Gly Ser Gly Gly Gly Gly Gly Ser Ser Arg Ser Ser Glu Val
145                 150                 155                 160

Gln Leu Val Glu Ser Gly Gly Leu Val Lys Pro Gly Gly Ser Leu
                165                 170                 175

Lys Leu Ser Cys Ala Ala Ser Gly Phe Thr Phe Ser Asn Tyr Ala Leu
            180                 185                 190

Ser Trp Val Arg Gln Thr Pro Glu Lys Arg Leu Glu Trp Val Ala Ser
        195                 200                 205

Ile Ser Ser Gly Gly Asn Thr Tyr Tyr Pro Asp Ser Val Lys Gly Arg
    210                 215                 220
```

```
Phe Thr Ile Ser Arg Asp Asn Ala Arg Asn Ile Leu Tyr Leu Gln Met
225                 230                 235                 240

Ser Ser Leu Arg Ser Glu Asp Thr Ala Met Phe Tyr Cys Thr Ser Arg
            245                 250                 255

Gly Asp Thr Thr Leu Ile Thr Thr Leu Phe Thr Tyr Trp Gly Gln Gly
        260                 265                 270

Thr Leu Val Thr Val Ser Ala
        275

<210> SEQ ID NO 69
<211> LENGTH: 266
<212> TYPE: PRT
<213> ORGANISM: Artificial Sequence
<220> FEATURE:
<223> OTHER INFORMATION: scFv Molecule Generated Antibody 5B3C11 (VL1)
<220> FEATURE:
<221> NAME/KEY: MISC_FEATURE
<222> LOCATION: (1)..(251)
<223> OTHER INFORMATION: scFv Molecule Generated Antibody 5B3C11 (VL1)
<220> FEATURE:
<221> NAME/KEY: MISC_FEATURE
<222> LOCATION: (252)..(266)
<223> OTHER INFORMATION: C-terminal Peptide

<400> SEQUENCE: 69

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Ser Ile Leu His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Ile Pro Trp Thr Phe Gly Gly Gly Thr Lys Leu Glu Ile Lys
            100                 105                 110

Ser Ser Gly Gly Gly Gly Ser Gly Gly Gly Gly Gly Ser Ser Arg
        115                 120                 125

Ser Ser Glu Val Gln Leu Val Glu Ser Gly Gly Gly Leu Val Lys Pro
    130                 135                 140

Gly Gly Ser Leu Lys Leu Ser Cys Ala Ala Ser Gly Phe Thr Phe Ser
145                 150                 155                 160

Asn Tyr Ala Leu Ser Trp Val Arg Gln Thr Pro Glu Lys Arg Leu Glu
                165                 170                 175

Trp Val Ala Ser Ile Ser Ser Gly Gly Asn Thr Tyr Tyr Pro Asp Ser
            180                 185                 190

Val Lys Gly Arg Phe Thr Ile Ser Arg Asp Asn Ala Arg Asn Ile Leu
        195                 200                 205

Tyr Leu Gln Met Ser Ser Leu Arg Ser Glu Asp Thr Ala Met Phe Tyr
    210                 215                 220

Cys Thr Ser Arg Gly Asp Thr Thr Leu Ile Thr Thr Leu Phe Thr Tyr
225                 230                 235                 240
```

Trp Gly Gln Gly Thr Leu Val Thr Val Ser Ala Ala Lys Thr Thr Pro
            245                 250                 255

Pro Ser Val Thr Ser Gly Gln Ala Gly Gln
        260                 265

<210> SEQ ID NO 70
<211> LENGTH: 257
<212> TYPE: PRT
<213> ORGANISM: Artificial Sequence
<220> FEATURE:
<223> OTHER INFORMATION: scFv Molecule Generated Antibody 5B3C11 (VL1)
<220> FEATURE:
<221> NAME/KEY: MISC_FEATURE
<222> LOCATION: (1)..(251)
<223> OTHER INFORMATION: scFv Molecule Generated Antibody 5B3C11 (VL1)
<220> FEATURE:
<221> NAME/KEY: MISC_FEATURE
<222> LOCATION: (252)..(257)
<223> OTHER INFORMATION: His Tag Peptide

<400> SEQUENCE: 70

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Ser Ile Leu His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Ile Pro Trp Thr Phe Gly Gly Gly Thr Lys Leu Glu Ile Lys
            100                 105                 110

Ser Ser Gly Gly Gly Gly Ser Gly Gly Gly Gly Gly Ser Ser Arg
        115                 120                 125

Ser Ser Glu Val Gln Leu Val Glu Ser Gly Gly Gly Leu Val Lys Pro
    130                 135                 140

Gly Gly Ser Leu Lys Leu Ser Cys Ala Ala Ser Gly Phe Thr Phe Ser
145                 150                 155                 160

Asn Tyr Ala Leu Ser Trp Val Arg Gln Thr Pro Glu Lys Arg Leu Glu
                165                 170                 175

Trp Val Ala Ser Ile Ser Ser Gly Gly Asn Thr Tyr Tyr Pro Asp Ser
            180                 185                 190

Val Lys Gly Arg Phe Thr Ile Ser Arg Asp Asn Ala Arg Asn Ile Leu
        195                 200                 205

Tyr Leu Gln Met Ser Ser Leu Arg Ser Glu Asp Thr Ala Met Phe Tyr
    210                 215                 220

Cys Thr Ser Arg Gly Asp Thr Thr Leu Ile Thr Thr Leu Phe Thr Tyr
225                 230                 235                 240

Trp Gly Gln Gly Thr Leu Val Thr Val Ser Ala His His His His
                245                 250                 255

His

<210> SEQ ID NO 71
<211> LENGTH: 263
<212> TYPE: PRT
<213> ORGANISM: Artificial Sequence

```
<220> FEATURE:
<223> OTHER INFORMATION: scFv Molecule Generated Antibody 5B3C11 (VL1)
<220> FEATURE:
<221> NAME/KEY: MISC_FEATURE
<222> LOCATION: (1)..(251)
<223> OTHER INFORMATION: scFv Molecule Generated Antibody 5B3C11 (VL1)
<220> FEATURE:
<221> NAME/KEY: MISC_FEATURE
<222> LOCATION: (252)..(263)
<223> OTHER INFORMATION: HA Tag Peptide

<400> SEQUENCE: 71
```

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Ser Ile Leu His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Ile Pro Trp Thr Phe Gly Gly Gly Thr Lys Leu Glu Ile Lys
            100                 105                 110

Ser Ser Gly Gly Gly Ser Gly Gly Gly Gly Ser Ser Arg
        115                 120                 125

Ser Ser Glu Val Gln Leu Val Glu Ser Gly Gly Leu Val Lys Pro
    130                 135                 140

Gly Gly Ser Leu Lys Leu Ser Cys Ala Ala Ser Gly Phe Thr Phe Ser
145                 150                 155                 160

Asn Tyr Ala Leu Ser Trp Val Arg Gln Thr Pro Glu Lys Arg Leu Glu
                165                 170                 175

Trp Val Ala Ser Ile Ser Ser Gly Gly Asn Thr Tyr Tyr Pro Asp Ser
            180                 185                 190

Val Lys Gly Arg Phe Thr Ile Ser Arg Asp Asn Ala Arg Asn Ile Leu
        195                 200                 205

Tyr Leu Gln Met Ser Ser Leu Arg Ser Glu Asp Thr Ala Met Phe Tyr
    210                 215                 220

Cys Thr Ser Arg Gly Asp Thr Thr Leu Ile Thr Thr Leu Phe Thr Tyr
225                 230                 235                 240

Trp Gly Gln Gly Thr Leu Val Thr Val Ser Ala Gly Ala Tyr Pro Tyr
                245                 250                 255

Asp Val Pro Asp Tyr Ala Ser
            260

```
<210> SEQ ID NO 72
<211> LENGTH: 284
<212> TYPE: PRT
<213> ORGANISM: Artificial Sequence
<220> FEATURE:
<223> OTHER INFORMATION: scFv Molecule Generated Antibody 5B3C11 (VL1)
<220> FEATURE:
<221> NAME/KEY: MISC_FEATURE
<222> LOCATION: (1)..(251)
<223> OTHER INFORMATION: scFv Molecule Generated Antibody 5B3C11 (VL1)
<220> FEATURE:
<221> NAME/KEY: MISC_FEATURE
<222> LOCATION: (252)..(284)
<223> OTHER INFORMATION: Preferred C-terminal Peptide
```

-continued

<400> SEQUENCE: 72

Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Ser Ile Leu His Ser
            20                  25                  30

Asn Gly Asn Thr Tyr Leu Asp Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65              70                  75                  80

Ser Arg Val Glu Ala Glu Asp Leu Gly Val Tyr Tyr Cys Phe Gln Gly
                85                  90                  95

Ser His Ile Pro Trp Thr Phe Gly Gly Gly Thr Lys Leu Glu Ile Lys
            100                 105                 110

Ser Ser Gly Gly Gly Gly Ser Gly Gly Gly Gly Gly Ser Ser Arg
            115                 120                 125

Ser Ser Glu Val Gln Leu Val Glu Ser Gly Gly Gly Leu Val Lys Pro
130                 135                 140

Gly Gly Ser Leu Lys Leu Ser Cys Ala Ala Ser Gly Phe Thr Phe Ser
145                 150                 155                 160

Asn Tyr Ala Leu Ser Trp Val Arg Gln Thr Pro Glu Lys Arg Leu Glu
                165                 170                 175

Trp Val Ala Ser Ile Ser Ser Gly Gly Asn Thr Tyr Tyr Pro Asp Ser
            180                 185                 190

Val Lys Gly Arg Phe Thr Ile Ser Arg Asp Asn Ala Arg Asn Ile Leu
        195                 200                 205

Tyr Leu Gln Met Ser Ser Leu Arg Ser Glu Asp Thr Ala Met Phe Tyr
    210                 215                 220

Cys Thr Ser Arg Gly Asp Thr Thr Leu Ile Thr Thr Leu Phe Thr Tyr
225                 230                 235                 240

Trp Gly Gln Gly Thr Leu Val Thr Val Ser Ala Ala Lys Thr Thr Pro
                245                 250                 255

Pro Ser Val Thr Ser Gly Gln Ala Gly Gln His His His His His His
            260                 265                 270

Gly Ala Tyr Pro Tyr Asp Val Pro Asp Tyr Ala Ser
        275                 280

<210> SEQ ID NO 73
<211> LENGTH: 294
<212> TYPE: PRT
<213> ORGANISM: Artificial Sequence
<220> FEATURE:
<223> OTHER INFORMATION: scFv Molecule Generated Antibody 5B3C11 (VL1)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated Antibody 5B3C11 (VL1)
<220> FEATURE:
<221> NAME/KEY: MISC_FEATURE
<222> LOCATION: (280)..(294)
<223> OTHER INFORMATION: C-terminal Peptide

<400> SEQUENCE: 73

```
Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Asn Gln Ser Ile Leu His Ser Asn Gly Asn Thr
    50                  55                  60

Tyr Leu Asp Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Arg Ile Ser Arg Val Glu
            100                 105                 110

Ala Glu Asp Leu Gly Val Tyr Tyr Cys Phe Gln Gly Ser His Ile Pro
        115                 120                 125

Trp Thr Phe Gly Gly Gly Thr Lys Leu Glu Ile Lys Ser Ser Gly Gly
130                 135                 140

Gly Gly Ser Gly Gly Gly Gly Ser Arg Ser Ser Glu Val
145                 150                 155                 160

Gln Leu Val Glu Ser Gly Gly Gly Leu Val Lys Pro Gly Gly Ser Leu
                165                 170                 175

Lys Leu Ser Cys Ala Ala Ser Gly Phe Thr Phe Ser Asn Tyr Ala Leu
            180                 185                 190

Ser Trp Val Arg Gln Thr Pro Glu Lys Arg Leu Glu Trp Val Ala Ser
        195                 200                 205

Ile Ser Ser Gly Gly Asn Thr Tyr Tyr Pro Asp Ser Val Lys Gly Arg
    210                 215                 220

Phe Thr Ile Ser Arg Asp Asn Ala Arg Asn Ile Leu Tyr Leu Gln Met
225                 230                 235                 240

Ser Ser Leu Arg Ser Glu Asp Thr Ala Met Phe Tyr Cys Thr Ser Arg
                245                 250                 255

Gly Asp Thr Thr Leu Ile Thr Thr Leu Phe Thr Tyr Trp Gly Gln Gly
            260                 265                 270

Thr Leu Val Thr Val Ser Ala Ala Lys Thr Thr Pro Pro Ser Val Thr
        275                 280                 285

Ser Gly Gln Ala Gly Gln
    290
```

<210> SEQ ID NO 74
<211> LENGTH: 285
<212> TYPE: PRT
<213> ORGANISM: Artificial Sequence
<220> FEATURE:
<223> OTHER INFORMATION: scFv Molecule Generated Antibody 5B3C11 (VL1)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated Antibody 5B3C11 (VL1)
<220> FEATURE:
<221> NAME/KEY: MISC_FEATURE
<222> LOCATION: (280)..(285)
<223> OTHER INFORMATION: His Tag Peptide

<400> SEQUENCE: 74

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Asn Gln Ser Ile Leu His Ser Asn Gly Asn Thr
    50                  55                  60

Tyr Leu Asp Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Arg Ile Ser Arg Val Glu
            100                 105                 110

Ala Glu Asp Leu Gly Val Tyr Tyr Cys Phe Gln Gly Ser His Ile Pro
        115                 120                 125

Trp Thr Phe Gly Gly Gly Thr Lys Leu Glu Ile Lys Ser Ser Gly Gly
    130                 135                 140

Gly Gly Ser Gly Gly Gly Gly Ser Ser Arg Ser Ser Glu Val
145                 150                 155                 160

Gln Leu Val Glu Ser Gly Gly Gly Leu Val Lys Pro Gly Gly Ser Leu
                165                 170                 175

Lys Leu Ser Cys Ala Ala Ser Gly Phe Thr Phe Ser Asn Tyr Ala Leu
            180                 185                 190

Ser Trp Val Arg Gln Thr Pro Glu Lys Arg Leu Glu Trp Val Ala Ser
        195                 200                 205

Ile Ser Ser Gly Gly Asn Thr Tyr Tyr Pro Asp Ser Val Lys Gly Arg
    210                 215                 220

Phe Thr Ile Ser Arg Asp Asn Ala Arg Asn Ile Leu Tyr Leu Gln Met
225                 230                 235                 240

Ser Ser Leu Arg Ser Glu Asp Thr Ala Met Phe Tyr Cys Thr Ser Arg
                245                 250                 255

Gly Asp Thr Thr Leu Ile Thr Thr Leu Phe Thr Tyr Trp Gly Gln Gly
            260                 265                 270

Thr Leu Val Thr Val Ser Ala His His His His His
        275                 280                 285

<210> SEQ ID NO 75
<211> LENGTH: 291
<212> TYPE: PRT
<213> ORGANISM: Artificial Sequence
<220> FEATURE:
<223> OTHER INFORMATION: scFv Molecule Generated Antibody 5B3C11 (VL1)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated Antibody 5B3C11 (VL1)
<220> FEATURE:
<221> NAME/KEY: MISC_FEATURE
<222> LOCATION: (280)..(291)
<223> OTHER INFORMATION: HA Tag Peptide

<400> SEQUENCE: 75

```
Ile Gln Glu Glu Phe Lys Met Lys Lys Thr Ala Ile Ala Ile Ala Val
1               5                   10                  15
Ala Leu Ala Gly Phe Ala Thr Val Ala Gln Ala Ala Asp Val Leu Met
            20                  25                  30
Thr Gln Thr Pro Leu Ser Leu Pro Val Ser Leu Gly Asp Gln Ala Ser
        35                  40                  45
Ile Ser Cys Arg Ser Asn Gln Ser Ile Leu His Ser Asn Gly Asn Thr
    50                  55                  60
Tyr Leu Asp Trp Tyr Leu Gln Lys Pro Gly Gln Ser Pro Lys Leu Leu
65                  70                  75                  80
Ile Tyr Lys Val Ser Asn Arg Phe Ser Gly Val Pro Asp Arg Phe Ser
                85                  90                  95
Gly Ser Gly Ser Gly Thr Asp Phe Thr Leu Arg Ile Ser Arg Val Glu
            100                 105                 110
Ala Glu Asp Leu Gly Val Tyr Tyr Cys Phe Gln Gly Ser His Ile Pro
        115                 120                 125
Trp Thr Phe Gly Gly Gly Thr Lys Leu Glu Ile Lys Ser Ser Gly Gly
    130                 135                 140
Gly Gly Ser Gly Gly Gly Gly Ser Ser Arg Ser Ser Glu Val
145                 150                 155                 160
Gln Leu Val Glu Ser Gly Gly Gly Leu Val Lys Pro Gly Gly Ser Leu
                165                 170                 175
Lys Leu Ser Cys Ala Ala Ser Gly Phe Thr Phe Ser Asn Tyr Ala Leu
            180                 185                 190
Ser Trp Val Arg Gln Thr Pro Glu Lys Arg Leu Glu Trp Val Ala Ser
        195                 200                 205
Ile Ser Ser Gly Gly Asn Thr Tyr Tyr Pro Asp Ser Val Lys Gly Arg
    210                 215                 220
Phe Thr Ile Ser Arg Asp Asn Ala Arg Asn Ile Leu Tyr Leu Gln Met
225                 230                 235                 240
Ser Ser Leu Arg Ser Glu Asp Thr Ala Met Phe Tyr Cys Thr Ser Arg
                245                 250                 255
Gly Asp Thr Thr Leu Ile Thr Thr Leu Phe Thr Tyr Trp Gly Gln Gly
            260                 265                 270
Thr Leu Val Thr Val Ser Ala Gly Ala Tyr Pro Tyr Asp Val Pro Asp
        275                 280                 285
Tyr Ala Ser
    290
```

<210> SEQ ID NO 76
<211> LENGTH: 312
<212> TYPE: PRT
<213> ORGANISM: Artificial Sequence
<220> FEATURE:
<223> OTHER INFORMATION: scFv Molecule Generated Antibody 5B3C11 (VL1)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated Antibody 5B3C11 (VL1)
<220> FEATURE:
<221> NAME/KEY: MISC_FEATURE
<222> LOCATION: (280)..(312)
<223> OTHER INFORMATION: Preferred C-terminal Peptide

<400> SEQUENCE: 76

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Asn Gln Ser Ile Leu His Ser Asn Gly Asn Thr
50                  55                  60

Tyr Leu Asp Trp Tyr Leu Gln Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Arg Ile Ser Arg Val Glu
            100                 105                 110

Ala Glu Asp Leu Gly Val Tyr Tyr Cys Phe Gln Gly Ser His Ile Pro
        115                 120                 125

Trp Thr Phe Gly Gly Gly Thr Lys Leu Glu Ile Lys Ser Ser Gly Gly
130                 135                 140

Gly Gly Ser Gly Gly Gly Gly Ser Ser Arg Ser Ser Glu Val
145                 150                 155                 160

Gln Leu Val Glu Ser Gly Gly Gly Leu Val Lys Pro Gly Gly Ser Leu
                165                 170                 175

Lys Leu Ser Cys Ala Ala Ser Gly Phe Thr Phe Ser Asn Tyr Ala Leu
            180                 185                 190

Ser Trp Val Arg Gln Thr Pro Glu Lys Arg Leu Glu Trp Val Ala Ser
        195                 200                 205

Ile Ser Ser Gly Gly Asn Thr Tyr Tyr Pro Asp Ser Val Lys Gly Arg
210                 215                 220

Phe Thr Ile Ser Arg Asp Asn Ala Arg Asn Ile Leu Tyr Leu Gln Met
225                 230                 235                 240

Ser Ser Leu Arg Ser Glu Asp Thr Ala Met Phe Tyr Cys Thr Ser Arg
                245                 250                 255

Gly Asp Thr Thr Leu Ile Thr Thr Leu Phe Thr Tyr Trp Gly Gln Gly
            260                 265                 270

Thr Leu Val Thr Val Ser Ala Ala Lys Thr Thr Pro Pro Ser Val Thr
        275                 280                 285

Ser Gly Gln Ala Gly Gln His His His His His Gly Ala Tyr Pro
290                 295                 300

Tyr Asp Val Pro Asp Tyr Ala Ser
305                 310

<210> SEQ ID NO 77
<211> LENGTH: 247
<212> TYPE: PRT
<213> ORGANISM: Artificial Sequence
<220> FEATURE:
<223> OTHER INFORMATION: scFv Molecule Generated Antibody 5B3C11 (VL2)

<400> SEQUENCE: 77

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

-continued

Tyr Leu His Trp Tyr Gln Gln Lys Ser Gly Ala Ser Pro Lys Leu Trp
            35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Gly Tyr Pro
                 85                  90                  95

Arg Thr Phe Gly Gly Gly Thr Lys Leu Glu Ile Lys Ser Ser Gly Gly
            100                 105                 110

Gly Gly Ser Gly Gly Gly Gly Ser Ser Arg Ser Ser Glu Val
            115                 120                 125

Gln Leu Val Glu Ser Gly Gly Gly Leu Val Lys Pro Gly Gly Ser Leu
130                 135                 140

Lys Leu Ser Cys Ala Ala Ser Gly Phe Thr Phe Ser Asn Tyr Ala Leu
145                 150                 155                 160

Ser Trp Val Arg Gln Thr Pro Glu Lys Arg Leu Glu Trp Val Ala Ser
                165                 170                 175

Ile Ser Ser Gly Gly Asn Thr Tyr Tyr Pro Asp Ser Val Lys Gly Arg
            180                 185                 190

Phe Thr Ile Ser Arg Asp Asn Ala Arg Asn Ile Leu Tyr Leu Gln Met
            195                 200                 205

Ser Ser Leu Arg Ser Glu Asp Thr Ala Met Phe Tyr Cys Thr Ser Arg
            210                 215                 220

Gly Asp Thr Thr Leu Ile Thr Thr Leu Phe Thr Tyr Trp Gly Gln Gly
225                 230                 235                 240

Thr Leu Val Thr Val Ser Ala
                245

<210> SEQ ID NO 78
<211> LENGTH: 275
<212> TYPE: PRT
<213> ORGANISM: Artificial Sequence
<220> FEATURE:
<223> OTHER INFORMATION: scFv Molecule Generated Antibody 5B3C11 (VL2)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(275)
<223> OTHER INFORMATION: scFv Molecule Generated Antibody 5B3C11 (VL2)

<400> SEQUENCE: 78

Ile Gln Glu Glu Phe Lys Met Lys Lys Thr Ala Ile Ala Ile Ala Val
 1               5                  10                  15

Ala Leu Ala Gly Phe Ala Thr Val Ala Gln Ala Glu Asn Val Leu
             20                  25                  30

Thr Gln Ser Pro Ala Ile Met Ser Ala Ser Pro Gly Glu Lys Val Thr
             35                  40                  45

Met Thr Cys Arg Ala Ser Ser Ser Val Ser Ser Ser Tyr Leu His Trp
 50                  55                  60

Tyr Gln Gln Lys Ser Gly Ala Ser Pro Lys Leu Trp Ile Tyr Ser Thr
 65                  70                  75                  80

Ser Asn Leu Ala Ser Gly Val Pro Ala Arg Phe Ser Gly Ser Gly Ser
                 85                  90                  95

```
Gly Thr Ser Tyr Ser Leu Thr Ile Ser Ser Val Glu Ala Glu Asp Ala
                100                 105                 110

Ala Thr Tyr Tyr Cys Gln Gln Tyr Ser Gly Tyr Pro Arg Thr Phe Gly
            115                 120                 125

Gly Gly Thr Lys Leu Glu Ile Lys Ser Ser Gly Gly Gly Ser Gly
        130                 135                 140

Gly Gly Gly Gly Ser Ser Arg Ser Ser Glu Val Gln Leu Val Glu
145                 150                 155                 160

Ser Gly Gly Gly Leu Val Lys Pro Gly Gly Ser Leu Lys Leu Ser Cys
                165                 170                 175

Ala Ala Ser Gly Phe Thr Phe Ser Asn Tyr Ala Leu Ser Trp Val Arg
            180                 185                 190

Gln Thr Pro Glu Lys Arg Leu Glu Trp Val Ala Ser Ile Ser Ser Gly
        195                 200                 205

Gly Asn Thr Tyr Tyr Pro Asp Ser Val Lys Gly Arg Phe Thr Ile Ser
    210                 215                 220

Arg Asp Asn Ala Arg Asn Ile Leu Tyr Leu Gln Met Ser Ser Leu Arg
225                 230                 235                 240

Ser Glu Asp Thr Ala Met Phe Tyr Cys Thr Ser Arg Gly Asp Thr Thr
                245                 250                 255

Leu Ile Thr Thr Leu Phe Thr Tyr Trp Gly Gln Gly Thr Leu Val Thr
            260                 265                 270

Val Ser Ala
    275

<210> SEQ ID NO 79
<211> LENGTH: 262
<212> TYPE: PRT
<213> ORGANISM: Artificial Sequence
<220> FEATURE:
<223> OTHER INFORMATION: scFv Molecule Generated Antibody 5B3C11 (VL2)
<220> FEATURE:
<221> NAME/KEY: MISC_FEATURE
<222> LOCATION: (1)..(247)
<223> OTHER INFORMATION: scFv Molecule Generated Antibody 5B3C11 (VL2)
<220> FEATURE:
<221> NAME/KEY: MISC_FEATURE
<222> LOCATION: (248)..(262)
<223> OTHER INFORMATION: C-terminal Peptide

<400> SEQUENCE: 79

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Arg Thr Phe Gly Gly Gly Thr Lys Leu Glu Ile Lys Ser Ser Gly Gly
            100                 105                 110

Gly Gly Ser Gly Gly Gly Gly Gly Ser Ser Arg Ser Ser Glu Val
        115                 120                 125
```

Gln Leu Val Glu Ser Gly Gly Gly Leu Val Lys Pro Gly Gly Ser Leu
    130                 135                 140

Lys Leu Ser Cys Ala Ala Ser Gly Phe Thr Phe Ser Asn Tyr Ala Leu
145                 150                 155                 160

Ser Trp Val Arg Gln Thr Pro Glu Lys Arg Leu Glu Trp Val Ala Ser
                165                 170                 175

Ile Ser Ser Gly Gly Asn Thr Tyr Tyr Pro Asp Ser Val Lys Gly Arg
            180                 185                 190

Phe Thr Ile Ser Arg Asp Asn Ala Arg Asn Ile Leu Tyr Leu Gln Met
        195                 200                 205

Ser Ser Leu Arg Ser Glu Asp Thr Ala Met Phe Tyr Cys Thr Ser Arg
210                 215                 220

Gly Asp Thr Thr Leu Ile Thr Thr Leu Phe Thr Tyr Trp Gly Gln Gly
225                 230                 235                 240

Thr Leu Val Thr Val Ser Ala Ala Lys Thr Thr Pro Pro Ser Val Thr
                245                 250                 255

Ser Gly Gln Ala Gly Gln
            260

<210> SEQ ID NO 80
<211> LENGTH: 253
<212> TYPE: PRT
<213> ORGANISM: Artificial Sequence
<220> FEATURE:
<223> OTHER INFORMATION: scFv Molecule Generated Antibody 5B3C11 (VL2)
<220> FEATURE:
<221> NAME/KEY: MISC_FEATURE
<222> LOCATION: (1)..(247)
<223> OTHER INFORMATION: scFv Molecule Generated Antibody 5B3C11 (VL2)
<220> FEATURE:
<221> NAME/KEY: MISC_FEATURE
<222> LOCATION: (248)..(253)
<223> OTHER INFORMATION: His Tag Peptide

<400> SEQUENCE: 80

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
                20                  25                  30

Tyr Leu His Trp Tyr Gln Gln Lys Ser Gly Ala Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Arg Thr Phe Gly Gly Gly Thr Lys Leu Glu Ile Lys Ser Ser Gly Gly
            100                 105                 110

Gly Gly Ser Gly Gly Gly Gly Ser Ser Arg Ser Ser Glu Val
        115                 120                 125

Gln Leu Val Glu Ser Gly Gly Gly Leu Val Lys Pro Gly Gly Ser Leu
    130                 135                 140

Lys Leu Ser Cys Ala Ala Ser Gly Phe Thr Phe Ser Asn Tyr Ala Leu
145                 150                 155                 160

Ser Trp Val Arg Gln Thr Pro Glu Lys Arg Leu Glu Trp Val Ala Ser
                165                 170                 175

```
Ile Ser Ser Gly Gly Asn Thr Tyr Tyr Pro Asp Ser Val Lys Gly Arg
            180                 185                 190

Phe Thr Ile Ser Arg Asp Asn Ala Arg Asn Ile Leu Tyr Leu Gln Met
        195                 200                 205

Ser Ser Leu Arg Ser Glu Asp Thr Ala Met Phe Tyr Cys Thr Ser Arg
    210                 215                 220

Gly Asp Thr Thr Leu Ile Thr Thr Leu Phe Tyr Trp Gly Gln Gly
225                 230                 235                 240

Thr Leu Val Thr Val Ser Ala His His His His His His
            245                 250

<210> SEQ ID NO 81
<211> LENGTH: 259
<212> TYPE: PRT
<213> ORGANISM: Artificial Sequence
<220> FEATURE:
<223> OTHER INFORMATION: scFv Molecule Generated Antibody 5B3C11 (VL2)
<220> FEATURE:
<221> NAME/KEY: MISC_FEATURE
<222> LOCATION: (1)..(247)
<223> OTHER INFORMATION: scFv Molecule Generated Antibody 5B3C11 (VL2)
<220> FEATURE:
<221> NAME/KEY: MISC_FEATURE
<222> LOCATION: (248)..(259)
<223> OTHER INFORMATION: HA Tag
<220> FEATURE:
<221> NAME/KEY: MISC_FEATURE
<222> LOCATION: (248)..(259)
<223> OTHER INFORMATION: HA Tag Peptide

<400> SEQUENCE: 81

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Arg Thr Phe Gly Gly Gly Thr Lys Leu Glu Ile Lys Ser Ser Gly Gly
            100                 105                 110

Gly Gly Ser Gly Gly Gly Gly Gly Ser Ser Arg Ser Ser Glu Val
        115                 120                 125

Gln Leu Val Glu Ser Gly Gly Gly Leu Val Lys Pro Gly Gly Ser Leu
    130                 135                 140

Lys Leu Ser Cys Ala Ala Ser Gly Phe Thr Phe Ser Asn Tyr Ala Leu
145                 150                 155                 160

Ser Trp Val Arg Gln Thr Pro Glu Lys Arg Leu Glu Trp Val Ala Ser
                165                 170                 175

Ile Ser Ser Gly Gly Asn Thr Tyr Tyr Pro Asp Ser Val Lys Gly Arg
            180                 185                 190

Phe Thr Ile Ser Arg Asp Asn Ala Arg Asn Ile Leu Tyr Leu Gln Met
        195                 200                 205

Ser Ser Leu Arg Ser Glu Asp Thr Ala Met Phe Tyr Cys Thr Ser Arg
    210                 215                 220
```

```
Gly Asp Thr Thr Leu Ile Thr Thr Leu Phe Thr Tyr Trp Gly Gln Gly
225                 230                 235                 240

Thr Leu Val Thr Val Ser Ala Gly Ala Tyr Pro Tyr Asp Val Pro Asp
            245                 250                 255

Tyr Ala Ser

<210> SEQ ID NO 82
<211> LENGTH: 280
<212> TYPE: PRT
<213> ORGANISM: Artificial Sequence
<220> FEATURE:
<223> OTHER INFORMATION: scFv Molecule Generated Antibody 5B3C11 (VL2)
<220> FEATURE:
<221> NAME/KEY: MISC_FEATURE
<222> LOCATION: (1)..(247)
<223> OTHER INFORMATION: scFv Molecule Generated Antibody 5B3C11 (VL2)
<220> FEATURE:
<221> NAME/KEY: MISC_FEATURE
<222> LOCATION: (248)..(280)
<223> OTHER INFORMATION: Preferred C-terminal Peptide

<400> SEQUENCE: 82

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Arg Thr Phe Gly Gly Gly Thr Lys Leu Glu Ile Lys Ser Ser Gly Gly
            100                 105                 110

Gly Gly Ser Gly Gly Gly Gly Gly Ser Ser Arg Ser Ser Glu Val
        115                 120                 125

Gln Leu Val Glu Ser Gly Gly Gly Leu Val Lys Pro Gly Gly Ser Leu
    130                 135                 140

Lys Leu Ser Cys Ala Ala Ser Gly Phe Thr Phe Ser Asn Tyr Ala Leu
145                 150                 155                 160

Ser Trp Val Arg Gln Thr Pro Glu Lys Arg Leu Glu Trp Val Ala Ser
                165                 170                 175

Ile Ser Ser Gly Gly Asn Thr Tyr Tyr Pro Asp Ser Val Lys Gly Arg
            180                 185                 190

Phe Thr Ile Ser Arg Asp Asn Ala Arg Asn Ile Leu Tyr Leu Gln Met
        195                 200                 205

Ser Ser Leu Arg Ser Glu Asp Thr Ala Met Phe Tyr Cys Thr Ser Arg
    210                 215                 220

Gly Asp Thr Thr Leu Ile Thr Thr Leu Phe Thr Tyr Trp Gly Gln Gly
225                 230                 235                 240

Thr Leu Val Thr Val Ser Ala Ala Lys Thr Thr Pro Pro Ser Val Thr
                245                 250                 255

Ser Gly Gln Ala Gly Gln His His His His His Gly Ala Tyr Pro
            260                 265                 270

Tyr Asp Val Pro Asp Tyr Ala Ser
        275                 280
```

<210> SEQ ID NO 83
<211> LENGTH: 290
<212> TYPE: PRT
<213> ORGANISM: Artificial Sequence
<220> FEATURE:
<223> OTHER INFORMATION: scFv Molecule Generated Antibody 5B3C11 (VL2)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(275)
<223> OTHER INFORMATION: scFv Molecule Generated Antibody 5B3C11 (VL2)
<220> FEATURE:
<221> NAME/KEY: MISC_FEATURE
<222> LOCATION: (275)..(290)
<223> OTHER INFORMATION: C-terminal Peptide

<400> SEQUENCE: 83

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Glu Asn Val Leu
            20                  25                  30

Thr Gln Ser Pro Ala Ile Met Ser Ala Ser Pro Gly Glu Lys Val Thr
        35                  40                  45

Met Thr Cys Arg Ala Ser Ser Val Ser Ser Ser Tyr Leu His Trp
    50                  55                  60

Tyr Gln Gln Lys Ser Gly Ala Ser Pro Lys Leu Trp Ile Tyr Ser Thr
65                  70                  75                  80

Ser Asn Leu Ala Ser Gly Val Pro Ala Arg Phe Ser Gly Ser Gly Ser
                85                  90                  95

Gly Thr Ser Tyr Ser Leu Thr Ile Ser Ser Val Glu Ala Glu Asp Ala
            100                 105                 110

Ala Thr Tyr Tyr Cys Gln Gln Tyr Ser Gly Tyr Pro Arg Thr Phe Gly
        115                 120                 125

Gly Gly Thr Lys Leu Glu Ile Lys Ser Gly Gly Gly Gly Ser Gly
130                 135                 140

Gly Gly Gly Gly Ser Ser Arg Ser Ser Glu Val Gln Leu Val Glu
145                 150                 155                 160

Ser Gly Gly Gly Leu Val Lys Pro Gly Gly Ser Leu Lys Leu Ser Cys
                165                 170                 175

Ala Ala Ser Gly Phe Thr Phe Ser Asn Tyr Ala Leu Ser Trp Val Arg
            180                 185                 190

Gln Thr Pro Glu Lys Arg Leu Glu Trp Val Ala Ser Ile Ser Ser Gly
        195                 200                 205

Gly Asn Thr Tyr Tyr Pro Asp Ser Val Lys Gly Arg Phe Thr Ile Ser
    210                 215                 220

Arg Asp Asn Ala Arg Asn Ile Leu Tyr Leu Gln Met Ser Ser Leu Arg
225                 230                 235                 240

Ser Glu Asp Thr Ala Met Phe Tyr Cys Thr Ser Arg Gly Asp Thr Thr
                245                 250                 255

Leu Ile Thr Thr Leu Phe Thr Tyr Trp Gly Gln Gly Thr Leu Val Thr
            260                 265                 270

Val Ser Ala Ala Lys Thr Thr Pro Pro Ser Val Thr Ser Gly Gln Ala
        275                 280                 285

Gly Gln
    290

```
<210> SEQ ID NO 84
<211> LENGTH: 281
<212> TYPE: PRT
<213> ORGANISM: Artificial Sequence
<220> FEATURE:
<223> OTHER INFORMATION: scFv Molecule Generated Antibody 5B3C11 (VL2)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(275)
<223> OTHER INFORMATION: scFv Molecule Generated Antibody 5B3C11 (VL2)
<220> FEATURE:
<221> NAME/KEY: MISC_FEATURE
<222> LOCATION: (276)..(281)
<223> OTHER INFORMATION: His Tag Peptide

<400> SEQUENCE: 84

Ile Gln Glu Glu Phe Lys Met Lys Lys Thr Ala Ile Ala Ile Ala Val
 1               5                  10                  15

Ala Leu Ala Gly Phe Ala Thr Val Ala Gln Ala Glu Asn Val Leu
             20                  25                  30

Thr Gln Ser Pro Ala Ile Met Ser Ala Ser Pro Gly Glu Lys Val Thr
         35                  40                  45

Met Thr Cys Arg Ala Ser Ser Ser Val Ser Ser Ser Tyr Leu His Trp
     50                  55                  60

Tyr Gln Gln Lys Ser Gly Ala Ser Pro Lys Leu Trp Ile Tyr Ser Thr
 65                  70                  75                  80

Ser Asn Leu Ala Ser Gly Val Pro Ala Arg Phe Ser Gly Ser Gly Ser
                 85                  90                  95

Gly Thr Ser Tyr Ser Leu Thr Ile Ser Ser Val Glu Ala Glu Asp Ala
            100                 105                 110

Ala Thr Tyr Tyr Cys Gln Gln Tyr Ser Gly Tyr Pro Arg Thr Phe Gly
        115                 120                 125

Gly Gly Thr Lys Leu Glu Ile Lys Ser Ser Gly Gly Gly Gly Ser Gly
    130                 135                 140

Gly Gly Gly Gly Ser Ser Arg Ser Ser Glu Val Gln Leu Val Glu
145                 150                 155                 160

Ser Gly Gly Gly Leu Val Lys Pro Gly Gly Ser Leu Lys Leu Ser Cys
                165                 170                 175

Ala Ala Ser Gly Phe Thr Phe Ser Asn Tyr Ala Leu Ser Trp Val Arg
            180                 185                 190

Gln Thr Pro Glu Lys Arg Leu Glu Trp Val Ala Ser Ile Ser Ser Gly
        195                 200                 205

Gly Asn Thr Tyr Tyr Pro Asp Ser Val Lys Gly Arg Phe Thr Ile Ser
    210                 215                 220

Arg Asp Asn Ala Arg Asn Ile Leu Tyr Leu Gln Met Ser Ser Leu Arg
225                 230                 235                 240

Ser Glu Asp Thr Ala Met Phe Tyr Cys Thr Ser Arg Gly Asp Thr Thr
                245                 250                 255

Leu Ile Thr Thr Leu Phe Thr Tyr Trp Gly Gln Gly Thr Leu Val Thr
            260                 265                 270

Val Ser Ala His His His His His His
        275                 280
```

```
<210> SEQ ID NO 85
<211> LENGTH: 287
<212> TYPE: PRT
<213> ORGANISM: Artificial Sequence
<220> FEATURE:
<223> OTHER INFORMATION: scFv Molecule Generated Antibody 5B3C11 (VL2)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(275)
<223> OTHER INFORMATION: scFv Molecule Generated Antibody 5B3C11 (VL2)
<220> FEATURE:
<221> NAME/KEY: MISC_FEATURE
<222> LOCATION: (276)..(287)
<223> OTHER INFORMATION: HA Tag
<220> FEATURE:
<221> NAME/KEY: MISC_FEATURE
<222> LOCATION: (276)..(287)
<223> OTHER INFORMATION: HA Tag Peptide

<400> SEQUENCE: 85

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Glu Asn Val Leu
            20                  25                  30

Thr Gln Ser Pro Ala Ile Met Ser Ala Ser Pro Gly Glu Lys Val Thr
        35                  40                  45

Met Thr Cys Arg Ala Ser Ser Ser Val Ser Ser Ser Tyr Leu His Trp
    50                  55                  60

Tyr Gln Gln Lys Ser Gly Ala Ser Pro Lys Leu Trp Ile Tyr Ser Thr
65                  70                  75                  80

Ser Asn Leu Ala Ser Gly Val Pro Ala Arg Phe Ser Gly Ser Gly Ser
                85                  90                  95

Gly Thr Ser Tyr Ser Leu Thr Ile Ser Ser Val Glu Ala Glu Asp Ala
            100                 105                 110

Ala Thr Tyr Tyr Cys Gln Gln Tyr Ser Gly Tyr Pro Arg Thr Phe Gly
        115                 120                 125

Gly Gly Thr Lys Leu Glu Ile Lys Ser Ser Gly Gly Gly Gly Ser Gly
    130                 135                 140

Gly Gly Gly Gly Ser Ser Arg Ser Ser Glu Val Gln Leu Val Glu
145                 150                 155                 160

Ser Gly Gly Gly Leu Val Lys Pro Gly Gly Ser Leu Lys Leu Ser Cys
                165                 170                 175

Ala Ala Ser Gly Phe Thr Phe Ser Asn Tyr Ala Leu Ser Trp Val Arg
            180                 185                 190

Gln Thr Pro Glu Lys Arg Leu Glu Trp Val Ala Ser Ile Ser Ser Gly
        195                 200                 205

Gly Asn Thr Tyr Tyr Pro Asp Ser Val Lys Gly Arg Phe Thr Ile Ser
    210                 215                 220

Arg Asp Asn Ala Arg Asn Ile Leu Tyr Leu Gln Met Ser Ser Leu Arg
225                 230                 235                 240

Ser Glu Asp Thr Ala Met Phe Tyr Cys Thr Ser Arg Gly Asp Thr Thr
                245                 250                 255

Leu Ile Thr Thr Leu Phe Thr Tyr Trp Gly Gln Gly Thr Leu Val Thr
            260                 265                 270

Val Ser Ala Gly Ala Tyr Pro Tyr Asp Val Pro Asp Tyr Ala Ser
        275                 280                 285
```

```
<210> SEQ ID NO 86
<211> LENGTH: 308
<212> TYPE: PRT
<213> ORGANISM: Artificial Sequence
<220> FEATURE:
<223> OTHER INFORMATION: scFv Molecule Generated Antibody 5B3C11 (VL2)
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(275)
<223> OTHER INFORMATION: scFv Molecule Generated Antibody 5B3C11 (VL2)
<220> FEATURE:
<221> NAME/KEY: MISC_FEATURE
<222> LOCATION: (276)..(308)
<223> OTHER INFORMATION: Preferred C-terminal Peptide

<400> SEQUENCE: 86

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Glu Asn Val Leu
            20                  25                  30

Thr Gln Ser Pro Ala Ile Met Ser Ala Ser Pro Gly Glu Lys Val Thr
        35                  40                  45

Met Thr Cys Arg Ala Ser Ser Val Ser Ser Ser Tyr Leu His Trp
50                  55                  60

Tyr Gln Gln Lys Ser Gly Ala Ser Pro Lys Leu Trp Ile Tyr Ser Thr
65                  70                  75                  80

Ser Asn Leu Ala Ser Gly Val Pro Ala Arg Phe Ser Gly Ser Gly Ser
                85                  90                  95

Gly Thr Ser Tyr Ser Leu Thr Ile Ser Ser Val Glu Ala Glu Asp Ala
            100                 105                 110

Ala Thr Tyr Tyr Cys Gln Gln Tyr Ser Gly Tyr Pro Arg Thr Phe Gly
        115                 120                 125

Gly Gly Thr Lys Leu Glu Ile Lys Ser Ser Gly Gly Gly Gly Ser Gly
    130                 135                 140

Gly Gly Gly Gly Ser Ser Arg Ser Ser Glu Val Gln Leu Val Glu
145                 150                 155                 160

Ser Gly Gly Gly Leu Val Lys Pro Gly Gly Ser Leu Lys Leu Ser Cys
                165                 170                 175

Ala Ala Ser Gly Phe Thr Phe Ser Asn Tyr Ala Leu Ser Trp Val Arg
            180                 185                 190

Gln Thr Pro Glu Lys Arg Leu Glu Trp Val Ala Ser Ile Ser Ser Gly
        195                 200                 205

Gly Asn Thr Tyr Tyr Pro Asp Ser Val Lys Gly Arg Phe Thr Ile Ser
    210                 215                 220

Arg Asp Asn Ala Arg Asn Ile Leu Tyr Leu Gln Met Ser Ser Leu Arg
225                 230                 235                 240

Ser Glu Asp Thr Ala Met Phe Tyr Cys Thr Ser Arg Gly Asp Thr Thr
                245                 250                 255

Leu Ile Thr Thr Leu Phe Thr Tyr Trp Gly Gln Gly Thr Leu Val Thr
            260                 265                 270

Val Ser Ala Ala Lys Thr Thr Pro Pro Ser Val Thr Ser Gly Gln Ala
        275                 280                 285
```

Gly Gln His His His His His Gly Ala Tyr Pro Tyr Asp Val Pro
    290                 295                 300

Asp Tyr Ala Ser
305

<210> SEQ ID NO 87
<211> LENGTH: 251
<212> TYPE: PRT
<213> ORGANISM: Artificial Sequence
<220> FEATURE:
<223> OTHER INFORMATION: scFv Molecule Generated from Antibody 5G2A3

<400> SEQUENCE: 87

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Arg
            20                  25                  30

Asn Gly Asn Thr Tyr Leu Asp Trp Phe Leu Leu Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Ser Gly Gly Ser Arg
        115                 120                 125

Ser Ser Glu Val Lys Leu Val Glu Ser Gly Gly Gly Leu Val Lys Pro
130                 135                 140

Gly Gly Ser Leu Thr Leu Ser Cys Ala Ala Ser Gly Phe Thr Phe Ser
145                 150                 155                 160

Ser Tyr Ala Met Ser Trp Val Arg Gln Thr Pro Glu Lys Ser Leu Glu
                165                 170                 175

Trp Val Ala Ser Ile Ser Ser Gly Gly Asn Thr Phe Tyr Pro Asp Thr
            180                 185                 190

Val Lys Gly Arg Phe Thr Ile Ser Arg Asp Asn Ala Arg Asn Ile Leu
        195                 200                 205

Tyr Leu Gln Met Ser Gly Leu Arg Ser Glu Asp Thr Ala Ile Tyr Tyr
    210                 215                 220

Cys Ala Arg Arg Gly Asp Pro Asn Met Ile Thr Thr Leu Phe Gly Tyr
225                 230                 235                 240

Trp Gly Gln Gly Thr Leu Val Thr Ile Ser Ala
                245                 250

<210> SEQ ID NO 88
<211> LENGTH: 279
<212> TYPE: PRT
<213> ORGANISM: Artificial Sequence
<220> FEATURE:
<223> OTHER INFORMATION: scFv Molecule Generated from Antibody 5G2A3
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated from Antibody 5G2A3

-continued

<400> SEQUENCE: 88

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Leu His Arg Asn Gly Asn Thr
    50                  55                  60

Tyr Leu Asp Trp Phe Leu Leu Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
            100                 105                 110

Ala Glu Asp Leu Gly Val Tyr Tyr Cys Phe Gln Gly Ser His Val Pro
        115                 120                 125

Trp Thr Phe Gly Gly Gly Thr Lys Leu Glu Ile Lys Ser Ser Gly Gly
    130                 135                 140

Gly Gly Ser Gly Gly Gly Gly Ser Ser Arg Ser Ser Glu Val
145                 150                 155                 160

Lys Leu Val Glu Ser Gly Gly Gly Leu Val Lys Pro Gly Gly Ser Leu
                165                 170                 175

Thr Leu Ser Cys Ala Ala Ser Gly Phe Thr Phe Ser Ser Tyr Ala Met
            180                 185                 190

Ser Trp Val Arg Gln Thr Pro Glu Lys Ser Leu Glu Trp Val Ala Ser
        195                 200                 205

Ile Ser Ser Gly Gly Asn Thr Phe Tyr Pro Asp Thr Val Lys Gly Arg
    210                 215                 220

Phe Thr Ile Ser Arg Asp Asn Ala Arg Asn Ile Leu Tyr Leu Gln Met
225                 230                 235                 240

Ser Gly Leu Arg Ser Glu Asp Thr Ala Ile Tyr Tyr Cys Ala Arg Arg
                245                 250                 255

Gly Asp Pro Asn Met Ile Thr Thr Leu Phe Gly Tyr Trp Gly Gln Gly
            260                 265                 270

Thr Leu Val Thr Ile Ser Ala
        275

<210> SEQ ID NO 89
<211> LENGTH: 266
<212> TYPE: PRT
<213> ORGANISM: Artificial Sequence
<220> FEATURE:
<223> OTHER INFORMATION: scFv Molecule Generated from Antibody 5G2A3
<220> FEATURE:
<221> NAME/KEY: MISC_FEATURE
<222> LOCATION: (1)..(251)
<223> OTHER INFORMATION: scFv Molecule Generated from Antibody 5G2A3
<220> FEATURE:
<221> NAME/KEY: MISC_FEATURE
<222> LOCATION: (252)..(266)
<223> OTHER INFORMATION: C-terminal Peptide

<400> SEQUENCE: 89

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Arg
            20                  25                  30

```
Asn Gly Asn Thr Tyr Leu Asp Trp Phe Leu Leu Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
                100                 105                 110

Ser Ser Gly Gly Gly Gly Ser Gly Gly Gly Gly Gly Ser Ser Arg
            115                 120                 125

Ser Ser Glu Val Lys Leu Val Glu Ser Gly Gly Gly Leu Val Lys Pro
130                 135                 140

Gly Gly Ser Leu Thr Leu Ser Cys Ala Ala Ser Gly Phe Thr Phe Ser
145                 150                 155                 160

Ser Tyr Ala Met Ser Trp Val Arg Gln Thr Pro Glu Lys Ser Leu Glu
                165                 170                 175

Trp Val Ala Ser Ile Ser Ser Gly Gly Asn Thr Phe Tyr Pro Asp Thr
                180                 185                 190

Val Lys Gly Arg Phe Thr Ile Ser Arg Asp Asn Ala Arg Asn Ile Leu
                195                 200                 205

Tyr Leu Gln Met Ser Gly Leu Arg Ser Glu Asp Thr Ala Ile Tyr Tyr
210                 215                 220

Cys Ala Arg Arg Gly Asp Pro Asn Met Ile Thr Thr Leu Phe Gly Tyr
225                 230                 235                 240

Trp Gly Gln Gly Thr Leu Val Thr Ile Ser Ala Ala Lys Thr Thr Pro
                245                 250                 255

Pro Ser Val Thr Ser Gly Gln Ala Gly Gln
                260                 265

<210> SEQ ID NO 90
<211> LENGTH: 257
<212> TYPE: PRT
<213> ORGANISM: Artificial Sequence
<220> FEATURE:
<223> OTHER INFORMATION: scFv Molecule Generated from Antibody 5G2A3
<220> FEATURE:
<221> NAME/KEY: MISC_FEATURE
<222> LOCATION: (1)..(251)
<223> OTHER INFORMATION: scFv Molecule Generated from Antibody 5G2A3
<220> FEATURE:
<221> NAME/KEY: MISC_FEATURE
<222> LOCATION: (252)..(257)
<223> OTHER INFORMATION: His Tag Peptide

<400> SEQUENCE: 90

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Leu His Arg
             20                  25                  30

Asn Gly Asn Thr Tyr Leu Asp Trp Phe Leu Leu Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Ser Ser Arg
        115                 120                 125

Ser Ser Glu Val Lys Leu Val Glu Ser Gly Gly Leu Val Lys Pro
    130                 135                 140

Gly Gly Ser Leu Thr Leu Ser Cys Ala Ala Ser Gly Phe Thr Phe Ser
145                 150                 155                 160

Ser Tyr Ala Met Ser Trp Val Arg Gln Thr Pro Glu Lys Ser Leu Glu
                165                 170                 175

Trp Val Ala Ser Ile Ser Ser Gly Gly Asn Thr Phe Tyr Pro Asp Thr
            180                 185                 190

Val Lys Gly Arg Phe Thr Ile Ser Arg Asp Asn Ala Arg Asn Ile Leu
        195                 200                 205

Tyr Leu Gln Met Ser Gly Leu Arg Ser Glu Asp Thr Ala Ile Tyr Tyr
    210                 215                 220

Cys Ala Arg Arg Gly Asp Pro Asn Met Ile Thr Thr Leu Phe Gly Tyr
225                 230                 235                 240

Trp Gly Gln Gly Thr Leu Val Thr Ile Ser Ala His His His His
                245                 250                 255

His
```

<210> SEQ ID NO 91
<211> LENGTH: 263
<212> TYPE: PRT
<213> ORGANISM: Artificial Sequence
<220> FEATURE:
<223> OTHER INFORMATION: scFv Molecule Generated from Antibody 5G2A3
<220> FEATURE:
<221> NAME/KEY: MISC_FEATURE
<222> LOCATION: (1)..(251)
<223> OTHER INFORMATION: scFv Molecule Generated from Antibody 5G2A3
<220> FEATURE:
<221> NAME/KEY: MISC_FEATURE
<222> LOCATION: (252)..(263)
<223> OTHER INFORMATION: HA Tag Peptide

<400> SEQUENCE: 91

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Arg
            20                  25                  30

Asn Gly Asn Thr Tyr Leu Asp Trp Phe Leu Leu Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Ser Ser Arg
        115                 120                 125

Ser Ser Glu Val Lys Leu Val Glu Ser Gly Gly Leu Val Lys Pro
    130                 135                 140
```

Gly Gly Ser Leu Thr Leu Ser Cys Ala Ala Ser Gly Phe Thr Phe Ser
145                 150                 155                 160

Ser Tyr Ala Met Ser Trp Val Arg Gln Thr Pro Glu Lys Ser Leu Glu
            165                 170                 175

Trp Val Ala Ser Ile Ser Ser Gly Gly Asn Thr Phe Tyr Pro Asp Thr
                180                 185                 190

Val Lys Gly Arg Phe Thr Ile Ser Arg Asp Asn Ala Arg Asn Ile Leu
            195                 200                 205

Tyr Leu Gln Met Ser Gly Leu Arg Ser Glu Asp Thr Ala Ile Tyr Tyr
        210                 215                 220

Cys Ala Arg Arg Gly Asp Pro Asn Met Ile Thr Thr Leu Phe Gly Tyr
225                 230                 235                 240

Trp Gly Gln Gly Thr Leu Val Thr Ile Ser Ala Gly Ala Tyr Pro Tyr
                245                 250                 255

Asp Val Pro Asp Tyr Ala Ser
            260

<210> SEQ ID NO 92
<211> LENGTH: 284
<212> TYPE: PRT
<213> ORGANISM: Artificial Sequence
<220> FEATURE:
<223> OTHER INFORMATION: scFv Molecule Generated from Antibody 5G2A3
<220> FEATURE:
<221> NAME/KEY: MISC_FEATURE
<222> LOCATION: (1)..(251)
<223> OTHER INFORMATION: scFv Molecule Generated from Antibody 5G2A3
<220> FEATURE:
<221> NAME/KEY: MISC_FEATURE
<222> LOCATION: (252)..(284)
<223> OTHER INFORMATION: Preferred C-terminal Peptide

<400> SEQUENCE: 92

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Arg
            20                  25                  30

Asn Gly Asn Thr Tyr Leu Asp Trp Phe Leu Leu Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Ser Ser Gly Gly Gly Gly Ser Gly Gly Gly Gly Gly Ser Ser Arg
        115                 120                 125

Ser Ser Glu Val Lys Leu Val Glu Ser Gly Gly Gly Leu Val Lys Pro
130                 135                 140

Gly Gly Ser Leu Thr Leu Ser Cys Ala Ala Ser Gly Phe Thr Phe Ser
145                 150                 155                 160

Ser Tyr Ala Met Ser Trp Val Arg Gln Thr Pro Glu Lys Ser Leu Glu
            165                 170                 175

Trp Val Ala Ser Ile Ser Ser Gly Gly Asn Thr Phe Tyr Pro Asp Thr
                180                 185                 190

```
Val Lys Gly Arg Phe Thr Ile Ser Arg Asp Asn Ala Arg Asn Ile Leu
            195                 200                 205

Tyr Leu Gln Met Ser Gly Leu Arg Ser Glu Asp Thr Ala Ile Tyr Tyr
210                 215                 220

Cys Ala Arg Arg Gly Asp Pro Asn Met Ile Thr Thr Leu Phe Gly Tyr
225                 230                 235                 240

Trp Gly Gln Gly Thr Leu Val Thr Ile Ser Ala Ala Lys Thr Thr Pro
                245                 250                 255

Pro Ser Val Thr Ser Gly Gln Ala Gly Gln His His His His His His
            260                 265                 270

Gly Ala Tyr Pro Tyr Asp Val Pro Asp Tyr Ala Ser
            275                 280
```

<210> SEQ ID NO 93
<211> LENGTH: 294
<212> TYPE: PRT
<213> ORGANISM: Artificial Sequence
<220> FEATURE:
<223> OTHER INFORMATION: scFv Molecule Generated from Antibody 5G2A3
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated from Antibody 5G2A3
<220> FEATURE:
<221> NAME/KEY: MISC_FEATURE
<222> LOCATION: (280)..(294)
<223> OTHER INFORMATION: C-terminal Peptide

<400> SEQUENCE: 93

```
Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Leu His Arg Asn Gly Asn Thr
50                  55                  60

Tyr Leu Asp Trp Phe Leu Leu Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
            100                 105                 110

Ala Glu Asp Leu Gly Val Tyr Tyr Cys Phe Gln Gly Ser His Val Pro
        115                 120                 125

Trp Thr Phe Gly Gly Gly Thr Lys Leu Glu Ile Lys Ser Ser Gly Gly
130                 135                 140

Gly Gly Ser Gly Gly Gly Gly Gly Ser Ser Arg Ser Ser Glu Val
145                 150                 155                 160

Lys Leu Val Glu Ser Gly Gly Leu Val Lys Pro Gly Gly Ser Leu
                165                 170                 175

Thr Leu Ser Cys Ala Ala Ser Gly Phe Thr Phe Ser Ser Tyr Ala Met
            180                 185                 190

Ser Trp Val Arg Gln Thr Pro Glu Lys Ser Leu Glu Trp Val Ala Ser
        195                 200                 205
```

Ile Ser Ser Gly Gly Asn Thr Phe Tyr Pro Asp Thr Val Lys Gly Arg
    210                 215                 220

Phe Thr Ile Ser Arg Asp Asn Ala Arg Asn Ile Leu Tyr Leu Gln Met
225                 230                 235                 240

Ser Gly Leu Arg Ser Glu Asp Thr Ala Ile Tyr Tyr Cys Ala Arg Arg
                245                 250                 255

Gly Asp Pro Asn Met Ile Thr Thr Leu Phe Gly Tyr Trp Gly Gln Gly
            260                 265                 270

Thr Leu Val Thr Ile Ser Ala Ala Lys Thr Thr Pro Pro Ser Val Thr
        275                 280                 285

Ser Gly Gln Ala Gly Gln
    290

<210> SEQ ID NO 94
<211> LENGTH: 285
<212> TYPE: PRT
<213> ORGANISM: Artificial Sequence
<220> FEATURE:
<223> OTHER INFORMATION: scFv Molecule Generated from Antibody 5G2A3
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated from Antibody 5G2A3
<220> FEATURE:
<221> NAME/KEY: MISC_FEATURE
<222> LOCATION: (280)..(285)
<223> OTHER INFORMATION: His Tag Peptide

<400> SEQUENCE: 94

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
        35                  40                  45

Ile Ser Cys Arg Ser Ser Gln Ser Ile Leu His Arg Asn Gly Asn Thr
    50                  55                  60

Tyr Leu Asp Trp Phe Leu Leu Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
            100                 105                 110

Ala Glu Asp Leu Gly Val Tyr Tyr Cys Phe Gln Gly Ser His Val Pro
        115                 120                 125

Trp Thr Phe Gly Gly Gly Thr Lys Leu Glu Ile Lys Ser Ser Gly Gly
    130                 135                 140

Gly Gly Ser Gly Gly Gly Gly Gly Ser Ser Arg Ser Ser Glu Val
145                 150                 155                 160

Lys Leu Val Glu Ser Gly Gly Gly Leu Val Lys Pro Gly Gly Ser Leu
                165                 170                 175

Thr Leu Ser Cys Ala Ala Ser Gly Phe Thr Phe Ser Ser Tyr Ala Met
            180                 185                 190

Ser Trp Val Arg Gln Thr Pro Glu Lys Ser Leu Glu Trp Val Ala Ser
        195                 200                 205

```
Ile Ser Ser Gly Gly Asn Thr Phe Tyr Pro Asp Thr Val Lys Gly Arg
    210                 215                 220

Phe Thr Ile Ser Arg Asp Asn Ala Arg Asn Ile Leu Tyr Leu Gln Met
225                 230                 235                 240

Ser Gly Leu Arg Ser Glu Asp Thr Ala Ile Tyr Tyr Cys Ala Arg Arg
                245                 250                 255

Gly Asp Pro Asn Met Ile Thr Thr Leu Phe Gly Tyr Trp Gly Gln Gly
                260                 265                 270

Thr Leu Val Thr Ile Ser Ala His His His His His
            275                 280                 285

<210> SEQ ID NO 95
<211> LENGTH: 291
<212> TYPE: PRT
<213> ORGANISM: Artificial Sequence
<220> FEATURE:
<223> OTHER INFORMATION: scFv Molecule Generated from Antibody 5G2A3
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated from Antibody 5G2A3
<220> FEATURE:
<221> NAME/KEY: MISC_FEATURE
<222> LOCATION: (280)..(291)
<223> OTHER INFORMATION: HA Tag Petide

<400> SEQUENCE: 95

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
                20                  25                  30

Thr Gln Thr Pro Leu Ser Leu Pro Val Ser Leu Gly Asp Gln Ala Ser
            35                  40                  45

Ile Ser Cys Arg Ser Ser Gln Ser Ile Leu His Arg Asn Gly Asn Thr
    50                  55                  60

Tyr Leu Asp Trp Phe Leu Leu Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
                100                 105                 110

Ala Glu Asp Leu Gly Val Tyr Tyr Cys Phe Gln Gly Ser His Val Pro
            115                 120                 125

Trp Thr Phe Gly Gly Gly Thr Lys Leu Glu Ile Lys Ser Ser Gly Gly
        130                 135                 140

Gly Gly Ser Gly Gly Gly Gly Gly Ser Ser Arg Ser Ser Glu Val
145                 150                 155                 160

Lys Leu Val Glu Ser Gly Gly Gly Leu Val Lys Pro Gly Gly Ser Leu
                165                 170                 175

Thr Leu Ser Cys Ala Ala Ser Gly Phe Thr Phe Ser Ser Tyr Ala Met
            180                 185                 190

Ser Trp Val Arg Gln Thr Pro Glu Lys Ser Leu Glu Trp Val Ala Ser
        195                 200                 205

Ile Ser Ser Gly Gly Asn Thr Phe Tyr Pro Asp Thr Val Lys Gly Arg
    210                 215                 220
```

```
Phe Thr Ile Ser Arg Asp Asn Ala Arg Asn Ile Leu Tyr Leu Gln Met
225                 230                 235                 240

Ser Gly Leu Arg Ser Glu Asp Thr Ala Ile Tyr Tyr Cys Ala Arg Arg
            245                 250                 255

Gly Asp Pro Asn Met Ile Thr Thr Leu Phe Gly Tyr Trp Gly Gln Gly
            260                 265                 270

Thr Leu Val Thr Ile Ser Ala Gly Ala Tyr Pro Tyr Asp Val Pro Asp
            275                 280                 285

Tyr Ala Ser
        290

<210> SEQ ID NO 96
<211> LENGTH: 312
<212> TYPE: PRT
<213> ORGANISM: Artificial Sequence
<220> FEATURE:
<223> OTHER INFORMATION: scFv Molecule Generated from Antibody 5G2A3
<220> FEATURE:
<221> NAME/KEY: MISC_FEATURE
<222> LOCATION: (1)..(28)
<223> OTHER INFORMATION: N-terminal Leader Peptide
<220> FEATURE:
<221> NAME/KEY: MISC_FEATURE
<222> LOCATION: (29)..(279)
<223> OTHER INFORMATION: scFv Molecule Generated from Antibody 5G2A3
<220> FEATURE:
<221> NAME/KEY: MISC_FEATURE
<222> LOCATION: (280)..(312)
<223> OTHER INFORMATION: Preferred C-terminal Peptide

<400> SEQUENCE: 96

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Asp Val Leu Met
            20                  25                  30

Thr Gln Thr Pro Leu Ser Leu Pro Val Ser Leu Gly Asp Gln Ala Ser
            35                  40                  45

Ile Ser Cys Arg Ser Ser Gln Ser Ile Leu His Arg Asn Gly Asn Thr
        50                  55                  60

Tyr Leu Asp Trp Phe Leu Leu Lys Pro Gly Gln Ser Pro Lys Leu Leu
65                  70                  75                  80

Ile Tyr Lys Val Ser Asn Arg Phe Ser Gly Val Pro Asp Arg Phe Ser
                85                  90                  95

Gly Ser Gly Ser Gly Thr Asp Phe Thr Leu Lys Ile Ser Arg Val Glu
            100                 105                 110

Ala Glu Asp Leu Gly Val Tyr Tyr Cys Phe Gln Gly Ser His Val Pro
        115                 120                 125

Trp Thr Phe Gly Gly Gly Thr Lys Leu Glu Ile Lys Ser Ser Gly Gly
130                 135                 140

Gly Gly Ser Gly Gly Gly Gly Gly Ser Ser Arg Ser Ser Glu Val
145                 150                 155                 160

Lys Leu Val Glu Ser Gly Gly Gly Leu Val Lys Pro Gly Gly Ser Leu
                165                 170                 175

Thr Leu Ser Cys Ala Ala Ser Gly Phe Thr Phe Ser Ser Tyr Ala Met
            180                 185                 190

Ser Trp Val Arg Gln Thr Pro Glu Lys Ser Leu Glu Trp Val Ala Ser
        195                 200                 205

Ile Ser Ser Gly Gly Asn Thr Phe Tyr Pro Asp Thr Val Lys Gly Arg
    210                 215                 220
```

```
Phe Thr Ile Ser Arg Asp Asn Ala Arg Asn Ile Leu Tyr Leu Gln Met
225                 230                 235                 240

Ser Gly Leu Arg Ser Glu Asp Thr Ala Ile Tyr Tyr Cys Ala Arg Arg
                245                 250                 255

Gly Asp Pro Asn Met Ile Thr Thr Leu Phe Gly Tyr Trp Gly Gln Gly
            260                 265                 270

Thr Leu Val Thr Ile Ser Ala Ala Lys Thr Thr Pro Pro Ser Val Thr
            275                 280                 285

Ser Gly Gln Ala Gly Gln His His His His His Gly Ala Tyr Pro
    290                 295                 300

Tyr Asp Val Pro Asp Tyr Ala Ser
305                 310

<210> SEQ ID NO 97
<211> LENGTH: 16
<212> TYPE: PRT
<213> ORGANISM: Artificial Sequence
<220> FEATURE:
<223> OTHER INFORMATION: Light Chain CDR1 Consensus Sequence
<220> FEATURE:
<221> NAME/KEY: MISC_FEATURE
<222> LOCATION: (3)..(3)
<223> OTHER INFORMATION: X1 (aa3) is N or S
<220> FEATURE:
<221> NAME/KEY: MISC_FEATURE
<222> LOCATION: (8)..(8)
<223> OTHER INFORMATION: X2 (aa8) is N or H
<220> FEATURE:
<221> NAME/KEY: MISC_FEATURE
<222> LOCATION: (9)..(9)
<223> OTHER INFORMATION: X3 (aa9) is A, R, N, Q, E, H, K, M, S or T
<220> FEATURE:
<221> NAME/KEY: MISC_FEATURE
<222> LOCATION: (16)..(16)
<223> OTHER INFORMATION: X4 (aa16) is E or D

<400> SEQUENCE: 97

Arg Ser Xaa Gln Ser Ile Leu Xaa Xaa Asn Gly Asn Thr Tyr Leu Xaa
1               5                   10                  15

<210> SEQ ID NO 98
<211> LENGTH: 7
<212> TYPE: PRT
<213> ORGANISM: Artificial Sequence
<220> FEATURE:
<223> OTHER INFORMATION: Light Chain CDR2 Consensus Sequence

<400> SEQUENCE: 98

Lys Val Ser Asn Arg Phe Ser
1               5

<210> SEQ ID NO 99
<211> LENGTH: 9
<212> TYPE: PRT
<213> ORGANISM: Artificial Sequence
<220> FEATURE:
<223> OTHER INFORMATION: Light Chain CDR3 Consensus Sequence
<220> FEATURE:
<221> NAME/KEY: MISC_FEATURE
<222> LOCATION: (6)..(6)
<223> OTHER INFORMATION: X1 (aa6) is V or I

<400> SEQUENCE: 99

Phe Gln Gly Ser His Xaa Pro Trp Thr
1               5
```

-continued

```
<210> SEQ ID NO 100
<211> LENGTH: 5
<212> TYPE: PRT
<213> ORGANISM: Artificial Sequence
<220> FEATURE:
<223> OTHER INFORMATION: Heavy Chain CDR1 Consensus Sequence
<220> FEATURE:
<221> NAME/KEY: MISC_FEATURE
<222> LOCATION: (1)..(1)
<223> OTHER INFORMATION: X1 (aa1) is N, D, Q, E or S
<220> FEATURE:
<221> NAME/KEY: MISC_FEATURE
<222> LOCATION: (2)..(2)
<223> OTHER INFORMATION: X2 (aa2) is A, R, N, D, C, Q, E, G, H, I, L, K,
      M, F, S, T, Y or V
<220> FEATURE:
<221> NAME/KEY: MISC_FEATURE
<222> LOCATION: (4)..(4)
<223> OTHER INFORMATION: X3 (aa4) is L or M

<400> SEQUENCE: 100

Xaa Xaa Ala Xaa Ser
1               5

<210> SEQ ID NO 101
<211> LENGTH: 16
<212> TYPE: PRT
<213> ORGANISM: Artificial Sequence
<220> FEATURE:
<223> OTHER INFORMATION: Heavy Chain CDR2 Consensus Sequence
<220> FEATURE:
<221> NAME/KEY: MISC_FEATURE
<222> LOCATION: (4)..(4)
<223> OTHER INFORMATION: X1 (aa1) is S or T
<220> FEATURE:
<221> NAME/KEY: MISC_FEATURE
<222> LOCATION: (7)..(7)
<223> OTHER INFORMATION: X2 (aa7) is A, R, N, D, Q, E, G, H, K, M, P, S,
      T or Y
<220> FEATURE:
<221> NAME/KEY: MISC_FEATURE
<222> LOCATION: (9)..(9)
<223> OTHER INFORMATION: X3 (aa9) is F or Y
<220> FEATURE:
<221> NAME/KEY: MISC_FEATURE
<222> LOCATION: (10)..(10)
<223> OTHER INFORMATION: X4 (aa10) is A, R, N, C, Q, E, H, I, L, K, M,
      F, S, T, Y or V
<220> FEATURE:
<221> NAME/KEY: MISC_FEATURE
<222> LOCATION: (13)..(13)
<223> OTHER INFORMATION: X5 (aa13) is A, R, N, D, Q, E, G, H, I, L, K,
      P, S or T
<220> FEATURE:
<221> NAME/KEY: MISC_FEATURE
<222> LOCATION: (14)..(14)
<223> OTHER INFORMATION: X6 (aa14) is I, L, M or V

<400> SEQUENCE: 101

Ser Ile Ser Xaa Gly Gly Xaa Thr Xaa Xaa Pro Asp Xaa Xaa Lys Gly
1               5                   10                  15

<210> SEQ ID NO 102
<211> LENGTH: 13
<212> TYPE: PRT
<213> ORGANISM: Artificial Sequence
<220> FEATURE:
<223> OTHER INFORMATION: Heavy Chain CDR3 Consensus Sequence
<220> FEATURE:
<221> NAME/KEY: MISC_FEATURE
<222> LOCATION: (3)..(3)
<223> OTHER INFORMATION: X1 (aa3) is absent or D
```

```
<220> FEATURE:
<221> NAME/KEY: MISC_FEATURE
<222> LOCATION: (4)..(4)
<223> OTHER INFORMATION: X2 (aa4) is absent or A, D, Q, E, K, P, S or T
<220> FEATURE:
<221> NAME/KEY: MISC_FEATURE
<222> LOCATION: (5)..(5)
<223> OTHER INFORMATION: X3 (aa5) is A, R, N, D, C, Q, E, G, H, I, L, K,
      M, F, P, S, T, Y or V
<220> FEATURE:
<221> NAME/KEY: MISC_FEATURE
<222> LOCATION: (6)..(6)
<223> OTHER INFORMATION: X4 (aa6) is A, R, C, I, L, K, M, F, S, T, Y or
      V
<220> FEATURE:
<221> NAME/KEY: MISC_FEATURE
<222> LOCATION: (7)..(7)
<223> OTHER INFORMATION: X5 (aa7) is A, C, I, L, M, F, S, T, Y or V
<220> FEATURE:
<221> NAME/KEY: MISC_FEATURE
<222> LOCATION: (8)..(8)
<223> OTHER INFORMATION: X6 (aa 8) is A, R, N, D, Q, E, G, H, I, L, K,
      P, S or T
<220> FEATURE:
<221> NAME/KEY: MISC_FEATURE
<222> LOCATION: (9)..(9)
<223> OTHER INFORMATION: X7 (aa9) is N, S or T
<220> FEATURE:
<221> NAME/KEY: MISC_FEATURE
<222> LOCATION: (12)..(12)
<223> OTHER INFORMATION: X8 (aa12) is A ,R ,N, D, C, Q, E, G, H, K, M,
      F, P, S, T, W, Y or V

<400> SEQUENCE: 102

Arg Gly Xaa Xaa Xaa Xaa Xaa Xaa Xaa Leu Phe Xaa Tyr
1               5                   10

<210> SEQ ID NO 103
<211> LENGTH: 467
<212> TYPE: PRT
<213> ORGANISM: Homo sapiens
<220> FEATURE:
<221> NAME/KEY: MISC_FEATURE
<222> LOCATION: (1)..(467)
<223> OTHER INFORMATION: Isoform 1 of PS1

<400> SEQUENCE: 103

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160
```

```
Val Ile His Ala Trp Leu Ile Ile Ser Ser Leu Leu Leu Phe Phe
                165                 170                 175

Phe Ser Phe Ile Tyr Leu Gly Glu Val Phe Lys Thr Tyr Asn Val Ala
        180                 185                 190

Val Asp Tyr Ile Thr Val Ala Leu Leu Ile Trp Asn Phe Gly Val Val
            195                 200                 205

Gly Met Ile Ser Ile His Trp Lys Gly Pro Leu Arg Leu Gln Gln Ala
        210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
        290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
        370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
        450                 455                 460

Phe Tyr Ile
465

<210> SEQ ID NO 104
<211> LENGTH: 448
<212> TYPE: PRT
<213> ORGANISM: Homo sapiens
<220> FEATURE:
<221> NAME/KEY: MISC_FEATURE
<222> LOCATION: (1)..(448)
<223> OTHER INFORMATION: Isoform 1 of PS2

<400> SEQUENCE: 104

Met Leu Thr Phe Met Ala Ser Asp Ser Glu Glu Glu Val Cys Asp Glu
1               5                   10                  15

Arg Thr Ser Leu Met Ser Ala Glu Ser Pro Thr Pro Arg Ser Cys Gln
            20                  25                  30
```

```
Glu Gly Arg Gln Gly Pro Glu Asp Gly Glu Asn Thr Ala Gln Trp Arg
            35                  40                  45

Ser Gln Glu Asn Glu Gly Asp Gly Glu Glu Asp Pro Asp Arg Tyr Val
 50                  55                  60

Cys Ser Gly Val Pro Gly Arg Pro Pro Gly Leu Glu Glu Glu Leu Thr
 65                  70                  75                  80

Leu Lys Tyr Gly Ala Lys His Val Ile Met Leu Phe Val Pro Val Thr
                 85                  90                  95

Leu Cys Met Ile Val Val Val Ala Thr Ile Lys Ser Val Arg Phe Tyr
                100                 105                 110

Thr Glu Lys Asn Gly Gln Leu Ile Tyr Thr Pro Phe Thr Glu Asp Thr
                115                 120                 125

Pro Ser Val Gly Gln Arg Leu Leu Asn Ser Val Leu Asn Thr Leu Ile
            130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
                180                 185                 190

Lys Thr Tyr Asn Val Ala Met Asp Tyr Pro Thr Leu Leu Leu Thr Val
            195                 200                 205

Trp Asn Phe Gly Ala Val Gly Met Val Cys Ile His Trp Lys Gly Pro
            210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
                260                 265                 270

Pro Leu Arg Met Leu Val Glu Thr Ala Gln Glu Arg Asn Glu Pro Ile
            275                 280                 285

Phe Pro Ala Leu Ile Tyr Ser Ser Ala Met Val Trp Thr Val Gly Met
            290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
            355                 360                 365

Phe Tyr Ser Val Leu Val Gly Lys Ala Ala Thr Gly Ser Gly Asp
            370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
            435                 440                 445
```

```
<210> SEQ ID NO 105
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Amino Acid Residues 407-423 of Tau Protein (SEQ
      ID NO:1)

<400> SEQUENCE: 105

His Leu Ser Asn Val Ser Ser Thr Gly Ser Ile Asp Met Val Asp Ser
1               5                   10                  15

Pro
```

ANTIBODY-BASED MOLECULES SPECIFIC FOR THE TRUNCATED ASP421 EPITOPE OF TAU AND THEIR USES IN THE DIAGNOSIS AND TREATMENT OF TAUOPATHY

CROSS-REFERENCE TO RELATED APPLICATIONS

This application is a § 371 Application of PCT/US2016/046513 (filed Aug. 11, 2016, now expired), which application claims priority to U.S. Provisional Patent Applns. Ser. No. 62/204,699 (filed on Aug. 13, 2015; now expired), and 62/211,123 (filed on Aug. 28, 2015; now expired), each of which application is hereby incorporated by reference herein in its entirety

STATEMENT REGARDING FEDERALLY SPONSORED RESEARCH OR DEVELOPMENT

This invention was made with government support under Grant Nos. NS077239, AG032611 and AG020197 awarded by the National Institutes of Health (NIH). The government has certain rights in the invention.

REFERENCE TO SEQUENCE LISTING

This application includes one or more Sequence Listings pursuant to 37 C.F.R. 1.821 et seq., which are disclosed in computer-readable media (file name: 1400-0008PCT_ST25.txt, created on Aug. 11, 2016, and having a size of 170,987 bytes), which file is herein incorporated by reference in its entirety.

FIELD OF THE INVENTION

The present invention relates to antibody-based molecules (including single domain antibody fragment, scFv molecules, antibodies, antibody fragments, diabodies, and the epitope-binding domains thereof) that are capable of immunospecifically and selectively binding to the truncated Asp421 epitope of Tau. Such antibody-based molecules are useful to detect pathological Tau protein conformer if present in a biological sample, especially in conjunction with the diagnosis and/or treatment of Alzheimer's disease or other tauopathy, and thus provide a diagnostic for Alzheimer's disease and other Tau pathologies. The antibody-based molecules of the present invention have particular utility as diagnostic markers for, Alzheimer's disease and related tauopathies and as pharmaceutical compositions for the treatment of such conditions.

BACKGROUND OF THE INVENTION

Alzheimer's disease is the most common form of dementia affecting more than 20 million people worldwide. Diagnosis of the disease, in particular at an early point, is troublesome and difficult and there exists a need for accurate diagnosis of tauopathies such as Alzheimer's disease. Antibody detection of abnormal Tau in cerebrospinal fluid has shown some promise (Blennow, K. et al. "*Cerebrospinal Fluid And Plasma Biomarkers In Alzheimer Disease*," Nat. Rev. Neurol. 6, 131-144 (2010) and Weiner et al. "*The Alzheimer's Disease Neuroimaging Initiative: A Review Of Papers Published Since Its Inception*," Alzheimers. Dement. 9, e111-e194 (2013)).

Over the years, antibody detection of phospho-Tau protein in cerebrospinal fluid has shown some utility for diagnosis of Alzheimer's disease (Blennow, K. et al. "*Cerebrospinal Fluid And Plasma Biomarkers In Alzheimer Disease*," Nat. Rev. Neurol. 6, 131-144 (2010); Lewis, J. et al. "*Neurofibrillary Tangles, Amyotrophy And Progressive Motor Disturbance In Mice Expressing Mutant (P301L) Tau Protein*," Nat. Genet. 25, 402-405; Weiner, M. W. et al. (2013) "*The Alzheimer's Disease Neuroimaging Initiative: A Review Of Papers Published Since Its Inception*," Alzheimers. Dement. 9: e111-e194), suggesting that further development in this arena is warranted (see, Congdon, E. E. (2014) "*Harnessing The Immune System For Treatment And Detection Of Tau Pathology*," J. Alzheimers. Dis. 40:S113-S121). However, CSF Tau levels in other tauopathies are usually not altered compared to controls (Theunis, C. et al. "*Efficacy And Safety Of A Liposome-Based Vaccine Against Protein Tau, Assessed In Tau.P301L Mice That Model Tauopathy*," PLoS. One. 8, e72301 (2013); Hales, C. M. et al. (2013) "*From Frontotemporal Lobar Degeneration Pathology To Frontotemporal Lobar Degeneration Biomarkers*," Int. Rev. Psychiatry 25:210-220), and imaging dyes may not detect pathological Tau in all tauopathies (Fodero-Tavoletti, M. T. et al. (2014) "*Assessing THK523 Selectivity For Tau Deposits In Alzheimer's Disease And Non Alzheimer's Disease Tauopathies*," Alzheimers. Res. Ther. 6:11). Imaging these Tau lesions in concert with amyloid-β (Aβ) is more likely to lead to accurate diagnosis as the regional pattern of Tau aggregates differs between the different tauopathies. Furthermore, all of them except Alzheimer's disease are in part defined by lack of Aβ deposition. In vivo imaging of Aβ plaques using compounds that bind well to β-sheets is already in clinical use (Mason, N. S. et al. (2013) "*Positron Emission Tomography Radioligands For In Vivo Imaging Of ABeta Plaques*," J. Labelled Comp. Radiopharm. 56:89-95). Several such dye-based Tau-binding ligands have been identified recently in preclinical studies and some of those are being evaluated (Fodero-Tavoletti, M. T. et al. (2014) "*Assessing THK523 Selectivity For Tau Deposits In Alzheimer's Disease And Non-Alzheimer's Disease Tauopathies*," Alzheimers. Res. Ther. 6:11; Fodero-Tavoletti, M. T. et al. (2011) "18*F-THK523: A Novel In Vivo Tau Imaging Ligand For Alzheimer's Disease*," Brain 134:1089-1100; Zhang, W. et al. (2012) "*A Highly Selective And Specific PET Tracer For Imaging Of Tau Pathologies*," J. Alzheimers. Dis. 31:601-612; Chien, D. T. et al. (2013) "*Early Clinical PET Imaging Results With The Novel PHF-Tau Radioligand [F-18]-T807*," J. Alzheimers. Dis. 34:457-468; Maruyama, M. H. et al. (2013) "*Imaging Of Tau Pathology In A Tauopathy Mouse Model And In Alzheimer Patients Compared To Normal Controls*," Neuron 79:1094-1108; Okamura, N. et al. (2005) "*Quinoline And Benzimidazole Derivatives: Candidate Probes For In Vivo Imaging Of Tau Pathology In Alzheimer's Disease*," J. Neurosci. 25:10857-10862; Harada, R., et al. (2013) "*Comparison Of The Binding Characteristics Of [18F]THK-523 And Other Amyloid Imaging Tracers To Alzheimer's Disease Pathology*," Eur. J. Nucl. Med. Mol. Imaging 40:125-132; Ono, M. et al. (2011) "*Rhodanine And Thiohydantoin Derivatives For Detecting Tau Pathology In Alzheimer's Brains*," ACS Chem. Neurosci. 2:269-275; Xia, C. F. et al. (2013) "[(18)F]T807, A Novel Tau Positron Emission Tomography Imaging Agent For Alzheimer's Disease," Alzheimers. Dement. 9:666-676; Chien, D. T. (2014) "*Early Clinical PET Imaging Results With The Novel PHF-Tau Radioligand [F18]-T808*," J. Alzheimers. Dis. 38:171-184; Villemagne, V. L. et al. (2014) "*In Vivo Evaluation Of A Novel Tau Imaging Tracer For Alzheimer's Disease*," Eur. J. Nucl. Med. Mol. Imaging 41:816-826; Okamura, N. et al.

(2014) "Non-Invasive Assessment Of Alzheimer's Disease Neurofibrillary Pathology Using 18F-THK5105 PET," Brain 137:1762-1771). The hope and promise for Tau based ligands is that they will be better than Aβ ligands to monitor the status and progression of neurodegeneration. Antibody-based probes are likely to provide greater specificity for detecting Tau lesions. In particular, smaller antibody fragments that bind to Tau are attractive as ligands for in vivo imaging to detect Tau lesions in patients with Alzheimer's disease or other tauopathies.

Within the cancer field, therapeutic antibodies have routinely been co-developed as imaging agents, and several such antibodies and Fab molecules are FDA approved for tumor imaging (Kaur, S. et al. "Recent Trends In Antibody-Based Oncologic Imaging," Cancer Lett. 315, 97-111 (2012)).

The present inventors have found antibody-derived molecules that provide excellent specificity for detecting Tau lesions, and in particular smaller single-chain variable antibody fragments (scFv molecules) which are attractive for in vivo imaging of Tau aggregates. It is envisaged that these antibody-derived imaging ligands can be useful in monitoring disease progression of Tau pathology, the efficacy of Tau-targeting therapies, and to identify Aβ negative tauopathies. Additionally, such antibody-derived molecules have utility as therapeutics in the prevention, treatment and management of Alzheimer's disease and other tauopathies.

SUMMARY OF THE INVENTION

The present invention relates to antibody-based molecules (including single domain antibody fragment, scFv molecules, antibodies, antibody fragments, diabodies, and the epitope-binding domains thereof) that are capable of immunospecifically and selectively binding to the truncated Asp421 epitope of Tau. Such antibody-based molecules are useful to detect pathological Tau protein conformer if present in a biological sample, especially in conjunction with the diagnosis and/or treatment of Alzheimer's disease or other tauopathy, and thus provide a diagnostic for Alzheimer's disease and other Tau pathologies. The antibody-based molecules of the present invention have particular utility as diagnostic markers for, Alzheimer's disease and related tauopathies and as pharmaceutical compositions for the treatment of such conditions.

In detail, the invention concerns a binding molecule that is capable of immunospecifically binding to the Truncated Asp421 Epitope of Tau, wherein the epitope is present on a peptide having the sequence of Tau 407-421 (SEQ ID NO:7): HLSNVSSTGSIDMVD.

The invention particularly concerns the embodiment of such binding molecule wherein the molecule competes for binding with an antibody selected from the group consisting of: Antibody 1G10D2, Antibody 1G11A10, Antibody 5B3C11 or Antibody 5G2A3/5G2G6.

The invention particularly concerns the embodiment of such binding molecule wherein the molecule comprises:
(a) (1) a Variable Light Chain CDR1, CDR2, CDR3 respectively having the amino acid sequence of SEQ ID NOs:9, 10 and 11; and
   (2) a Variable Heavy Chain CDR1, CDR2, CDR3 respectively having the amino acid sequence of SEQ ID NOs:13, 14 and 15;
(b) (1) a Variable Light Chain CDR1, CDR2, CDR3 respectively having the amino acid sequence of SEQ ID NOs:17, 18 and 19; and
   (2) a Variable Heavy Chain CDR1, CDR2, CDR3 respectively having the amino acid sequence of SEQ ID NOs:21, 22 and 23;
(c) (1) a Variable Light Chain CDR1, CDR2, CDR3 respectively having the amino acid sequence of SEQ ID NOs:25, 26 and 27; and
   (2) a Variable Heavy Chain CDR1, CDR2, CDR3 respectively having the amino acid sequence of SEQ ID NOs:33, 34 and 35;
(d) (1) a Variable Light Chain CDR1, CDR2, CDR3 respectively having the amino acid sequence of SEQ ID NOs:29, 30 and 31; and
   (2) a Variable Heavy Chain CDR1, CDR2, CDR3 respectively having the amino acid sequence of SEQ ID NOs:33, 34 and 35;
or
(e) (1) a Variable Light Chain CDR1, CDR2, CDR3 respectively having the amino acid sequence of SEQ ID NOs:37, 38 and 39; and
   (2) a Variable Heavy Chain CDR1, CDR2, CDR3 respectively having the amino acid sequence of SEQ ID NOs:41, 42 and 43.

The invention particularly concerns the embodiment of any of the above-described binding molecules wherein the molecule comprises:
(a) a Variable Light Chain CDR1, CDR2, CDR3 respectively having the amino acid sequence of SEQ ID NOs:97, 98 and 99; and
(2) a Variable Heavy Chain CDR1, CDR2, CDR3 respectively having the amino acid sequence of SEQ ID NOs: 100, 101 and 102.

The invention particularly concerns the embodiment of any of the above-described binding molecules wherein upon peripheral injection into a recipient, the molecule substantially co-localizes with a Tau aggregate.

The invention particularly concerns the embodiment of any of the above-described binding molecules wherein the molecule is an antibody, a diabody, an scFv, or comprises an epitope-binding fragment of an antibody, diabody or scFv.

The invention particularly concerns the embodiment of any of the above-described binding molecules wherein the molecule is an antibody.

The invention particularly concerns the embodiment of any of the above-described binding molecules wherein the molecule is a humanized antibody or comprises an epitope-binding fragment of a humanized antibody.

The invention particularly concerns the embodiment of any of the above-described binding molecules wherein the molecule is an scFv.

The invention particularly concerns the embodiment of any of the above-described binding molecules wherein the molecule is detectably labeled, and especially wherein the detectable label is a fluorescent label, a chemoluminescent label, a paramagnetic label, a radioisotopic label or an enzyme label.

The invention additionally concerns the use of any of such antibody-based molecules for detecting or measuring the presence or amount of the truncated Tau protein in the brain, cerebrospinal fluid, blood, serum or plasma of a recipient subject.

The invention particularly concerns the embodiment of such use, wherein the detection or measurement comprises in vivo or ex vivo imaging of the antibody-based molecule bound to the truncated Tau protein.

The invention particularly concerns the embodiments of such uses wherein the detection or measurement is for diagnosing Alzheimer's disease or another tauopathy of a subject.

The invention additionally concerns an in vivo medicament for the treatment of Alzheimer's disease or another tauopathy of a subject, wherein the medicament comprises any of the above-described antibody-based molecules in an amount effective to treat the Alzheimer's disease or other tauopathy, and one or more carriers, diluents and/or stabilizers.

The invention additionally concerns the use of such in vivo medicament for the treatment of Alzheimer's disease or another tauopathy of the subject.

The invention particularly concerns the embodiments of such uses wherein the subject is a human.

The invention additionally concerns a kit for detecting or measuring the presence or amount of the truncated Tau protein in the brain of a subject, or for diagnosing Alzheimer's disease or another tauopathy in a subject, wherein the kit comprises an above-described antibody-based molecule.

The invention particularly concerns the embodiments of any of such uses, medicaments or kits wherein the tauopathy is selected from the group comprising frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

BRIEF DESCRIPTION OF THE DRAWINGS

FIG. 5A: The mixed cortical cultures treated with Antibody 5G2A3 (10 μg/ml) for 48 h, 72 h and 96 h demonstrated very significant decrease in the phospho-Tau levels against Ser199 epitope i.e. 66%, 81% and 94% with p<0.0001 respectively when compared to the control cells, whereas the cells treated with Antibody 1G11A10 (10 μg/ml) were unable to significantly decrease the phospho-Tau levels. The PHF treated mixed cortical cultures incubated with IgG (10 μg/ml) were considered as control for this set of experiment. FIG. 5B: Antibody 5G2A3 proved very effective in reducing phospho-Tau levels in primary neurons at Ser199 epitope by demonstrating 90%, 89%, 76% and 68% reduction for 24 h, 48 h, 72 h and 96 h respectively, with p<0.0001. Antibody 1G11A10 treatment at 10 μg/ml also demonstrated 68%, 67% and 68% reduction in phospho-Tau levels from 24 h up to 72 h, p<0.05, which subsided at 96 h showing only 9% reduction.

FIG. 6A: Antibody 5G2A3 treatment using mixed cortical culture was able to reduce the total Tau levels i.e. up to 54% until 96 h, p<0.05, whereas Antibody 1G11A10 treatment demonstrated significant reduction in total Tau levels only at 24 h (41%) and 96 h (36%), p<0.0001 when compared to the control cells that were treated with IgG (10 μg/ml). FIG. 6A: Antibody 5G2A3 treatment in primary neurons proved effective in significantly reducing total Tau levels at 24 h (58%), 48 h (45%) and 96 h (43%) with p<0.05 when compared with the control, whereas Antibody 1G11A10 demonstrated significant reduction in the levels of total Tau only at 48 h showing 65% reduction, p<0.05 in primary neuronal culture.

DETAILED DESCRIPTION OF THE INVENTION

Figure 1A:
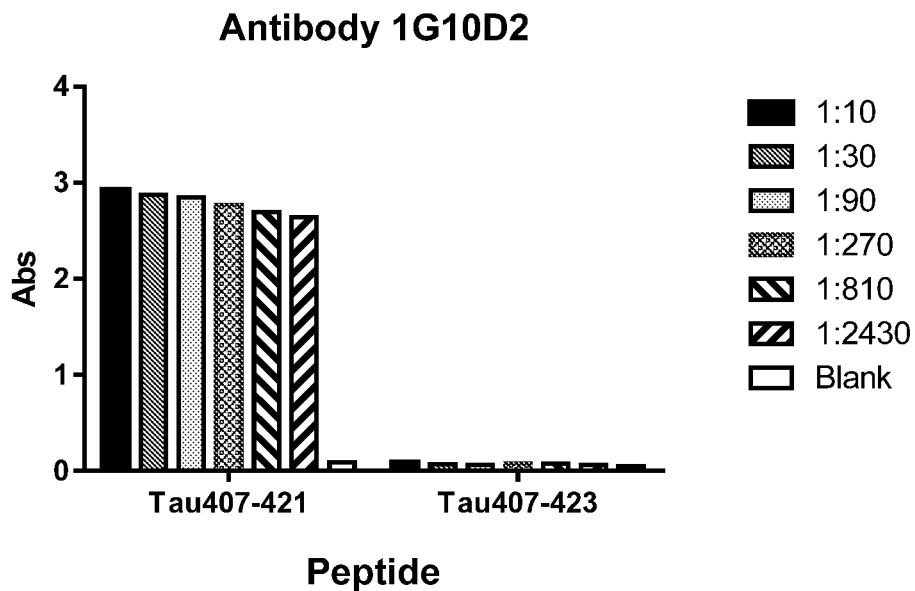
FIGS. 1A-1E show the immunospecificity of Antibodies 1G10D2 (FIG. 1A), Antibody 1G11A10 (FIG. 1B), Antibody 5B3C11 (FIG. 1C), Antibody 5G2A3 (FIG. 1D) and Antibody 5G2G6 (FIG. 1E) for the Truncated Asp421 Epitope of Tau at dilutions of hybridoma culture supernatants of 1:10, 1:30, 1:90, 1:270, 1:810 and 1:2430.

The present invention relates to antibody-based molecules (including single domain antibody fragment, scFv molecules, antibodies, antibody fragments, diabodies, and the epitope-binding domains thereof) that are capable of immunospecifically and selectively binding to the truncated Asp421 epitope of Tau. Such antibody-based molecules are useful to detect pathological Tau protein conformer if present in a biological sample, especially in conjunction with the diagnosis and/or treatment of Alzheimer's disease or other tauopathy, and thus provide a diagnostic for Alzheimer's disease and other Tau pathologies. The antibody-based molecules of the present invention have particular utility as diagnostic markers for, tauopathy (and in particular for Alzheimer's disease and related tauopathies) and as pharmaceutical compositions for the treatment of such conditions.

The term "tauopathy," as used herein, encompasses any neurodegenerative disease that involves the pathological aggregation of the microtubule protein Tau within the brain. Accordingly, in addition to both familial and sporadic Alzheimer's disease, the tauopathies of the present invention include, without limitation, frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

The antibody-based molecules of the present invention provide greater specificity than β-sheet dyes for detecting Tau lesions in patients with AD or other tauopathies. In particular, smaller antibody fragments that bind to Tau are attractive as ligands for in vivo imaging. Their smaller size compared to antibodies leads to better access to Tau aggregates. Another advantage is their relatively rapid clearance from the circulation compared to unmodified antibodies that have longer half-lives. Within the cancer field, therapeutic antibodies have routinely been co-developed as imaging agents, and several such antibodies and Fab's or smaller diabodies and scFv molecules with better pharmacokinetic properties approved or proposed as tumor imaging agents (see, Kaur, S. et al. (2012) "*Recent Trends In Antibody Based Oncologic Imaging*," Cancer Lett. 315:97-111; Olafsen, T. et al. (2010) "*Antibody Vectors For Imaging*," Semin. Nucl. Med. 40:167-181).

I. Tau and the Preferred Immunogenic Tau Peptides of the Present Invention

As used herein, the term "Tau" is synonymous with the Tau protein and refers to any of the Tau protein isoforms (identified in for example UniProt as P10636, 1-9). Tau is a soluble microtubule-associated protein that is dynamically phosphorylated and dephosphorylated by a host of kinase enzymes during the cell cycle. Tau's ability to stabilize microtubules is dependent on the extent of its phosphorylation. In its dephosphorylated form, the protein is able to interact with tubulin to stabilize microtubules and promote tubulin assembly into microtubules (which form the cytoskeleton of the cell and are the major constituents of the mitotic spindles that pull apart eukaryotic chromosomes in mitosis). In its phosphorylated form, Tau is able to dissociate from microtubules, thereby permitting mitosis to occur. The phosphorylation of Tau acts thus as a direct microtubule association-dissociation switch within the neuron (Pedersen, J. T. et al. (2015) "*Tau Immunotherapy For Alzheimer's Disease*," Trends Mol. Med. 2015 Apr. 3. pii: S1471-4914 (15)00058-1; pages 1-9, hereby incorporated by reference herein in its entirety).

The amino acid numbering of Tau residues provided herein is given with respect to SEQ ID NO:1, as shown below, with methionine being the first amino acid residue thereof.

SEQ ID NO: 1:
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR IPAKTPPAPK TPPSSGEPPK SGDRSGYSSP

GSPGTPGSRS RTPSLPTPPT REPKKVAVVR TPPKSPSSAK

SRLQTAPVPM PDLKNVKSKI GSTENLKHQP GGGKVQIINK

KLDLSNVQSK CGSKDNIKHV PGGGSVQIVY KPVDLSKVTS

KCGSLGNIHH KPGGGQVEVK SEKLDFKDRV QSKIGSLDNI

THVPGGGNKK IETHKLTFRE NAKAKTDHGA EIVYKSPVVS

GDTSPRHLSN VSSTGSIDMV DSPQLATLAD EVSASLAKQG L

The term "Phospho-Tau" or "P-Tau" refers to a Tau protein or peptide that has been phosphorylated at one or more serine or threonine residues. As used herein, the notation "$^{\{p\}}$Ser" or "$^{\{p\}}$OS" denote the amino acid residue phosphoserine. For example, the notation "$^{\{p\}}$Ser199" refers to a polypeptide portion of SEQ ID NO:1 wherein the residue that corresponds to residue 199 of SEQ ID NO:1 is a phosphoserine residue. In contrast, the notation "Ser199" refers to a polypeptide portion of SEQ ID NO:1 wherein the residue that corresponds to residue 199 of SEQ ID NO:1 is a serine residue.

Hyperphosphorylation of Tau can result in the formation of insoluble self-assembling "tangles," referred to herein as "Tau aggregates," of paired helical filaments and straight filaments. Such Tau aggregates may be intracellular (e.g., intraneuronal), but may also form outside of the cells. The presence of Tau aggregates impairs Tau's ability to stabilize microtubules and thus leads to microtubule disassembly, dendritic spinal collapse, and the degeneration of axons. Normal Tau contains, on average two phosphorylated sites; the hyperphosphorylated Tau filaments average seven to eight phosphorylated sites. Hyperphosphorylated Tau is the main constituent of the intracellular neurofibrillary tangles that are a main hallmark of Alzheimer's Disease and other tauopathies. As used herein, the term "Pathological Tau" refers to the hyperphosphorylated Tau that is characteristic of Alzheimer's Disease and other tauopathies.

II. The Preferred Antibody-Based Molecules of the Present Invention

The "antibody-based molecules" of the present invention include antibodies that are capable of immunospecifically and selectively binding to the Asp421 Epitope of Tau, as well as fragments and derivatives thereof that exhibit such binding immunospecificity and selectively. As used herein, a molecule is said to be a "fragment" of another molecule if it is obtained through the actual fragmenting of such parental molecule (for example, a Fab or (Fab)$_2$ fragment), or if it comprises an amino acid sequence that comprises a portion of the amino acid sequence of such parental molecule. As used herein, a molecule is said to be a "derivative" of another molecule (or relevant portion thereof) if it is obtained through the actual chemical modification of such parental molecule or portion thereof, or if it comprises an amino acid sequence that is substantially similar to the amino acid sequence of such parental molecule or relevant portion thereof (for example differing by less than 30%, less than 20%, less than 10%, or less than 5% from such parental molecule or such relevant portion thereof, or by 10 amino acid residues, or by fewer than 10, 9, 8, 7, 6, 5, 4, 3 or 2 amino acid residues from such parental molecule or relevant portion thereof).

As used herein, the term "antibody" refers to an intact immunoglobulin as well as a molecule having an epitope-binding fragment thereof. As used herein, the terms "fragment," "region" and "domain" are generally intended to be synonymous, unless the context of their use indicates otherwise. Naturally occurring antibodies typically comprise a tetramer which is usually composed of at least two heavy (H) chains and at least two light (L) chains. Each heavy chain is comprised of a heavy chain variable region (abbreviated herein as a "VH region") and a heavy chain constant region, usually comprised of three domains (CH1, CH2 and CH3 domains). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable region (abbreviated herein as a "VL region") and a light chain constant region (CL). Light chains include kappa chains and lambda chains. The heavy and light chain variable region is typically responsible for antigen recognition, while the heavy and light chain constant region may mediate the binding of the immunoglobulin to host tissues or factors, including various cells of the immune system (e.g., effector cells) and the first component (C1q) of the classical complement system. The VH and VL regions can be further subdivided into regions of hypervariability, termed "complementarity determining regions," or "CDRs," that are interspersed with regions of more conserved sequence, termed "framework regions" (FR). Each VH and VL region is composed of three CDR Domains and four FR Domains arranged from amino-terminus to carboxy-terminus in the following order: FR1-CDR1-FR2-CDR2-FR3-CDR3-FR4. The variable regions of the heavy and light chains contain a binding domain that interacts with an antigen. Of particular relevance are antibodies and their epitope-binding fragments that have been "isolated" so as to exist in a physical milieu distinct from that in which it may occur in nature or that have been modified so as to differ from a naturally-occurring antibody in amino acid sequence.

Fragments of antibodies (including Fab and (Fab)$_2$ fragments) that exhibit epitope-binding ability can be obtained, for example, by protease cleavage of intact antibodies. More preferably, such fragments will be single domain antibody fragments, scFv molecules, and the epitope-binding domains of antibodies, etc., that are formed using recombinant techniques. For example, although the two domains of the Fv fragment, the VL region and the VH region, are encoded by separate genes, such gene sequences or their encoding cDNA can be joined, using recombinant methods, by a flexible linker (typically of about 10, 12, 15 or more amino acid residues) that enables them to be made as a single protein chain in which the VL and VH regions associate to form monovalent epitope-binding molecules (known as single chain Fv (scFv) molecules; see e.g., Bird et al. (1988) "*Single-Chain Antigen Binding Proteins*," Science 242:423-426; and Huston et al. (1988) "*Protein Engineering Of Antibody Binding Sites: Recovery Of Specific Activity In An Anti-Digoxin Single-Chain Fv Analogue Produced In Escherichia coli*," Proc. Natl. Acad. Sci. (U.S.A.) 85:5879-5883). Alternatively, by employing a flexible linker that is too short (e.g., less than about 9 residues) to enable the VL and VH regions of a single polypeptide chain to associate together, one can form a bispecific antibody, diabody, or similar molecule (in which two such polypeptide chains associate together to form a bivalent epitope-binding molecule) (see for instance Holliger, P. et al. (1993) "*Diabodies*': *Small Bivalent And Bispecific Antibody Fragments*," Proc. Natl. Acad. Sci. (U.S.A.) 90(14), 6444-8 (1993) for a description of diabodies). Single domain antibody fragments possess only one variable domain (e.g., VL or VH). Examples of the epitope-binding fragments encompassed within the present invention include (i) Fab' or Fab fragments, a monovalent fragment consisting of the VL, VN, CL and CH1 domains, or a monovalent antibody as described in WO2007059782; (ii) F(ab')$_2$ fragments, bivalent fragments comprising two Fab fragments linked by a disulfide bridge at the hinge region; (iii) Fd fragments consisting essentially of the VH and CH1 domains; (iv) Fv fragments consisting essentially of a VL and VH domain, (v) dAb fragments (Ward, E. S. et al. "*Binding Activities Of A Repertoire Of Single Immunoglobulin Variable Domains Secreted From Escherichia coli*," Nature 341:544-546 (1989)), which consist essentially of a VH domain and also called domain antibodies (Holt, L. J. et al. (2003) "*Domain Antibodies: Proteins For Therapy*," Trends Biotechnol. 21(11):484-490); (vi) camelid or nanobodies (Revets, H. et al. (2005) "*Nanobodies As Novel Agents For Cancer Therapy*," Expert Opin. Biol. Ther. 5(1):111-124) and (vii) isolated complementarity determining regions (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single-chain antibodies or single-chain Fv (scFv), see for instance Bird et al. (1988) "*Single-Chain Antigen-Binding Proteins*," Science 242:423-426 and Huston et al. (1988) "*Protein Engineering Of Antibody Binding Sites: Recovery Of Specific Activity In An Anti-Digoxin Single-Chain Fv Analogue Produced In Escherichia coli*," Proc. Natl. Acad. Sci. (U.S.A.) 85:5879-5883). These and other useful antibody fragments in the context of the present invention are discussed further herein. It also should be understood that the term antibody, unless specified otherwise, also includes antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3, IgG4, IgD, IgA, IgE, or IgM) that is encoded by heavy chain constant region genes. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-Tau antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1, κ.

Such antibody fragments are obtained using conventional techniques known to those of skill in the art. For example, F(ab')2 fragments may be generated by treating antibody with pepsin. The resulting F(ab')2 fragment may be treated to reduce disulfide bridges to produce Fab' fragments. Fab fragments may be obtained by treating an IgG antibody with papain; Fab' fragments may be obtained with pepsin digestion of IgG antibody. An F(ab') fragment may also be produced by binding Fab' described below via a thioether bond or a disulfide bond. A Fab' fragment is an antibody fragment obtained by cutting a disulfide bond of the hinge region of the F(ab')$_2$. A Fab' fragment may be obtained by treating an F(ab')$_2$ fragment with a reducing agent, such as dithiothreitol. Antibody fragment may also be generated by expression of nucleic acids encoding such fragments in recombinant cells (see for instance Evans, M. J. et al. (1995) "*Rapid Expression Of An Anti-Human C5 Chimeric Fab Utilizing A Vector That Replicates In COS And 293 Cells*," J. Immunol. Meth. 184:123-38). For example, a chimeric gene encoding a portion of an F(ab')$_2$ fragment could include DNA sequences encoding the CH1 domain and hinge region of the H chain, followed by a translational stop codon to yield such a truncated antibody fragment molecule. Suitable fragments capable of binding to a desired epitope may be readily screened for utility in the same manner as an intact antibody.

In one embodiment, such antibody fragments are a monovalent antibody, preferably a monovalent antibody as described in PCT Publication WO 2007/059782 (which is incorporated herein by reference in its entirety) having a deletion of the hinge region. Such an antibody may be constructed by a method comprising: i) providing a nucleic acid construct encoding the light chain of said monovalent antibody, said construct comprising a nucleotide sequence encoding the VL region of a selected antigen-specific anti-alpha-synuclein antibody and a nucleotide sequence encoding the constant CL region of an Ig, wherein said nucleotide sequence encoding the VL region of a selected antigen-specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen-specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulfide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen-specific antibody and said nucleotide sequence encoding the CH region of said Ig are operably linked together; iii) providing a cell expression system for producing said monovalent antibody;

iv) producing said monovalent antibody by co-expressing the nucleic acid constructs of (i) and (ii) in cells of the cell expression system of (iii).

Similarly, in one embodiment, the antibody is a monovalent antibody, which comprises:
(i) a variable region of an antibody of the invention as described herein or an antigen-binding part of the said region, and
(ii) a CH region of an immunoglobulin or a fragment thereof comprising the CH2 and CH3 regions, wherein the CH region or fragment thereof has been modified such that the region corresponding to the hinge region and, if the immunoglobulin is not an IgG4 subtype, other regions of the CH region, such as the CH3 region, do not comprise any amino acid residues, which are capable of forming disulfide bonds with an identical CH region or other covalent or stable non-covalent inter-heavy chain bonds with an identical CH region in the presence of polyclonal human IgG.

In a further embodiment, the heavy chain of the monovalent antibody has been modified such that the entire hinge has been deleted.

In another further embodiment, the sequence of said monovalent antibody has been modified so that it does not comprise any acceptor sites for N-linked glycosylation.

As used herein, an antibody or an epitope-binding fragment thereof is said to "immunospecifically" bind a region of another molecule (i.e., an epitope) if it reacts or associates more frequently, more rapidly, with greater duration and/or with greater affinity or avidity with that epitope relative to alternative epitopes. It is also understood by reading this definition that, for example, an antibody or an epitope-binding fragment thereof that immunospecifically binds to a first target may or may not specifically or preferentially bind to a second target.

As used herein, the term "binding" in the context of the binding of an antibody or binding fragment thereof to a predetermined antigen typically refers to binding with an affinity corresponding to a $K_D$ of about $10^{-7}$ M or less, such as about $10^{-8}$ M or less, such as about $10^{-9}$ M or less when determined by, for instance, surface plasmon resonance (SPR) technology in a BIAcore 3000 instrument (preferably using the antibody as the ligand and the antigen as the analyte), and which binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., bovine serum albumin ("BSA"), casein, etc.) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. The term "$k_d$" ($sec^{-1}$ or 1/s), as used herein, refers to the dissociation rate constant of a particular antibody-antigen interaction. Said value is also referred to as the $k_{off}$ value. The term "$k_a$" ($M^{-1} \times sec^{-1}$ or 1/M), as used herein, refers to the association rate constant of a particular antibody-antigen interaction. The term "$K_D$" (M), as used herein, refers to the dissociation equilibrium constant of a particular antibody-antigen interaction and is obtained by dividing the $k_d$ by the $k_a$. The term "$K_A$" ($M^{-1}$ or 1/M), as used herein, refers to the association equilibrium constant of a particular antibody-antigen interaction and is obtained by dividing the $k_a$ by the $k_d$.

As used herein, an antibody or an epitope-binding fragment thereof is said to "selectively" bind to a truncated peptide epitope if it immunospecifically binds to such epitope with higher affinity than it binds (if it binds at all) to the non-truncated peptide epitope. As used herein, the term "truncated epitope" denotes an epitope that is a portion of a naturally-occurring ("non-truncated") epitope, such that the non-truncated epitope possesses one or more amino acid residues extending from the C-terminus and/or the N-terminus of the truncated epitope. Most preferably, such higher affinity will be at least 10-fold higher, at least 30-fold higher, at least 100-fold higher, at least 300-fold higher, at least 1,000-fold higher, at least 3,000-fold higher, or at least 10,000-fold higher. The extent of "selectivity" of an antibody, or of an epitope-binding fragment thereof, for truncated Tau is determined by comparing, via ELISA or Biacore, the affinity with which it immunospecifically binds to the truncated epitope relative to the non-truncated epitope thereof. For example, a polypeptide that comprises a "Non-Truncated Asp421 Epitope" possesses a Tau epitope that comprises position Asp421 of SEQ ID NO:1. A polypeptide that comprises a "Truncated Asp421 Epitope" possesses a Tau epitope that comprises position Asp421 of SEQ ID NO:1, wherein such Asp421 residue is the N-terminal or C-terminal Tau residue of such polypeptide. An antibody that exhibits immunospecificity for the Truncated Asp421 Epitope exhibits enhanced immunospecificity to the Truncated Asp421 Epitope relative to a Non-Truncated Asp421 Epitope. Thus, an antibody that exhibits immunospecificity for the Truncated Asp421 Epitope exhibits substantially diminished binding to polypeptides that contain Tau sequence C-terminal to position Asp421 of Tau (SEQ ID NO:1).

The term "epitope" refers to an antigenic determinant capable of being immunospecifically bound to an antibody. Epitopes usually comprise surface groupings of molecules such as amino acids or sugar side chains and usually have specific three dimensional structural characteristics, as well as specific charge characteristics. Conformational and non-conformational epitopes are distinguished in that the binding to the former, but not the latter, is lost in the presence of denaturing solvents. An epitope may comprise amino acid residues directly involved in the binding (also called the immunodominant component of the epitope) and other amino acid residues, which are not directly involved in the binding, such as amino acid residues that are effectively blocked by the specific antigen-binding peptide (in other words, the amino acid residue is within the footprint of the specific antigen-binding peptide).

As used herein, the term "epitope-binding fragment of an antibody" means a fragment of an antibody capable of immunospecifically binding to an epitope. An epitope-binding fragment may contain 1, 2, 3, 4, 5 or all 6 of the CDR Domains of such antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino-terminus and a carboxyl terminus (e.g., a diabody, an Fab fragment, an (Fab)$_2$ fragment, etc.).

The antibody-based molecules of the present invention, and their Tau epitope-binding fragments will preferably be "humanized," particularly if they are to be employed for therapeutic purposes. The term "humanized" refer to a chimeric molecule, generally prepared using recombinant techniques, having an antigen binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild-type (e.g., fully human) or they may be modified to contain one or more amino acid substitutions not found in the human antibody whose sequence has served as the basis for humanization. Humanization lessens or eliminates the likelihood that a constant region of the molecule will act as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332: 323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody. The ability to humanize an antigen is well-known (see, e.g., U.S. Pat. Nos. 5,225,539; 5,530,101; 5,585,089; 5,859,205; 6,407,213; 6,881,557).

In one embodiment, an antibody-based molecule of the invention is a human antibody. Suitable human antibodies may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice."

The HuMAb mouse contains a human immunoglobulin gene minilocus that encodes unrearranged human heavy variable and constant (μ and Υ) and light variable and constant (K) chain immunoglobulin sequences, together with targeted mutations that inactivate the endogenous μ and K chain loci (Lonberg, N. et al. (1994) "*Antigen-Specific Human Antibodies From Mice Comprising Four Distinct Genetic Modifications*," Nature 368:856-859). Accordingly, such mice exhibit reduced expression of mouse IgM or IgK and in response to immunization, the introduced human heavy and light chain transgenes, undergo class switching and somatic mutation to generate high affinity human IgG, monoclonal antibodies (Lonberg, N. et al. (1994) "*Antigen-Specific Human Antibodies From Mice Comprising Four Distinct Genetic Modifications*," Nature 368:856-859; Lonberg, N. (1994) "*Human Monoclonal Antibodies from Transgenic Mice*," In: HANDBOOK EXPERIMENTAL PHARMACOLOGY, Volume 181 (Starke, K. et al., Eds.) Springer-Verlag Berlin Heidelberg; Lonberg, N. et al. (1995) "*Human Antibodies From Transgenic Mice*," Intern. Rev. Immunol. 13(1):65-93; Harding, F. et al. (1995) "*Class Switching In Human Immunoglobulin Transgenic Mice*," Ann. N.Y. Acad. Sci 764:536-546). The preparation of HuMAb mice is described in detail in Taylor, L. et al. (1992) "*A Transgenic Mouse That Expresses A Diversity Of Human Sequence Heavy And Light Chain Immunoglobulins*," Nucl. Acids Res. 20(23):6287-6295; Chen, J. et al. (1993) "*Immunoglobulin Gene Rearrangement In B Cell Deficient Mice Generated By Targeted Deletion Of The JH Locus*," Int'l. Immunol. 5:647-656; Tuaillon, N. et al. (1994) "*Biased Utilization Of DHQ52 And JH4 Gene Segments In A Human Ig Transgenic Minilocus Is Independent Of Antigenic Selection*," J. Immunol. 152: 2912-2920; Taylor, L. et al. (1994) "*Human Immunoglobulin Transgenes Undergo Rearrangement, Somatic Mutation And Class Switching In Mice That Lack Endogenous IgM*," Int'l. Immunol. 6:579-591; Fishwild, D. et al. (1996) "*High Avidity Human IgG Kappa Monoclonal Antibodies From A Novel* Strain *Of Minilocus Transgenic Mice*," Nature Biotechnol. 14:845-851; see also U.S. Pat. Nos. 5,545,806; 5,569,825; 5,625,126; 5,633,425; 5,789,650; 5,877,397; 5,661,016; 5,814,318; 5,874,299; 5,770,429; 5,545,807; PCT Publications WO 98/24884, WO 94/25585, WO 93/1227, WO 92/22645, WO 92/03918 and WO 01/09187).

The HCo7 mice have a JKD disruption in their endogenous light chain (kappa) genes (as described in Chen et al. (1993) "*B Cell Development In Mice That Lack One Or Both Immunoglobulin Kappa Light Chain Genes*," EMBO J. 12:821-830), a CMD disruption in their endogenous heavy chain genes (as described in Example 1 of PCT Publication WO 01/14424), a KCo5 human kappa light chain transgene (as described in Fishwild, D. et al. (1996) "*High-Avidity Human Igg Kappa Monoclonal Antibodies From A Novel* Strain *Of Minilocus Transgenic Mice*," Nature Biotechnol. 14:845-851), and a HCo7 human heavy chain transgene (as described in U.S. Pat. No. 5,770,429).

The HCo12 mice have a JKD disruption in their endogenous light chain (kappa) genes (as described in Chen et al.

(1993) "*B Cell Development In Mice That Lack One Or Both Immunoglobulin Kappa Light Chain Genes*," EMBO J. 12:821-830), a CMD disruption in their endogenous heavy chain genes (as described in Example 1 of PCT Publication WO 01/14424), a KCo5 human kappa light chain transgene (as described in Fishwild, D. et al. (1996) "*High-Avidity Human Igg Kappa Monoclonal Antibodies From A Novel Strain Of Minilocus Transgenic Mice*," Nature Biotechnol. 14:845-851), and a HCol2 human heavy chain transgene (as described in Example 2 of PCT Publication WO 01/14424).

In the KM mouse strain, the endogenous mouse kappa light chain gene has been homozygously disrupted as described in Chen et al. (1993) "*B Cell Development In Mice That Lack One Or Both Immunoglobulin Kappa Light Chain Genes*," EMBO J. 12:821-830) and the endogenous mouse heavy chain gene has been homozygously disrupted as described in Example 1 of PCT Publication WO 01/09187. This mouse strain carries a human kappa light chain transgene, KCo5, as described in Fishwild, D. et al. (1996) "*High-Avidity Human Igg Kappa Monoclonal Antibodies From A Novel* Strain *Of Minilocus Transgenic Mice*," Nature Biotechnol. 14:845-851). This mouse strain also carries a human heavy chain transchromosome composed of chromosome 14 fragment hCF (SC20) as described in PCT Publication WO 02/43478.

Splenocytes from these transgenic mice may be used to generate hybridomas that secrete human monoclonal antibodies according to well-known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690; 5,756,687; 5,750,172 and 5,741,957.

In some antibodies only part of a CDR, namely the subset of CDR residues required for binding, termed the "SDRs," are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (see, Kabat et al. (1992) SEQUENCES OF PROTEINS OF IMMUNOLOGICAL INTEREST, National Institutes of Health Publication No. 91-3242; Chothia, C. et al. (1987) "*Canonical Structures For The Hypervariable Regions Of Immunoglobulins*," J. Mol. Biol. 196:901-917), by molecular modeling and/or empirically, or as described in Gonzales, N. R. et al. (2004) "*SDR Grafting Of A Murine Antibody Using Multiple Human Germline Templates To Minimize Its Immunogenicity*," Mol. Immunol. 41:863-872. In such humanized antibodies at positions in which one or more donor CDR residues is absent or in which an entire donor CR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The fact that a single amino acid alteration of a CDR residue can result in loss of functional binding (Rudikoff, S. et al. (1982) "*Single Amino Acid Substitution Altering Antigen Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "*Where Did The BLOSUM62 Alignment Score Matrix Come From?*," Nature Biotech. 22(8):1035-1036; Henikoff, J. G. (1992) "Amino acid substitution matrices from protein blocks," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). Table 1 presents the BLOSUM62.iij substitution scores (the higher the score the more conservative the substitution and thus the more likely the substitution will not affect function). If an antigen-binding fragment comprising the resultant CDR fails to bind to ROR1, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |

TABLE 1-continued

|   | A  | R  | N  | D  | C  | Q  | E  | G  | H  | I  | L  | K  | M  | F  | P  | S  | T  | W   | Y  | V  |
|---|----|----|----|----|----|----|----|----|----|----|----|----|----|----|----|----|----|-----|----|----|
| G | 0  | -2 | 0  | -1 | -3 | -2 | -2 | +6 | -2 | -4 | -4 | -2 | -3 | -3 | -2 | 0  | -2 | -2  | -3 | -3 |
| H | -2 | 0  | +1 | -1 | -3 | 0  | 0  | -2 | +8 | -3 | -3 | -1 | -2 | -1 | -2 | -1 | -2 | -2  | +2 | -3 |
| I | -1 | -3 | -3 | -3 | -1 | -3 | -3 | -4 | -3 | +4 | +2 | -3 | +1 | 0  | -3 | -2 | -1 | -3  | -1 | +3 |
| L | -1 | -2 | -3 | -4 | -1 | -2 | -3 | -4 | -3 | +2 | +4 | -2 | +2 | 0  | -3 | -2 | -1 | -2  | -1 | +1 |
| K | -1 | +2 | 0  | -1 | -3 | +1 | +1 | -2 | -1 | -3 | -2 | +5 | -1 | -3 | -1 | 0  | -1 | -3  | -2 | -2 |
| M | -1 | -1 | -2 | -3 | -1 | 0  | -2 | -3 | -2 | +1 | +2 | -1 | +5 | 0  | -2 | -1 | -1 | -1  | -1 | +1 |
| F | -2 | -3 | -3 | -3 | -2 | -3 | -3 | -3 | -1 | 0  | 0  | -3 | 0  | +6 | -4 | -2 | -2 | +1  | +3 | -1 |
| P | -1 | -2 | -2 | -1 | -3 | -1 | -1 | -2 | -2 | -3 | -3 | -1 | -2 | -4 | +7 | -1 | -1 | -4  | -3 | -2 |
| S | +1 | -1 | +1 | 0  | -1 | 0  | 0  | 0  | -1 | -2 | -2 | 0  | -1 | -2 | -1 | +4 | +1 | -3  | -2 | -2 |
| T | 0  | -1 | 0  | -1 | -1 | -1 | -1 | -2 | -2 | -1 | -1 | -1 | -1 | -2 | -1 | +1 | +5 | -2  | -2 | 0  |
| W | -3 | -3 | -4 | -4 | -2 | -2 | -3 | -2 | -2 | -3 | -2 | -3 | -1 | +1 | -4 | -3 | -2 | +11 | +2 | -3 |
| Y | -2 | -2 | -2 | -3 | -2 | -1 | -2 | -3 | +2 | -1 | -1 | -2 | -1 | +3 | -3 | -2 | -2 | +2  | +7 | -1 |
| V | 0  | -3 | -3 | -3 | -1 | -2 | -2 | -3 | -3 | +3 | +1 | -2 | +1 | -1 | -2 | -2 | 0  | -3  | -1 | +4 |

The invention thus contemplates the use of guided or random mutagenesis to identify improved CDRs.

In the context of the present invention, conservative substitutions may be defined by substitutions within the classes of amino acids reflected in one or more of the following three tables:

Amino Acid Residue Classes For Conservative Substitutions:

TABLE 2

| Acidic Residues | Asp (D) and Glu (E) |
|---|---|
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 3

| 1 | A | S | T |
|---|---|---|---|
| 2 | D | E |   |
| 3 | N | Q |   |
| 4 | R | K |   |
| 5 | I | L | M |
| 6 | F | Y | W |

Alternative Physical and Functional Classifications of Amino Acid Residues:

TABLE 4

| Alcohol Group-Containing Residues | S and T |
|---|---|
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |
| Small Residues | A, C, D, G, N, P, S, T and V |
| Very Small Residues | A, G and S |
| Residues Involved In Turn Formation | A, C, D, E, G, H, K, N, Q, R, S, P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) PROTEINS: STRUCTURE AND MOLECULAR PROPERTIES (2d Ed. 1993), W. H. Freeman and Company.

Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (See, e.g. Glaser et al. (1992) "Antibody Engineering By Codon-Based Mutagenesis In A Filamentous Phage Vector System," J. Immunology 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu, H. et al. (1998) "Stepwise In Vitro Affinity Maturation Of Vitaxin, An Alphav Beta3-Specific Humanized Mab," Proc. Natl. Acad. Sci. (U.S.A.) 95:6037-6042; Yelton et al. (1995) "Affinity Maturation Of The BR96 Anti-Carcinoma Antibody By Codon-Based Mutagenesis," J. Immunology 155:1994). CDR walking, which randomizes the Light Chain, may be used (see, Schier, R. et al. (1996) "Isolation Of Picomolar Affinity Anti-c-erbB-2 Single-Chain Fv By Molecular Evolution Of The Complementarity Determining Regions In The Center Of The Antibody Binding Site," J. Mol. Biol. 263:551-567).

Methods for accomplishing such affinity maturation are described for example in: Krause, J. C. et al. (2011) "An Insertion Mutation That Distorts Antibody Binding Site Architecture Enhances Function Of A Human Antibody," MBio. 2(1) pii: e00345-10. doi: 10.1128/mBio.00345-10; Kuan, C. T. et al. (2010) "Affinity Matured Anti-Glycoprotein NMB Recombinant Immunotoxins Targeting Malignant Gliomas And Melanomas," Int. J. Cancer 10.1002/ijc.25645; Hackel, B. J. et al. (2010) "Stability And CDR Composition Biases Enrich Binder Functionality Landscapes," J. Mol. Biol. 401(1):84-96; Montgomery, D. L. et al. (2009) "Affinity Maturation And Characterization Of A Human Monoclonal Antibody Against HIV-1 gp41," MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525: 353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "*Affinity Maturation Of Antibodies Assisted By In Silico Modeling*," Proc. Natl. Acad. Sci. (USA) 105(26): 9029-9034.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-Tau antibody when immunized with Tau antigen and/or cells expressing Tau. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in PCT Publication WO 02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching.

The use of the antibody-based molecules of the present invention as Tau imaging probes has great potential due to their specificity. Because of the general impermeability of the blood-brain barrier, smaller single-chain variable antibody fragments (scFv molecules) have been found to be preferred as in vivo imaging ligands to detect Tau lesions. scFv molecules are formed as a fusion protein of the variable regions of the heavy (H) and light chains (L) domains of an antibody, connected to one another via a short linker peptide of from about 10 to about 25 amino acid residues. The linker is usually rich in glycine for flexibility (e.g., GGGGSGGGGSGGGGS (SEQ ID NO:2) (Fisher, A. et al. (2009) "*Efficient Isolation Of Soluble Intracellular Single-Chain Antibodies Using The Twin Arginine Translocation Machinery*," J. Nol. Biol. 385(1):299-311; Bird, R. E. et al. (1988) "*Single-Chain Antigen Binding Proteins*," Science 242:423-426; Huston, J. S. et al. (1988) "*Protein Engineering Of Antibody Binding Sites: Recovery Of Specific Activity In An Anti-Digoxin Single-Chain Fv Analogue Produced In Escherichia coli*," Proc. Natl. Acad. Sci. (U.S.A.) 85:5879-5883), as well as serine or threonine for solubility, and can either connect the N-terminus of the Heavy Chain Variable Domain with the C-terminus of the Light Chain Variable Domain VL, or vice versa (Huang, L. et al. (2013) "*Single-Chain Fragment Variable Passive Immunotherapies For Neurodegenerative Diseases*," Int. J. Mol. Sci. 14(9):19109-19127; Ahmad, Z. A. et al. (2012) "*scFv Antibody: Principles And Clinical Application*," Clin. Dev. Immunol. 2012: 980250; Huhalov, A. et al. (2004) "*Engineered Single-Chain Antibody Fragments For Radioimmunotherapy*," Q. J. Nucl. Med. Mol. Imaging 48(4):279-288). An example of such a linker is GSTSGSGKPGSGEGSTKG (SEQ ID NO:3) (Whitlow, M. et al. (1993) "*An Improved Linker For Single-Chain Fv With Reduced Aggregation And Enhanced Proteolytic Stability*," Protein Eng. 6:989-995). A particularly preferred linker for the present invention has the amino acid sequence (SEQ ID NO:4): SSGGGGSGGGGGGSSRSS.

In order to facilitate purification and/or recovery, the scFv may include a poly histidine ("His-Tag") (e.g., (SEQ ID NO:5) HHHHHH). The imidazole side chains of the histidine residues of the His-Tag can engage in reversible coordinative bonds to certain transition metal ions, such as $Co^{2+}$, $Zn^{2+}$ and especially $Ni^{+2}$. Thus, when His-tagged scFv molecules are applied to a matrix containing such metal ions, they specifically bind to the matrix, while most untagged proteins do not. The scFv may additionally or alternatively include an "HA-Tag" such as (SEQ ID NO:6) GAYPYDVPDYAS. Human influenza hemagglutinin (HA) is a surface glycoprotein required for the infectivity of the human virus. The HA-tag is derived from the human influenza hemagglutinin (HA) surface glycoprotein, and permits detection of the scFv using an anti-HA-Tag antibody (Millipore).

scFv molecules may be expressed directly or as a fusion protein that is linked to an N-terminal leader peptide that is cleaved in order to yield the scFv (see, e.g., Huston, J. S. et al. (1988) "*Protein Engineering Of Antibody Binding Sites: Recovery Of Specific Activity In An Anti Digoxin Single-Chain Fv Analogue Produced In Escherichia coli*," Proc. Natl. Acad. Sci. (U.S.A.) 85:5879-5883). For example, the scFv may be fused to the modified trp LE leader peptide (MLE)), and cleaved away by acid cleavage of the Asp-Pro peptide bond (Piszkiewicz, D. et al. (1970) "*Anomalous Cleavage Of Aspartyl-Proline Peptide Bonds During Amino Acid Sequence Determinations*," Biochem. Biophys. Res. Commun. 40(5):1173-1178; Fraser, K. J. et al. (1972) "*Specific Cleavage Between Variable And Constant Domains Of Rabbit Antibody Light Chains By Dilute Acid Hydrolysis*," Biochemistry 11(26):4974-4977; Poulsen, K. et al. (1972) "*An Active Derivative Of Rabbit Antibody Light Chain Composed Of The Constant And The Variable Domains Held Together Only By A Native Disulfide Bond*," Proc. Natl. Acad. Sci. (U.S.A.) 69(9):2495-2499).

In a further embodiment, an scFv can be linked to another scFv (which may be the same or different) in order to form a bivalent molecule. This can be done by producing a single peptide chain with two VH and two VL regions, yielding tandem scFv molecules (Xiong, C.-Y. et al. (2006) "*Development Of Tumor Targeting Anti-MUC-1 Multimers Effects Of di-scFv Unpaired Cysteine Location On PEGylation And Tumor Binding*," Protein Engineering Design and Selection 19(8):359-367; Kufer, P. et al. (2004) "*A Revival Of Bispecific Antibodies*," Trends in Biotechnology 22(5):238-24). Alternatively, by forming an scFv whose Heavy Chain Variable Domain is separated from its Light Chain Variable Domain by a linker that is too short to permit such domains to complex with one another and form an epitope-binding site, one can force two scFv molecules to dimerize as a diabody (Hollinger, P. et al. (1993) "*Diabodies": Small Bivalent And Bispecific Antibody Fragments*," Proc. Natl. Acad. Sci. (U.S.A.) 90(14):6444-6448). Diabodies have been shown to have dissociation constants up to 40-fold lower than corresponding scFv molecules, meaning that they have a much higher affinity to their target. Consequently, diabody drugs could be dosed much lower than other therapeutic antibodies and are capable of highly specific targeting of tumors in vivo (Adams, G. P. et al. (1998) "*Prolonged in vivo Tumour Retention Of A Human Diabody Targeting The Extracellular Domain Of Human HER2/neu*," Brit. J. Cancer 77(9):1405-1412). Still shorter linkers (one or two amino acids) lead to the formation of trimers, so-called triabodies or tribodies. Tetrabodies have also been produced. They exhibit an even higher affinity to their targets than diabodies (Le Gall, F. et al. (1999) "*Di-, Tri-And Tetrameric Single-Chain Fv Antibody Fragments Against Human CD19: Effect Of Valency On Cell Binding*," FEBS Letters 453(1):164-168). All of these formats can be composed from variable scFv molecules so as to form dimers, trimers, etc. having specificity for two or more different epitopes (i.e., bispecific diabodies, etc.) (Dincq, S. et al. (2001) "*Expression And Purification Of Monospecific And Bispecific Recombinant Antibody Fragments Derived From Antibodies That Block The CD80/CD86-CD28 Costimulatory Pathway*," Protein Express. Purificat. 22(1):11-24).

As discussed above, the formation of neurofibrillary tangles (NFT), which comprise an accumulation of hyperphosphorylated Tau protein, is a characteristic feature of neurodegenerative diseases such as Alzheimer's disease, Pick's disease and progressive supranuclear palsy. The proteolytic cleavage of Tau at Asp421 (i.e., at residue D421 of SEQ ID NO:1) as an effect of caspase activation results in the generation of truncated Tau that is known to further stimulate Tau polymerization and accelerate the development of NFTs. Thus, such cleavage is considered one of several mechanisms associated with the accumulation of hyperphosphorylated Tau (see Pedersen, J. T. et al. (2015) "*Tau Immunotherapy For Alzheimer's Disease*," Trends Mol. Med. 2015 Apr. 3. pii: S1471-4914(15)00058-1; pages 1-9, Jarero-Basulto, J. J. et al. (2013) "*Luna Proteolytic Cleavage Of Polymeric Tau Protein By Caspase-3: Implications For Alzheimer Disease*," J. Neuropathol. Exp. Neurol. 72(12):1145-1161; Mondragon-Rodriguez, S. et al. (2014) "*Phosphorylation Of Tau Protein At Sites Ser(396-404) Is One Of The Earliest Events In Alzheimer's Disease And Down Syndrome*," Neuropathol. Appl. Neurobiol. 40(2):121-135; Lerchundi, R. et al. (2011) "*Tau Cleavage At D421 By Caspase-3 Is Induced In Neurons And Astrocytes Infected With Herpes Simplex Virus Type 1*," J. Alzheimers Dis. 23(3):513-520; Quintanilla, R. A. et al. (2009) "*Caspase-Cleaved Tau Expression Induces Mitochondrial Dysfunction In Immortalized Cortical Neurons: Implications For The Pathogenesis Of Alzheimer Disease*," J. Biol. Chem. 284(28):18754-18766; Mondragon-Rodriguez, S. et al. (2008) "*Cleavage And Conformational Changes Of Tau Protein Follow Phosphorylation During Alzheimer's Disease*," Int. J. Exp. Pathol. 89(2):81-90; Mondragon-Rodriguez, S. et al. (2008) "*Conformational Changes And Cleavage Of Tau In Pick Bodies Parallel The Early Processing Of Tau Found In Alzheimer Pathology*," Neuropathol. Appl. Neurobiol. 34(1):62-75; Guillozet-Bongaarts, A. L. et al. (2006) "*Pseudophosphorylation Of Tau At Serine 422 Inhibits Caspase Cleavage: In Vitro Evidence And Implications For Tangle Formation in vivo*," J. Neurochem. 97(4):1005-1014; Fasulo, L. et al. (2005) "*Apoptotic Effect Of Caspase-3 Cleaved Tau In Hippocampal Neurons And Its Potentiation By Tau FTDP-Mutation N279K*," J. Alzheimers. Dis. 7(1):3-13; Guillozet-Bongaarts, A. L. et al. (2005) "*Tau Truncation During Neurofibrillary Tangle Evolution In Alzheimer's Disease*," Neurobiol. Aging; 26(7): 1015-1022; Cho, J. H. et al. (2004) "*Glycogen Synthase Kinase 3 Beta Induces Caspase-Cleaved Tau Aggregation In Situ*," J. Biol. Chem. 279(52):54716-54723; and Berry, R. W. et al. (2003) "*Inhibition Of Tau Polymerization By Its Carboxy-Terminal Caspase Cleavage Fragment*," Biochemistry 42(27):8325-8331, each of which references is hereby incorporated by reference herein in its entirety).

The antibody-based molecules of the present invention exhibit immunospecificity to the "Truncated Asp421 Epitope." Although any immunogen containing a free Asp421 residue (of SEQ ID NO:1) may be employed to isolate and characterize such antibodies, it is preferred to employ a peptide having the amino acid sequence of HLSNVSSTGSIDMVD (SEQ ID NO:7) which corresponds to amino acid residues 407-421 of Tau (SEQ ID NO:1). The employed immunogen may contain this peptide, and is preferably modified to contain an N-terminal cysteine residue that is conjugated to keyhole limpet hemocyanin (KLH). To screen antibodies that selectively recognize the free Asp421 residue, binding to this immunogen can be compared to a peptide that does not contain a free Asp421 residue such as HLSNVSSTGSIDMVDSP (SEQ ID NO:105), which corresponds to amino acid residues 407-423 of Tau (SEQ ID NO:1). Antibody 1G10D2, Antibody 1G11A10, Antibody 5B3C11, Antibody 5G2A3 and Antibody 5G2G6 are illustrative antibodies that exhibit immunospecificity to the Truncated Asp421 Epitope.

A. Antibody 1G10D2, Antibody 1G11A10, Antibody 5B3C11, Antibody 5G2A3 and Antibody 5G2G6

Such efforts led to the isolation of Antibody 1G10D2, Antibody 1G11A10, Antibody 5B3C11, Antibody 5G2A3 and Antibody 5G2G6, which immunospecifically binds to the Asp421 Epitope. Antibody 1G10D2, Antibody 5B3C11, Antibody 5G2A3 and Antibody 5G2G6 target the Truncated Asp421 Epitope and bind with a high affinity as determined by ELISA. Antibody 5G2A3 binds the Truncated Asp421 Epitope with high affinity ($10^{-9}$M) as determined using Biacore analysis. In contrast, Antibody 1G11A10 binds the Truncated Asp421 Epitope with lower affinity ($10^{-6}$ M) as determined using Biacore analysis. Upon sequence analysis, Antibody 5G2A3 and Antibody 5G2G6 were found to be identical in sequence. Thus, further references to such antibodies will refer only to Antibody 5G2A3.

1. Antibody 1G10D2

The Light Chain Variable Domain of Antibody 1G10D2 has the amino acid sequence (SEQ ID NO:8; CDRs are underlined):

DVLMTQTPLS LPVSLGDQAS ISC<u>RSSQSIL</u> <u>NSNGNTYLE</u>W

YLQKPGQSPK LLIY<u>KVSNRF</u> <u>S</u>GVPDRFSGS GSGTDFTLKI

SRVEAEDLGV YYC<u>FQGSHVP</u> <u>WT</u>FGGGTKLE IK

The Light Chain Variable Domain CDR1 of Antibody 1G10D2 thus has the amino acid sequence (SEQ ID NO:9): RSSQSILNSNGNTYLE The Light Chain Variable Domain CDR2 of Antibody 1G10D2 thus has the amino acid sequence (SEQ ID NO:10): KVSNRFS The Light Chain Variable Domain CDR3 of Antibody 1G10D2 thus has the amino acid sequence (SEQ ID NO:11): FQGSHVPWT The Heavy Chain Variable Domain of Antibody 1G10D2 has the amino acid sequence (SEQ ID NO:12; CDRs are underlined):

```
EVKLVESGGD LVTPGGSLKV SCAASGLTFS DSAMSWVRLT

PEKRLEWVAS ISTGGATYYP DGLKGRFTIS RDDARNILFL

QMNSLRSEDT AMYYCTRRGV SSGNLFTYWG QGTLVTVSA
```

Thus, the Heavy Chain Variable Domain CDR1 of Antibody 1G10D2 has the amino acid sequence (SEQ ID NO:13): DSAMS Thus, the Heavy Chain Variable Domain CDR2 of Antibody 1G10D2 has the amino acid sequence (SEQ ID NO:14): SISTGGATYYPDGLKG Thus, the Heavy Chain Variable Domain CDR3 of Antibody 1G10D2 has the amino acid sequence (SEQ ID NO:15): RGVSSGNLFTY 2. Antibody 1G11A10

The Light Chain Variable Domain of Antibody 1G11A10 has the amino acid sequence (SEQ ID NO:16; CDRs are underlined):

```
DVLMTQTPLS LPVSLGDQAS ISCRSSQSII NSNGNTYLEW

YLQKPGQSPK LLIYKVSNRF SGVPDRFSGS GSGTDFTLKI

SRVETEDLGI YYCFQGSHVP WTFGGGTKLE IK
```

The Light Chain Variable Domain CDR1 of Antibody 1G11A10 thus has the amino acid sequence (SEQ ID NO:17): RSSQSIINSNGNTYLE The Light Chain Variable Domain CDR2 of Antibody 1G11A10 thus has the amino acid sequence (SEQ ID NO:18): KVSNRFS The Light Chain Variable Domain CDR3 of Antibody 1G11A10 thus has the amino acid sequence (SEQ ID NO:19): FQGSHVPWT The Heavy Chain Variable Domain of Antibody 1G11A10 has the amino acid sequence (SEQ ID NO:20; CDRs are underlined):

```
EVKLVESGGG LMKPGGSLKL SCAASGFTFS SYAMSWVRQS

PEKRLEWVAS ISSGGQTYSP DSVKGRFTIS RDNARNILYL

QMRNLRSEDT AMYYCASRGD PTMTATLFVY WGQGTLVTVS
```

Thus, the Heavy Chain Variable Domain CDR1 of Antibody 1G11A10 has the amino acid sequence (SEQ ID NO:21): SYAMS Thus, the Heavy Chain Variable Domain CDR2 of Antibody 1G11A10 has the amino acid sequence (SEQ ID NO:22): SISSGGQTYSPDSVKG Thus, the Heavy Chain Variable Domain CDR3 of Antibody 1G11A10 has the amino acid sequence (SEQ ID NO:23): RGDPTMTATLFVY 3. Antibody 5B3C11

Occasionally, more than one antibody sequences may be expressed by the same hybridoma cell, which may result from the hybridoma being non-monoclonal or from a rearrangement issue or from the genetic background of fusion partner. In this case, two Light Chain Variable Domains were identified for Antibody 5B3C11: Light Chain VL1 and Light Chain VL2.

a. Light Chain VL1 of Antibody 5B3C11

The Light Chain VL1 of Antibody 5B3C11 has the amino acid sequence (SEQ ID NO:24; CDRs are underlined):

```
DVLMTQTPLS LPVSLGDQAS ISCRSNQSIL HSNGNTYLDW

YLQKPGQSPK LLIYKVSNRF SGVPDRFSGS GSGTDFTLRI

SRVEAEDLGV YYCFQGSHIP WTFGGGTKLE IK
```

The Light Chain VL1 Variable Domain CDR1 of Antibody 5B3C11 thus has the amino acid sequence (SEQ ID NO:25): RSNQSILHSNGNTYLD The Light Chain VL1 Variable Domain CDR2 of Antibody 5B3C11 thus has the amino acid sequence (SEQ ID NO:26): KVSNRFS The Light Chain VL1 Variable Domain CDR3 of Antibody 5B3C11 thus has the amino acid sequence (SEQ ID NO:27): FQGSHIPWT b. Light Chain VL2 of Antibody 5B3C11

The Light Chain VL2 of Antibody 5B3C11 has the amino acid sequence (SEQ ID NO:28; CDRs are underlined):

```
ENVLTQSPAI MSASPGEKVT MTCRASSSVS SSYLHWYQQK

SGASPKLWIY STSNLASGVP ARFSGSGSGT SYSLTISSVE

AEDAATYYCQ QYSGYPRTFG GGTKLEIK
```

The Light Chain VL2 Variable Domain CDR1 of Antibody 5B3C11 thus has the amino acid sequence (SEQ ID NO:29): RASSSVSSSYLH The Light Chain VL2 Variable Domain CDR2 of Antibody 5B3C11 thus has the amino acid sequence (SEQ ID NO:30): STSNLAS The Light Chain VL2 Variable Domain CDR3 of Antibody 5B3C11 thus has the amino acid sequence (SEQ ID NO:31): QQYSGYPRT The Heavy Chain Variable Domain of Antibody 5B3C11 has the amino acid sequence (SEQ ID NO:32; CDRs are underlined):

```
EVQLVESGGG LVKPGGSLKL SCAASGFTFS NYALSWVRQT

PEKRLEWVAS ISSGGNTYYP DSVKGRFTIS RDNARNILYL

QMSSLRSEDT AMFYCTSRGD TTLITTLFTY WGQGTLVTVS A
```

Thus, the Heavy Chain Variable Domain CDR1 of Antibody 5B3C11 has the amino acid sequence (SEQ ID NO:33): NYALS Thus, the Heavy Chain Variable Domain CDR2 of Antibody 5B3C11 has the amino acid sequence (SEQ ID NO:34): SISSGGNTYYPDSVKG Thus, the Heavy Chain Variable Domain CDR3 of Antibody 5B3C11 has the amino acid sequence (SEQ ID NO:35): RGDTTLITTLFTY 4. Antibody 5G2A3

The Light Chain Variable Domain of Antibody 5G2A3 has the amino acid sequence (SEQ ID NO:36; CDRs are underlined):

```
DVLMTQTPLS LPVSLGDQAS ISCRSSQSIL HRNGNTYLDW

FLLKPGQSPK LLIYKVSNRF SGVPDRFSGS GSGTDFTLKI

SRVEAEDLGV YYCFQGSHVP WTFGGGTKLE IK
```

The Light Chain Variable Domain CDR1 of Antibody 5G2A3 thus has the amino acid sequence (SEQ ID NO:37): RSSQSILHRNGNTYLD The Light Chain Variable Domain CDR2 of Antibody 5G2A3 thus has the amino acid sequence (SEQ ID NO:38): KVSNRFS The Light Chain Variable Domain CDR3 of Antibody 5G2A3 thus has the amino acid sequence (SEQ ID NO:39): FQGSHVPWT The Heavy Chain Variable Domain of Antibody 5G2A3 has the amino acid sequence (SEQ ID NO:40; CDRs are underlined):

```
EVKLVESGGG LVKPGGSLTL SCAASGFTFS SYAMSWVRQT
PEKSLEWVAS ISSGGNTFYP DTVKGRFTIS RDNARNILYL
QMSGLRSEDT AIYYCARRGD PNMITTLFGY WGQGTLVTIS A
```

Thus, the Heavy Chain Variable Domain CDR1 of Antibody 5G2A3 has the amino acid sequence (SEQ ID NO:41): SYAMS Thus, the Heavy Chain Variable Domain CDR2 of Antibody 5G2A3 has the amino acid sequence (SEQ ID NO:42): SISSGGNTFYPDTVKG Thus, the Heavy Chain Variable Domain CDR3 of Antibody 5G2A3 has the amino acid sequence (SEQ ID NO:43): RGDPNMITTLFGY B. scFv Molecules scFv molecules may be generated from Antibody 1G10D2, Antibody 1G11A10, Antibody 5B3C11 or Antibody 5G2A3, and will possess the same Light and Heavy Chain Variable Domains CDR1, CDR2 and CDR3 as such antibody. Peripheral injection of such scFv molecules results in a strong in vivo brain signal in transgenic tauopathy mice but not in wild-type or amyloid-β plaque mice. The imaging signal correlates very well with co-localization of the probe with intraneuronal Tau aggregates, and is associated with markers of endosomes, autophagosomes and lysosomes, suggesting their interaction in these degradation pathways. scFv molecules derived from Antibody 1G10D2, Antibody 1G11A10, Antibody 5B3C11 or Antibody 5G2A3 have great potential as diagnostic markers for AD and related tauopathies.

In a preferred embodiment, such scFv molecules are prepared as a fusion protein that includes an N-terminal leader peptide portion having the amino acid sequence (SEQ ID NO:44): IQEEFKMKKTAIAIAVALAGFATVAQAA, and/or a C-terminal sequence peptide portion. The C-terminal peptide portion may include: an antibody constant domain, such as (SEQ ID NO:45): AKTTPPSVTSGQAGQ (Hussein, A. H. et al. (2007) "*Construction and Characterization of Single-Chain Variable Fragment Antibodies Directed against the Bordetella pertussis Surface Adhesins Filamentous Hemagglutinin and Pertactin*," Infect. Immun. 75(11):5476-5482), a His-Tag, such as (SEQ ID NO:5): HHHHHH), and/or an HA-Tag such as (SEQ ID NO:6): GAYPYDVPDYAS, or any combination or sub-combination thereof, and in any order. A preferred C-terminal peptide portion has the amino acid sequence (SEQ ID NO:46): AKTTPPSVTSGQAGQHHHHHHGAYPYDVPDYAS, and thus includes (in the N-terminus to C-Terminus direction) SEQ ID NO:45, SEQ ID NO:5, and SEQ ID NO:6.

1. scFv Molecules Generated From Antibody 1G10D2

The complete sequence of an exemplary scFv molecule generated from Antibody 1G10D2 is (SEQ ID NO:47) (CDR residues are underlined):

```
DVLMTQTPLS LPVSLGDQAS ISCRSSQSIL NSNGNTYLEW

YLQKPGQSPK LLIYKVSNRF SGVPDRFSGS GSGTDFTLKI

SRVEAEDLGV YYCFQGSHVP WTFGGGTKLE IKssggggsg ggggssrss EVKLVESGGD LVTPGGSLKV SCAASGLTFS

DSAMSWVRLT PEKRLEWVAS ISTGGATYYP DGLKGRFTIS

RDDARNILFL QMNSLRSEDT AMYYCTRRGV SSGNLFTYWG

QGTLVTVSA
``` wherein amino acid residues 1-112 are the amino acid residues of the Light Chain Variable Domain of Antibody 1G10D2 (SEQ ID NO:8), amino acid residues 113-130 are the amino acid residues of the linker (SEQ ID NO:4) (shown in lowercase italics), and amino acid residues 131-249 are the amino acid residues of the Heavy Chain Variable Domain of Antibody 1G10D2 (SEQ ID NO:12).

Thus, in preferred embodiments, such scFv fusion proteins will comprise the amino acid sequence of any of SEQ ID NOs:48-56 (in which the N-terminal and/or C-Terminal peptide portions of the ScFv fusion are underlined):

```
SEQ ID NO: 48 (a fusion of SEQ ID NOs: 44 and 57):
IQEEFKMKKT AIAIAVALAG FATVAQAADV LMTQTPLSLP VSLGDQASIS

CRSSQSILNS NGNTYLEWYL QKPGQSPKLL IYKVSNRFSG VPDRFSGSGS

GTDFTLKISR VEAEDLGVYY CFQGSHVPWT FGGGTKLEIK ssggggsggg gggssrssEV KLVESGGDLV TPGGSLKVSC AASGLTFSDS AMSWVRLTPE

KRLEWVASIS TGGATYYPDG LKGRFTISRD DARNILFLQM NSLRSEDTAM

YYCTRRGVSS GNLFTYWGQG TLVTVSA

SEQ ID NO: 49 (a fusion of SEQ ID NOs: 47 and 45):
DVLMTQTPLS LPVSLGDQAS ISCRSSQSIL NSNGNTYLEW YLQKPGQSPK

LLIYKVSNRF SGVPDRFSGS GSGTDFTLKI SRVEAEDLGV YYCFQGSHVP

WTFGGGTKLE IKssggggsg ggggssrss EVKLVESGGD LVTPGGSLKV

SCAASGLTFS DSAMSWVRLT PEKRLEWVAS ISTGGATYYP DGLKGRFTIS

RDDARNILFL QMNSLRSEDT AMYYCTRRGV SSGNLFTYWG QGTLVTVSAA

KTTPPSVTSG QAGQ
```

SEQ ID NO: 50 (a fusion of SEQ ID NOs: 47 and 5):
DVLMTQTPLS LPVSLGDQAS ISCRSSQSIL NSNGNTYLEW YLQKPGQSPK

LLIYKVSNRF SGVPDRFSGS GSGTDFTLKI SRVEAEDLGV YYCFQGSHVP

WTFGGGTKLE IK*ssggggsg gggggssrss* EVKLVESGGD LVTPGGSLKV

SCAASGLTFS DSAMSWVRLT PEKRLEWVAS ISTGGATYYP DGLKGRFTIS

RDDARNILFL QMNSLRSEDT AMYYCTRRGV SSGNLFTYWG QGTLVTVSAH

HHHHH

SEQ ID NO: 51 (a fusion of SEQ ID NOs: 47 and 6):
DVLMTQTPLS LPVSLGDQAS ISCRSSQSIL NSNGNTYLEW YLQKPGQSPK

LLIYKVSNRF SGVPDRFSGS GSGTDFTLKI SRVEAEDLGV YYCFQGSHVP

WTFGGGTKLE IK*ssggggsg gggggssrss* EVKLVESGGD LVTPGGSLKV

SCAASGLTFS DSAMSWVRLT PEKRLEWVAS ISTGGATYYP DGLKGRFTIS

RDDARNILFL QMNSLRSEDT AMYYCTRRGV SSGNLFTYWG QGTLVTVSAG

AYPYDVPDYA S

SEQ ID NO: 52 (a fusion of SEQ ID NOs: 47 and 46):
DVLMTQTPLS LPVSLGDQAS ISCRSSQSIL NSNGNTYLEW YLQKPGQSPK

LLIYKVSNRF SGVPDRFSGS GSGTDFTLKI SRVEAEDLGV YYCFQGSHVP

WTFGGGTKLE IK*ssggggsg gggggssrss* EVKLVESGGD LVTPGGSLKV

SCAASGLTFS DSAMSWVRLT PEKRLEWVAS ISTGGATYYP DGLKGRFTIS

RDDARNILFL QMNSLRSEDT AMYYCTRRGV SSGNLFTYWG QGTLVTVSAA

KTTPPSVTSG QAGQHHHHHH GAYPYDVPDY AS

SEQ ID NO: 53 (a fusion of SEQ ID NOs: 44, 47 and 45):
IQEEFKMKKT AIAIAVALAG FATVAQAADV LMTQTPLSLP VSLGDQASIS

CRSSQSILNS NGNTYLEWYL QKPGQSPKLL IYKVSNRFSG VPDRFSGSGS

GTDFTLKISR VEAEDLGVYY CFQGSHVPWT FGGGTKLEIK *ssggggsggg*

*gggssrss*EV KLVESGGDLV TPGGSLKVSC AASGLTFSDS AMSWVRLTPE

KRLEWVASIS TGGATYYPDG LKGRFTISRD DARNILFLQM NSLRSEDTAM

YYCTRRGVSS GNLFTYWGQG TLVTVSAAKT TPPSVTSGQA GQ

SEQ ID NO: 54 (a fusion of SEQ ID NOs: 44, 47 and 5):
IQEEFKMKKT AIAIAVALAG FATVAQAADV LMTQTPLSLP VSLGDQASIS

CRSSQSILNS NGNTYLEWYL QKPGQSPKLL IYKVSNRFSG VPDRFSGSGS

GTDFTLKISR VEAEDLGVYY CFQGSHVPWT FGGGTKLEIK *ssggggsggg*

*gggssrss*EV KLVESGGDLV TPGGSLKVSC AASGLTFSDS AMSWVRLTPE

KRLEWVASIS TGGATYYPDG LKGRFTISRD DARNILFLQM NSLRSEDTAM

YYCTRRGVSS GNLFTYWGQG TLVTVSAHHH HHH

SEQ ID NO:55 (a fusion of SEQ ID NOs: 44, 47 and 6):
IQEEFKMKKT AIAIAVALAG FATVAQAADV LMTQTPLSLP VSLGDQASIS

CRSSQSILNS NGNTYLEWYL QKPGQSPKLL IYKVSNRFSG VPDRFSGSGS

GTDFTLKISR VEAEDLGVYY CFQGSHVPWT FGGGTKLEIK *ssggggsggg*

*gggssrss*EV KLVESGGDLV TPGGSLKVSC AASGLTFSDS AMSWVRLTPE

KRLEWVASIS TGGATYYPDG LKGRFTISRD DARNILFLQM NSLRSEDTAM

YYCTRRGVSS GNLFTYWGQG TLVTVSAGAY PYDVPDYAS

SEQ ID NO: 56 (a fusion of SEQ ID NOs: 44, 47 and 46):
IQEEFKMKKT AIAIAVALAG FATVAQAADV LMTQTPLSLP VSLGDQASIS

CRSSQSILNS NGNTYLEWYL QKPGQSPKLL IYKVSNRFSG VPDRFSGSGS

GTDFTLKISR VEAEDLGVYY CFQGSHVPWT FGGGTKLEIK *ssggggsggg*

*ssggggsg*EV KLVESGGDLV TPGGSLKVSC AASGLTFSDS AMSWVRLTPE

KRLEWVASIS TGGATYYPDG LKGRFTISRD DARNILFLQM NSLRSEDTAM

YYCTRRGVSS GNLFTYWGQG TLVTVSAAKT TPPSVTSGQA GQHHHHHGA

YPYDVPDYAS

2. scFv Molecules Generated from Antibody 1G11A10

The complete sequence of an exemplary scFv molecule generated from Antibody 1G11A10 is (SEQ ID NO:57) (CDR residues are underlined):

DVLMTQTPLS LPVSLGDQAS ISC<u>RSSQSII</u> <u>NSNGNTYLEW</u>

YLQKPGQSPK LLIY<u>KVSNRF</u> <u>S</u>GVPDRFSGS GSGTDFTLKI

SRVETEDLGI YYC<u>FQGSHVP</u> <u>WT</u>FGGGTKLE IK*ssggggsg*

*gggggssrss* EVKLVESGGG LMKPGGSLKL SCAASGFTFS

<u>SYAMS</u>WVRQS PEKRLEWVA<u>S</u> <u>ISSGGQTYSP</u> <u>DSVKG</u>RFTIS

-continued
RDNARNILYL QMRNLRSEDT AMYYCAS<u>RGD</u> PTMTATLFVY

WGQGTLVTVS wherein amino acid residues 1-112 are the amino acid residues of the Light Chain Variable Domain of Antibody 1G11A10 (SEQ ID NO:16), amino acid residues 113-130 are the amino acid residues of the linker (SEQ ID NO:4) (shown in lowercase italics), and amino acid residues 131-250 are the amino acid residues of the Heavy Chain Variable Domain of Antibody 1G11A10 (SEQ ID NO:20).

Thus, in preferred embodiments, such scFv fusion proteins will comprise the amino acid sequence of any of SEQ ID NOs:58-66 (in which the N-terminal and/or C-Terminal peptide portions of the ScFv fusion are underlined):

SEQ ID NO: 58 (a fusion of SEQ ID NOs: 44 and 57)
IQEEFKMKKT AIAIAVALAG FATVAQAADV LMTQTPLSLP VSLGDQASIS

CRSSQSIINS NGNTYLEWYL QKPGQSPKLL IYKVSNRFSG VPDRFSGSGS

GTDFTLKISR VETEDLGIYY CFQGSHVPWT FGGGTKLEIK *ssggggsggg*

*gggssrss*EV KLVESGGGLM KPGGSLKLSC AASGFTFSSY AMSWVRQSPE

KRLEWVASIS SGGQTYSPDS VKGRFTISRD NARNILYLQM RNLRSEDTAM

YYCASRGDPT MTATLFVYWG QGTLVTVS

SEQ ID NO: 59 (a fusion of SEQ ID NOs: 57 and 45):
DVLMTQTPLS LPVSLGDQAS ISCRSSQSII NSNGNTYLEW YLQKPGQSPK

LLIYKVSNRF SGVPDRFSGS GSGTDFTLKI SRVETEDLGI YYCFQGSHVP

WTFGGGTKLE IK*ssggggsg ggggssrss* EVKLVESGGG LMKPGGSLKL

SCAASGFTFS SYAMSWVRQS PEKRLEWVAS ISSGGQTYSP DSVKGRFTIS

RDNARNILYL QMRNLRSEDT AMYYCASRGD PTMTATLFVY WGQGTLVTVS

AKTTPPSVTS GQAGQ

SEQ ID NO: 60 (a fusion of SEQ ID NOs: 57 and 5):
DVLMTQTPLS LPVSLGDQAS ISCRSSQSII NSNGNTYLEW YLQKPGQSPK

LLIYKVSNRF SGVPDRFSGS GSGTDFTLKI SRVETEDLGI YYCFQGSHVP

WTFGGGTKLE IK*ssggggsg ggggssrss* EVKLVESGGG LMKPGGSLKL

SCAASGFTFS SYAMSWVRQS PEKRLEWVAS ISSGGQTYSP DSVKGRFTIS

RDNARNILYL QMRNLRSEDT AMYYCASRGD PTMTATLFVY WGQGTLVTVS

HHHHHH

SEQ ID NO: 61 (a fusion of SEQ ID NOs: 57 and 6):
DVLMTQTPLS LPVSLGDQAS ISCRSSQSII NSNGNTYLEW YLQKPGQSPK

LLIYKVSNRF SGVPDRFSGS GSGTDFTLKI SRVETEDLGI YYCFQGSHVP

WTFGGGTKLE IK*ssggggsg gggggssrss* EVKLVESGGG LMKPGGSLKL

SCAASGFTFS SYAMSWVRQS PEKRLEWVAS ISSGGQTYSP DSVKGRFTIS

RDNARNILYL QMRNLRSEDT AMYYCASRGD PTMTATLFVY WGQGTLVTVS

GAYPYDVPDY AS

SEQ ID NO: 62 (a fusion of SEQ ID NOs: 57 and 46):
DVLMTQTPLS LPVSLGDQAS ISCRSSQSII NSNGNTYLEW YLQKPGQSPK

LLIYKVSNRF SGVPDRFSGS GSGTDFTLKI SRVETEDLGI YYCFQGSHVP

WTFGGGTKLE IK*ssggggsg gggggssrss* EVKLVESGGG LMKPGGSLKL

SCAASGFTFS SYAMSWVRQS PEKRLEWVAS ISSGGQTYSP DSVKGRFTIS

RDNARNILYL QMRNLRSEDT AMYYCASRGD PTMTATLFVY WGQGTLVTVS

AKTTPPSVTS GQAGQHHHHH HGAYPYDVPD YAS

SEQ ID NO: 63 (a fusion of SEQ ID NOs: 44, 57 and 45):
IQEEFKMKKT AIAIAVALAG FATVAQAADV LMTQTPLSLP VSLGDQASIS

CRSSQSIINS NGNTYLEWYL QKPGQSPKLL IYKVSNRFSG VPDRFSGSGS

GTDFTLKISR VETEDLGIYY CFQGSHVPWT FGGGTKLEIK *ssggggsggg*

*gggssrss*EV KLVESGGGLM KPGGSLKLSC AASGFTFSSY AMSWVRQSPE

KRLEWVASIS SGGQTYSPDS VKGRFTISRD NARNILYLQM RNLRSEDTAM

YYCASRGDPT MTATLFVYWG QGTLVTVSAK TTPPSVTSGQ AGQ

SEQ ID NO: 64 (a fusion of SEQ ID NOs: 44, 57 and 5):
IQEEFKMKKT AIAIAVALAG FATVAQAADV LMTQTPLSLP VSLGDQASIS

CRSSQSIINS NGNTYLEWYL QKPGQSPKLL IYKVSNRFSG VPDRFSGSGS

GTDFTLKISR VETEDLGIYY CFQGSHVPWT FGGGTKLEIK *ssggggsggg*

*gggssrss*EV KLVESGGGLM KPGGSLKLSC AASGFTFSSY AMSWVRQSPE

KRLEWVASIS SGGQTYSPDS VKGRFTISRD NARNILYLQM RNLRSEDTAM

YYCASRGDPT MTATLFVYWG QGTLVTVSHH HHHH

SEQ ID NO: 65 (a fusion of SEQ ID NOs: 44, 57 and 6):
IQEEFKMKKT AIAIAVALAG FATVAQAADV LMTQTPLSLP VSLGDQASIS

CRSSQSIINS NGNTYLEWYL QKPGQSPKLL IYKVSNRFSG VPDRFSGSGS

GTDFTLKISR VETEDLGIYY CFQGSHVPWT FGGGTKLEIK *ssggggsggg*

*gggssrss*EV KLVESGGGLM KPGGSLKLSC AASGFTFSSY AMSWVRQSPE

KRLEWVASIS SGGQTYSPDS VKGRFTISRD NARNILYLQM RNLRSEDTAM

YYCASRGDPT MTATLFVYWG QGTLVTVSGA YPYDVPDYAS

SEQ ID NO: 66 (a fusion of SEQ ID NOs: 44, 57 and 46):
IQEEFKMKKT AIAIAVALAG FATVAQAADV LMTQTPLSLP VSLGDQASIS

CRSSQSIINS NGNTYLEWYL QKPGQSPKLL IYKVSNRFSG VPDRFSGSGS

GTDFTLKISR VETEDLGIYY CFQGSHVPWT FGGGTKLEIK *ssggggsggg*

*gggssrss*EV KLVESGGGLM KPGGSLKLSC AASGFTFSSY AMSWVRQSPE

KRLEWVASIS SGGQTYSPDS VKGRFTISRD NARNILYLQM RNLRSEDTAM

YYCASRGDPT MTATLFVYWG QGTLVTVSAK TTPPSVTSGQ AGQHHHHHHG

AYPYDVPDYA S

3. scFv Molecules Generated from Antibody 5B3C11 a. scFv Molecules Generated from Light Chain VL1 of Antibody 5B3C11

The complete sequence of an exemplary scFv molecule generated from Antibody 5B3C11 using the VL1 Light Chain Variable Domain) is (SEQ ID NO:67) (CDR residues are underlined):

```
DVLMTQTPLS LPVSLGDQAS ISCRSNQSIL HSNGNTYLDW

YLQKPGQSPK LLIYKVSNRF SGVPDRFSGS GSGTDFTLRI

SRVEAEDLGV YYCFQGSHIP WTFGGGTKLE IKssggggsg ggggssrss  EVQLVESGGG LVKPGGSLKL SCAASGFTFS

NYALSWVRQT PEKRLEWVAS ISSGGNTYYP DSVKGRFTIS

RDNARNILYL QMSSLRSEDT AMFYCTSRGD TTLITTLFTY

WGQGTLVTVS A
``` wherein amino acid residues 1-112 are the amino acid residues of the VL1 Light Chain Variable Domain of the Antibody 5B3C11 (SEQ ID NO:28), amino acid residues 113-130 are the amino acid residues of the linker (SEQ ID NO:4) (shown in lowercase italics), and amino acid residues 131-251 are the amino acid residues of the Heavy Chain Variable Domain of Antibody 5B3C11 (SEQ ID NO:32).

Thus, in preferred embodiments, such scFv fusion proteins will comprise the amino acid sequence of any of SEQ ID NOs:68-76 (in which the N-terminal and/or C-Terminal peptide portions of the ScFv fusion are underlined):

```
SEQ ID NO: 68 (a fusion of SEQ ID NOs: 44 and 67)
IQEEFKMKKT AIAIAVALAG FATVAQAADV LMTQTPLSLP VSLGDQASIS

CRSNQSILHS NGNTYLDWYL QKPGQSPKLL IYKVSNRFSG VPDRFSGSGS

GTDFTLRISR VEAEDLGVYY CFQGSHIPWT FGGGTKLEIK ssggggsggg gggssrssEV QLVESGGGLV KPGGSLKLSC AASGFTFSNY ALSWVRQTPE

KRLEWVASIS SGGNTYYPDS VKGRFTISRD NARNILYLQM SSLRSEDTAM

FYCTSRGDTT LITTLFTYWG QGTLVTVSA

SEQ ID NO: 69 (a fusion of SEQ ID NOs: 67 and 45):
DVLMTQTPLS LPVSLGDQAS ISCRSNQSIL HSNGNTYLDW YLQKPGQSPK

LLIYKVSNRF SGVPDRFSGS GSGTDFTLRI SRVEAEDLGV YYCFQGSHIP

WTFGGGTKLE IKssggggsg ggggssrss  EVQLVESGGG LVKPGGSLKL

SCAASGFTFS NYALSWVRQT PEKRLEWVAS ISSGGNTYYP DSVKGRFTIS

RDNARNILYL QMSSLRSEDT AMFYCTSRGD TTLITTLFTY WGQGTLVTVS

AAKTTPPSVT SGQAGQ

SEQ ID NO: 70 (a fusion of SEQ ID NOs: 67 and 5):
DVLMTQTPLS LPVSLGDQAS ISCRSNQSIL HSNGNTYLDW YLQKPGQSPK

LLIYKVSNRF SGVPDRFSGS GSGTDFTLRI SRVEAEDLGV YYCFQGSHIP

WTFGGGTKLE IKssggggsg ggggssrss  EVQLVESGGG LVKPGGSLKL

SCAASGFTFS NYALSWVRQT PEKRLEWVAS ISSGGNTYYP DSVKGRFTIS

RDNARNILYL QMSSLRSEDT AMFYCTSRGD TTLITTLFTY WGQGTLVTVS

AHHHHHH

SEQ ID NO: 71 (a fusion of SEQ ID NOs: 67 and 6):
DVLMTQTPLS LPVSLGDQAS ISCRSNQSIL HSNGNTYLDW YLQKPGQSPK

LLIYKVSNRF SGVPDRFSGS GSGTDFTLRI SRVEAEDLGV YYCFQGSHIP

WTFGGGTKLE IKssggggsg ggggssrss  EVQLVESGGG LVKPGGSLKL

SCAASGFTFS NYALSWVRQT PEKRLEWVAS ISSGGNTYYP DSVKGRFTIS

RDNARNILYL QMSSLRSEDT AMFYCTSRGD TTLITTLFTY WGQGTLVTVS

AGAYPYDVPD YAS

SEQ ID NO: 72 (a fusion of SEQ ID NOs: 67 and 46):
DVLMTQTPLS LPVSLGDQAS ISCRSNQSIL HSNGNTYLDW YLQKPGQSPK

LLIYKVSNRF SGVPDRFSGS GSGTDFTLRI SRVEAEDLGV YYCFQGSHIP

WTFGGGTKLE IKssggggsg ggggssrss  EVQLVESGGG LVKPGGSLKL
```

-continued

```
SCAASGFTFS NYALSWVRQT PEKRLEWVAS ISSGGNTYYP DSVKGRFTIS

RDNARNILYL QMSSLRSEDT AMFYCTSRGD TTLITTLFTY WGQGTLVTVS

AAKTTPPSVT SGQAGQHHHH HHGAYPYDVP DYAS

SEQ ID NO: 73 (a fusion of SEQ ID NOs: 44, 67 and 45):
IQEEFKMKKT AIAIAVALAG FATVAQAADV LMTQTPLSLP VSLGDQASIS

CRSNQSILHS NGNTYLDWYL QKPGQSPKLL IYKVSNRFSG VPDRFSGSGS

GTDFTLRISR VEAEDLGVYY CFQGSHIPWT FGGGTKLEIK *ssggggsggg*

*gggssrss*EV QLVESGGGLV KPGGSLKLSC AASGFTFSNY ALSWVRQTPE

KRLEWVASIS SGGNTYYPDS VKGRFTISRD NARNILYLQM SSLRSEDTAM

FYCTSRGDTT LITTLFTYWG QGTLVTVSAA KTTPPSVTSG QAGQ

SEQ ID NO: 74 (a fusion of SEQ ID NOs: 44, 67 and 5):
IQEEFKMKKT AIAIAVALAG FATVAQAADV LMTQTPLSLP VSLGDQASIS

CRSNQSILHS NGNTYLDWYL QKPGQSPKLL IYKVSNRFSG VPDRFSGSGS

GTDFTLRISR VEAEDLGVYY CFQGSHIPWT FGGGTKLEIK *ssggggsggg*

*gggssrss*EV QLVESGGGLV KPGGSLKLSC AASGFTFSNY ALSWVRQTPE

KRLEWVASIS SGGNTYYPDS VKGRFTISRD NARNILYLQM SSLRSEDTAM

FYCTSRGDTT LITTLFTYWG QGTLVTVSAH HHHHH

SEQ ID NO: 75 (a fusion of SEQ ID NOs: 44, 67 and 6):
IQEEFKMKKT AIAIAVALAG FATVAQAADV LMTQTPLSLP VSLGDQASIS

CRSNQSILHS NGNTYLDWYL QKPGQSPKLL IYKVSNRFSG VPDRFSGSGS

GTDFTLRISR VEAEDLGVYY CFQGSHIPWT FGGGTKLEIK *ssggggsggg*

*gggssrss*EV QLVESGGGLV KPGGSLKLSC AASGFTFSNY ALSWVRQTPE

KRLEWVASIS SGGNTYYPDS VKGRFTISRD NARNILYLQM SSLRSEDTAM

FYCTSRGDTT LITTLFTYWG QGTLVTVSAG AYPYDVPDYA S

SEQ ID NO: 76 (a fusion of SEQ ID NOs: 44, 67 and 46):
IQEEFKMKKT AIAIAVALAG FATVAQAADV LMTQTPLSLP VSLGDQASIS

CRSNQSILHS NGNTYLDWYL QKPGQSPKLL IYKVSNRFSG VPDRFSGSGS

GTDFTLRISR VEAEDLGVYY CFQGSHIPWT FGGGTKLEIK *ssggggsggg*

*gggssrss*EV QLVESGGGLV KPGGSLKLSC AASGFTFSNY ALSWVRQTPE

KRLEWVASIS SGGNTYYPDS VKGRFTISRD NARNILYLQM SSLRSEDTAM

FYCTSRGDTT LITTLFTYWG QGTLVTVSAA KTTPPSVTSG QAGQHHHHHH

GAYPYDVPDY AS
``` b. scFv Molecules Generated from Light Chain VL2 of Antibody 5B3C11

The complete sequence of an exemplary scFv molecule generated from Antibody 5B3C11 using the VL2 Light Chain Variable Domain) is (SEQ ID NO:77) (CDR residues are underlined):

```
ENVLTQSPAI MSASPGEKVT MTCRASSSVS SSYLHWYQQK

SGASPKLWIY STSNLASGVP ARFSGSGSGT SYSLTISSVE

AEDAATYYCQ QYSGYPRTFG GGTKLEIK*ss ggggsggggg*

*gssrss*EVQL VESGGGLVKP GGSLKLSCAA SGFTFSNYAL

SWVRQTPEKR LEWVASISSG GNTYYPDSVK GRFTISRDNA
```

-continued
```
RNILYLQMSS LRSEDTAMFY CTSRGDTTLI TTLFTYWGQG

TLVTVSA
``` wherein amino acid residues 1-108 are the amino acid residues of the VL2 Light Chain Variable Domain of Antibody 5B3C11 (SEQ ID NO:28), amino acid residues 109-126 are the amino acid residues of the linker (SEQ ID NO:4) (shown in lowercase italics), and amino acid residues 127-247 are the amino acid residues of the Heavy Chain Variable Domain of Antibody 5B3C11 (SEQ ID NO:32).

Thus, in preferred embodiments, such scFv fusion proteins will comprise the amino acid sequence of any of SEQ ID NOs:78-86 (in which the N-terminal and/or C-Terminal peptide portions of the ScFv fusion are underlined):

SEQ ID NO: 78 (a fusion of SEQ ID NOs: 44 and 77)
IQEEFKMKKT AIAIAVALAG FATVAQAAEN VLTQSPAIMS ASPGEKVTMT

CRASSSVSSS YLHWYQQKSG ASPKLWIYST SNLASGVPAR FSGSGSGTSY

SLTISSVEAE DAATYYCQQY SGYPRTFGGG TKLEIK*ssgg ggsgggggggs*

*srss*EVQLVE SGGGLVKPGG SLKLSCAASG FTFSNYALSW VRQTPEKRLE

WVASISSGGN TYYPDSVKGR FTISRDNARN ILYLQMSSLR SEDTAMFYCT

SRGDTTLITT LFTYWGQGTL VTVSA

SEQ ID NO: 79 (a fusion of SEQ ID NOs: 77 and 45):
ENVLTQSPAI MSASPGEKVT MTCRASSSVS SSYLHWYQQK SGASPKLWIY

STSNLASGVP ARFSGSGSGT SYSLTISSVE AEDAATYYCQ QYSGYPRTFG

GGTKLEIK*ss gggggsggggg gssrss*EVQL VESGGGLVKP GGSLKLSCAA

SGFTFSNYAL SWVRQTPEKR LEWVASISSG GNTYYPDSVK GRFTISRDNA

RNILYLQMSS LRSEDTAMFY CTSRGDTTLI TTLFTYWGQG TLVTVSAAKT

TPPSVTSGQA GQ

SEQ ID NO: 80 (a fusion of SEQ ID NOs: 77 and 5):
ENVLTQSPAI MSASPGEKVT MTCRASSSVS SSYLHWYQQK SGASPKLWIY

STSNLASGVP ARFSGSGSGT SYSLTISSVE AEDAATYYCQ QYSGYPRTFG

GGTKLEIK*ss gggggsggggg gssrss*EVQL VESGGGLVKP GGSLKLSCAA

SGFTFSNYAL SWVRQTPEKR LEWVASISSG GNTYYPDSVK GRFTISRDNA

RNILYLQMSS LRSEDTAMFY CTSRGDTTLI TTLFTYWGQG TLVTVSAHHH

HHH

SEQ ID NO: 81 (a fusion of SEQ ID NOs: 77 and 6):
ENVLTQSPAI MSASPGEKVT MTCRASSSVS SSYLHWYQQK SGASPKLWIY

STSNLASGVP ARFSGSGSGT SYSLTISSVE AEDAATYYCQ QYSGYPRTFG

GGTKLEIK*ss gggggsggggg gssrss*EVQL VESGGGLVKP GGSLKLSCAA

SGFTFSNYAL SWVRQTPEKR LEWVASISSG GNTYYPDSVK GRFTISRDNA

RNILYLQMSS LRSEDTAMFY CTSRGDTTLI TTLFTYWGQG TLVTVSAGAY

PYDVPDYAS

SEQ ID NO: 82 (a fusion of SEQ ID NOs: 77 and 46):
ENVLTQSPAI MSASPGEKVT MTCRASSSVS SSYLHWYQQK SGASPKLWIY

STSNLASGVP ARFSGSGSGT SYSLTISSVE AEDAATYYCQ QYSGYPRTFG

GGTKLEIK*ss gggggsggggg gssrss*EVQL VESGGGLVKP GGSLKLSCAA

SGFTFSNYAL SWVRQTPEKR LEWVASISSG GNTYYPDSVK GRFTISRDNA

RNILYLQMSS LRSEDTAMFY CTSRGDTTLI TTLFTYWGQG TLVTVSAKT

TPPSVTSGQA GQHHHHHGA YPYDVPDYAS

SEQ ID NO: 83 (a fusion of SEQ ID NOs: 44, 77 and 45):
IQEEFKMKKT AIAIAVALAG FATVAQAAEN VLTQSPAIMS ASPGEKVTMT

CRASSSVSSS YLHWYQQKSG ASPKLWIYST SNLASGVPAR FSGSGSGTSY

SLTISSVEAE DAATYYCQQY SGYPRTFGGG TKLEIK*ssgg ggsgggggggs*

*srss*EVQLVE SGGGLVKPGG SLKLSCAASG FTFSNYALSW VRQTPEKRLE

WVASISSGGN TYYPDSVKGR FTISRDNARN ILYLQMSSLR SEDTAMFYCT

SRGDTTLITT LFTYWGQGTL VTVSAAKTTP PSVTSGQAGQ

-continued

SEQ ID NO: 84 (a fusion of SEQ ID NOs: 44, 77 and 5):
IQEEFKMKKT AIAIAVALAG FATVAQAAEN VLTQSPAIMS ASPGEKVTMT

CRASSSVSSS YLHWYQQKSG ASPKLWIYST SNLASGVPAR FSGSGSGTSY

SLTISSVEAE DAATYYCQQY SGYPRTFGGG TKLEIK*ssgg ggsgggggs*

*srss*EVQLVE SGGGLVKPGG SLKLSCAASG FTFSNYALSW VRQTPEKRLE

WVASISSGGN TYYPDSVKGR FTISRDNARN ILYLQMSSLR SEDTAMFYCT

SRGDTTLITT LFTYWGQGTL VTVSAHHHHH H

SEQ ID NO: 85 (a fusion of SEQ ID NOs: 44, 77 and 6):
IQEEFKMKKT AQAQAVALAG FATVAQAAEN VLTQSPAIMS ASPGEKVTMT

CRASSSVSSS YLHWYQQKSG ASPKLWIYST SNLASGVPAR FSGSGSGTSY

SLTISSVEAE DAATYYCQQY SGYPRTFGGG TKLEIK*ssgg ggsgggggs*

*srss*EVQLVE SGGGLVKPGG SLKLSCAASG FTFSNYALSW VRQTPEKRLE

WVASISSGGN TYYPDSVKGR FTISRDNARN ILYLQMSSLR SEDTAMFYCT

SRGDTTLITT LFTYWGQGTL VTVSAGAYPY DVPDYAS

SEQ ID NO: 86 (a fusion of SEQ ID NOs: 44, 77 and 46):
IQEEFKMKKT AQAQAVALAG FATVAQAAEN VLTQSPAIMS ASPGEKVTMT

CRASSSVSSS YLHWYQQKSG ASPKLWIYST SNLASGVPAR FSGSGSGTSY

SLTISSVEAE DAATYYCQQY SGYPRTFGGG TKLEIK*ssgg ggsgggggs*

*srss*EVQLVE SGGGLVKPGG SLKLSCAASG FTFSNYALSW VRQTPEKRLE

WVASISSGGN TYYPDSVKGR FTISRDNARN ILYLQMSSLR SEDTAMFYCT

SRGDTTLITT LFTYWGQGTL VTVSAAKTTP PSVTSGQAGQ HHHHHHGAYP

YDVPDYAS

4. scFv Molecules Generated from Antibody 5G2A3

The complete sequence of an exemplary scFv molecule generated from Antibody 5G2A3 (or Antibody 5G2G6, which has the same sequence) is (SEQ ID NO:87) (CDR residues are underlined):

DVLMTQTPLS LPVSLGDQAS ISCRSSQSIL HRNGNTYLDW

FLLKPGQSPK LLIYKVSNRF SGVPDRFSGS GSGTDFTLKI

SRVEAEDLGV YYCFQGSHVP WTFGGGTKLE IK*ssggggsg*

*ggggssrss* EVKLVESGGG LVKPGGSLTL SCAASGFTFS

SYAMSWVRQT PEKSLEWVAS ISSGGNTFYP DTVKGRFTIS

RDNARNILYL QMSGLRSEDT AIYYCARRGD PNMITTLFGY

WGQGTLVTIS A wherein amino acid residues 1-112 are the amino acid residues of the Light Chain Variable Domain of Antibody 5G2A3 (SEQ ID NO:36), amino acid residues 113-130 are the amino acid residues of the linker (SEQ ID NO:4) (shown in lowercase italics), and amino acid residues 131-251 are the amino acid residues of the Heavy Chain Variable Domain of Antibody 5G2A3 (SEQ ID NO:40).

Thus, in preferred embodiments, such scFv fusion proteins will comprise the amino acid sequence of any of SEQ ID NOs:96-104 (in which the N-terminal and/or C-Terminal peptide portions of the ScFv fusion are underlined):

SEQ ID NO: 88 (a fusion of SEQ ID NOs: 44 and 87)
IQEEFKMKKT AIAIAVALAG FATVAQAADV LMTQTPLSLP VSLGDQASIS

CRSSQSILHR NGNTYLDWFL LKPGQSPKLL IYKVSNRFSG VPDRFSGSGS

GTDFTLKISR VEAEDLGVYY CFQGSHVPWT FGGGTKLEIK *ssggggsggg*

*gggssrss*EV KLVESGGGLV KPGGSLTLSC AASGFTFSSY AMSWVRQTPE

KSLEWVASIS SGGNTFYPDT VKGRFTISRD NARNILYLQM SGLRSEDTAI

YYCARRGDPN MITTLFGYWG QGTLVTISA

SEQ ID NO: 89 (a fusion of SEQ ID NOs: 87 and 45):
DVLMTQTPLS LPVSLGDQAS ISCRSSQSIL HRNGNTYLDW FLLKPGQSPK

LLIYKVSNRF SGVPDRFSGS GSGTDFTLKI SRVEAEDLGV YYCFQGSHVP

-continued

WTFGGGTKLE IK*ssggggsg gggggssrss* EVKLVESGGG LVKPGGSLTL

SCAASGFTFS SYAMSWVRQT PEKSLEWVAS ISSGGNTFYP DTVKGRFTIS

RDNARNILYL QMSGLRSEDT AIYYCARRGD PNMITTLFGY WGQGTLVTIS

AAKTTPPSVT SGQAGQ

SEQ ID NO: 90 (a fusion of SEQ ID NOs: 87 and 5):
DVLMTQTPLS LPVSLGDQAS ISCRSSQSIL HRNGNTYLDW FLLKPGQSPK

LLIYKVSNRF SGVPDRFSGS GSGTDFTLKI SRVEAEDLGV YYCFQGSHVP

WTFGGGTKLE IK*ssggggsg gggggssrss* EVKLVESGGG LVKPGGSLTL

SCAASGFTFS SYAMSWVRQT PEKSLEWVAS ISSGGNTFYP DTVKGRFTIS

RDNARNILYL QMSGLRSEDT AIYYCARRGD PNMITTLFGY WGQGTLVTIS

AHHHHHH

SEQ ID NO: 91 (a fusion of SEQ ID NOs: 87 and 6):
DVLMTQTPLS LPVSLGDQAS ISCRSSQSIL HRNGNTYLDW FLLKPGQSPK

LLIYKVSNRF SGVPDRFSGS GSGTDFTLKI SRVEAEDLGV YYCFQGSHVP

WTFGGGTKLE IK*ssggggsg gggggssrss* EVKLVESGGG LVKPGGSLTL

SCAASGFTFS SYAMSWVRQT PEKSLEWVAS ISSGGNTFYP DTVKGRFTIS

RDNARNILYL QMSGLRSEDT AIYYCARRGD PNMITTLFGY WGQGTLVTIS

AGAYPYDVPD YAS

SEQ ID NO: 92 (a fusion of SEQ ID NOs: 87 and 46):
DVLMTQTPLS LPVSLGDQAS ISCRSSQSIL HRNGNTYLDW FLLKPGQSPK

LLIYKVSNRF SGVPDRFSGS GSGTDFTLKI SRVEAEDLGV YYCFQGSHVP

WTFGGGTKLE IK*ssggggsg gggggssrss* EVKLVESGGG LVKPGGSLTL

SCAASGFTFS SYAMSWVRQT PEKSLEWVAS ISSGGNTFYP DTVKGRFTIS

RDNARNILYL QMSGLRSEDT AIYYCARRGD PNMITTLFGY WGQGTLVTIS

AAKTTPPSVT SGQAGQHHHH HHGAYPYDVP DYAS

SEQ ID NO: 93 (a fusion of SEQ ID NOs: 44, 87 and 45):
IQEEFKMKKT AIAIAVALAG FATVAQAADV LMTQTPLSLP VSLGDQASIS

CRSSQSILHR NGNTYLDWFL LKPGQSPKLL IYKVSNRFSG VPDRFSGSGS

GTDFTLKISR VEAEDLGVYY CFQGSHVPWT FGGGTKLEIK *ssggggsgggg*

*ggssrss*EV KLVESGGGLV KPGGSLTLSC AASGFTFSSY AMSWVRQTPE

KSLEWVASIS SGGNTFYPDT VKGRFTISRD NARNILYLQM SGLRSEDTAI

YYCARRGDPN MITTLFGYWG QGTLVTISAA KTTPPSVTSG QAGQ

SEQ ID NO: 94 (a fusion of SEQ ID NOs: 44, 87 and 5):
IQEEFKMKKT AIAIAVALAG FATVAQAADV LMTQTPLSLP VSLGDQASIS

CRSSQSILHR NGNTYLDWFL LKPGQSPKLL IYKVSNRFSG VPDRFSGSGS

GTDFTLKISR VEAEDLGVYY CFQGSHVPWT FGGGTKLEIK *ssggggsgggg*

*ggssrss*EV KLVESGGGLV KPGGSLTLSC AASGFTFSSY AMSWVRQTPE

KSLEWVASIS SGGNTFYPDT VKGRFTISRD NARNILYLQM SGLRSEDTAI

YYCARRGDPN MITTLFGYWG QGTLVTISAH HHHH

SEQ ID NO: 95 (a fusion of SEQ ID NOs: 44, 87 and 6):
IQEEFKMKKT AIAIAVALAG FATVAQAADV LMTQTPLSLP VSLGDQASIS

CRSSQSILHR NGNTYLDWFL LKPGQSPKLL IYKVSNRFSG VPDRFSGSGS

GTDFTLKISR VEAEDLGVYY CFQGSHVPWT FGGGTKLEIK *ssggggsgggg*

*ggssrss*EV KLVESGGGLV KPGGSLTLSC AASGFTFSSY AMSWVRQTPE

```
                            -continued
KSLEWVASIS SGGNTFYPDT VKGRFTISRD NARNILYLQM SGLRSEDTAI

YYCARRGDPN MITTLFGYWG QGTLVTISAG AYPYDVPDYA S

SEQ ID NO: 96 (a fusion of SEQ ID NOs: 44, 87 and 46):
IQEEFKMKKT AIAIAVALAG FATVAQAADV LMTQTPLSLP VSLGDQASIS

CRSSQSILHR NGNTYLDWFL LKPGQSPKLL IYKVSNRFSG VPDRFSGSGS

GTDFTLKISR VEAEDLGVYY CFQGSHVPWT FGGGTKLEIK ssggggsggg gggssrssEV KLVESGGGLV KPGGSLTLSC AASGFTFSSY AMSWVRQTPE

KSLEWVASIS SGGNTFYPDT VKGRFTISRD NARNILYLQM SGLRSEDTAI

YYCARRGDPN MITTLFGYWG QGTLVTISAA KTTPPSVTSG QAGQHHHHHH

GAYPYDVPDY AS
```

Although scFv are able to transit across the blood-brain barrier, various ancillary approaches may be used to further promote such transit (Huang, L. et al. (2013) "*Single-Chain Fragment Variable Passive Immunotherapies For Neurodegenerative Diseases*," Int. J. Mol. Sci. 14(9):19109-19127). A limited set of proteins and peptides are transported across the blood-brain barrier via receptor-mediated transcytosis (Hervé, F. et al. (2008) "*CNS Delivery Via Adsorptive Transcytosis*," AAPS J. 10(3):455-472), the three best-studied ligands being insulin, iron-transferrin and LDL-cholesterol (Bickel, U. et al. (2001) "*Delivery Of Peptides And Proteins Through The Blood-Brain Barrier*," Adv. Drug Deliv. Rev. 46:247-279; Tuma, P. L. et al. (2003) "*Transcytosis: Crossing Cellular Barriers*," Physiol. Rev. 83:871-932). Thus, transport of an scFv across the blood-brain barrier can be promoted by fusing the scFv to an antibody, or an epitope-binding fragment thereof, that is immunospecific for a receptor of such ligands (e.g., the human insulin receptor (HIR), the transferrin receptor (TfR), low density lipoprotein receptor-related proteins 1 (LRP1) and 2 (LRP2), non-toxic diphtheria toxin receptor/Heparin binding epidermal growth factor-like growth factor, etc). The resulting fusion protein can be transported across the blood-brain barrier through its binding to the receptor (Boado, R. J. et al. (2010) "*IgG-Single-Chain Fv Fusion Protein Therapeutic For Alzheimer's Disease: Expression In CHO cells And Pharmacokinetics And Brain Delivery In The Rhesus Monkey*," Biotechnol. Bioeng. 105:627-635; Jones, A. R. et al. (2007) "*Blood-Brain Barrier Transport Of Therapeutics Via Receptor-Mediation*," Pharm. Res. 24(9):1759-1771; Wang, Y. Y. et al. (2009) "*Receptor-Mediated Therapeutic Transport Across The Blood-Brain Barrier*," Immunotherapy 1(6):983-993; Lajoie, J. M. et al. (2015) "*Targeting Receptor-Mediated Transport For Delivery Of Biologics Across The Blood-Brain Barrier*," Annu. Rev. Pharmacol. Toxicol. 55:613-631; Pardridge, W. M. (2102) "*Drug Transport Across The Blood-Brain Barrier*," J. Cereb. Blood Flow Metab. 32(11):1959-1972; Bhaskar, S. et al. (2010) "*Multifunctional Nanocarriers For Diagnostics, Drug Delivery And Targeted Treatment Across Blood-Brain Barrier: Perspectives On Tracking And Neuroimaging*," Part. Fibre. Toxicol. 7:3 pp. 1-25).

The scFv may be augmented to contain a polycationic peptide that facilitates adsorptive-mediated transcytosis. Suitable polycationic peptides include hexamethylene-diamine, putrescine, spermidine and spermine (Hervé, F. et al. (2008) "*CNS Delivery Via Adsorptive Transcytosis*," AAPS J. 10(3):455-472; Kandimalla, K. K. et al. (2006) "*Physiological And Biophysical Factors That Influence Alzheimer's Disease Amyloid Plaque Targeting Of Native And Putrescine Modified Human Amyloid Beta40*," J. Pharmacol. Exp. Ther. 318:17-25). The scFv may be augmented to comprise polycationic groups via treatment that amidates some or all of its carboxylic groups (i.e., the carboxy-terminal group, or the carboxylic side chains of glutamate or aspartate residue(s) of the scFv).

Alternatively, the scFv may be augmented to contain a cell-penetrating peptide ("CPP") (Rao, K. S. et al. (2009) "*Targeting Anti-HIV Drugs To The CNS*," Expert Opin. Drug Deliv. 6(8):771-784; Mathupala, S. P. et al. (2009) "*Delivery Of Small-Interfering RNA (siRNA) To The Brain*," Expert Opin. Ther. Pat. 19(2):137-140; Hervé, F. et al. (2008) "*CNS Delivery Via Adsorptive Transcytosis*," AAPS J. 10(3):455-472). Such peptides include the HIV-1 trans-activating transcriptional activator (TAT) peptide, the Herpes Simplex Virus type-1 transcription factor (HSV VP-22) peptide, antennapedia and penetratin (Wadia, J. S. et al. (2004) "*Transducible TAT-HA Fusogenic Peptide Enhances Escape Of TAT-Fusion Proteins After Lipid Raft Macropinocytosis*," Nat. Med. 10:310-315; Richard, J. P. et al. (2003) "*Cell-Penetrating Peptides. A Reevaluation Of The Mechanism Of Cellular Uptake*," J. Biol. Chem. 278:585-590; Temsamani, J. et al. (2004) "*The Use Of Cell-Penetrating Peptides For Drug Delivery*," Drug Discov. Today 9:1012-1019).

C. Consensus CDR Sequences

Analyses of the CDRs of the identified antibodies were conducted in order to identify consensus CDR sequences and likely variant CDR sequences that would provide binding attributes similar to those of Antibody 1G10D2, Antibody 1G11A10, Antibody 5B3C11 and/or Antibody 5G2A3. Such variant CDRs were computed using Blosum62.iij analysis according to Table 1. Table 1 presents the Blosum62.iij substitution scores. The higher the score the more conservative the substitution and thus the more likely the substitution will not affect function.

The present invention permits the formation of novel antibodies and antigen-binding fragments having 1, 2, 3, 4, 5 or 6 variant CDRs. Because the methods of the present invention have identified a substantial number of distinct CDRs, the invention permits a recognition of CDR residues that are likely to be required in any variant of a particular identified CDR. Such residues are shown in boldface in Table 5 and Table 6. For those residues that are found to vary among the compared CDRs, the substitution scores of Table 1 provide a means for determining the identities of likely substitutions. For example, if a particular residue of a particular CDR is found to vary as R or S, then since R and S have a substitution score of −1, any substitution for R or S having a substitution score of −1 or greater are as likely as the observed variants (R or S) (or are more likely than R or S) to create a variant CDR having binding attributes that are sufficiently similar to those of the particular CDR to permit the variant CDR to be employed in lieu thereof so as to form a functional antibody or antigen-binding fragment. For each position, the selection of a residue having a higher substitution score is preferred over the selection of a residue having a lower substitution score.

Table 5 presents an analysis of the light chain CDRs of Antibody 1G10D2, Antibody 1G11A10, Antibody 5B3C11 and Antibody 5G2A3 and provides the consensus sequence of the observed light chain CDRs of the disclosed antibodies of the present invention.

TABLE 5

Light Chain Consensus CDRs

Light Chain CDR1

| Antibody | Variant | Sequence | SEQ ID NO |
|---|---|---|---|
| 1G10D2 | | RSS QSILN S NGNTYLE | 9 |
| 1G11A10 | | RSS QSIIN S NGNTYLE | 17 |
| 5B3C11 | 1 | RSN QSILH S NGNTYLD | 25 |
| 5G2A3 | | RSS QSILH R NGNTYLD | 37 |
| Light Chain CDR1 Consensus Sequence: | | RS$\mathbf{X_1}$QSIL$\mathbf{X_2}$$\mathbf{X_3}$NGNTYL$\mathbf{X_4}$ | 97 |

$X_1$ are substitutions of N/S or substitutions having an equal or greater substitution score (i.e., ≥+1): N or S $X_2$ are substitutions of N/H or substitutions having an equal or greater substitution score (i.e., ≥+1): N or H $X_3$ are substitutions of S/R, or substitutions having an equal or greater substitution score (i.e., ≥−1): A, R, N, Q, E, H, K, M, S, or T $X_4$ are substitutions of E/D or substitutions having an equal or greater substitution score (i.e., ≥+2): E or D Light Chain CDR2

| Antibody | Variant | Sequence | SEQ ID NO |
|---|---|---|---|
| 1G10D2 | | KVSNRFS | 10 |
| 1G11A10 | | KVSNRFS | 18 |
| 5B3C11 | 1 | KVSNRFS | 26 |
| 5G2A3 | | KVSNRFS | 38 |
| Light Chain CDR2 Consensus Sequence: | | KVSNRFS | 98 |

Light Chain CDR3

| Antibody | Variant | Sequence | SEQ ID NO |
|---|---|---|---|
| 1G10D2 | | FQGSHV PWT | 11 |
| 1G11A10 | | FQGSHV PWT | 19 |
| 5B3C11 | 1 | FQGSHI PWT | 27 |
| 5G2A3 | | FQGSHV PWT | 39 |
| Light Chain CDR3 Consensus Sequence: | | FQGSH$\mathbf{X_1}$PWT | 99 |

$X_1$ are substitutions of V/I or substitutions having an equal or greater substitution score (i.e., ≥+3): V or I Table 6 presents an analysis of the heavy chain CDRs of Antibody 1G10D2, Antibody 1G11A10, Antibody 5B3C11 and Antibody 5G2A3 and provides the consensus sequence of the observed heavy chain CDRs of the disclosed antibodies of the present invention.

TABLE 6

Heavy Chain Consensus CDRs

Heavy Chain CDR1

| Antibody | Variant | Sequence | SEQ ID NO |
|---|---|---|---|
| 1G10D2 | | D S AM S | 13 |
| 1G11A10 | | S Y AM S | 21 |
| 5B3C11 | 1 | N Y AL S | 33 |
| 5G2A3 | | S Y AM S | 41 |
| Heavy Chain CDR1 Consensus Sequence: | | $X_1X_2AX_3S$ | 100 |

$X_1$ are substitutions of D/N/S or substitutions having an equal or greater substitution score (i.e., ≥0): N, D, Q, E or S $X_2$ are substitutions of S/Y or substitutions having an equal or greater substitution score (i.e., ≥-2): A, R, N, D, C, Q, E, G, H, I, L, K, M, F, S, T, Y or V $X_3$ are substitutions of L/M, or substitutions having an equal or greater substitution score (i. e., ≥+2): L or M

Heavy Chain CDR2

| Antibody | Variant | Sequence | SEQ ID NO |
|---|---|---|---|
| 1G10D2 | | SIST GGA TY Y PDG L KG | 14 |
| 1G11A10 | | SISS GGQ TY S PDS V KG | 22 |
| 5B3C11 | 1 | SISS GGN TY Y PDS V KG | 34 |
| 5G2A3 | | SISS GGN TF Y PDT V KG | 42 |
| Heavy Chain CDR2 Consensus Sequence: | | $SISX_1GGX_2TX_3X_4PDX_5X_6KG$ | 101 |

$X_1$ are substitutions of S/T or substitutions having an equal or greater substitution score (i.e., ≥+1): S or T $X_2$ are substitutions of A/Q/N or substitutions having an equal or greater substitution score (i. e., ≥-2): A, R, N, D, Q, E, G, H, K, M, P, S, T or Y $X_3$ are substitutions of F/Y or substitutions having an equal or greater substitution score (i.e., ≥+3): F or Y $X_4$ are substitutions of S/Y or substitutions having an equal or greater substitution score (i.e., ≥-2): A, R, N, C, Q, E, H, I, L, K, M, F, S, T, Y or V $X_5$ are substitutions of G/S/T or substitutions having an equal or greater substitution score (i.e., ≥-2): A, R, N, D, Q, E, G, H, I, L, K, P, S or T $X_6$ are substitutions of L/V or substitutions having an equal or greater substitution score (i.e., ≥+1): I, L, M or V

Heavy Chain CDR3

| Antibody | Variant | Sequence | SEQ ID NO |
|---|---|---|---|
| 1G10D2 | | RG V S S G N LFT Y | 15 |
| 1G11A10 | | RGD P T M T A T LFV Y | 23 |
| 5B3C11 | | RGD T T L I T T LFT Y | 35 |
| 5G2A3 | | RGD P N M I T T LFG Y | 43 |
| Heavy Chain CDR3 Consensus Sequence: | | $RGX_1X_2X_3X_4X_5X_6X_7LFX_8Y$ | 102 |

$X_1$ is absent or D $X_2$ is absent or are substitutions of P/T or substitutions having an equal or greater substitution score (i.e., ≥-1): A, D, Q, E, K, P, S or T TABLE 6-continued Heavy Chain Consensus CDRs $X_3$ are substitutions of V/T/N or substitutions having an equal or greater substitution score (i.e., ≥-3):
A, R, N, D, C, Q, E, G, H, I, L, K, M, F, P, S, T, Y or V $X_4$ are substitutions of S/L/M or substitutions having an equal or greater substitution score (i.e., ≥-2):
A, R, C, I, L, K, M, F, S, T, Y or V $X_5$ are substitutions of S/T/I or substitutions having an equal or greater substitution score (i.e., ≥-2):
A, C, I, L, M, F, S, T, Y or V $X_6$ are substitutions of G/A/T or substitutions having an equal or greater substitution score (i.e., ≥-2):
A, R, N, D, Q, E, G, H, I, L, K, P, S or T $X_7$ are substitutions of N/T or substitutions having an equal or greater substitution score (i.e., ≥0):
N, S or T $X_8$ are substitutions of T/V/G or substitutions having an equal or greater substitution score (i.e., ≥-3):
A, R, N, D, C, Q, E, G, H, K, M, F, P, S, T, W, Y or V Thus, in addition to antibodies and antigen-binding fragments thereof that possess the CDRs of Antibody 1G10D2, Antibody 1G11A10, Antibody 5B3C11 or Antibody 5G2A3, the invention additionally provides antibodies and antigen-binding fragments thereof that possess CDRs having amino acid sequences deduced from such light and/or heavy chain consensus CDR sequences.

Although scFv are able to transit across the blood-brain barrier, various ancillary approaches may be used to further promote such transit (Huang, L. et al. (2013) "*Single-Chain Fragment Variable Passive Immunotherapies For Neurodegenerative Diseases*," Int. J. Mol. Sci. 14(9):19109-19127). A limited set of proteins and peptides are transported across the blood-brain barrier via receptor-mediated transcytosis (Hervé, F. et al. (2008) "*CNS Delivery Via Adsorptive Transcytosis*," AAPS J. 10(3):455-472), the three best-studied ligands being insulin, iron-transferrin and LDL-cholesterol (Bickel, U. et al. (2001) "*Delivery Of Peptides And Proteins Through The Blood-Brain Barrier*," Adv. Drug Deliv. Rev. 46:247-279; Tuma, P. L. et al. (2003) "*Transcytosis: Crossing Cellular Barriers*," Physiol. Rev. 83:871-932). Thus, transport of an scFv across the blood-brain barrier can be promoted by fusing the scFv to an antibody, or an epitope-binding fragment thereof, that is immunospecific for a receptor of such ligands (e.g., the human insulin receptor (HIR), the transferrin receptor (TfR), low density lipoprotein receptor-related proteins 1 (LRP1) and 2 (LRP2), non-toxic diphtheria toxin receptor/Heparin binding epidermal growth factor-like growth factor, etc). The resulting fusion protein can be transported across the blood-brain barrier through its binding to the receptor (Boado, R. J. et al. (2010) "*IgG-Single-Chain Fv Fusion Protein Therapeutic For Alzheimer's Disease: Expression In CHO cells And Pharmacokinetics And Brain Delivery In The Rhesus Monkey*," Biotechnol. Bioeng. 105:627-635; Jones, A. R. et al. (2007) "*Blood-Brain Barrier Transport Of Therapeutics Via Receptor-Mediation*," Pharm. Res. 24(9):1759-1771; Wang, Y. Y. et al. (2009) "*Receptor-Mediated Therapeutic Transport Across The Blood-Brain Barrier*," Immunotherapy 1(6):983-993; Lajoie, J. M. et al. (2015) "*Targeting Receptor-Mediated Transport For Delivery Of Biologics Across The Blood-Brain Barrier*," Annu. Rev. Pharmacol. Toxicol. 55:613-631; Pardridge, W. M. (2102) "*Drug Transport Across The Blood-Brain Barrier*," J. Cereb. Blood Flow Metab. 32(11):1959-1972; Bhaskar, S. et al. (2010) "*Multifunctional Nanocarriers For Diagnostics, Drug Delivery And Targeted Treatment Across Blood-Brain Barrier: Perspectives On Tracking And Neuroimaging*," Part. Fibre. Toxicol. 7:3 pp. 1-25).

The scFv may be augmented to contain a polycationic peptide that facilitates adsorptive-mediated transcytosis. Suitable polycationic peptides include hexamethylene-diamine, putrescine, spermidine and spermine (Hervé, F. et al. (2008) "*CNS Delivery Via Adsorptive Transcytosis*," AAPS J. 10(3):455-472; Kandimalla, K. K. et al. (2006) "*Physiological And Biophysical Factors That Influence Alzheimer's Disease Amyloid Plaque Targeting Of Native And Putrescine Modified Human Amyloid Beta40*," J. Pharmacol. Exp. Ther. 318:17-25). The scFv may be augmented to comprise polycationic groups via treatment that amidates some or all of its carboxylic groups (i.e., the carboxy-terminal group, or the carboxylic side chains of glutamate or aspartate residue(s) of the scFv).

Alternatively, the scFv may be augmented to contain a cell-penetrating peptide ("CPP") (Rao, K. S. et al. (2009) "*Targeting Anti-HIV Drugs To The CNS*," Expert Opin. Drug Deliv. 6(8):771-784; Mathupala, S. P. et al. (2009) "*Delivery Of Small-Interfering RNA (siRNA) To The Brain*," Expert Opin. Ther. Pat. 19(2):137-140; Hervé, F. et al. (2008) "*CNS Delivery Via Adsorptive Transcytosis*," AAPS J. 10(3):455-472). Such peptides include the HIV-1 trans-activating transcriptional activator (TAT) peptide, the Herpes Simplex Virus type-1 transcription factor (HSV VP-22) peptide, antennapedia and penetratin (Wadia, J. S. et al. (2004) "*Transducible TAT-HA Fusogenic Peptide Enhances Escape Of TAT-Fusion Proteins After Lipid Raft Macropinocytosis*," Nat. Med. 10:310-315; Richard, J. P. et al. (2003) "*Cell-Penetrating Peptides. A Reevaluation Of The Mechanism Of Cellular Uptake*," J. Biol. Chem. 278:585-590; Temsamani, J. et al. (2004) "*The Use Of Cell-Penetrating Peptides For Drug Delivery*," Drug Discov. Today 9:1012-1019).

III. Uses of the Antibodies and Antibody Fragments of the Present Invention

The present invention relates to the use of antibody-based molecules that are immunospecific for the Asp421 Epitope to diagnose and/or treat Alzheimer's disease or tauopathy in a subject patient. With respect to such diagnostic utility, such uses may involve detecting, in the subject (i.e., in vivo), the presence of a pathological Tau conformer using, for example, Antibody 1G10D2, Antibody 1G11A10, Antibody 5B3C11 or Antibody 5G2A3, or an Asp421 Epitope-binding fragment thereof (and especially an scFv fragment thereof), that has preferably been detectably labeled (such molecules being collectively referred to herein as the diagnostic molecules of the present invention). Alternatively, such uses may involve detecting the presence of a pathological Tau conformer ex vivo (e.g., in a biopsy sample, or post-mortem) using the diagnostic molecules of the present invention.

In one embodiment, the Asp421 Epitope-specific antibody-based molecules of the present invention may be humanized antibodies.

With respect to the therapeutic utility of the Asp421 Epitope-specific antibody-based molecules of the present invention, such utility may involve the administration of a therapeutically effective amount of such an antibody-based molecule (e.g., Antibody 1G10D2, Antibody 1G11A10, Antibody 5B3C11, Antibody 5G2A3 or Antibody 5G2G6, and more particularly, an scFv fragment thereof) to a patient having one or more symptoms of Alzheimer's disease or such tauopathy, and thus in need of such therapy, or it may involve the administration of a prophylactically effective amount of such antibody-based molecules to a patient not exhibiting such symptoms, or exhibiting symptoms of mild dementia or pre-tauopathy that is indicative of incipient Alzheimer's disease or tauopathy, such molecules being collectively referred to herein as the therapeutic molecules of the present invention.

The Asp421 Epitope-specific antibody-based molecules of the present invention may be used in concert for diagnostic and/or therapeutic purposes with antibodies and antibody-based molecules having immunospecificity for epitopes other than the Asp421 Epitope.

IV. Production of the Tau-Binding Molecules of the Present Invention

The Tau-binding molecules of the present invention are preferably produced via the recombinant expression of a nucleic acid molecule that encodes their constituent polypeptide chain(s). The invention thus accordingly also relates to an expression vector encoding such one or more polypeptide chains of an antibody of the invention or a fragment thereof.

An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-Tau antibody-encoding nucleic acid is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski et al., MoI Ther 3, 793-800 (2001)), or as a precipitated nucleic acid vector construct, such as a CaPO4-precipitated construct (as described in, for instance, WO 00/46147, Benvenisty and Reshef, PNAS USA 83, 9551-55 (1986), Wigler et al., Cell 14, 725 (1978), and Coraro and Pearson, Somatic Cell Genetics 2, 603 (1981)). Such nucleic acid vectors and the usage thereof are well-known in the art (see for instance U.S. Pat. Nos. 5,589,466 and 5,973,972).

In one embodiment, the vector is suitable for the expression of an Asp421 Epitope-specific antibody-based molecule of the present invention in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison, Wis.) and the like). An expression vector may also or alternatively be a vector suitable for expression of such antibody-based molecules in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. CURRENT PROTOCOLS IN MOLECULAR BIOLOGY, Greene Publishing and Wiley InterScience New York (1987), and Grant et al., Methods in Enzymol 153, 516-544 (1987)).

In an expression vector of the invention, a nucleic acid molecule encoding an Asp421 Epitope-specific antibody-based molecule of the present invention may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In an even further aspect, the invention relates to a recombinant eukaryotic or prokaryotic host cell, such as a transfectoma, that produces an Asp421 Epitope-specific antibody-based molecule of the present invention. Examples of host cells include yeast, bacteria, and mammalian cells, such as CHO or HEK cells. For example, in one embodiment, the present invention provides a cell comprising a nucleic acid stably integrated into the cellular genome that comprises a sequence coding for expression of an Asp421 Epitope-specific antibody-based molecule of the present invention. In another embodiment, the present invention provides a cell comprising a non-integrated nucleic acid, such as a plasmid, cosmid, phagemid, or linear expression element, that which comprises a sequence coding for expression of an Asp421 Epitope-specific antibody-based molecule of the present invention.

In a further aspect, the invention relates to a method for producing an Asp421 Epitope-specific antibody-based molecule of the present invention, said method comprising the steps of a) culturing a hybridoma or a host cell of the invention as described herein above, and b) purifying the antibody of the invention from the culture media.

In general, an Asp421 Epitope-specific antibody-based molecule of the present invention may be modified by inclusion of any suitable number of modified amino acids and/or associations with such conjugated substituents. Suitability in this context is generally determined by the ability to at least substantially retain the immunospecificity for the Asp421 Epitope associated with the non-derivatized parent anti-Tau antibody. The presence of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N—X—S/T motifs during expression in mammalian cells) or modified by synthetic means. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On CD-Rom, Humana Press, Totowa, N.J. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

As indicated above, when it is desired to increase the half-life of an administered therapeutic molecule of the present invention, such molecules may be formed to comprise carbohydrate moieties, such as polyoxyethylated polyols or polyethylene glycol (PEG) (e.g., a PEG with a molecular weight of between about 1,000 and about 40,000, such as between about 2,000 and about 20,000, e.g., about 3,000-12,000 g/mol) (Moosmann, A. et al. (2014) "*Purification Of PEGylated Proteins, With The Example Of PEGylated Lysozyme and PEGylated scFv*," Methods Mol. Biol. 1129:527-538; Jevsevar, S. et al. (2010) "*PEGylation Of Therapeutic Proteins*," Biotechnol. J. 5:113-228), or through glycosylation or by adding or associating proteins such as human serum albumin (Müller, M. R. et al. (2012) "*Improving The Pharmacokinetic Properties Of Biologics By Fusion To An Anti HSA Shark VNAR Domain*," MAbs. 4(6):673-685; Stork, R. et al. (2008) "*N-Glycosylation As Novel Strategy To Improve Pharmacokinetic Properties Of Bispecific Single-Chain Diabodies*," J. Biol. Chem. 283:7804-7812; Alt, M. et al. (1999) "*Novel Tetravalent And Bispecific IgG-like Antibody Molecules Combining Single-Chain Diabodies With The Immunoglobulin Gamma*1 *Fc or CH*3 *Region*," FEBS Lett. 454:90-94; Peters T. et al. (1985) "*Serum Albumin*," Adv. Protein Chem. 37:161-245). Illustrative polymers and methods to attach them to peptides, are known, (see, for example, U.S. Pat. Nos. 4,766,106; 4,179,337; 4,495,285 and 4,609,546).

V. Pharmaceutical Compositions of the Present Invention

The Asp421 Epitope-specific antibody-based molecules of the present invention are advantageously administered as pharmaceutical compositions comprising an active therapeutic agent and one or more of a variety of other pharmaceutically acceptable components. See REMINGTON: THE SCIENCE AND PRACTICE OF PHARMACY (21$^{st}$ Edition) (2005) (Troy, D. B. et al. (Eds.) Lippincott Williams & Wilkins (Publs.), Baltimore Md.), which is hereby incorporated by reference in its entirety. The preferred form depends on the intended mode of administration and therapeutic application. The compositions can also include, depending on the formulation desired, pharmaceutically acceptable, non-toxic carriers, excipients, diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition, and which are vehicles commonly used to formulate pharmaceutical compositions for animal or human administration. The diluent is selected to not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. Examples of suitable aqueous and non-aqueous carriers which may be employed in the pharmaceutical compositions of the present invention include water, saline, phosphate-buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well-known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Suitability for carriers and other components of pharmaceutical compositions is determined based on the lack of significant negative impact on the desired biological properties of the chosen compound or pharmaceutical composition of the present invention (e.g., less than a substantial impact (e.g., 10% or less relative inhibition, 5% or less relative inhibition, etc.)) on antigen binding.

The pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well-known in the art. Methods for the preparation of such formulations are generally known to those skilled in the art. See, e.g., SUSTAINED AND CONTROLLED RELEASE DRUG DELIVERY SYSTEMS, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

For parenteral administration, agents of the present invention are typically formulated as injectable dosages of a solution or suspension of the substance in a physiologically acceptable diluent with a pharmaceutical carrier that can be a sterile liquid such as water, oil, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin. Peanut oil, soybean oil, and mineral oil are all examples of useful materials. In general, glycols, such as propylene glycol or polyethylene glycol, are preferred liquid carriers, particularly for injectable solutions. Agents of the invention can be administered in the form of a depot injection or implant preparation which can be formulated in such a manner as to permit a sustained release of the active ingredient. An exemplary composition comprises an scFv at about 5 mg/mL, formulated in aqueous buffer consisting of 50 mM L-histidine, 150 mM NaCl, adjusted to pH 6.0 with HCl.

Typically, compositions are thus prepared as injectables, either as liquid solutions or suspensions; solid forms suitable for solution in, or suspension in, liquid vehicles prior to injection can also be prepared. The preparation also can be emulsified or encapsulated in liposomes or micro particles, such as polylactide, polyglycolide, or copolymer, for enhanced adjuvant effect (Langer, et al., Science 249:1527 (1990); Hanes, et al., Advanced Drug Delivery Reviews 28:97-119 (1997), which are hereby incorporated by reference in their entirety). Additional formulations suitable for other modes of administration include oral, intranasal, and pulmonary formulations, suppositories, and transdermal applications.

VI. Administration of the Pharmaceutical Compositions of the Present Invention

The molecules of the present invention can be administered by parenteral, topical, oral or intranasal means for prophylactic and/or therapeutic treatment. Intramuscular injection (for example, into the arm or leg muscles) and intravenous infusion are preferred methods of administration of the molecules of the present invention. In some methods, such molecules are administered as a sustained release composition or device, such as a Medipad™ device (Elan Pharm. Technologies, Dublin, Ireland). In some methods, the molecules of the present invention are injected directly into a particular tissue where deposits have accumulated, for example intracranial injection.

In one embodiment, a pharmaceutical composition of the present invention is administered parenterally. The phrases "parenteral administration" and "administered parenterally" as used herein denote modes of administration other than enteral and topical administration, usually by injection, and include epidermal, intravenous, intramuscular, intraarterial, intrathecal, intracapsular, intracranial, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection, subcutaneous and infusion. In one embodiment that pharmaceutical composition is administered by intravenous or subcutaneous injection or infusion.

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presented during development of the disease.

In therapeutic applications (i.e., in applications involving a patient who has been diagnosed as having Alzheimer's disease or other tauopathy) the therapeutic molecules of the present invention are administered to such patient in an amount sufficient to cure, treat, or at least partially arrest, the symptoms of the disease (as adduced by biochemical, histologic and/or behavioral assessment), including its complications and intermediate pathological phenotypes in development of the disease. In some embodiments, the administration of the therapeutic molecules of the present invention reduces or eliminates mild cognitive impairment in patients that have not yet developed characteristic Alzheimer's pathology.

Effective doses of the provided therapeutic molecules of the present invention, for the treatment of the above-described conditions may vary depending upon many different factors, including means of administration, target site, physiological state of the patient, other medications administered, and whether treatment is prophylactic or therapeutic. Treatment dosages are typically titrated to optimize their safety and efficacy. On any given day that a dosage is given, the dosage may range from about 0.0001 to about 100 mg/kg, and more usually from about 0.01 to about 10 mg/kg, of the host body weight. For example, dosages can be 1 mg/kg body weight or 10 mg/kg body weight or within the range of 1-10 mg/kg body weight. Exemplary dosages thus include: from about 0.1 to about 10 mg/kg/body weight, from about 0.1 to about 5 mg/kg/body weight, from about 0.1 to about 2 mg/kg/body weight, from about 0.1 to about 1 mg/kg/body weight, for instance about 0.15 mg/kg/body weight, about 0.2 mg/kg/body weight, about 0.5 mg/kg/body weight, about 1 mg/kg/body weight, about 1.5 mg/kg/body weight, about 2 mg/kg/body weight, about 5 mg/kg/body weight, or about 10 mg/kg/body weight A physician or veterinarian having ordinary skill in the art may readily determine and prescribe the effective amount of the pharmaceutical composition required. For example, the physician or veterinarian could start doses of the anti-Tau antibody or fragment employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

An exemplary treatment regime entails administration once per every two weeks or once a month or once every 3 to 6 months. In some methods, one, two or more antibodies (or epitope-binding fragments thereof) will be administered in conjunction with the administration of the therapeutic molecules of the present invention, in which case the dosage of each such administered molecule falls within the ranges indicated.

The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered such therapeutic molecule using a prophylactic dosage regime.

For therapeutic purposes, the molecules of the present invention are usually administered on multiple occasions. Intervals between single dosages (e.g., a bolus or infusion) can be weekly, monthly, or yearly. In some methods, dosage is adjusted to achieve a plasma concentration of 1-1000 μg/mL and in some methods 25-300 μg/mL. Alternatively, the therapeutic molecules of the present invention can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and non-human antibodies. scFv molecules generally have short serum half-lives.

Another aspect of the present invention is a combination therapy wherein an additional antibody, or an epitope-binding fragment thereof, recognizing the Tau protein, or an immunogenic epitope thereof, is administered in combination with a therapeutic molecule of the present invention. In the case of amyloidogenic diseases such as, Alzheimer's disease and Down's syndrome, immune modulation to clear amyloid-beta (Aβ) deposits is an emerging therapy. Immunotherapies targeting Aβ have consistently resulted in cognitive improvements. It is likely that Tau and Aβ pathologies are synergistic. Therefore, a combination therapy targeting the clearance of both pathologies at the same time may be more effective than targeting each individually. In the case of Parkinson's Disease and related neurodegenerative diseases, immune modulation to clear aggregated forms of the α-synuclein protein is also an emerging therapy. A combination therapy which targets the clearance of both Tau and α-synuclein proteins simultaneously may be more effective than targeting each individually.

VII. Utility of the Tau-Binding Molecules of the Present Invention

A. Diagnostic Utility

Detecting the presence of a pathological Tau conformer in a subject using an Asp421 Epitope-specific antibody-based diagnostic molecule of the present invention can be achieved by obtaining a biological sample from the subject (e.g., blood, urine, cerebral spinal fluid), contacting the biological sample with said diagnostic antibody, and detecting binding of the diagnostic molecule to a pathological Tau protein conformer in the sample from the subject. Assays for carrying out the detection of a pathological Tau protein in a biological sample that may be readily adapted to the detection of the diagnostic molecules of the present invention are well-known in the art and include, without limitation, ELISA, immunohistochemistry, Western blot, etc.

Alternatively, detecting the presence of a pathological Tau protein conformer in a subject using an Asp421 Epitope-specific antibody-based diagnostic molecule of the present invention can be achieved using in vivo imaging techniques. In vivo imaging involves administering to the subject the diagnostic antibody having antigenic specificity for a pathological Tau peptide and detecting binding of the diagnostic antibody reagent to the pathological Tau protein conformer in vivo.

The Asp421 Epitope-specific antibody-based diagnostic molecules of the present invention can be administered by injection (e.g., intravenous injection, intracarotid injection, etc.) into the body of the patient, or directly into the brain by intracranial injection. The dosage of such molecule should be from about 0.0001 mg/kg to about 100 mg/kg, and more usually from about 0.01 mg/kg to about 5 mg/kg, of the host body weight. For example, dosages can be about 1 mg/kg body weight or about 10 mg/kg body weight or within the range of about 1-10 mg/kg.

Typically, an Asp421 Epitope-specific antibody-based diagnostic molecule of the present invention is labeled, although in some methods, the molecule may be unlabeled and a secondary labeling agent is used to bind to such molecule (coupled or conjugated either directly to the molecule or indirectly, through an intermediate (such as, for example, a linker known in the art) using techniques known in the art). The choice of label depends on the means of detection. For example, a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, is suitable for optical detection. Chemoluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin. Paramagnetic labels and radioisotopic labels can also be employed, and are preferably detected using Positron Emission Tomography (PET) or Single-Photon Emission Computed Tomography (SPECT). Radiolabels include, but are not limited to, bismuth ($^{213}$Bi) ($^{11}$C, $^{13}$C, carbon $^{14}$C) chromium ($^{51}$Cr) cobalt ($^{57}$Co, $^{60}$Co), copper ($^{64}$Cu), dysprosium ($^{165}$Dy), erbium ($^{169}$Er), fluorine ($^{18}$F), gadolinium ($^{153}$Gd, $^{159}$Gd), gallium ($^{68}$Ga, $^{67}$Ga), germanium ($^{68}$Ge), gold ($^{198}$Au), holmium ($^{166}$Ho) hydrogen ($^{3}$H), indium ($^{111}$In, $^{112}$In, $^{113}$In, $^{115}$In), iodine ($^{121}$I, $^{123}$I, $^{124}$I, $^{125}$I, $^{131}$I) iridium ($^{192}$Ir), iron ($^{59}$Fe), krypton ($^{81m}$Kr), lanthanium ($^{140}$La), lutelium ($^{177}$Lu), manganese ($^{54}$Mn), molybdenum ($^{99}$Mo), nitrogen ($^{13}$N, $^{15}$N), oxygen ($^{15}$O), palladium ($^{103}$Pd), phosphorus ($^{32}$P), potassium ($^{42}$K), praseodymium ($^{142}$Pr) promethium ($^{149}$Pm), rhenium ($^{186}$Re, $^{188}$Re), rhodium ($^{105}$Rh), rubidium ($^{81}$Rb, $^{82}$Rb), ruthenium ($^{82}$Ru, $^{97}$Ru), samarium ($^{153}$Sm), scandium ($^{47}$Sc), selenium ($^{75}$Se), sodium ($^{24}$Na), strontium ($^{85}$Sr, $^{89}$Sr, $^{92}$Sr), sulfur ($^{35}$S), technetium ($^{99}$Tc), thallium ($^{201}$Tl), tin ($^{113}$Sn, $^{117}$Sn), xenon ($^{133}$Xe), ytterbium ($^{169}$Yb, $^{175}$Yb, $^{177}$Yb), yttrium ($^{90}$Y), and zinc ($^{65}$Zn) and zirconium ($^{89}$Zr); positron emitting metals using various positron emission tomographies, and non-radioactive paramagnetic metal ions (such as paramagnetic ions of Aluminum (Al), Barium (Ba), Calcium (Ca), Cerium (Ce), Dysprosium (Dy), Erbium (Er), Europium (Eu), Gandolinium (Gd), Holmium (Ho), Iridium (Ir), Lithium (Li), Magnesium (Mg), Manganese (Mn), Molybdenum (M), Neodymium (Nd), Osmium (Os), Oxygen (O), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zr), and particularly, $Co^{+2}$, $CR^{+2}$, $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$). Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581; 4,735,210; 5,101,827; 5,102,990; RE 35,500; 5,648,471 and 5,697,902. For example, a radioisotope may be conjugated by a chloramine-T method (Lindegren, S. et al. (1998) "*Chloramine-T In High-Specific-Activity Radioiodination Of Antibodies Using N-Succinimidyl-3-(Trimethylstannyl) Benzoate As An Intermediate,*" Nucl. Med. Biol. 25(7):659-665; Kurth, M. et al. (1993) "*Site-Specific Conjugation Of A Radioiodinated Phenethylamine Derivative To A Monoclonal Antibody Results In Increased Radioactivity Localization In Tumor,*" J. Med. Chem. 36(9):1255-1261; Rea, D. W. et al. (1990) "*Site-specifically radioiodinated antibody for targeting tumors,*" Cancer Res. 50(3 Suppl):857s-861s).

Diagnosis is performed by comparing the number, size, and/or intensity of labeled pathological Tau conformers, Tau aggregates, and/or neurofibrillary tangles in a sample from the subject, or in the subject, to corresponding baseline values. The base line values can represent the mean levels in a population of non-diseased individuals. Baseline values can also represent previous levels determined in the same subject.

The diagnostic methods described above can also be used to monitor a subject's response to therapy. In this embodiment, detecting the presence of pathological Tau in a subject is determined prior to the commencement of treatment. The level of pathological Tau in the subject at this time point is used as a baseline value. At various times during the course of treatment the detection of pathological Tau protein conformers, Tau aggregates, and/or neurofibrillary tangles is repeated, and the measured values thereafter compared with the baseline values. A decrease in values relative to baseline signals a positive response to treatment. Values can also increase temporarily in biological fluids as pathological Tau is being cleared from the brain.

The present invention is further directed to a kit for performing the above-described diagnostic and monitoring methods. Typically, such kits contain the diagnostic antibody of the present invention. The kit can also include a detectable label. The diagnostic antibody itself may contain the detectable label (e.g., fluorescent molecule, biotin, etc.) which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for measuring pathological Tau protein in a biological sample, the antibodies of the kit may be supplied pre-bound to a solid phase, such as to the wells of a microtiter dish.

The presence of labeled anti-Tau antibodies or their Tau-binding fragments may be detected in vivo for diagnosis purposes. In one embodiment, such diagnosis comprises: a) administering to a subject an effective amount of such labeled molecule; b) waiting for a time interval following administration in order to allow the labeled molecule to concentrate at sites (if any) of aggregated Tau and to allow unbound labeled molecule to be cleared to a background level; c) determining a background level; and d) detecting such labeled molecule in the subject, such that detection of labeled molecule above the background level is indicative that the subject has a tauopathy, or is indicative of the severity of such tauopathy. In accordance with such embodiment, the antibody is labeled with an imaging moiety suitable for detection using a particular imaging system known to those skilled in the art. Background levels may be determined by various methods known in the art, including comparing the amount of labeled molecule detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MM), and sonography.

B. Therapeutic Utility

As indicated above, one aspect of the present invention relates to a method of preventing or treating Alzheimer's disease or other tauopathy in a subject via the administration of an effective amount of an Asp421 Epitope-specific antibody-based molecule of the present invention (especially Antibody 1G10D2, Antibody 1G11A10, Antibody 5B3C11 or Antibody 5G2A3, or an scFv fragment thereof) in an amount effective to prevent or treat such Alzheimer's disease or other tauopathy. Such administration may be provided in order to promote the clearance of Tau aggregates from the brain of a subject or may be provided in order to slow a tangle-related behavioral phenotype in a subject. Additionally, such administration may be provided prophylactically in order to delay, impede, attenuate or prevent the onset of Alzheimer's disease, or other tauopathy associated with the neurofibrillary tangle.

The term "treatment" or "treating" as used herein means ameliorating, slowing or reversing the progress or severity of a disease or disorder, or ameliorating, slowing or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total, detectable or undetectable.

An "effective amount," when applied to an antibody of the invention, refers to an amount sufficient, at dosages and for periods of time necessary, to achieve an intended biological effect or a desired therapeutic result including, without limitation, clinical results. The phrase "therapeutically effective amount" when applied to an antibody of the invention is intended to denote an amount of the antibody that is sufficient to ameliorate, palliate, stabilize, reverse, slow or delay the progression of a disorder or disease state, or of a symptom of the disorder or disease. In an embodiment, the method of the present invention provides for administration of the antibody in combinations with other compounds. In such instances, the "effective amount" is the amount of the combination sufficient to cause the intended biological effect.

An amount adequate to accomplish therapeutic or prophylactic treatment is defined, respectively, as a therapeutically effective dose or a prophylactically effective dose. In both prophylactic and therapeutic regimes, agents are usually administered in several dosages until a sufficient immune response has been achieved. Typically, the immune response is monitored and repeated dosages are given if the immune response starts to wane. A therapeutically effective or prophylactically effective dose of such an antibody or epitope-binding fragment thereof may vary according to factors such as the disease state, age, sex, and weight of the individual, and the ability of the molecule to elicit a desired response in the subject. A therapeutically effective amount is also one in which any toxic or detrimental effects of the antibody or antibody portion are outweighed by the therapeutically beneficial effect.

Patients amenable to treatment include individuals having Alzheimer's disease or such other tauopathy who show clinically recognized symptoms or indications of such conditions, as well as patients not presently showing symptoms of such conditions. Although Alzheimer's disease is definitively diagnosed only post-mortem biopsy, individuals suffering from Alzheimer's disease are clinically diagnosed using the "Alzheimer's Disease and Related Disorders Association ("ADRDA") Criteria (Carrillo, M. C. et al. (2013) "*Revisiting The Framework Of The National Institute On Aging-Alzheimer's Association Diagnostic Criteria,*" Alzheimers Dement. 9(5):594-601; Budson, A. E. et al. (2012) "*New Criteria For Alzheimer Disease And Mild Cognitive Impairment: Implications For The Practicing Clinician,*" Neurologist 18(6):356-363; Sarazin, M. et al. (2012) "*Clinical And Research Diagnostic Criteria For Alzheimer's Disease,*" Neuroimaging Clin. N. Amer. 22(1): 23-32; Husain, M. M. (2005) "*Clinical Diagnosis And Management Of Alzheimer's Disease,*" Neuroimaging Clin. N. Amer. 15(4):767-777; Small, G. W. et al. (1997) "*Diagnosis And Treatment Of Alzheimer Disease And Related Disorders. Consensus Statement Of The American Association For Geriatric Psychiatry, The Alzheimer's Association, And The American Geriatrics Society,*" JAMA 278(16): 1363-1371). Such individuals can alternatively be distinguished from those having diseases or conditions that are un-related to Alzheimer's disease or other tauopathy by the presence of correlated risk factors (i.e., one or more factors that have been found to possess greater than 50% coincidence with Alzheimer's disease or such other tauopathy). Such correlated risk factors include the finding that a patient has had relatives who have experienced Alzheimer's disease or such other tauopathy, or present a family history of hypercholesterolemia or atherosclerosis. Such correlated risk factors particularly include the finding that a patient possesses one or more genetic or biochemical markers that have been correlated with (i.e., found to possess greater than 50% coincidence with) the occurrence of such actual disease. Examples of such genetic markers of risk toward Alzheimer's disease include correlated mutations in the APP gene, for example, mutations at position 717 and positions 670 and 671 of the APP gene (referred to as the Hardy and Swedish mutations respectively). Other suitable markers of known genetic risk include correlated mutations in the presenilin genes (PS1 and PS2) and in the ApoE4 gene (Bekris, L. M. et al. (2010) "*Genetics of Alzheimer Disease,*" J. Geriatr. Psychiatry Neurol. 23(4):213-227).

The amino acid sequence of isoform 1 of PS1 is (SEQ ID NO:103):

```
MTELPAPLSY FQNAQMSEDN HLSNTVRSQN DNRERQEHND
RRSLGHPEPL SNGRPQGNSR QVVEQDEEED EELTLKYGAK
```

-continued

```
HVIMLFVPVT LCMVVVVATI KSVSFYTRKD GQLIYTPFTE

DTETVGQRAL HSILNAAIMI SVIVVMTILL VVLYKYRCYK

VIHAWLIISS LLLLFFFSFI YLGEVFKTYN VAVDYITVAL

LIWNFGVVGM ISIHWKGPLR LQQAYLIMIS ALMALVFIKY

LPEWTAWLIL AVISVYDLVA VLCPKGPLRM LVETAQERNE

TLFPALIYSS TMVWLVNMAE GDPEAQRRVS KNSKYNAEST

ERESQDTVAE NDDGGFSEEW EAQRDSHLGP HRSTPESRAA

VQELSSSILA GEDPEERGVK LGLGDFIFYS VLVGKASATA

SGDWNTTIAC FVAILIGLCL TLLLLAIFKK ALPALPISIT

FGLVFYFATD YLVQPFMDQL AFHQFYI
```

Such PS1 mutations include the substitutions: R35Q; A79V; V82L; L85P; V89L; V94M; V96F; V97L; F105I; F105L; F105V; L113P; L113Q; Y115C; Y115D; Y115H; T116I; T116N; P117A; P117L; P117R; P117S; E120D; E120D; E120G; E120K; E123K; N135D; N135S; A136G; M139I; M139I; M139K; M139T; M139V; I143F; I143M; I143N; I143T; I143V; M146I; M146I; M146I; M146L; M146L; M146V; T147I; L153V; Y154C; Y154N; H163R; H163Y; W165C; W165G; L166H; L166P; L166R; S169L; S169P; S170F; L171P; L173F; L173W; L174M; L174R; F175S; F177L; F177S; S178P; G183V; E184D; V191A; G206A; G206D; G206S; G206V; G209E; G209R; G209V; S212Y; I213F; I213L; I213T; H214D; H214Y; G217D; G217R; L219F; L219P; Q222H; Q222R; Q223R; L226F; L226R; I229F; A231T; A231V; M233I; M233L; M233L; M233T; M233V; L235P; L235V; F237I; F237L; K239N; T245P; A246E; L248R; L250S; L250V; Y256S; A260V; V261F; V261L; L262F; C263F; C263R; P264L; G266S; P267L; P267S; R269G; R269H; L271V; V272A; E273A; T274R; R278I; R278K; R278S; R278T; E280A; E280G; L282F; L282R; L282V; P284L; P284S; A285V; L286P; L286V; T291P; E318G; R358Q; S365A; R377M; G378E; G378V; L381V; G384A; F386S; S390I; V391F; L392P; L392V; G394V; N405S; A409T; C410Y; V412I; L418F; L420R; L424F; L424H; L424R; L424V; A426P; A431E; A431V; A434C; L435F; P436Q; P436S; and I439S.

The amino acid sequence of isoform 1 of PS2 is (SEQ ID NO:104):

```
MLTFMASDSE EEVCDERTSL MSAESPTPRS CQEGRQGPED

GENTAQWRSQ ENEEDGEEDP DRYVCSGVPG RPPGLEEELT

LKYGAKHVIM LFVPVTLCMI VVVATIKSVR FYTEKNGQLI

YTPFTEDTPS VGQRLLNSVL NTLIMISVIV VMTIFLVVLY

KYRCYKFIHG WLIMSSLMLL FLFTYIYLGE VLKTYNVAMD

YPTLLLTVWN FGAVGMVCIH WKGPLVLQQA YLIMISALMA

LVFIKYLPEW SAWVILGAIS VYDLVAVLCP KGPLRMLVET

AQERNEPIFP ALIYSSAMVW TVGMAKLDPS SQGALQLPYD

PEMEEDSYDS FGEPSYPEVF EPPLTGYPGE ELEEEERGV

KLGLGDFIFY SVLVGKAAAT GSGDWNTTLA CFVAILIGLC

LTLLLLAVFK KALPALPISI TFGLIFYFST DNLVRPFMDT

LASHQLYI
```

Such PS2 mutations include the substitutions: R29H; G34S; R62C; R62H; R71W; A85V; T122P; T122R; S130L; V139M; N141I; L143H; V148I; R163H; M174V; S175C; Y231C; Q228L; M239V; M230I; A252T; P334R; T430M; and D439A.

Such ApoE4 alleles include the ε4 allele, ε3 allele and ε2 allele (Verghese, P. B. et al. (2011) "*Apolipoprotein E In Alzheimer's Disease And Other Neurological Disorders*," Lancet Neurol. 10(3):241-252).

In addition, a number of diagnostic tests are available for identifying individuals who have Alzheimer's disease. These include measurement of CSF Tau and Aβ42 levels. Elevated Tau and decreased Aβ42 levels signify the presence of Alzheimer's disease.

In the case of Alzheimer's disease, virtually anyone is at risk of suffering from Alzheimer's disease. Therefore, the therapeutic molecules of the present invention can be administered prophylactically to the general population without the need for any assessment of the risk of the subject patient. The present methods are especially useful for the prophylactic treatment of individuals who do have a known genetic risk of Alzheimer's disease. In asymptomatic patients, treatment can begin at any age (e.g., 10, 20, 30). Usually, however, it is not necessary to begin treatment until a patient reaches 40, 50, 60, 70, 80 or 90 years of age. Treatment typically entails the administration of multiple dosages over a period of time. Treatment can be monitored by assaying antibody, or activated T-cell or B-cell responses to the therapeutic agent over time. If the response falls, a booster dosage is indicated. In the case of potential Down's syndrome patients, treatment can begin ante-natally by administering the therapeutic agent to the mother during pregnancy or shortly after the patient's birth.

The present invention provides:
1. A binding molecule that is capable of immunospecifically binding to the Truncated Asp421 Epitope of Tau.
2. The embodiment of such binding molecule wherein the molecule competes for binding with an antibody selected from the group consisting of: Antibody 1G10D2, Antibody 1G11A10, Antibody 5B3C11 and 5G2A3.
3. The embodiment of such binding molecule wherein the molecule comprises:
   (a) (1) a Variable Light Chain CDR1, CDR2, CDR3 respectively having the amino acid sequence of SEQ ID NOs:9, 10 and 11; and
   (2) a Variable Heavy Chain CDR1, CDR2, CDR3 respectively having the amino acid sequence of SEQ ID NOs:13, 14 and 15;
   (b) (1) a Variable Light Chain CDR1, CDR2, CDR3 respectively having the amino acid sequence of SEQ ID NOs:17, 18 and 19; and
   (2) a Variable Heavy Chain CDR1, CDR2, CDR3 respectively having the amino acid sequence of SEQ ID NOs:21, 22 and 23;
   (c) (1) a Variable Light Chain CDR1, CDR2, CDR3 respectively having the amino acid sequence of SEQ ID NOs:25, 26 and 27; and
   (2) a Variable Heavy Chain CDR1, CDR2, CDR3 respectively having the amino acid sequence of SEQ ID NOs:33, 34 and 35;
   (d) (1) a Variable Light Chain CDR1, CDR2, CDR3 respectively having the amino acid sequence of SEQ ID NOs:29, 30 and 31; and
   (2) a Variable Heavy Chain CDR1, CDR2, CDR3 respectively having the amino acid sequence of SEQ ID NOs:33, 34 and 35;

(e) (1) a Variable Light Chain CDR1, CDR2, CDR3 respectively having the amino acid sequence of SEQ ID NOs:37, 38 and 39; and
    (2) a Variable Heavy Chain CDR1, CDR2, CDR3 respectively having the amino acid sequence of SEQ ID NOs:41, 42 and 43;
(f) (1) a Variable Light Chain CDR1, CDR2, CDR3 respectively having the amino acid sequence of SEQ ID NOs:45, 46 and 47; and
    (2) a Variable Heavy Chain CDR1, CDR2, CDR3 respectively having the amino acid sequence of SEQ ID NOs:49, 50 and 51.

4. The embodiment of such binding molecule wherein the molecule comprises:
   (a) a Variable Light Chain CDR1, CDR2, CDR3 respectively having the amino acid sequence of SEQ ID NOs:115, 116 and 117; and
   (2) a Variable Heavy Chain CDR1, CDR2, CDR3 respectively having the amino acid sequence of SEQ ID NOs:118, 119 and 120.

5. The embodiment of any such binding molecules wherein upon peripheral injection into a recipient, the molecule substantially co-localizes with a Tau aggregate.

6. The embodiment of any such binding molecules wherein the molecule is an antibody, a diabody, an scFv, or comprises an epitope-binding fragment of an antibody, diabody or scFv.

7. The embodiment of any such binding molecules wherein the molecule is an antibody.

8. The embodiment of any such binding molecules, wherein the molecule is the Antibody 1G10D2, the Antibody 1G11A10, the Antibody 5B3C11 or the Antibody 5G2A3.

9. The embodiment of any of the above-described binding molecules, wherein the molecule immunospecifically binds to the Tau 407-421 peptide (SEQ ID NO:7): HLSNVSSTGSIDMVD.

10. The embodiment of any of the above-described binding molecules, which is detectably labeled.

11. The embodiment of any of the above-described detectably labeled binding molecules, wherein the detectable label is a fluorescent label, a chemoluminescent label, a paramagnetic label, a radioisotopic label or an enzyme label.

12. (A) The embodiment of any of the above-described detectably labeled binding molecules for use in the manufacture of a medicament for detecting or measuring the presence or amount of pathological Tau protein in the brain of, or in a biological sample of, a recipient subject, or
    (B) the use of any of the above-described detectably embodiments of labeled binding molecules for detecting or measuring the presence or amount of the pathological Tau protein in the brain of, or in a biological sample of, a recipient subject.

13. (A) The embodiment of any of the above-described detectably labeled binding molecules for use in the manufacture of a medicament for detecting or measuring the presence or amount of pathological Tau protein in the brain of, or in a biological sample of, a recipient subject, or
    (B) the use of any of the above-described embodiments of detectably labeled binding molecules for detecting or measuring the presence or amount of the pathological Tau protein in the brain of, or in a biological sample of, a recipient subject;
    wherein the detection or measurement comprises in vivo imaging of the binding molecule bound to the truncated Tau protein.

14. (A) The embodiment of any of the above-described detectably labeled binding molecules for use in the manufacture of a medicament for detecting or measuring the presence or amount of pathological Tau protein in the brain of, or in a biological sample of, a recipient subject, or
    (B) the use of any of the above-described embodiments of detectably labeled binding molecules for detecting or measuring the presence or amount of the pathological Tau protein in the brain of, or in a biological sample of, a recipient subject;
    wherein the detection or measurement comprises ex vivo imaging of the binding molecule bound to the truncated Tau protein.

15. (A) (1) The embodiment of any of the above-described binding molecules, which is detectably labeled; or
    (2) the embodiment of any of the above-described detectably labeled binding molecules, wherein the detectable label is a fluorescent label, a chemoluminescent label, a paramagnetic label, a radioisotopic label or an enzyme label;
    for use in the manufacture of a medicament for diagnosing Alzheimer's disease or another tauopathy of a subject; or
    (B) (1) the use of any of the above-described embodiments of detectably labeled binding molecules for diagnosing Alzheimer's disease or another tauopathy of a subject; or
    (2) the use of any of the above-described embodiments of detectably labeled binding molecules, wherein the detectable label is a fluorescent label, a chemoluminescent label, a paramagnetic label, a radioisotopic label or an enzyme label, for diagnosing Alzheimer's disease or another tauopathy of a subject.

16. (A) (1) The embodiment of any of the above-described binding molecules, which is detectably labeled; or
    (2) the embodiment of any of the above-described detectably labeled binding molecules, wherein the detectable label is a fluorescent label, a chemoluminescent label, a paramagnetic label, a radioisotopic label or an enzyme label;
    for use in the manufacture of a medicament for diagnosing Alzheimer's disease or another tauopathy of a subject; or
    (B) (1) the use of any of the above-described embodiments of detectably labeled binding molecules for diagnosing Alzheimer's disease or another tauopathy of a subject; or
    (2) the use of any of the above-described embodiments of detectably labeled binding molecules, wherein the detectable label is a fluorescent label, a chemoluminescent label, a paramagnetic label, a radioisotopic label or an enzyme label, for diagnosing Alzheimer's disease or another tauopathy of a subject;
    wherein the medicament is an in vivo medicament that is administered to the subject.

17. (A) (1) The embodiment of any of the above-described binding molecules, which is detectably labeled; or
    (2) the embodiment of any of the above-described detectably labeled binding molecules, wherein the detectable label is a fluorescent label, a chemoluminescent label, a paramagnetic label, a radioisotopic label or an enzyme label;
    for use in the manufacture of a medicament for diagnosing Alzheimer's disease or another tauopathy of a subject; or
    (B) (1) the use of any of the above-described embodiments of detectably labeled binding molecules for diagnosing Alzheimer's disease or another tauopathy of a subject; or (2) the use of any of the above-described embodiments of detectably labeled binding molecules, wherein the detectable label is a fluorescent label, a chemoluminescent label, a paramagnetic label, a radioisotopic label or an enzyme label, for diagnosing Alzheimer's disease or another tauopathy of a subject;
wherein the medicament is incubated ex vivo with a biopsy sample of the subject.

18. The embodiment of any of such uses, wherein the tauopathy is selected from the group comprising frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

EXAMPLES

The following examples illustrate various methods for compositions in the diagnostic or treatment methods of the invention. The examples are intended to illustrate, but in no way limit, the scope of the invention.

Example 1

Figure 1B:
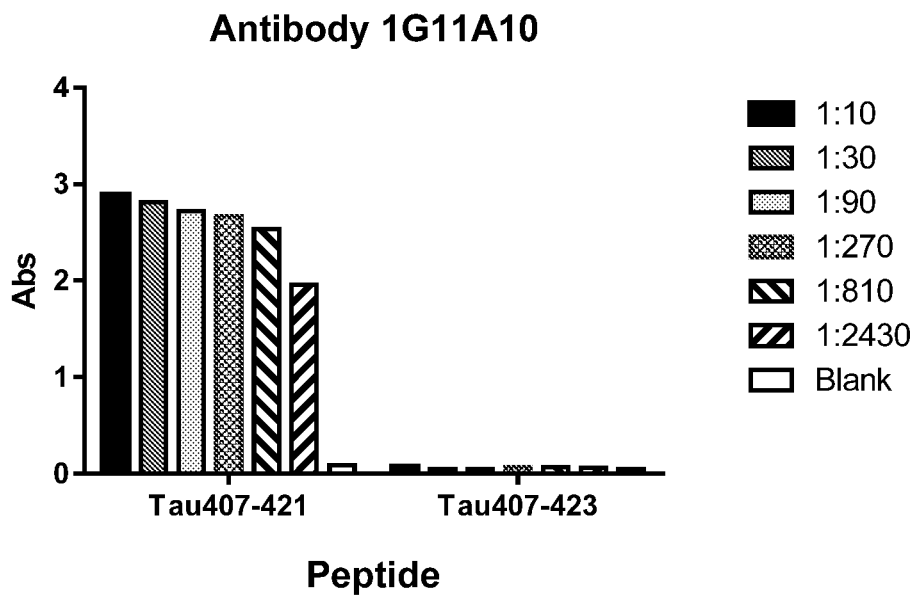
Figure 1C:
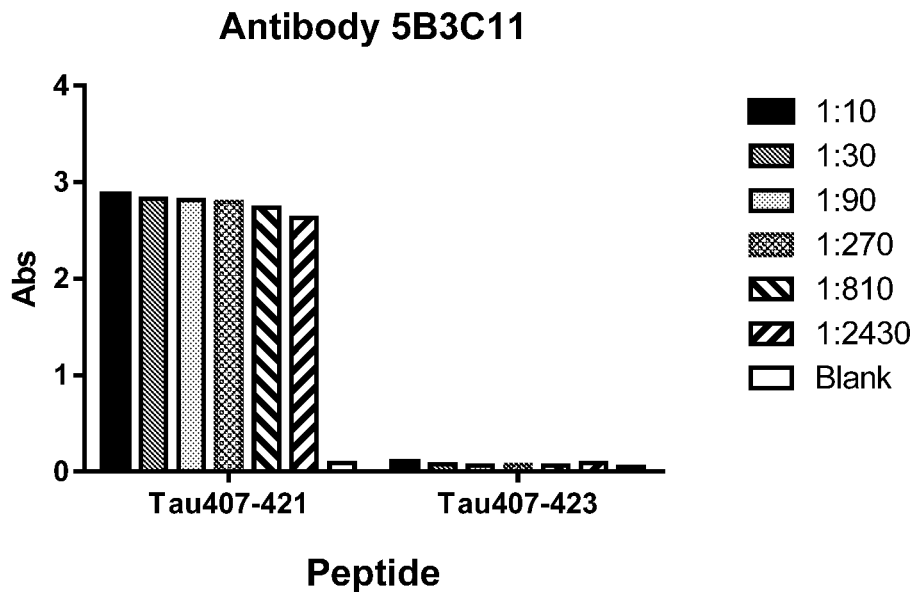
Figure 1D:
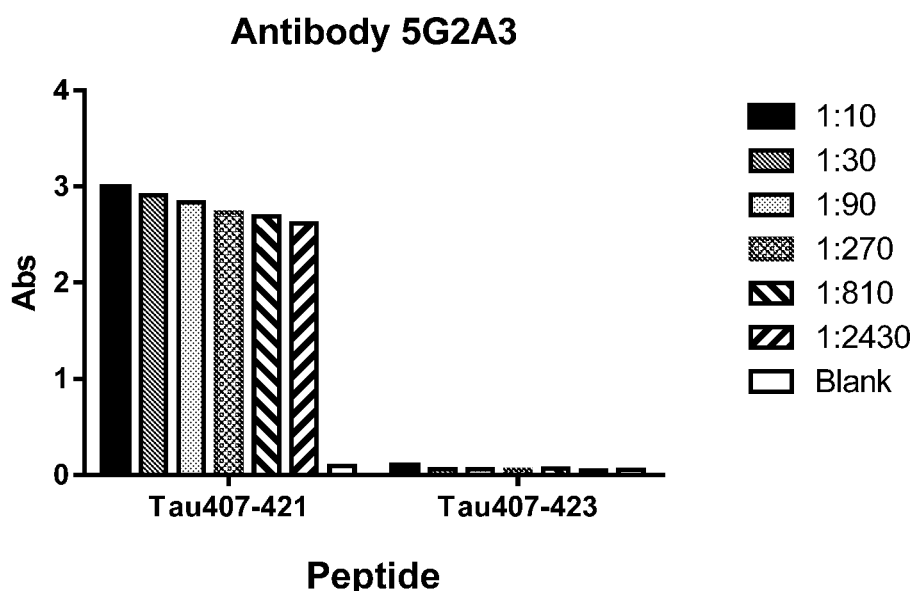
Figure 1E:
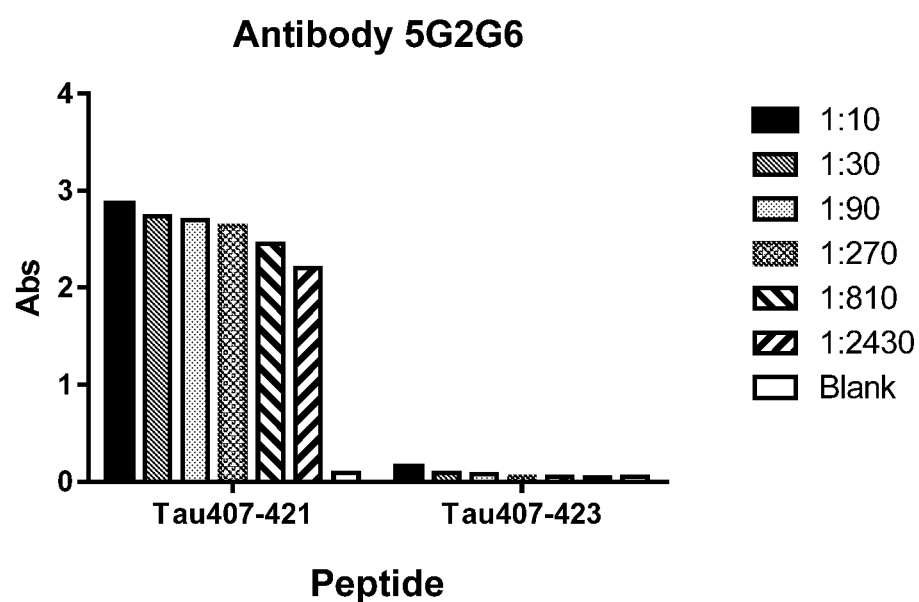

Specificity of Antibody 1G10D2, Antibody 1G11A10, Antibody 5B3C11, Antibody 5G2A3 (or Antibody 5G2G6) for the Truncated Asp421 Epitope of Tau In order to demonstrate the ability of Antibodies Antibody 1G10D2, Antibody 1G11A10, Antibody 5B3C11, Antibody 5G2A3/5G2G6 to immunospecifically bind to the Truncated Asp421 Epitope of Tau, antibody preparations were incubated in the presence of an immobilized peptide corresponding either to Tau residues 407-421 (SEQ ID NO:7) or 407-423 (SEQ ID NO:105) (corresponding, respectively, to residues 407-421 and 407-423, respectively of SEQ ID NO:1), and the amount of antibody bound to the immobilized peptide was determined via ELISA. Antibody 1G10D2 (FIG. 1A), Antibody 1G11A10 (FIG. 1B), Antibody 5B3C11 (FIG. 1C), Antibody 5G2A3 (FIG. 1D) and Antibody 5G2G6 (FIG. 1E) were each found to be capable of strongly binding to the truncated (Tau 407-421) peptide (SEQ ID NO:7), but incapable of binding a peptide (Tau 407-423; SEQ ID NO:105) that contained the non-truncated epitope. The data thus confirms the ability of Antibodies 1G11A10, 5G2A3 and 5G2G6 to immunospecifically bind to the Truncated Asp421 Epitope of Tau.

Figure 2A:
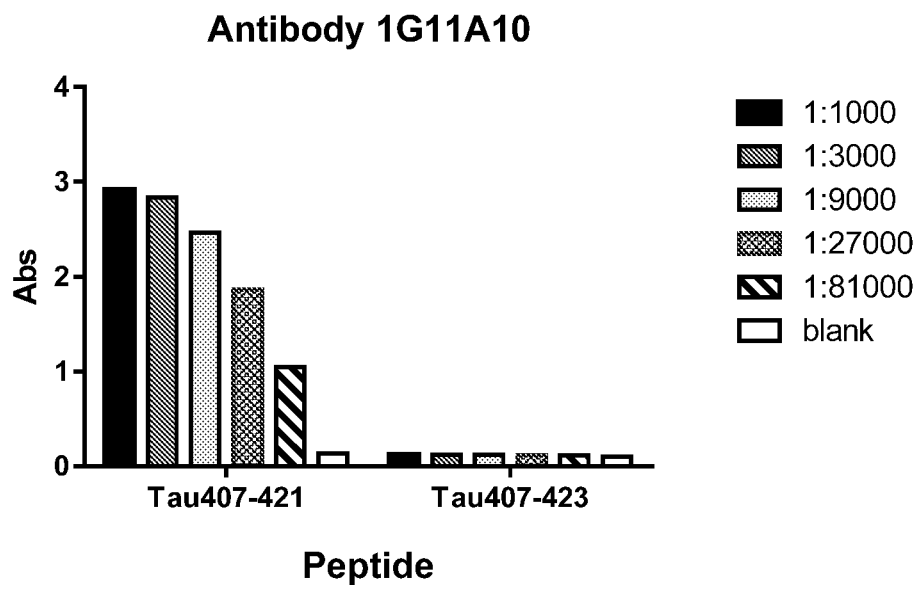
FIGS. 2A-2B show the immunospecificity of Antibodies 1G11A10 (FIG. 2A) and 5G2A3 (FIG. 2C) for the Truncated Asp421 Epitope of Tau at antibody dilutions of 1:1000, 1:3000, 1:9000, 1:27000 and 1:81000.
Figure 2B:
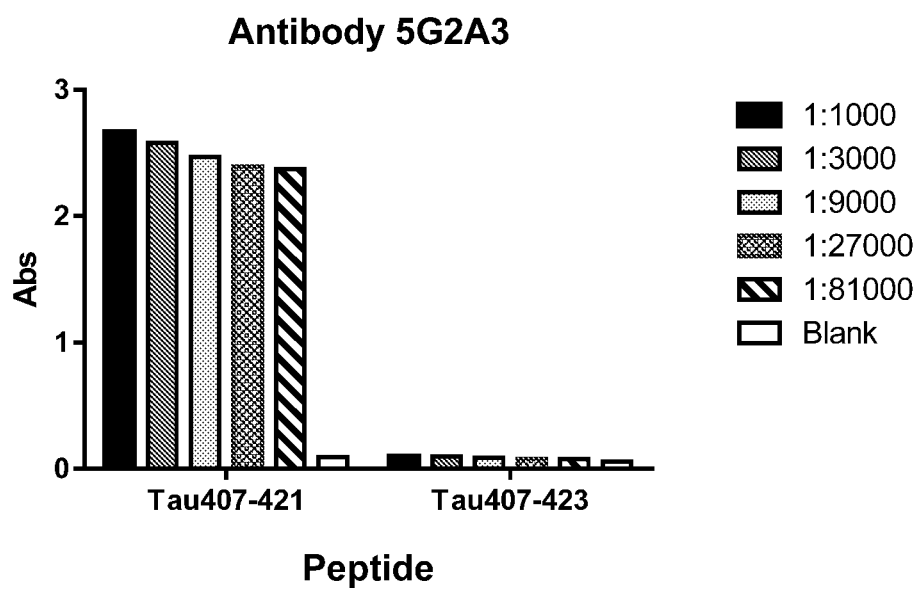

As shown in FIGS. 2A-2B, the binding affinity profiles of Antibodies 1G11A10 and 5G2A3 differ, with Antibody 1G11A10 binding to the Truncated Asp421 Epitope with lower affinity, such that less binding is observed at higher antibody dilution (FIG. 2A), relative to Antibody 5G2A3 which exhibits high affinity binding to the Truncated Asp421 Epitope even at very low antibody concentration (FIG. 2B).

The binding affinity inferred from the ELISA data was confirmed by Biacore analysis. The results of the analysis are shown in Table 7.

TABLE 7

| Analyte | Antibody 5G2A3 | Antibody 1G11A10 |
|---|---|---|
| Tau407-421 (SEQ ID NO: 7) | $7.46 \times 10^{-9}$ | $1.07 \times 10^{-6}$ |
| Tau407-423 (SEQ ID NO: 105) | $5.07 \times 10^{-6}$ | No Binding |

Thus, Antibody 5G2A3 targets the Truncated Asp421 Epitope and binds with a high affinity ($10^{-9}$ M). In contrast, antibody 1G11A10 binds the Truncated Asp421 Epitope with lower affinity ($10^{-6}$ M), but does not detectably bind to the non-truncated epitope.

Example 2

Ability of Antibodies Recognizing the Asp421 Epitope of Tau to Clear Pathological Tau Immunotherapy using monoclonal antibodies against Tau epitopes such as the "$^{\{P\}}$Ser396/$^{\{P\}}$Ser404 Tau Epitope," which involves Tau having phosphoserine residues at positions 396 and 404 ($^{\{P\}}$Ser396 and $^{\{P\}}$SerSer404), has demonstrated a reduction in the hyperphosphorylated Tau levels and the pathology associated with it. In order to further demonstrate the therapeutic capabilities of the Truncated Tau Epitope-binding molecules of the present invention, the ability of monoclonal Antibodies 5G2A3/5G2G6 and 1G11A10, which immunospecifically bind to the Truncated Asp421 Epitope to affect hyperphosphorylated Tau was explored using primary neuronal cultures. In addition, the ability of Antibodies 5G2A3 and 1G11A10 to affect hyperphosphorylated Tau was explored using mixed cortical cultures.

Accordingly, primary neurons and mixed cortical cultures from Day 0 JNPL3 mice were pretreated with PHF (1 μg/mL) for 24 h followed by the addition of Antibody 5G2A3/5G2G6 (only pure neuronal cultures) or Antibody 1G11A10 (10 μg/mL) for an additional 24 h, 48 h, 72 h or 96 h. Immunoblots were undertaken against antibody PHF-1 (which binds a $^{\{P\}}$Ser396/$^{\{P\}}$Ser404 epitope), anti-human Tau antibody (Dako) and phosphorylated Tau ($^{\{P\}}$Ser199).

Table 8 shows the results of this experiment for the mixed neuronal cultures pretreated with PHF.

TABLE 8

| | 24 hr | 48 hr | 72 hr | 96 hr |
|---|---|---|---|---|
| | PHF-Treated Cells (PHF-1 Chemoluminescent Signal Values) | | | |
| | 751300 | 1224982 | 1622299 | 1828209 |
| | 688635 | 1321391 | 1523903 | 1729813 |
| | 670977 | 1449190 | 1637642 | 1843552 |
| | 645829 | 1507930 | 1629707 | 1835617 |
| | 649657 | 1380862 | 1595397 | 1801307 |
| | 425133 | 1354053 | 1648179 | 1854089 |
| Mean | 638588.5 | 1373068 | 1609521 | 1815431 |
| SD | 111351.5 | 98999.8 | 45576.12 | 45576.14 |
| | IgG-Treated Cells (PHF-1 Chemoluminescent Signal Values) | | | |
| | 583074 | 1422041 | 1443397 | 2201538 |
| | 641161 | 1417630 | 1464404 | 1814748 |
| | 708202 | 1457702 | 1662020 | 1766616 |
| | 688516 | 1373635 | 1521455 | 1679659 |
| | 687360 | 1320653 | 1834901 | 1629244 |
| | 622845 | 1417484 | 1512274 | 1574982 |
| Mean | 655193 | 1401524 | 1573075 | 1818361 |
| SD | 47748.37 | 47768 | 149299.2 | 225335.3 |

TABLE 8-continued

|  | 24 hr | 48 hr | 72 hr | 96 hr |
|---|---|---|---|---|
| | 5G2A3-Treated Cells | | | |
| | (PHF-1 Chemoluminescent Signal Values) | | | |
| | 571503 | 435510.8 | 543829.3 | 229600 |
| | 399505 | 418450.8 | 533115.5 | 212540 |
| | 413940 | 418883.4 | 445210 | 212973 |
| | 413921 | 464627.2 | 539038.1 | 258717 |
| | 408297 | 434414.7 | 425200.4 | 228504 |
| | 322745 | 471881.4 | 535928.9 | 265971 |
| Mean | 421651.8 | 440628 | 503720.4 | 234717.5 |
| SD | 81272.39 | 22725.25 | 53565.64 | 22725.4 |
| | 1G11A10-Treated Cells | | | |
| | (PHF-1 Chemoluminescent Signal Values) | | | |
| | 351671 | 414222.4 | 606166.6 | 543586 |
| | 568261 | 423511.5 | 595803.6 | 636088 |
| | 436208 | 425164.2 | 570901.7 | 918583 |
| | 382948 | 432781.3 | 630724.7 | 1165849 |
| | 313133 | 435635.4 | 559424.1 | 1209264 |
| | 257632 | 460723.8 | 556335.5 | 1141208 |
| Mean | 384975.5 | 432006.4 | 586559.4 | 935763 |
| SD | 108359.9 | 15960.63 | 29378.37 | 287698.8 |

Figure 3A:
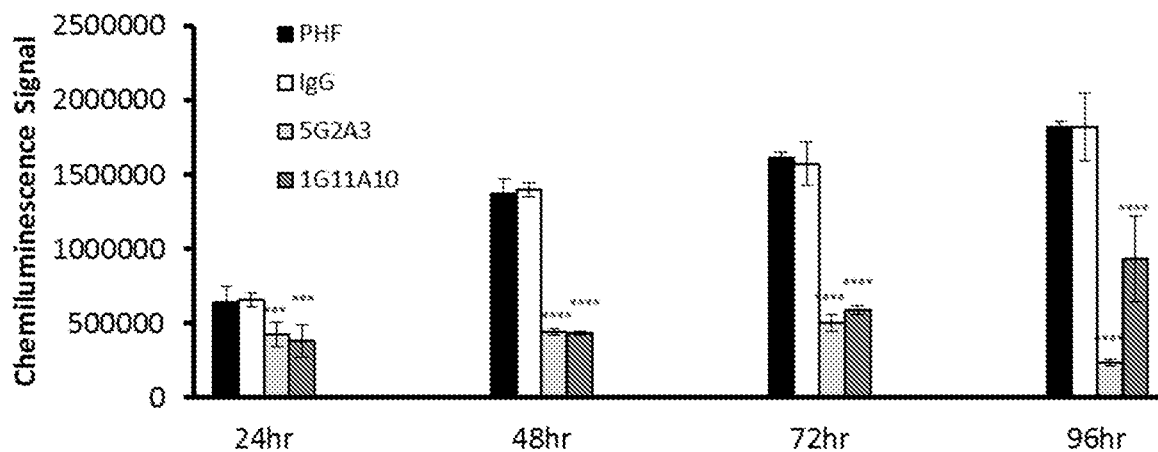
FIGS. 3A-3B show the effect of Antibody 5G2A3 and Antibody 1G11A10 (10 μg/mL), over time, on phosphorylated Tau levels of mixed cortical (FIG. 3A) or pure neuronal (FIG. 3B) cultures of JNPL3 mice that were pre-treated with PHF (1 μg/mL). Antibody 5G2G6 was also tested in the pure neuronal culture. The results presented in FIG. 3A are obtained from Western blot analysis using detection antibody PHF-1 (Table 6). The PHF-treated mixed cultures that were incubated with IgG (10 μg/mL) were considered as control for this set of experiment. The results presented in FIG. 3B are obtained from Western blot analysis using detection antibody specific for $^{\{P\}}$Ser199 Tau, with IgG-treated controls set at 100%. The data is not normalized.

The data of Table 8 are shown graphically in FIG. 3A. The data show that such cells (postnatal day 0) have significantly decreased levels of PHF-1 ($^{\{P\}}$Ser396/$^{\{P\}}$Ser404) after treatment with antibody 5G2A3 and 1G11A10 when compared to control cells, $p<0.0001$.

Table 9 shows the results of this experiment for the mixed neuronal cultures immunoblotted with anti-human Tau antibody (Dako) to thus show total Tau.

TABLE 9

|  | 24 hr | 48 hr | 72 hr | 96 hr |
|---|---|---|---|---|
| | PHF-Treated (Total Tau values) | | | |
| | 1273302 | 2097159 | 1771592 | 2651642 |
| | 1361667 | 1949165 | 1749614 | 2463713 |
| | 1389425 | 1631917 | 2058003 | 2738844 |
| | 1315507 | 1827079 | 1916164 | 2308258 |
| | 1403872 | 1893961 | 2156769 | 2442688 |
| | 1431630 | 1873666 | 1672630 | 3030670 |
| Mean | 1380420 | 1878825 | 1930428 | 2605969 |
| SD | 58959.05 | 152653 | 190270.9 | 259091.5 |
| | IgG-Treated (Total Tau values) | | | |
| | 1510411 | 1809605 | 1824976 | 2575640 |
| | 1403872 | 2030118 | 1918718 | 2726928 |
| | 1347143 | 1807288 | 1864949 | 2688261 |
| | 1402882 | 1824177 | 2019845 | 2617819 |
| | 1415410 | 1982228 | 1810848 | 2657325 |
| | 1390445 | 1927370 | 2058342 | 2700656 |
| Mean | 1420475 | 1896798 | 1916280 | 2661105 |
| SD | 53881.43 | 96845.96 | 102956.8 | 56261.23 |
| | 5G2A3-Treated (Total Tau values) | | | |
| | 1101694 | 1108014 | 1222242 | 883267.9 |
| | 991056 | 1090107 | 1145993 | 1042934 |
| | 1015557 | 1140544 | 1238038 | 1147477 |
| | 984736 | 1102489 | 1251133 | 974776 |
| | 985154 | 1029836 | 1133375 | 1242680 |
| | 1101469 | 1079134 | 527897 | 2025784 |
| Mean | 1029944 | 1091687 | 1198156 | 1219487 |
| SD | 56626.95 | 36758.35 | 54531.71 | 414713.6 |
| | 1G11A10-Treated (Total Tau values) | | | |
| | 1036131 | 1533105 | 1374552 | 1717181 |
| | 982975 | 1502506 | 1751198 | 1750701 |
| | 916187 | 1547973 | 1606475 | 1798726 |
| | 968581 | 1464179 | 1446938 | 1763811 |
| | 978434 | 1464597 | 1790780 | 1628009 |
| | 1047353 | 1580912 | 1255174 | 1569623 |

TABLE 9-continued

|  | 24 hr | 48 hr | 72 hr | 96 hr |
|---|---|---|---|---|
| Mean | 988276.8 | 1515545 | 1537520 | 1704675 |
| SD | 47937.2 | 46982.87 | 214026.5 | 88016.1 |

Figure 4A:
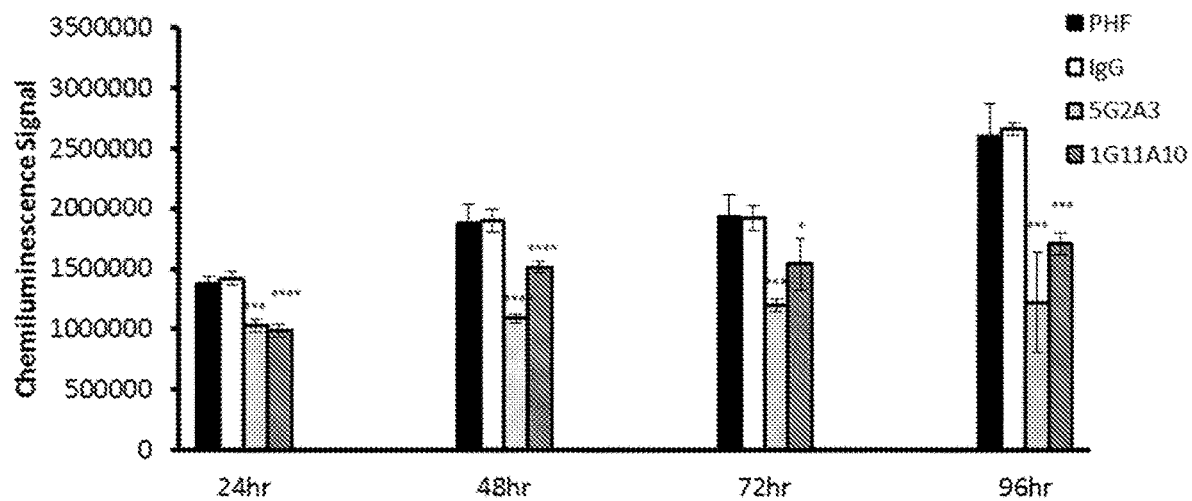
FIGS. 4A-4B show the effect of Antibody 5G2A3 and Antibody 1G11A10 (10 μg/mL), over time, on intracellular Tau using mixed cortical (FIG. 4A) or pure neuronal (FIG. 4B) cultures of JNPL3 mice that were pre-treated with PHF (1 μg/mL). Antibody 5G2G6 was also tested in the pure neuronal culture. The results presented in FIG. 4A (Table 7) and FIG. 4B are obtained from Western blot analysis using anti-human Tau antibody (Dako). The PHF-treated cultures that were incubated with IgG (10 μg/mL) were considered as control for both sets of experiments and are presented in FIGS. 3A-3B. The data is not normalized.

The data of Table 9 are shown graphically in FIG. 4A. The data show that 5G2A3 treatment was more effective in reducing the total Tau levels (54%, $p<0.0001$) at 96 h than 1G11A10 (36%, $p<0.05$) when compared to the control cells treated with IgG.

Figure 3B:
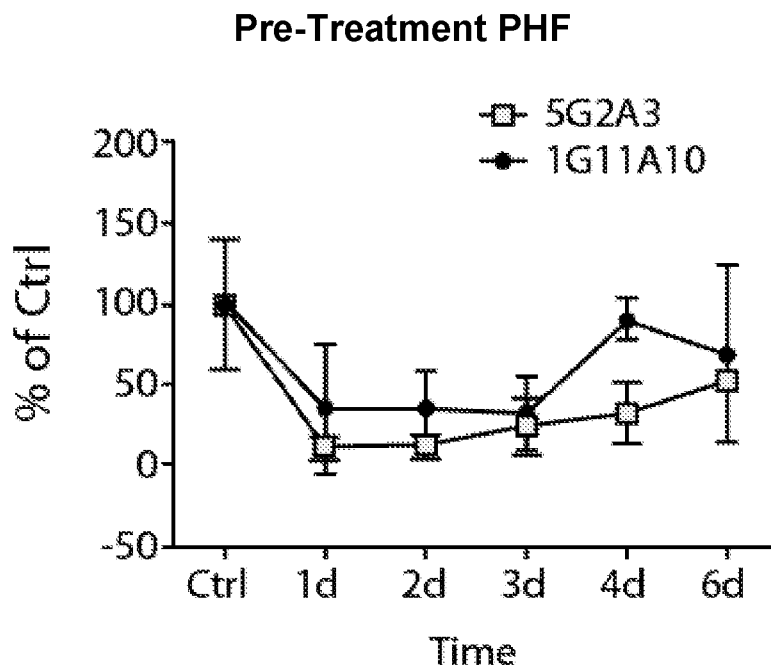
Figure 4B:
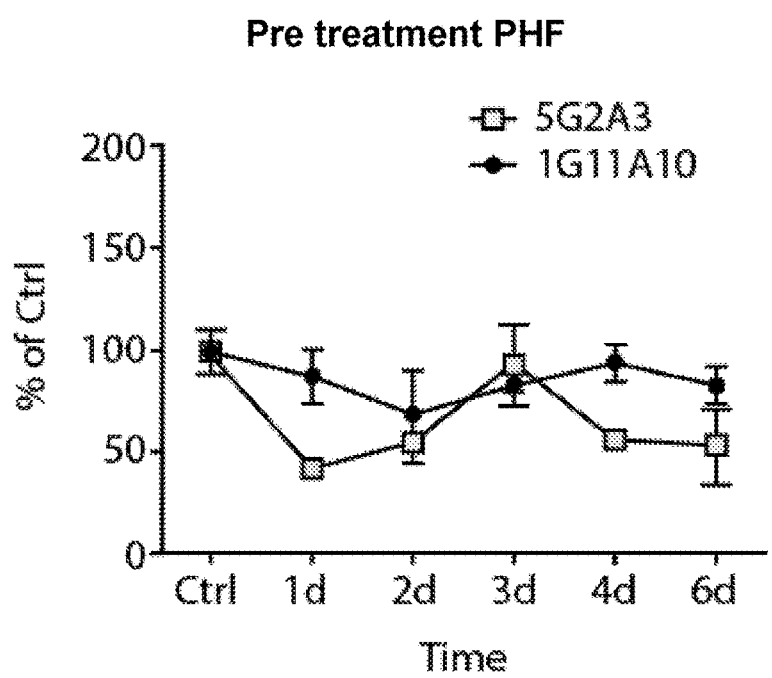

The presence of the higher affinity antibody specific for the Truncated Asp421 Epitope (Antibody 5G2A3) led to significant and sustained reduction in both phospho-Tau (up to 87% at 96 h, $p<0.001$) and total Tau (up to 54% at 96 h, $p<0.0001$) in the mixed culture, compared to control IgG which had no effect (FIGS. 3A and 4A). This tau antibody had a pronounced effect in the primary neurons at 24 and 48 h (phospho-Tau: 89% reduction at both time points, $p<0.001$; total Tau: 58% at 24 h, $p=0.001$ and 45% at 48 h, $p=0.005$) that subsided slightly at the later time points (phospho-Tau: 75% reduction, $p=0.003$ at 72 h and 68% reduction at 96 h, $p=0.008$; total Tau: 6% reduction, $p>0.05$ at 72 h and 43% reduction, $p=0.006$ at 96 h; FIGS. 3B and 4B).

The presence of the lower affinity antibody specific for the Truncated Asp421 Epitope (Antibody 1G11A10) was less efficacious in reducing phospho-Tau and total Tau (up to 49% reduction at 96 h, $p<0.0001$ and 36% reduction at 96 h, respectively, $p<0.0001$) in the mixed cortical culture (FIGS. 3A and 4A), and was ineffective in the primary neuronal culture to reduce either phospho-Tau or total Tau (FIGS. 3B and 4B).

In conclusion, this study clearly shows: 1) the therapeutic efficacy of targeting Tau protein truncated at Asp421; 2) that higher affinity antibody against this particular epitope is more efficacious, and; 3) that greater efficacy is observed in mixed cortical cultures than in primary neurons, presumably because of contribution from phagocytic microglia that promote degradation of tau-antibody complexes. Neurons in mixed cultures are also healthier and, therefore, likely to be better suited to clear/degrade such complexes.

This study clearly demonstrates the ability of Antibody 5G2A3 to mediate a significant reduction of hyperphosphorylated Tau level, as well as significant reduction of total intracellular Tau level, in both mixed cortical cells and primary neuronal cells. This finding thus demonstrates the importance of the Asp421 epitope as a therapeutic target for Tau immunotherapy.

These data indicate that multiple mechanisms are occurring, and that both extracellular blockage and promotion of intracellular clearance are valid methods for preventing seeding of tau pathology and associated toxicity. Antibodies that can affect both pathways are likely to be more efficacious than those acting only within one compartment.

Example 3

Treatment with Antibodies Targeting Asp421 of the Tau Protein Prevents Toxicity of, and Clears, Pathological Tau, with Associated Reduction in Microgliosis To elucidate the effects of antibodies that are capable of immunospecifically binding to the Truncated Asp421 Epitope of Tau, mixed cortical cultures and primary neurons were both pretreated with PHF (1 µg/ml) for 24 h followed by administration of Antibody 5G2A3 and Antibody 1G11A10 at 10 µg/ml for a further 24 h, 48 h, 72 h or 96 h and the effect of such treatment on the clearance of intracellular Tau was assessed.

The extent of intracellular Tau clearance was determined by undertaking Western immunoblot analysis on mixed cortical culture and primary neuronal culture from day 0 JNPL3 pups against phospho Ser 199 epitope. Both the mixed cortical and primary neuronal culture were pretreated with PHF (1 µg/ml) for 24 h followed by treatment with Antibody 5G2A3 (10 µg/ml) or Antibody 1G11A10 (10 µg/ml) antibodies for a further 24 h, 48 h, 72 h or 96 h. Antibody 5G2A3 illustrated reduction in the levels of phospho-Tau in both the mixed cortical as well as primary neurons.

Figure 5A:
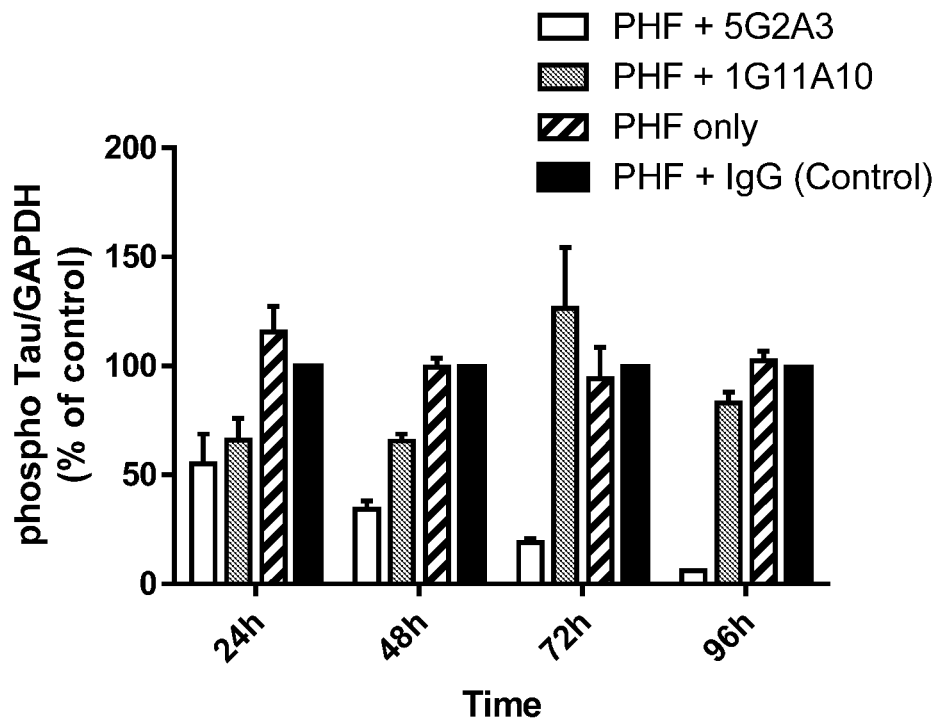
FIGS. 5A-5B show that Antibody 5G2A3 proved to be more effective than Antibody 1G11A10 in reducing the phospho-Tau levels in mixed cortical (FIG. 5A) and primary neuronal (FIG. 5B) culture.
Figure 5B:
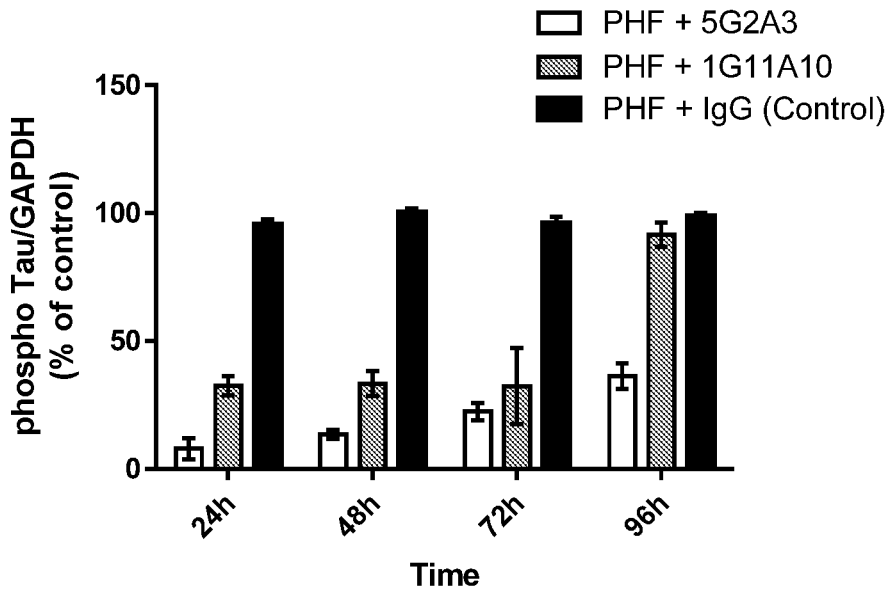

Total and phospho-Tau values were standardized against GAPDH to determine the effects of Antibody 5G2A3 and Antibody 1G11A10 in the clearance of PHF. A comparative analysis between the mixed cortical culture and primary neurons illustrated that Antibody 5G2A3 proved effective in reducing phospho-Tau in both the cell models with the maximum reduction observed at 96 h (94%) (FIG. 5A) for mixed cortical culture. In the primary neurons (FIG. 5B), although the administration of Antibody 5G2A3 was found to be associated with a significant decrease in the levels of phospho Tau for all the time points, i.e., from 24 h until 96 h, compared to the control cells that are treated with IgG (10 µg/ml), a subtle increase in the levels of phospho Tau for the respective time points were observed plausibly depicting the inability of Antibody 5G2A3 in sustaining the reduction of phospho Tau levels within the primary neurons when compared with the mixed cortical culture.

Antibody 1G11A10 treatment only proved effective in reducing phospho-Tau levels in primary neurons showing ~68% reduction from 24 h until 72 h, however, Antibody 1G11A10 treatment was found to be unable to significantly reduce the levels of phospho Tau in mixed cortical culture.

Figure 6A:
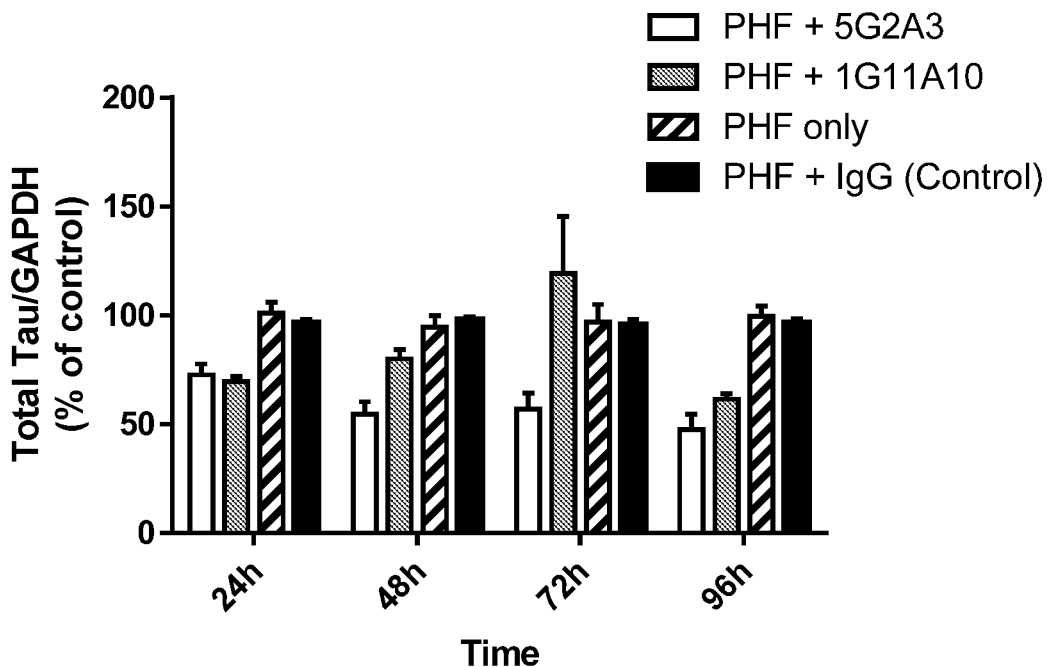
FIGS. 6A-6B show that Antibody 5G2A3 proved to be effective in reducing total Tau in mixed cortical and primary neuronal culture whereas Antibody 1G11A10 was more effective in reducing total Tau levels in primary neuronal culture.
Figure 6B:
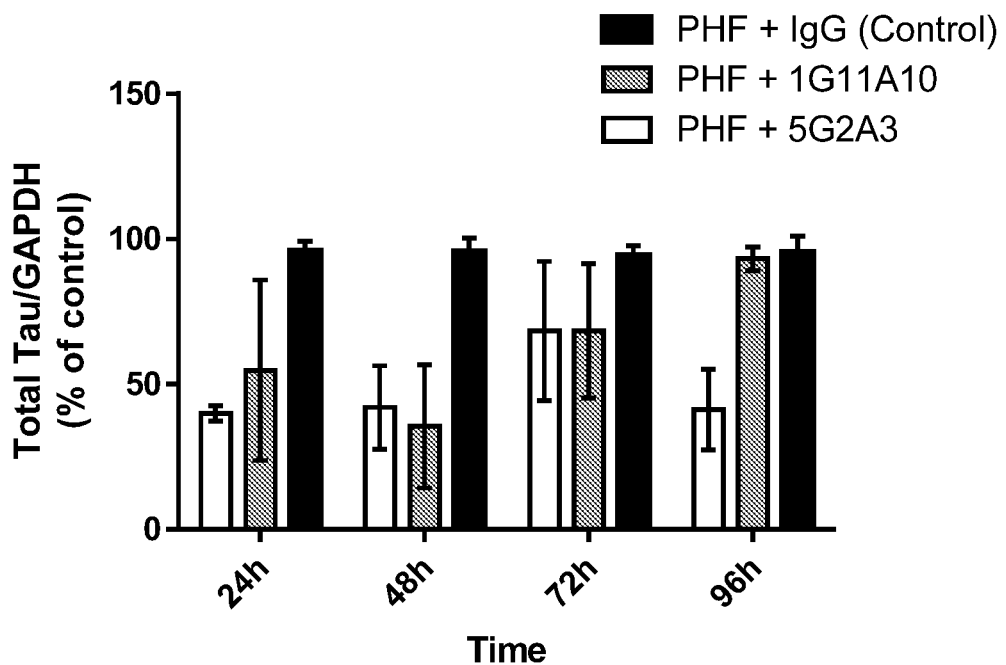

A comparative analysis between mixed cortical culture and primary neurons illustrated reduction in the total Tau levels in both the cell types after Antibody 5G2A3 treatment. Western blots were undertaken against total Tau (Dako) both in the mixed cortical and primary neuronal cultures from day 0 JNPL3 mice. Both the cortical and primary neuronal culture were pretreated with PHF (1 µg/ml) for 24 h followed by treatment with Antibody 5G2A3 (10 µg/ml) or Antibody 1G11A10 (10 µg/ml) for further 24 h, 48 h, 72 h or 96 h. The cells treated with IgG (10 µg/ml) were considered as control for both the mixed cortical culture and primary neurons. A sustained reduction (54%) in the total Tau levels from 48 h until 96 h was illustrated in the mixed cortical culture after Antibody 5G2A3 treatment (FIG. 6A), whereas ~50% reduction was observed in the primary neurons at 24 h, 48 h and 96 h (FIG. 6B) illustrating the beneficial effect of Antibody 5G2A3 in reducing the total Tau levels in both the mixed cortical and primary neuronal culture.

Antibody 1G11A10 proved effective in reducing the total Tau levels in the mixed cortical culture for 24 h (41%) and 96 h (36%) (FIG. 6A), but a significant reduction in the levels of total Tau was only evident at 48 h (65%) in the primary neurons (FIG. 6B) when compared to the control.

GAPDH was considered as a loading control for all the experiments. GAPDH levels did not change after Antibody 5G2A3 or Antibody 1G11A10 treatment in the mixed cortical and primary neurons. The mixed cortical culture and primary neuronal culture pretreated with PHF (1 µg/ml) followed by Antibody 5G2A3 or Antibody 1G11A10 treatment at 10 µg/ml each did not demonstrate any significant alteration in the levels of GAPDH levels, p>0.05 for 24 h, 48 h, 72 h and 96 h when compared to the IgG treated control.

Figure 7:
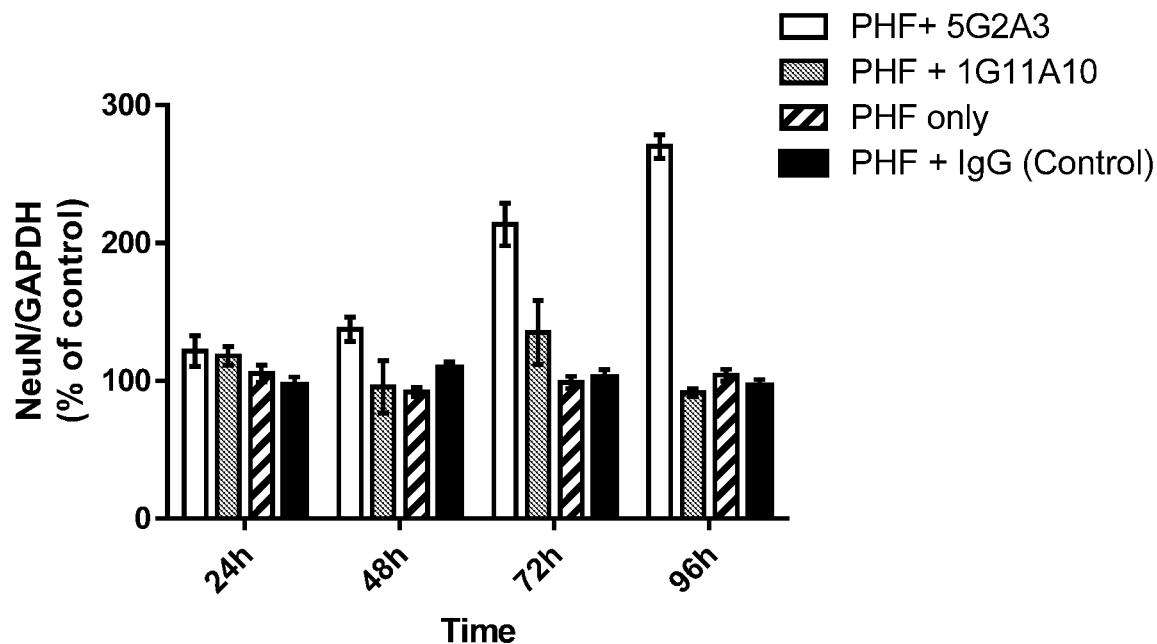
FIG. 7 shows that Antibody 5G2A3 treatment increased NeuN levels in the mixed cortical cultures. Mixed cortical cultures from day 0 JNPL3 mice were pretreated with PHF (1 μg/ml) followed by Antibody 5G2A3 (10 μg/ml) and Antibody 1G11A10 (10 μg/ml) treatment for further 24 h, 48 h, 72 h or 96 h. A western blot analysis undertaken against NeuN, which is a neuronal nuclei marker, demonstrated a significant increase in the levels of NeuN for 72 h (114%) and 96 h (170%) compared to the IgG (10 μg/ml) treated control cells. Antibody 1G11A10 treatment did not show any significant alteration in the levels of NeuN.

In order to further characterize the effects of antibodies that are capable of immunospecifically binding to the Truncated Asp421 Epitope of Tau, NeuN and Iba1 levels were measured in the mixed cortical culture treated with Antibody 5G2A3 or Antibody 1G11A10. NeuN is used as a post-mitotic neuronal marker to determine the morpho-functional state of neurons, such that a decrease in the NeuN levels is suggestive of neuronal loss or damage. The Antibody 5G2A3-treated cells demonstrated a gradual increase in NeuN levels from 24 h until 96 h, with a statistically significant increase observed at 72 h and 96 h when compared to the control cells that were treated with IgG for the respective time points (FIG. 7). No significant alteration in the levels of NeuN was observed for the Antibody 1G11A10-treated cells when compared to the control or cells treated with PHF only.

Figure 8:
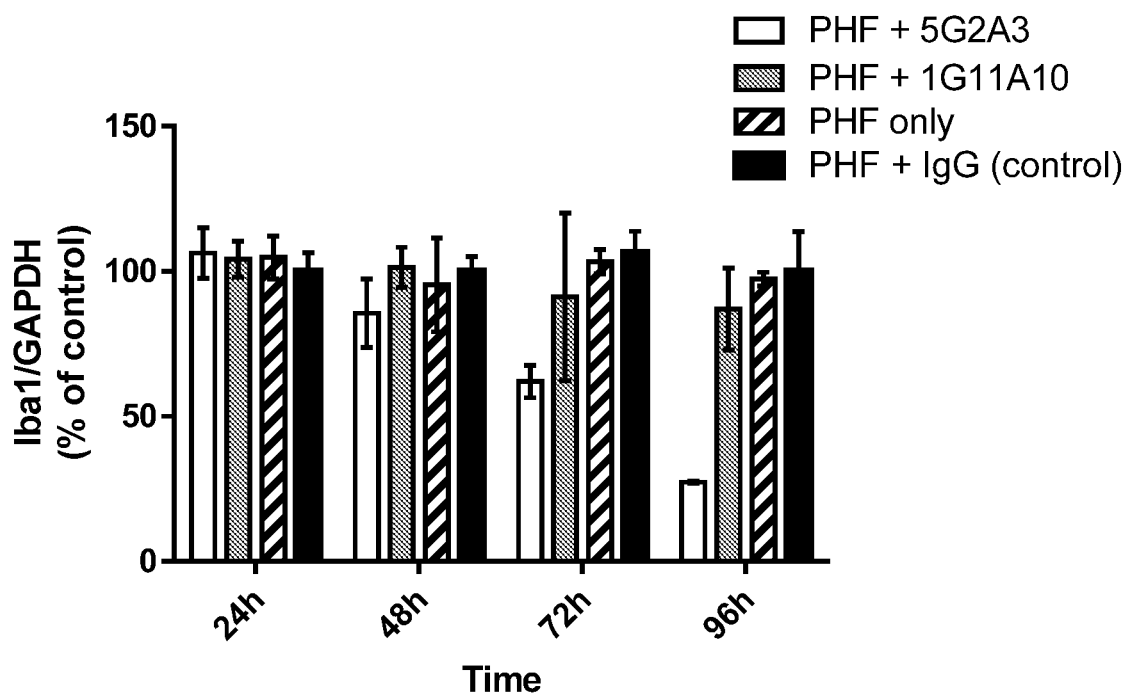
FIG. 8 shows that Iba1 expression was reduced after Antibody 5G2A3 treatment in mixed cortical culture. The mixed cortical cells from day 0 JNPL3 mice were pretreated with PHF (1 μg/ml) followed by treatment with Antibody 5G2A3 or Antibody 1G11A10 (10 μg/ml each) for 24 h, 48 h, 72 h or 96 h, respectively. Immunoblots undertaken against Iba1 antibody, a microglia specific marker, demonstrated a significant decrease in the levels of Iba1 at 72 h (38%, p<0.05) and 96 h (73%, p=0.0004), when compared to control for the respective time points, whereas Antibody 1G11A10 treatment was unable to demonstrate any significant difference in the Iba1 expression for any time points. The cells treated with IgG (10 μg/ml) were considered as control for both the mixed cortical and primary neuronal cultures.

Iba1 is a glial specific marker that is known to be upregulated in the activated microglia. Iba1 was used as marker to investigate the effect of microglial activation as a result of PHF and antibody treatment. A significant decrease in the levels of Iba1 was observed in the Antibody 5G2A3-treated mixed cortical culture at 72 h and 96 h (FIG. 8), relative to the control and cells treated with PHF only. Tau aggregates are known to activate microglia that in turn is known to cause stimulation of cytokine further leading to increased inflammatory response. Although increased microglial activation would further help in the clearance of PHF, a sustained increase in the microglia and inflammatory cytokines is also known to add to the overall pathology by causing elevated cellular injury. A decrease in Iba1 expression after Antibody 5G2A3 treatment is suggestive of a reduction in the inflammatory response mechanism following microglia-mediated clearance of antibody-tau complexes, whereas the less effective Antibody 1G11A10 treatment was unable to illustrate any significant alteration in the levels of Iba1 when compared to the control.

A significant decrease in the phospho Tau (pSer199), total Tau and Iba1 levels with an increase in the NeuN levels in the Antibody 5G2A3-treated mixed cortical culture is possibly suggestive of the beneficial effect of Antibody 5G2A3 in the clearance of PHF by further reducing microglial activation, inflammatory response and maintaining the neuronal physiology that was observed through an increase in the NeuN expression.

Example 4

Figure 9:
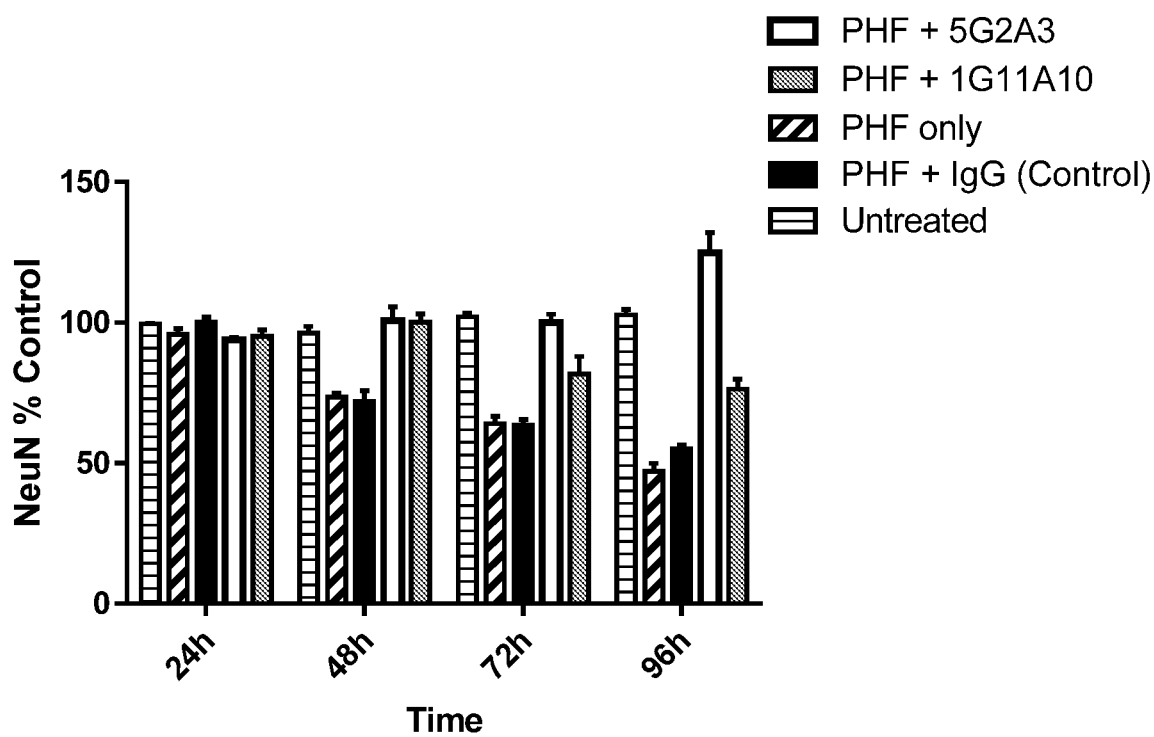
FIG. 9 shows the effect on NeuN levels of co-incubation of high dose PHF (10 μg/ml) with antibodies that are immunospecific for the Truncated Asp421 Epitope of Tau (10 μg/ml) in mixed cortical cultures, as measured by changes in NeuN levels. Under these more toxic conditions (higher PHF dose), a similar pattern is observed as in Example 3 with Antibody 5G2A3 being very effective in clearing pathological tau and preventing its toxicity, whereas the lower affinity Antibody 1G11A10 is less effective.

Co-Incubation of High Dose PHF (10 µg/Ml) with Antibodies that are Immunospecific for the Truncated Asp421 Epitope of Tau (10 µg/Ml) in Mixed Cortical Cultures To further elucidate the effects of antibodies that are capable of immunospecifically binding to the Truncated Asp421 Epitope of Tau, mixed neuronal cultures from Day 0 postnatal JNPL3 mice were co-incubated with PHF (10 µg/ml) and Antibody 5G2A3 (10 µg/ml) or Antibody 1G11A10 (10 µg/ml) for a duration of 24 h, 48 h, 72 h or 96 h. Western immunoblots were performed against NeuN, and demonstrated a significant decrease in the levels of NeuN at 48 h (27%), 72 h (37%) and 96 h (53%) for the cells treated with PHF only as well as for the PHF+IgG co-incubated cells, when compared to the untreated cells, p<0.0001. No significant alteration in the NeuN level was observed for the Antibody 5G2A3 co-incubated cells from 24 h until 72 h, p=0.18, whereas a sudden increase (122%, p<0.0001) was observed at 96 h when compared to the untreated cells. The cells co-incubated with Antibody 1G11A10 and PHF demonstrated no significant alteration in the levels of NeuN until 48 h followed by a gradual decrease in the NeuN levels at 72 h (18%) and 96 h (24%) when compared to the untreated cells. The results of this investigation are shown in FIG. 9.

Figure 10:
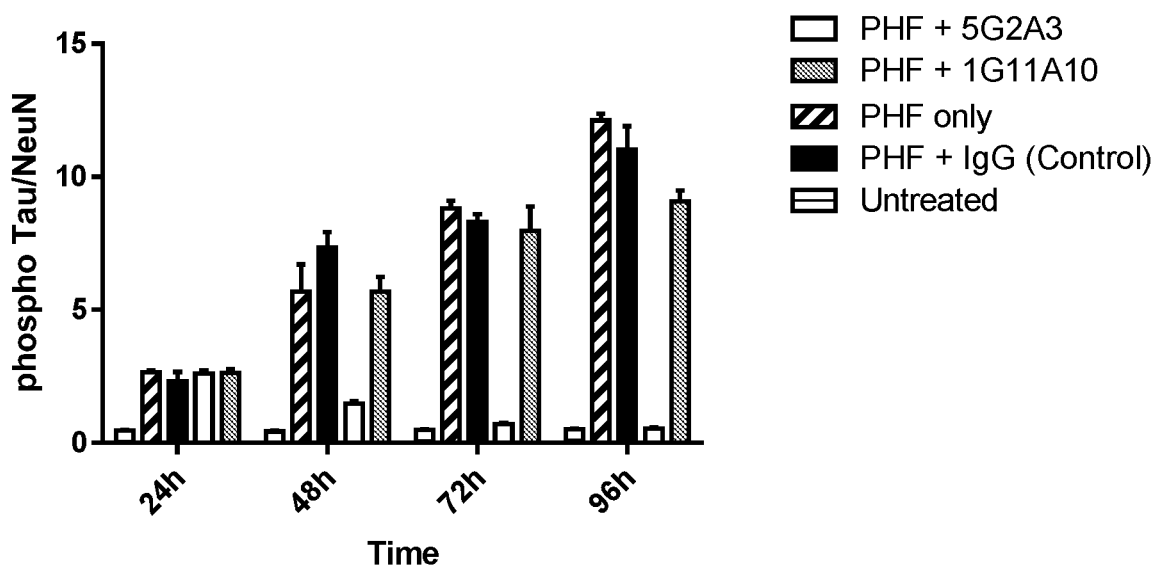
FIG. 10 shows the effect on phosphorylated Tau levels, normalized to NeuN levels, seen upon co-incubation of high dose PHF (10 μg/ml) with antibodies that are immunospecific for the Truncated Asp421 Epitope of Tau (10 μg/ml) in mixed cortical cultures, as measured by changes in binding to the Ser199 epitope, normalized to NeuN levels. The co-incubation of Antibody 5G2A3 antibody with PHF demonstrated a significant decrease in the level of phospho-Tau compared to the cells treated with PHF alone and PHF+IgG, whereas co-incubation of Antibody 1G11A10 antibody with PHF was unable to demonstrate any such alteration in the levels of phospho-Tau.

To further elucidate the effects of antibodies that are capable of immunospecifically binding to the Truncated Asp421 Epitope of Tau, mixed neuronal cultures from Day 0 postnatal JNPL3 mice were co-incubated with PHF (10 µg/ml) and Antibody 5G2A3 (10 µg/ml) or Antibody 1G11A10 (10 µg/ml) for a duration of 24 h, 48 h, 72 h or 96 h. Immunoblots were performed against Ser199 epitope and were normalized against NeuN levels (FIG. 10). The co-incubation of Antibody 5G2A3 antibody with PHF demonstrated significant decrease in the levels of phospho-Tau at 48 h (78%), 72 h (92%) and 96 h (95%) compared to the cells treated with PHF only and PHF+IgG, p<0.0001, whereas when compared with the untreated cells for the respective time points no significant alteration was observed in phospho-Tau levels for the cells co-incubated with Antibody 5G2A3 and PHF. The co-incubation of Antibody 1G11A10 antibody with PHF was unable to demonstrate any significant alteration in the levels of phospho-Tau when compared to the cells treated with PHF only and PHF+IgG for all time points.

Figure 11:
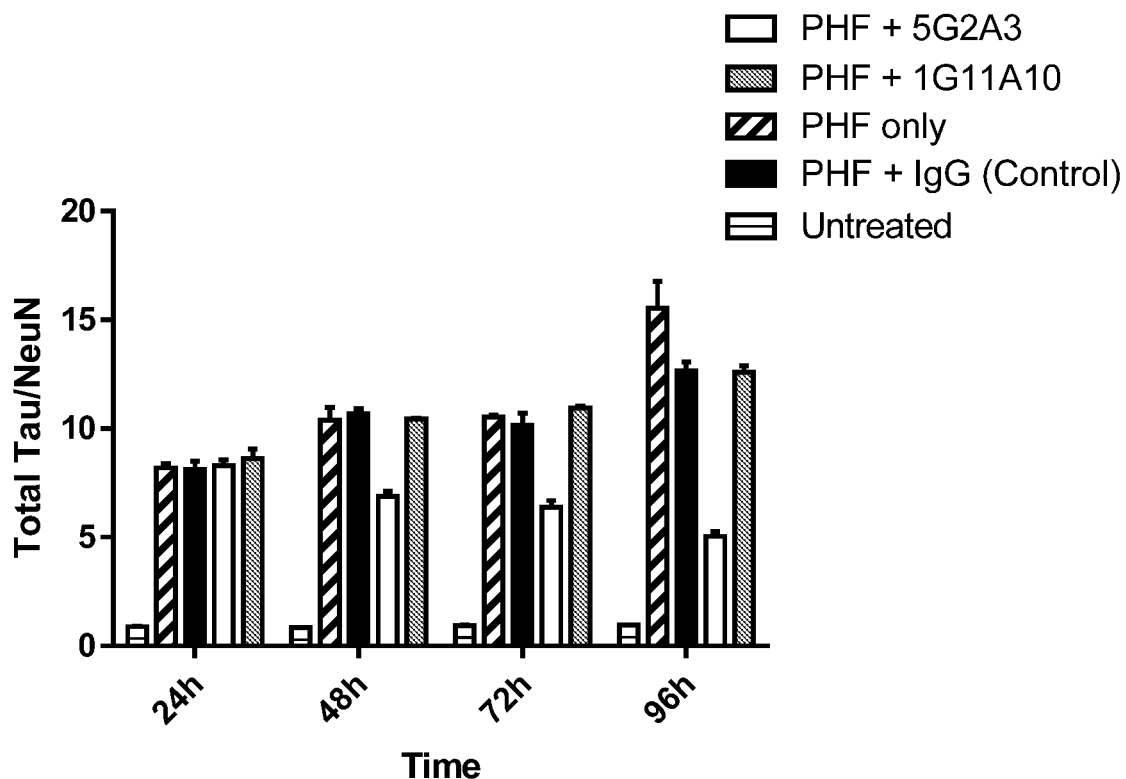
FIG. 11 shows the effect on total Tau (both phosphorylated as well as non-phosphorylated tau), normalized to NeuN levels, seen upon co-incubating a high dose of PHF (10 μg/ml) with antibodies that are capable of immunospecifically binding to the Truncated Asp421 Epitope of Tau.

Mixed neuronal cultures from Day 0 postnatal JNPL3 mice were also co-incubated with PHF (10 µg/ml) and antibodies that are capable of immunospecifically binding to the Truncated Asp421 Epitope of Tau (Antibody 5G2A3 (10 µg/ml) and Antibody 1G11A10 (10 µg/ml)) for a duration of 24 h, 48 h, 72 h or 96 h. Immunoblots were performed against Tau (Dako) which recognizes both phosphorylated as well as non-phosphorylated tau species within the cells. The values were normalized against NeuN (FIG. 11). Amongst the Antibody 5G2A3 and Antibody 1G11A10 antibodies, only Antibody 5G2A3 proved effective in reducing the total Tau levels, demonstrating 32%, 37% and 91% reduction at 48 h, 72 h and 96 h respectively compared to the control cells (cells treated with PHF+IgG) with p<0.0001. Antibody 1G11A10 was ineffective in reducing the total Tau levels for all the time points when compared to the control cells.

Figure 12:
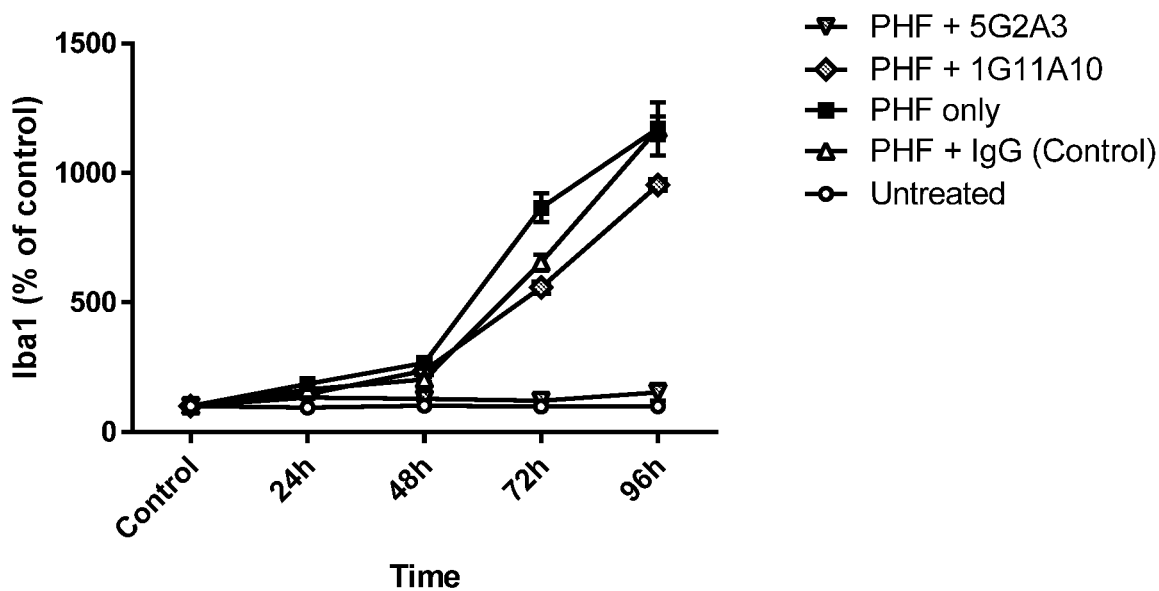
FIG. 12 shows the effect on Iba1 levels seen upon co-incubating a high dose of PHF (10 μg/ml) with antibodies that are capable of immunospecifically binding to the Truncated Asp421 Epitope of Tau.

Mixed neuronal cultures from Day 0 postnatal JNPL3 mice were also co-incubated with PHF (10 µs/ml) and Antibody 5G2A3 (10 µg/ml) or Antibody 1G11A10 (10 µg/ml) for a duration of 24 h, 48 h, 72 h or 96 h and immunoblots were performed against Iba1 to demonstrate the effect of such antibody administration on microglial activity. The co-incubation of Antibody 5G2A3 antibody with PHF did not demonstrate any significant alteration in Iba1 levels when compared to the untreated control cells, whereas a significant increase in the levels of Iba1 was observed for the cells treated with PHF only, PHF+IgG and PHF+Antibody 1G11A10 for 72 h and 96 h, p<0.0001 (FIG. 12).

Example 5

Figure 13A:
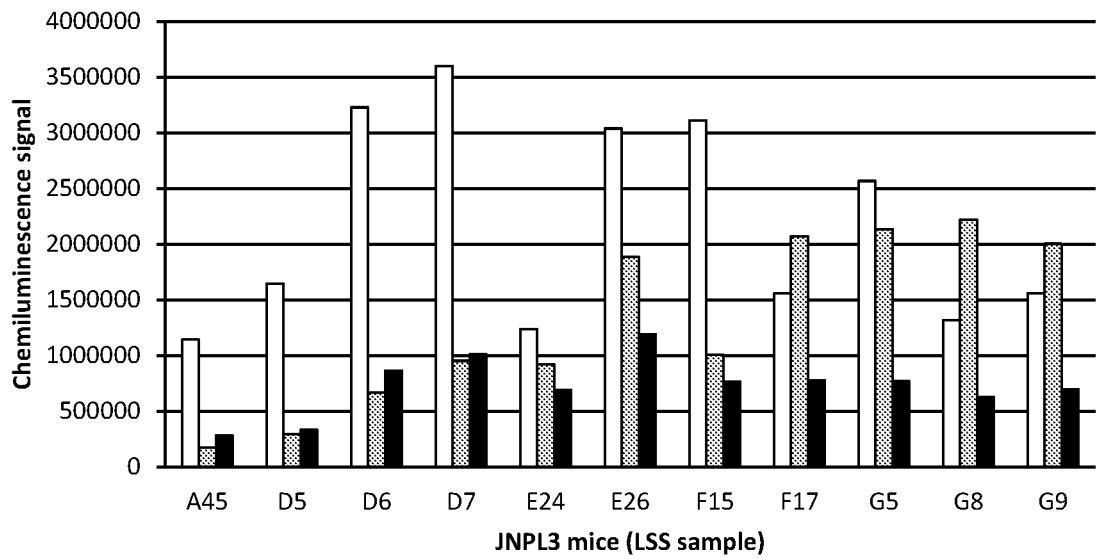
FIGS. 13A-13B show the tissue reactivity of antibodies that are immunospecific for the Truncated Asp421 Epitope of Tau in JNPL3 tauopathy mice (FIG. 13A) and hTau tauopathy mice (FIG. 13B). Low speed supernatant (LSS) samples from such mice were evaluated. The ordinate values of the Figures are the codenames of the specific mice being analyzed. White bars, Antibody 5G2A3; gray bars, Antibody 1G11A10; black bars, anti-Tau antibody C3.
Figure 13B:
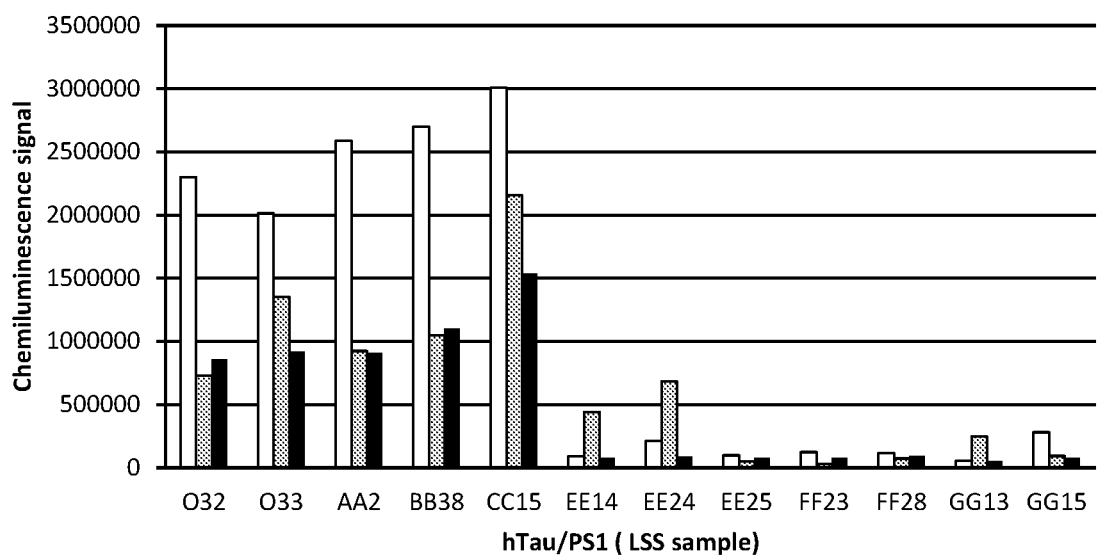

Tissue Reactivity in Tauopathy Mice of Antibodies that are Immunospecific for the Truncated Asp421 Epitope of Tau In order to assess the tissue reactivity of antibody that are immunospecific for the Truncated Asp421 Epitope of Tau, a dot blot analysis was conducted on brain supernatant samples from JNPL3 tauopathy mice (FIG. 13A) and from hTau tauopathy mice (FIG. 13B).

With regard to the JNPL3 tauopathy mice (FIG. 13A), a stronger signal was detected in most of the mice with the higher affinity Antibody 5G2A3. However, the lower affinity Antibody 1G11A10 gave a stronger signal in some of the mice, suggesting that the exact epitope recognized by these two antibodies differed. The anti-Tau antibody, C3, a commerically available antibody (Millipore Sigma; Abcam; Delobel, P. et al. (2008) "Analysis of Tau Phosphorylation and Truncation in a Mouse Model of Human Tauopathy," Am. J. Pathol. 172(1):123-131) against the same epitope, showed the lowest signal in nearly all the samples.

Example 6

Figure 14:
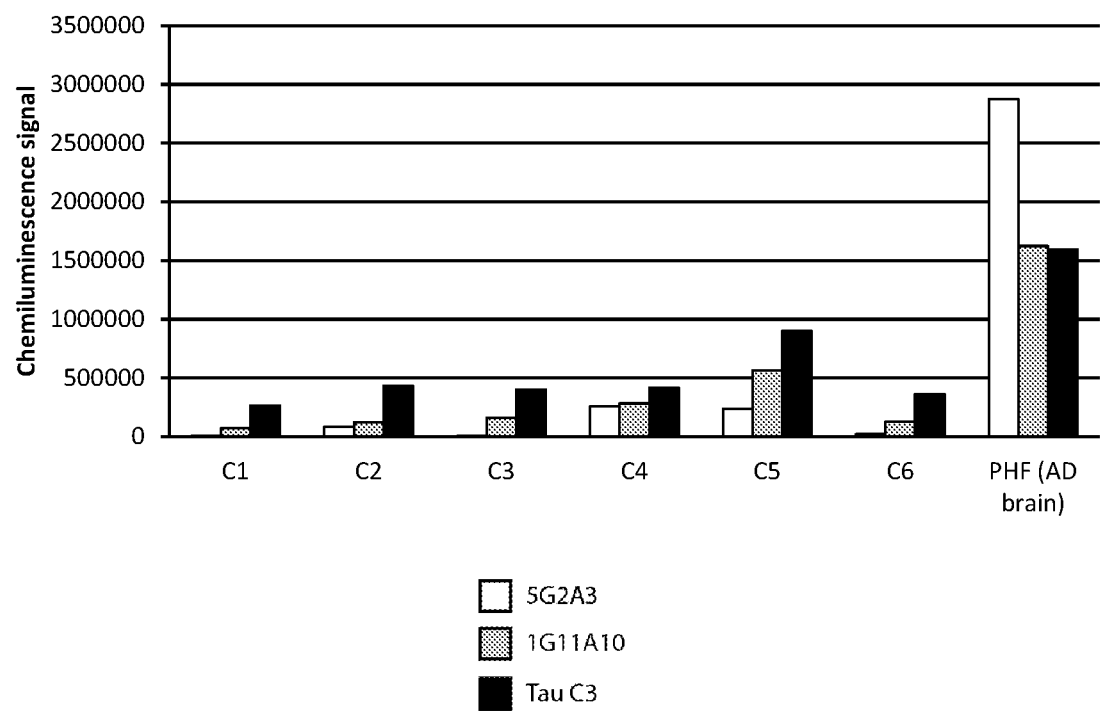
FIG. 14 shows the tissue reactivity of antibodies that are immunospecific for the Truncated Asp421 Epitope of Tau in brain supernatant samples from human (control) brain and purified PHF from human AD brain. The ordinate values of the Figure are the codenames of the specific subject being analyzed. White bars, Antibody 5G2A3; gray bars, Antibody 1G11A10; black bars, anti-Tau antibody C3.

Tissue Reactivity in Brain Supernatant Samples from Human (Control) Brain and Purified PHF from Human AD Brain An assessment of the tissue reactivity of antibody that are immunospecific for the Truncated Asp421 Epitope of Tau was also conducted on brain supernatant samples from human (control) brain and from PHF that had been purified from human AD brain. The results of this investigation are shown in FIG. 14. In human samples, Antibody 5G2A3 gives the strongest signal detecting PHF material isolated from an Alzheimer's brain. It also has the best specificity as it has a low signal in control brain supernatant (C1-C6). Antibody 1G11A10 and commercial C3 antibody have comparable signal detecting pathological PHF material, but Antibody 1G11A10 has better specificity as it has lower signal than C3 in control brains.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An antibody-based molecule that is capable of immunospecifically binding to the Truncated Asp421 Epitope of Tau, wherein said epitope is present on a peptide having the sequence of Tau 407-421 (SEQ ID NO:7): HLSNVSSTGSIDMVD,
wherein:
(A) said aspartate residue of SEQ ID NO:7 is the C-terminal Tau residue of said polypeptide;
(B) relative to said immunospecific binding, said antibody-based molecule exhibits substantially diminished binding to a polypeptide that contains additional Tau sequence residues C-terminal to said aspartate residue of SEQ ID NO:7; and
(C) said antibody-based molecule comprises:
  (i) a Variable Light Chain CDR1, CDR2, CDR3 having the amino acid sequence of SEQ ID NOs:37, 38 and 39, respectively; and
  (ii) a Variable Heavy Chain CDR1, CDR2, CDR3 respectively having the amino acid sequence of SEQ ID NOs:41, 42 and 43, respectively.

2. The antibody-based molecule of claim 1, wherein upon peripheral injection into a recipient, said molecule is capable of co-localizing with a Tau aggregate.

3. A pharmaceutical composition for the treatment of Alzheimer's disease or another tauopathy of a subject in need thereof, wherein said pharmaceutical composition comprises an effective amount of the antibody-based molecule of claim 1, and one or more carriers, diluents and/or stabilizers.

4. The pharmaceutical composition of claim 3, wherein said tauopathy is selected from the group consisting of frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

5. The antibody-based molecule of claim 1, wherein said molecule is an antibody, a diabody, an scFv, or comprises an epitope-binding fragment of an antibody, diabody or scFv.

6. The antibody-based molecule of claim 5, wherein said molecule is an antibody.

7. The antibody-based molecule of claim 5, wherein said molecule is a humanized antibody or comprises an epitope-binding fragment of a humanized antibody.

8. The antibody-based molecule of claim 5, wherein said molecule is an scFv.

9. The antibody-based molecule of any of claim 1, which is detectably labeled.

10. The antibody-based molecule of claim 9, wherein said detectable label is a fluorescent label, a chemoluminescent label, a paramagnetic label, a radioisotopic label or an enzyme label.

11. A kit for detecting or measuring the presence or amount of said truncated Tau protein in the brain of a subject, or for diagnosing Alzheimer's disease or another tauopathy in a subject, wherein said kit comprises the antibody-based molecule of claim 9.

12. A method for detecting or measuring the presence or amount of truncated Tau protein in the brain, cerebrospinal fluid, blood, serum or plasma of a recipient subject, wherein said method comprises contacting said brain, cerebrospinal fluid, blood, serum or plasma of said subject with the antibody-based molecule of claim 9 and detecting or measuring binding between said truncated Tau protein and said antibody-based molecule.

13. The method of claim 12, wherein said detection or measurement is for diagnosing Alzheimer's disease or another tauopathy of a subject.

14. The method of claim 13, wherein said tauopathy is selected from the group consisting of frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

15. The method of claim 12, wherein said detection or measurement comprises in vivo or ex vivo imaging of said antibody-based molecule bound to said truncated Tau protein.

16. The method of claim 15, wherein said detection or measurement is for the treatment of Alzheimer's disease or another tauopathy of said subject.

17. The method of claim 16, wherein said tauopathy is selected from the group consisting of frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

* * * * *

UNITED STATES PATENT AND TRADEMARK OFFICE
CERTIFICATE OF CORRECTION

PATENT NO.      : 10,988,528 B2
APPLICATION NO. : 15/750975
DATED           : April 27, 2021
INVENTOR(S)     : Einar Sigurdsson It is certified that error appears in the above-identified patent and that said Letters Patent is hereby corrected as shown below:

In the Claims

Column 203, Line 37, the word "respectively" should be deleted.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*